United States Patent [19]

Friden

[11] Patent Number: 6,015,555
[45] Date of Patent: *Jan. 18, 2000

[54] TRANSFERRIN RECEPTOR SPECIFIC ANTIBODY-NEUROPHARMACEUTICAL OR DIAGNOSTIC AGENT CONJUGATES

[75] Inventor: Phillip M. Friden, Bedford, Mass.

[73] Assignee: Alkermes, Inc., Cambridge, Mass.

[*] Notice: This patent is subject to a terminal disclaimer.

[21] Appl. No.: 08/444,644

[22] Filed: May 19, 1995

Related U.S. Application Data

[60] Division of application No. 08/232,246, filed as application No. PCT/US92/10206, Nov. 24, 1992, which is a continuation-in-part of application No. 07/800,458, which is a continuation-in-part of application No. PCT/US90/05077, Sep. 7, 1990, abandoned, which is a continuation-in-part of application No. 07/404,089, Sep. 7, 1989, Pat. No. 5,154,924.

[51] Int. Cl.⁷ .......................... A61K 39/395; C12N 5/20; C07K 16/28

[52] U.S. Cl. .................................. 424/133.1; 530/387.3; 530/388.22; 424/143.1; 435/7.21; 435/69.6; 435/69.7; 435/328; 435/334

[58] Field of Search ........................ 530/387.3, 388.22, 530/391.5, 391.7, 866, 867; 424/178.1, 182.1, 801, 809, 133.1, 143.1; 435/7.21, 69.6, 69.7, 328, 334

[56] References Cited

U.S. PATENT DOCUMENTS

| | | | |
|---|---|---|---|
| 4,292,425 | 9/1981 | Buckler et al. | 536/4 |
| 4,434,156 | 2/1984 | Trowbridge . | |
| 4,444,744 | 4/1984 | Goldenberg | 424/1.1 |
| 4,545,985 | 10/1985 | Pastan et al. . | |
| 4,569,789 | 2/1986 | Blattler et al. . | |
| 4,626,507 | 12/1986 | Trowbridge et al. . | |
| 4,631,190 | 12/1986 | Shen et al. . | |
| 4,801,575 | 1/1989 | Pardridge | 514/4 |
| 4,816,567 | 3/1989 | Cabilly et al. | 530/387 |
| 4,892,827 | 1/1990 | Pastan et al. | 435/193 |
| 4,902,505 | 2/1990 | Pardridge et al. | 424/85.7 |
| 4,992,255 | 2/1991 | Pardridge | 424/1.1 |
| 5,004,697 | 4/1991 | Pardridge | 436/547 |
| 5,028,697 | 7/1991 | Johnson et al. | 530/388 |
| 5,087,616 | 2/1992 | Myers et al. | 514/21 |
| 5,091,513 | 2/1992 | Huston et al. | 530/387 |
| 5,130,129 | 7/1992 | Pardridge | 424/85.8 |
| 5,132,405 | 7/1992 | Huston et al. | 530/387.3 |
| 5,141,736 | 8/1992 | Iwasa et al. | 530/387.3 |
| 5,154,924 | 10/1992 | Friden . | |
| 5,182,107 | 1/1993 | Friden . | |
| 5,527,527 | 6/1996 | Friden | 424/178.1 |

FOREIGN PATENT DOCUMENTS

| | | |
|---|---|---|
| 0094844 | 11/1983 | European Pat. Off. . |
| 0175560 | 3/1986 | European Pat. Off. . |
| 0253202 | 1/1988 | European Pat. Off. . |
| 0286418 | 10/1988 | European Pat. Off. . |
| 0286441 | 10/1988 | European Pat. Off. . |
| 0305967 | 3/1989 | European Pat. Off. . |
| 0324625 | 7/1989 | European Pat. Off. . |
| 0327169 | 8/1989 | European Pat. Off. . |
| 0328147 | 8/1989 | European Pat. Off. . |
| 0336383 | 10/1989 | European Pat. Off. . |
| 0449769 | 10/1991 | European Pat. Off. . |
| 1564666 | 4/1980 | United Kingdom . |
| 86/01409 | 3/1986 | WIPO . |
| 88/07365 | 10/1988 | WIPO . |
| 91/03259 | 3/1991 | WIPO . |
| 91/04753 | 4/1991 | WIPO . |
| 91/09965 | 7/1991 | WIPO . |
| 91/14438 | 10/1991 | WIPO . |
| 92/13570 | 8/1992 | WIPO . |

OTHER PUBLICATIONS

Hoogenboom, H.R. et al., "Cloning and Expression of a Chimeric Antibody Directed Against the Human Transferrin Receptor," *J. Immunology*, 144 (8): 3211–3217, (Apr. 15, 1990).

Trowbridge, I.S. et al., "Anti–transferrin Receptor Monoclonal Antibody and Toxin–antibody Conjugates Affect Growth of Human Tumour Cells," *Nature*, 294 : 171–173 (Nov. 1981).

Domingo, D.L. et al., "Transferrin Receptor as a Target for Antibody–drug Conjugates," *Methods in Enzymology*, 112: 238–247 (1985).

Zovickian, J. et al., "Potent and Specific Killing of Human Malignant Brain Tumor Cells by an Anti–Transferrin Receptor Antibody–Ricin Immunotoxin," *J. Neurosurg.*, 66 : 850–861 (1987).

Jeffries, W.A. et al., "Transferrin Receptor on Endothelium of Brain Capillaries," *Nature*, 312 : 162–163 (nov. 8, 1984).

Raso, V. et al., "Monensin is Obligatory for the Cytotoxic Action of a Disulfide Linked Methotrexate–Anti–Transferrin Receptor Conjugate," *Biochem. Biophy. Res. Comm.*, 150 (1): 104–110 (Jan. 15, 1988).

Alkan, S.S. et al., "Antiviral and Antiproliferative Effects of Interferons Delivered via Monoclonal Antibodies," *J. Interferon Res.*, 4 (3): 355–363 (1984).

Capon, D.J. et al., "Designing CD4 Immunoadhesins for AIDS Therapy," *Nature*, 337 : 525–531 (Feb. 9, 1989).

(List continued on next page.)

*Primary Examiner*—Julie Burke
*Attorney, Agent, or Firm*—Hamilton, Brook, Smith & Reynolds, P.C.

[57] ABSTRACT

The present invention pertains to a method for delivering a neuropharmaceutical or diagnostic agent across the blood brain barrier to the brain of a host. The method comprises administering to the host a therapeutically effective amount of an antibody-neuropharmaceutical or diagnostic agent conjugate wherein the antibody is reactive with a transferrin receptor and the antibody is a chimera between the variable region from one animal source and the constant region from a different animal source. Other aspects of this invention include a delivery system comprising an antibody reactive with a transferrin receptor linked to a neuropharmaceutical or diagnostic agent and methods for treating hosts afflicted with a disease associated with a neurological disorder.

6 Claims, 77 Drawing Sheets

OTHER PUBLICATIONS

Pietersz, G.A. et al., "Novel Synthesis and in Vitro Characterization of Disulfide–Linked Ricin–Monoclonal Antibody Conjugates Devoid of Galactose Binding Activity," *Cancer Res.,* 48 : 4469–4476 (Aug. 15, 1988).

Pietersz, G.A. et al., "The Use of Monoclonal Antibody Conjugates for the Diagnosis and Treatment of Cancer," *Immunol. and Cell. Biol.,* 65 (pt. 2): 111–125 (1987).

Gascoigne, N.R.J. et al., "Secretion of a Chimeric T–Cell Receptor–Immunoglobulin Protein," *Proc. Nat'l Acad. Sci. USA* 84 : 2936–2940 (May 1987).

Baldwin, R.W. et al., "Monoclonal Antibodies for Radioimmunodetection of Tumours and for Targeting," *Bull. Cancer* (Paris) 70(2): 132–136 (1983).

Bryn, R.A. et al., "Biological Properties of a CD4 Immunoadhesin," *Nature,* 344 : 667–670 (Apr. 12, 1990).

Dautry–Varsat, A. et al., "pH and the Recycling of Transferrin During Receptor Mediated Endocytosis," *Proc. Nat'l. Acad. Sci. USA* 80 : 2258–2262 (Apr. 1983).

Pardridge, W.M., "Receptor–Mediated Peptide Transport through the Blood–Brain Barrier," *Endocrine Reviews,* 7 (3): 314–330.

Friden, P.M. et al., "Anti–Transferrin Receptor Antibody and Antibody–Drug Conjugates Cross the Blood–Brain Barrier," *Proc. Nat'l Acad. Sci. USA,* 88 (11): 4771–4775 (Jun. 1, 1991).

Huston, J.M. et al., "Protein Engineering of Antibody Binding Sites: Recovery of Specific Activity in an Anti–Digoxin Single–Chain Fv Analogue Produced in *Escherichia coli*," *Proc. Natl. Acad. Sci. USA* 85: 5879–5883 (Aug. 1988).

Riechmann, L. et al., "Reshaping Human Antibodies for Therapy," *Nature 332 (Issue No. 6162):* 323–327 (Mar. 1988).

Morrison, S.L. et al., "Chimeric Human Antibody Molecules:Mouse Antigen–Binding Domains with Human ConstantRegion Domains," *Proc. Natl. acad. Sci. USA* 81 : 6851–6855 (Nov. 1984).

Boulianne, G.L. et al. "Production of Functional Chimeric Mouse/Human Antibody," *Nature 312*:643–646 (Dec. 13, 1984).

Jeffries, W.A. et al., "Analysis of Lymphopoietic Stem Cells with a Monoclonal Antibody to the Rat Transferrin Receptor," *Immunology* 54: 333–341 (1985).

Roitt, I.M., "Essential Immunology," *Blackwell Scientific Publications* pp. 65–68 & 74 (1991).

Bach, J.F. et al., "Safety and Efficacy of Therapeutic Monoclonal Antibodies in Clinical Therapy," *Immunology Today* 14(9): 421–425 (1993).

Gregoriadis, G. and A.T. Florence, "Recent Advances in Drug Targeting," *Trends in Biotech* 11: 440–42 (Nov. 1993).

Thorpe, R., "Monoclonal Antibodies: Clinical andRegulatory Issues," *Trends in Biotech 11*: 40–42 (Feb. 1993).

Hoogenboom, H.R. et al., "Construction and Expression of Antibody–Tumor Necrosis Factor Fusion Proteins," *Molecular Immunology,* 28(9) : 1027–1037 (Sep. 1991).

Shen, W.–C. et al., "Cis–Aconityl Spacer between Daunomycin and Macromolecular Carriers: A Model of pH–Sensitive Linkage Releasing Drug from a Lysosomotropic Conjugate," *Biochem. & Biophy. Res. Comm.* 102(3): 1048–1054, (Oct. 15, 1981).

Fishman, J.B. et al., "Receptor–Mediated Transcytosis of Transferrin Across the Blood–Brain Barrier," *J. Neur. Res., 18*: 299–304 (1987).

Pardridge, W.M. et al., "Selective Transport of an Anti––Transferrin Receptor Antibody through the Blood–Brain Barrier in Vivo," *J. Pharmacol. and Exp. Therapeutics, 259*(1): 66–70 (1991).

Sutherland, R. et al., "Ubiquitous Cell–Surface Glycoprotein on Tumor Cells is Proliferation–Associated Receptor for Transferrin," *Proc. Nat'l Acad. Sci. USA,* 78(7): 4515–4519 (Jul. 1981).

Batra, J.K. et al., "Antitumor Activity in Mice of an Immunotoxin made with Anti–Transferrin Receptor and a Recombinant Form of Pseudomonas Exotoxin," *Proc. Nat'l Acad. Sci. USA,* 86: 8545–8549 (Nov. 1989).

Batra, J.K. et al., "Single–Chain Immunotoxins Directed at the Human Transferrin Receptor Containing Pseudomonas Exotoxin A or Diphtheria Toxin: Anti–TFR(Fv)–PE40 and DT388–Anti–TFR(Fv)," *Mol. and Cell. Biol.* 11(4): 2200–2205 (Apr. 1991).

Friden, P.M. et al., "Blood–Brain Barrier Penetration and in Vivo Activity of an NGF Conjugate," *Science* 259: 373–377 (Jan. 15, 1993).

Cazzola, M. et al., "Cytotoxic Activity of an Anti–Transferrin Receptor Immunotoxin on Normal and Leukemic Human Hematopoietic Progenitors," *Cancer Res.* 51: 536–541 (Jan. 15, 1991).

Bjorn, M. et al., "Immunotoxins to the Murine Transferrin Receptor: Intracavitary Therapy of Mice Bearing Syngeneic Paritoneal Tumors," *Cancer Res.* 47: 6639–6645 (Dec. 15, 1987).

Smyth, M.J. et al., "The Mode of Action of Methotrexate––Monoclonal Antibody Conjugates," *Immun. and Cell Biol.* 65(Pt. 2): 189–200 (1987).

Griffin, T.W. et al., "In Vitro Cytotoxicity of Recombinant Ricin A Chain–Antitransferrin Receptor Immunotoxin Against Human Adenocarcinomas of the Colon and Pancreas," *J. of Biological Response Modifiers* 7(6): 559–567 (1988).

Pirker, R. et al., "Anti–Transferrin Receptor Antibody Linked to Pseudomonas Exotoxin as a Model Immunotoxin in Human Ovarian Carcinoma Cell Lines," *Cancer Res.* 45: 751–757 (Feb. 1985).

Morrison, S.L. et al., "Genetically Engineered Antibody Molecules: New Tools for Cancer Therapy," *Cancer Investigation* 6(2): 185–192 (1988).

```
CGTTGTCAGAAGTAAGTTGGCCGCAGTGTTATCACTCATGGTTATGGCAGCACTGCATAATTCTCTTACTGTCATGCCAT
CCGTAAGATGCTTTCTGTGACTTGGTGACTACTCAACCAAGTCATTCTGAGAATAGTGTATGCGGCGACCGAGTTGCTCT
TGCCCGGCGTCAACACGGGATAATACCGCGCCACATAGCAGAACTTTAAAAGTGCTCATCATTGGAAAACGTTCTTCGGG
GCGAAAACTCTCAAGGATCTTACCGCTGTTGAGATCCAGTTCGATGTAACCCACTCGTGCACCCAACTGATCTTCAGCAT
CTTTTACTTTCACCAGCGTTTCTGGGTGAGCAAAAACAGGAAGGCAAAATGCCGCAAAAAAGGGAATAAGGGCGACACGG
AAATGTTGAATACTTCATACTCTCCTTTTCAATATTATTGAAGCATTTATCAGGTTATTGTCTCATGAGCGGATACAT
ATTTGAATGTATTTAGAAAAATAAACAAATAGGGGTTCCGCGCACATTTCCCCGAAAAGTGCCACCTGACGTCTAAGAAA
CCATTATTATCATGACATTAACCTAT                EcoRI

AAAAATAGGCGTATCACCGAGGCCCCTTTCGTCTTCAAGAATTCAGAGAGGTCTGGTGGAGCCTGCAAAAGTCCAGCTTTCA
AAGGAACACAGAAGTATGTGATGGAATATTAGAAGAGATGTCTGCTTTATTTTTTTAAATGTCCAAAATTTTGTCAATCAATTGAG
ATACTGTGACTTAAAATGTGAGAGGTTTCAAGTACTCATTTTTTAAGTCCGAGGAATGGGAGTGAGGCTCTCATACCCTATTCAGAAC
GTCTGTTGTGTAGAACTGACATTACTTAAGTTTAAAATATTTTAAGAATGAATTGAGCAATGTGAGTGAGTCAAG
TGACTTTTAACAATAAATAAGTTTAAAATATTTTAAGAATGAATTGAGCAATGTGAGTTGAGTCAAG
                    PvuII

ATGGCCGATCAGAACCGGAACACCTGCAGCAGGTGGCAGGAAGCAGGTCATGTGGCAAGGCTATTTGGGGAAGGAAAAT
AAACCACTAGGTAAACTTGTAGCTGTGGTTTGAAGAAGTGGTTTGAAACACTCTGTCCAGCCCCACCAAACCGAAAGT
CCAGGCTGAGCAAAACACCACCTGGGTAATTTGCATTTCTAAAATAAGTTGAGGATTCAGCCGAAACTGGAGAGGTCCTC
TTTTAACTTATTGAGTTCAACCTTTTAATTTAGCTTGAGTAGTTCTGAGTAGTTCCCCAACTTAAGTTTATCGACTTCTAA
AATGT      EcoRI

ATTTAGAATTCCTTTGCCTAATATTAATGAGGACTTAACCTGTGGAAATATTTTGATGTGGGAAGCTGTTACTGTTAAAA
CTGAGGTTATTGGGTAACTGCTATGTTAAACTTGCATTGTCTGTGTTGTGTGGTGGTCAGGACTTGCATTCAGGGAACCTTGCATCAGGGAACCC
ATTCAAGGGTCAAATTTCATTTCTGCTTGTGGTGGTGGGAAATGCTACAGTTGACAGTCAGCAGTAAAATGAACACTAGATATTTTGAACC
CAAATATCCTGCTCAAATGTAACCCCAAAAAATGCTACAGTTGACAGTCAGCAGATGAACAACTGACCACAAGGCTGTTT
TGGATAAGGATAAATGCTTATCCAGTGGAGTGCTGGGTTCCTGATCCAAGTAAACACACAGTGCTGCTTGATGAGCAGGTGT
TACACAGGTGGGGAAAATGCCCTCGTTTTGCACATTACTAACACAGCAACCACAGTGCTGCTTACCAACACTTCTGAACAC
TGGGCCCTTGTCGCAAAGCTGACAGCTTGTATGTTTCTGCTGTTGACATTGCTGCTGCTGTGAAAACCCCTACCCAATTTCCTTT
AGCAGTGGAAGGACTTCCCAGATATTTTAAAATTACCCTTGAAAAGCGGTTCGTGAAAAACCCCTACCCAATTTCCTTT
TGTTAAGTGACCTAATTAACAGGAGGACACAGAGGGTGGGCAGCCTATGATTGGAATGTCCTCTCAAGT
```

FIG. 11A

```
                          BamHI
AGAGGAGGTTAGGGTTTATGAGGACACAGAGGAGCTTCCTGGGATCCGATCCNNNNNNNNNNNNNNNNNNNNNNNN
NNNNNNNNNNNNNNNNNNNNNNNNNNNNNNNNNNNNNNNNNNNNNNNNNNNNNNNNNNNNNNNNNNNNNNNNNNNN
NNNNNNNNNNNNNNNNNNNNNNNNNNNNNNNNNNNNNNNNNNNNNNNNNNNNNNNNNNNNNNNNNNNNNNNNNNNN
NNNNNNNNNNNNNNNNNNNNNNNNNNNNNNNNNNNNNNNNNNNNNNNNNNNNNNNNNNNNNNNNNNNNNNNNNNNN
NNNNNNNNNNNNNNNNNNNNNNNNNNNNNNNNNNNNNNNNNNNNNNNNNNNNNNNNNNNNNNNNNNNNNNNNNNNN
NNNNNNNNNNNNNNNNNNNNNNNNNNNNNNNNNNNNNNNNNNNNNNNNNNNNNNNNNNNNNNNNNNNNNNNNNNNN
NNNNNNNNNNNNNNNNNNNNNNNNNNNNNNNNNNNNNNNNNNNNNNNNNNNNNNNNNNNNNNNNNNNNNNNNNNNN
NNNNNNNNNNNNNNNNNNNNNNNNNNNNNNNNNNNNNNNNNNNNNNNNNNNNNNNNNNNNNNNNNNNNNNNNNNNN
NNNNNNNNNNNNNNNNNNNNNNNNNNNNNNNNNNNNNNNNNNNNNNNNNNNNNNNNNNNNNNNNNNNNNNNNNNNN
NNNNNNNNNNNNNNNNNNNNNNNNNNNNNNNNNNNNNNNNNNNNNNNNNNNNNNNNNNNNNNNNNNNNNNNNNNNN
NNNNNNNNNNNNNNNNNNNNNNNNNNNNNNNNNNNNNNNNNNNNNNNNNNNNNNNNNNNNNNNNNNNNNNNNNNNN
NNNNNNNNNNNNNNNNNNNNNNNNNNNNNNNNNNNNNNNNNNNNNNNNNNNNNNNNNNNNNNNNNNNNNNNNNNNN
NNNNNNNNNNNNNNNNNNNNNNNNNNNNNNNNNNNNNNNNNNNNNNNNNNNNNNNNNNNNNNNNNNNNNNNNNNNN
NNNNNNNNNNNNNNNNNNNNNNNNNNNNNNNNNNNNNNNNNNNNNNNNNNNNNNNNNNNNNNNNNNNNNATATAGC
ACAAAGACATGCAA
```

FIG. 11B

```
                                HindIII
ATAATATTCCCTATGCTCATAAAAACAGCCCTGACCATGAAGCTTTGACAGAGCCACAACCCTG
                                         EcoRV
GACTCCCAAGTCTTTCTTCTTCAGTGACAAACAGACATAGGATATCCACCATGGAATGGAGCTG
                                                        PvuII
GGTAATGCTCTTCCTCCTGTCAGGAACTGCAGGTGTCCGCTCAGGTCCAGCTGCAACAGTCTGACCTGAACTGGTGA
AGCCTGGAGCTTCAATGAAGATTTCCTGCAAGGTCTTGTTACTCTCACTGGCTACACCATGAACTGGTGAAGCAG
AGCCATGGAGAGAACCTTGAGTGGATTGGATATTAATCCTCACAATGGTGTACTGACTACAACCAGAAGTTCAAGGA
CAAGGCCCCTTTAACTGTAGACAAGTCATCCAACACAGCCTACATGGAGCTCCTCAGTCTGACATCTGAGGACTCTGCAG
TCTATTACTGTGCAAGAGGCTACTATTACTTTCTTTGGACTACTGGGGTCAAGGAACCTCAGTCACCGT
     NheI
CTCCTCAGCTAGCACCAAGGGCCCATCGGTCTTCCCCCTGGCACCCTCTGGGGGCACAGCGGCCC
TGGGCTGCCTGGTCAAGGACTACTTCCCCGAACCGGTGACGGTGTCGTGGAACTCAGGCGCCCTGACCAGCGGCGTGCAC
ACCTTCCCGGCTGTCCTACAGTCCTCAGGACTCTACTCCCTCAGCAGCGTGGTGACCGTGCCCTCCAGCAGCTTGGGCAC
CCAGACCTACATCTGCAACGTGAATCACAAGCCCAGCAACACCAAGGTGGACAAGAAAGTTGTGAGAGGCCAGCACAGG
GAGGGAGGGTGTCTGCTGGAAGCAGGCTCCTCTTCACCGGAGCGCATCCGACCCACTCATGCTCAGCCACGCAGGCAGC
AAGGCAGGCCCCGTCTGGGCAGGCAGCCAGTCAGGGCCCAAGGGCCAGTGTCCAGTGGGTCTTCTGGCTTTTT
CCCAGGCTCTGGGCAGGCACAGTCCCAGGATTCCACCCTGGAGCCTAAGGGCCCAAACTCTCCACTCCCTCAGCTCGG
GCCAAGAGCCATATCCGTGGGAGGACCCTGCCCCTGACCTAGCAACTCTTCTCTGCAGAGCCCAGGACTGTGCTGGACCT
ACACCTTCTCTCCTCCCAGATTCCAGTAACTCTTCCAGGCCTCGGGACACGTAAGCCAGGTACCTGCCCTAGAGTAGCCTGCATC
GCCAACCGTGCCCAGGTAAGCCACCGGTGCTGACAGGACCCCAAAACCTGAGGTTCCTCCAGCCCCTGAACTCCTGGGGGACCGTCAG
CAGGGACAGGCCCCAGCCCGGTGCTGACAAGGACACCCTCATGATCTCCCGGACCCCTGAGGTCACATGCGTGGTGGTGGACGTG
TCTTCCTCTTCCCCCCAAAACCCTGAGGTCAAGTTCAACTGGTACGTGGACGGCGTGCATAATGCCAAGACAAAGCCGCGGGA
AGCCACGAAGAGCACCTACAAGAGCAGTACAACAGCACGTACCGGGTGGTCAGCGTCCTCACCGTCCTGCACCAGGACTGGCTG
AGTGCAAGGTCTCCAACAAAGCCCTCCCAGCCCCCATCGAGAAAACCATCTCCAAAGCCAAAGGTGGGACCCGTGGGGTG
CGAGGGCCACAGTGGACAGAGGCCGGCTCGGCCCGGCTACCCTGAGAGTGACCAGTGGCCCTGTACCAACCTCTGTCCTACAGG
```

FIG. 11C

```
GCAGCCCCGAGAACCACAGGTGTACACCCTGCCCCCATCCCGGGATGAGCTGACCAAGAACCAGGTCAGCCTGACCTGCC
TGGTCAAAGGCTTCTATCCCAGCGACATCGCCGTGGAGTGGGAGAGCAATGGGCAGCCGGAGAACAACTACAAGACCACG
CCTCCCGTGCTGGACTCCGACGGCTCCTTCTTCCTCTACAGCAAGCTCACCGTGGACAAGAGCAGGTGGCAGCAGGGGAA
CGTCTTCTCATGCTCCGTGATGCATGAGGCTCTGCACAACCACTACACGCAGAAGAGCCTCTCCCTGTCTCCGGGTAAAT
GAGTGCGACGGCCGCGCAAGCCCCGCCCAGCATGAGCGCACGAGGATGCTTGGCACGTACCCCCTGTACATAC
TTCCCGGGCGCCGAGTCTGAGGCCTGAGTGGCATGGAGGAGCAGAGGGGTCAANNNNNNNNNNNNNNNNNNNNNNNN
TCAGGCCGAGTCTGAGGCCTGAGTGGCATGGAGGAGCAGAGCGGGTCAANNNNNNNNNNNNNNNNNNNNNNNN
NNNNNNNNNNNNNNNNNNNNNNNNNNNNNNNNNNNNNNNNNNNNNNNNNNNNNNNNNNNNNNNNNNNNNNNNNNNN
NNNNNNNNNNNNNNNNNNNNNNNNNNNNNNNNNNNNNNNNNNNNNNNNNNNNNNNNNNNNNNNNNNNNNNNNNNNN
NNNNNNNNNNNNNNNNNNNNNNNNNNNNNNNNNNNNNNNNNNNNNNNNNNNNNNNNNNNNNNNNNNNNNNNNNNNN
NNNNNNNNNNNNNNNNNNNNNNNNNNNNNNNNNNNNNNNNNNNNNNNNNNNNNNNNNNNNNNNNNNNNNNNNNNNN
NNNNNNNNNNNNNNNNNNNNNNNNNNNNNNNNNNNNNNNNNNNNNNNNNNNNNNNNNNNNNNNNNNNNNNNNNNNN
NNNNNNNNNNNNNNNNNNNNNNNNNNNNNNNNNNNNNNNNNNNNNNNNNNNNNNNNNNNNNNNNNNNNNNNNNNNN
NNNNNNNNNNNNNNNNNNNNNNNNNNNNNNNNNNNNNNNNNNNNNNNNNNNNNNNNNNNNNNNNNNNNNNNNNNNN
NNNNNNNNNNNNNNNNNNNNNNNNNNNNNNNNNNNNNNNNNNNNNNNNNNNNNNNNNNNNNNNNNNNNNNNNNNNN
NNNNNNNNNNNNNNNNNNNNNNNNNNNNNNNNNNNNNNNNNNNNNNNNNNNNNNNNNNNNNNNNNNNNNNNNNNNN
NNNNNNNNNNNNNNNNNNNNNNNNNNNNNNNNNNNNNNNNNNNNNNNNNNNNNNNNN
    MboI
    BamHI
NNGGATCCAGACACATGATAAGATACATTGATGAGTTTGGACAAACCACAACTAGAATGCAGTGAAAAAATGCTTTATTTG
TGAAATTTGTGATGCTATTGCTTTATTGTAACCATTATAAGCTGCAATA
```

FIG. 11D

HpaI
AACAAGTTAACAACAACAATTGCATTCATTTATGTTTCAGGTTCAGGGGGGAGGTGTGGAGGTT
TTTAAGCAAGTAAAACCTCTACAAATGTGGTATGGCTGATTATGATCTCTAGTCAAGGCACTATACATCAAATATCC
                                    MboI
TTATTAACCCCTTTACAAATTAAAAGCTAAAGCTACACAATTTTGAGCATAGTTATTAATAGCAGACACTCTATGCCT
GTGTGGAGTAAGAAAAACAGTATGTTATGATTATAAACTGTTATGCCTACTATAAAGGTTACAGAATATTTTCCATAA
TTTTCTTGTATAGCAGTGCAGCTTTTTCCTTGTGGTGTAAATAGCAAAGCAAGAGTTCTATTACTAAACACAGCA
TGACTCAAAAAACTTAGCAATTCTGAAGGAAAGTCCCTGGGCTCTTCTTACCTTCTCTTCTTTTTGGAGGAGTAGAATG
TTGAGAGTCAGCAGTAGCCTCATCATCACTAGAGTTGGAATCTAAAAACAGGTTTTCCTCATTAAAGGCATTCC
ACCACTGCTCCCATTCATCAGTTCCATAGGTTGGAATCTAAAATACACAAACAATTAGAATCAGTAGTTTAACACATTAT
ACACTTAAAATTTTATATTTACCTTATAGCTTTAAATCTCTGTAGTAGTTGTCCAATTATGTCACCACAGAAGTA
AGGTTCCTTC
        MboI                                                           HpaI
ACAAAGATCCGGNNNNNNNNNNNNNNNNNNNNNTCATGCTTGCTCCTTGAGGGCGTTAACGCGCAAGGTAACGGCA
TTTTTATGGGCGGTCAGACGTTCGGCGGCGCGTTCGGTGTTTCTATGGTTGAAGCCACCGCGAGAACCCCTCTTTCGACAG
TTCCTGTACGGTCATACGCTTCTGGAAATCTGCCAGCCCGAGGCTGGAACAGGTGGCGGTTAACCGTAAGTCGGTAGAA
CGTGGTTGGTTCCGAGGCGTTCACGGGCGTTGCGGGTCTGAATGATCAGGTGCCTGGGCGGGCGGTTTCGCACGCGGTTTCCGCCAGTT
CTATCGACCAGTTCACGGGCGTTGCGGGTCTGAATGATCAGGTGCCTGGGCGGGCGGTTTCGCACGCGGTTCCGCCAGTT
CGCTGAATCTTTAGTCACGATCAGGCGGCTACGCGCAACGCGGCGACGCGCCATATCAGCAGCGGGCGTCAGTAGAATCACCTGTGAGTCCGGCCGTGT
GGCGTTCGACGGCCTCGGCAACGCCCTCGACGTTCGCTTCCGCGGTTCCGCTTCCGCCAGTTCCGCCAGT
TCAGCCCTGAGAGAGCAAATCAGAAG
                                                                    ClaI
CCACGAAATCCGGCGTTGCGCCGCTGTCAGCAATCACCAGCACTCCGACGGCCTGCGGGCATATCGATCTCCGCACCG
TCCAGACGCTGGCTCACCTGACGTTCGCTTCGACAAAGGCGTTACCCGGCCCGAAGATTTGTCCACTTTGCAC
GGATTCCGTACCAAACGCCAGTGCGGCAAT

FIG. 11E

```
                    PvuII
GGCCTGTGCGCCGCCGACGTTGAACACGTCCTGCACACCGCACAGCTGCGCTGCCGCCGCATAAAGGATCTCATCGGCAATCGGCG
GCGGTGAGCACAGCACCACTTTTTACAGCCCGCAATACGGCCGGAGTCGCCAGCATTAATACCGTTGAGAAGAGCGGG
GCGAGCCCGCCAGAATATACAACCAACTGAAGCTACCGGACGCGTGCTGGCAACGCACCGCCTGGCTGCGTTTC
TACATCTACCGGCGGCAGTTTTTGCGCAGGCGGCGGCAGTGTGTGGAAGGTTTCAATATTCTTACTGCCACCGCCATCGCCTGTTTAGCT
CGTCGCTCAGGCGTTCGCTGGCGGCGATCTCCTGCAGATCTCCTGCAGAGACCTTCAGCGCGGTAACCGTGTTTTATCAAACTTC
GCGCTGTATTCCCGCAGGCCCTCATCGCCGCCGCGCTGCTTATCGAGAATATCGTTAACAGTGCGGTAATGCTTT
CAGAGGCGGAAATCGCCGGCGCGTAACAGCTGGCGTGTTGCACCGCAGTACAGCTATTCCAGTCAATGATTGTTA
              PvuII
AAGCTCATNNNCCGGATCAGCTTTTTGCATAAATAAAAAAGCCTCCAAAAGCCTCCTCACTACTTCTGAATAGCTCAG
AGGCCGAGGCGCCCTCGGCGCTCTGCAGTAGGGGCGGAGAATGGCCGGAATGCTGGGCGCGGAACTGGGCGGAG
TTAGGGCGGGATGGGCGGAGTTTCCACACCTGGTTGCTGACTAATTGAGATGCTTTGCATACTTCTGCCTGCTGGGA
GCTGGGAGCCTGGGACTTTCCACACCCTAACTGACACACATTCCACAGCTGCCTCGCGTTTCGGTGATGACGGTGAAAACCTCT
GACACATGCAGCTCCCGAGACGTCACAGCTTGTCTGTAAGCGGATGCCGGGAGCAGACAAGCCCCTCAGGCGCCGTCA
GCGCGTGTTGGCGGTGTCGGGCGCAGCCAGCCATGAGAGTGCACCATATGCCGGTGAAATACCGGCTAGCGGAGTATACTGGCTTAACTATGCG
GCATCAGAGCAGATTGTACTGAGAGTGCACCATATGCCGCTCGCCGAGCGGTATCAGCTCACTCAA
CAGGCGCTCTTCCGCTTCCTCGCGCTCACAGAATCAGGGGATAACGCCAGGAAAGAACATGTGAGCAAAAGGCCAGG
AGGCGGTAATACGGTTATCCACAGAATCAGGGGATAACGCCAGGAAAGAACATCACAAAATCGACGCTCAAG
AACCGTAAAAAGGCCGCGTTGCTGGCGTTTTTCCATAGGCTCCGCCCCCTGACGAGCATCACAAAAATCGACGCTCAAG
TCAGAGGTGGCGAAACCCGACAGGACTATAAAGATACCAGGCGTTTCCCCCTGGAAGCTCCCTCGTGCGCTCTCCTGTTC
CGACCCTGCCGCTTACCGGATACCTGTCGTTTCGCCAAGCTGGGCTGTGTGCACGAACCCCCCGTTCAGCCCGACCGCTGCGCCTT
TATCTCAGTTCGGTGTAGGTCGTTCGCTCCAAGCTGGGCTGTGTGCACGAACCCCCCCGTTCAGCCCGACCGCTGCGCCTT
ATCCGGTAACTATCGTCTTGAGTCCAACCCGGTAAGACACGACTTATCGCCACTGGCAGCAGCCACTGGTAACAGGATTA
GCAGAGCGAGGTATGTAGGCGGTGCTACAGAGTTCTTGAAGTGGTGGCCTAACTACGGCTACACTAGAAGGACAGTATTT
GGTATCTGCGCTCTGCTGAAGCCAGTTACCTTCGGAAAAAGAGTTGGTAGCTCTTGATCCGGCAAACAAACCACCGCTGG
TAGCGGTGGTTTTTTTGTTTGCAAGCAGCAGATTACGCGCAGAAAAAAGGATCTCAAGAAGATCCTTTGATCTTTTCTA
```

FIG. 11F

CGGGGTCTGACGCTCAGTGGAACGAAAACTCACGTTAAGGGATTTGGTCATGAGATTATCAAAAAGGATCTTCACCTAG
ATCCTTTTAAATTAAAATGAAGTTTTAAATCAATCTAAAGTATATATGAGTAAACTTGGTCTGACAGTTACCAATGCTT
AATCAGTGAGGCACCTATCTCAGCGATCTGTCTATTTCGTTCATCCATAGTTGCCTGACTCCCCGTCGTGTAGATAACTA
CGATACGGGAGGGCTTACCATCTGGCCCCAGTGCTGCAATGATACCGCGAGACCCACGCTCACCGGCTCCAGATTTATCA
GCAATAAACCAGCCAGCGGAAGGGCCGAGCGCAGAAGTGGTCCTGCAACTTTATCCGCCTCCATCCAGTCTATTAATTG
TTGCCGGGAAGCTAGAGTAAGTAGTTCGCC
                        PstI
AGTTAATAGTTTGCGCAACGTTGTTGCCATTGCTGCTCCAGGCATCGTCGTGTCACGCTCGTCGTTTGGTATGGCTTCATTCA
GCTCCGGTTCCCAACGATCAAGGCGAGTTACATGATCCCCCATGTTGTGCAAAAAGCGGTTAGCTCCT
    PvuI
TCGGTCCTCCG

FIG. 11G

|     |     |     |     |     |     |     |     |     | ATG | GAA | TGG |
|-----|-----|-----|-----|-----|-----|-----|-----|-----|-----|-----|-----|
|     |     |     |     |     |     |     |     |     | Met | Glu | Trp |
|     |     |     |     |     |     |     |     |     | 1   |     |     |

AGC TGG GTA ATG CTC TTC CTC CTG TCA GGA ACT GCA GGT GTC CGC TCT
Ser Trp Val Met Leu Phe Leu Leu Ser Gly Thr Ala Gly Val Arg Ser
    5                          10                     15

GAG GTC CAG CTG CAA CAG TCT GGA CCT GAA CTG GTG AAG CCT GGA GCT
Glu Val Gln Leu Gln Gln Ser Gly Pro Glu Leu Val Lys Pro Gly Ala
20                    25                  30                  35

TCA ATG AAG ATT TCC TGC AAG GCT TCT GGT TAC TCA TTC ACT GGC TAC
Ser Met Lys Ile Ser Cys Lys Ala Ser Gly Tyr Ser Phe Thr Gly Tyr
                   40                  45                  50

ACC ATG AAC TGG GTG AAG CAG AGC CAT GGA GAG AAC CTT GAG TGG ATT
Thr Met Asn Trp Val Lys Gln Ser His Gly Glu Asn Leu Glu Trp Ile
            55                  60                65

GGA CGT ATT AAT CCT CAC AAT GGT GGT ACT GAC TAC AAC CAG AAG TTC
Gly Arg Ile Asn Pro His Asn Gly Gly Thr Asp Tyr Asn Gln Lys Phe
        70                    75                  80

AAG GAC AAG GCC CCT TTA ACT GTA GAC AAG TCA TCC AAC ACA GCC TAC
Lys Asp Lys Ala Pro Leu Thr Val Asp Lys Ser Ser Asn Thr Ala Tyr
85                    90                  95

ATG GAG CTC CTC AGT CTG ACA TCT GAG GAC TCT GCA GTC TAT TAC TGT
Met Glu Leu Leu Ser Leu Thr Ser Glu Asp Ser Ala Val Tyr Tyr Cys
100                105               110            115

GCA AGA GGC TAC TAT TAC TAT TCT TTG GAC TAC TGG GGT CAA GGA ACC
Ala Arg Gly Tyr Tyr Tyr Tyr Ser Leu Asp Tyr Trp Gly Gln Gly Thr
                120               125            130

TCA GTC ACC GTC TCC TCA GCT AGC ACC AAG GGC CCA TCG GTC TTC CCC
Ser Val Thr Val Ser Ser Ala Ser Thr Lys Gly Pro Ser Val Phe Pro
            135               140              145

CTG GCA CCC TCC TCC AAG AGC ACC TCT GGG GGC ACA GCG GCC CTG GGC
Leu Ala Pro Ser Ser Lys Ser Thr Ser Gly Gly Thr Ala Ala Leu Gly
        150                 155            160

TGC CTG GTC AAG GAC TAC TTC CCC GAA CCG GTG ACG GTG TCG TGG AAC
Cys Leu Val Lys Asp Tyr Phe Pro Glu Pro Val Thr Val Ser Trp Asn
     165               170               175

TCA GGC GCC CTG ACC AGC GGC GTG CAC ACC TTC CCG GCT GTC CTA CAG
Ser Gly Ala Leu Thr Ser Gly Val His Thr Phe Pro Ala Val Leu Gln
180               185               190            195

FIG. 11H

```
TCC TCA GGA CTC TAC TCC CTC AGC AGC GTG GTG ACC GTG CCC TCC AGC
Ser Ser Gly Leu Tyr Ser Leu Ser Ser Val Val Thr Val Pro Ser Ser
            200                 205                 210

AGC TTG GGC ACC CAG ACC TAC ATC TGC AAC GTG AAT CAC AAG CCC AGC
Ser Leu Gly Thr Gln Thr Tyr Ile Cys Asn Val Asn His Lys Pro Ser
            215                 220                 225

AAC ACC AAG GTG GAC AAG AAA GTT
Asn Thr Lys Val Asp Lys Lys Val
            230             235
```

FIG. 11I

```
GAG CCC AAA TCT TGT GAC AAA ACT CAC ACA TGC CCA CCG TGC CCA
Glu Pro Lys Ser Cys Asp Lys Thr His Thr Cys Pro Pro Cys Pro
 1           5                   10                      15
```

FIG. 11J

```
GCA CCT GAA CTC CTG GGG GGA CCG TCA GTC TTC CTC TTC CCC CCA AAA
Ala Pro Glu Leu Leu Gly Gly Pro Ser Val Phe Leu Phe Pro Pro Lys
 1           5                       10                    15

CCC AAG GAC ACC CTC ATG ATC TCC CGG ACC CCT GAG GTC ACA TGC GTG
Pro Lys Asp Thr Leu Met Ile Ser Arg Thr Pro Glu Val Thr Cys Val
             20                  25                  30

GTG GTG GAC GTG AGC CAC GAA GAC CCT GAG GTC AAG TTC AAC TGG TAC
Val Val Asp Val Ser His Glu Asp Pro Glu Val Lys Phe Asn Trp Tyr
         35                  40                  45

GTG GAC GGC GTG GAG GTG CAT AAT GCC AAG ACA AAG CCG CGG GAG GAG
Val Asp Gly Val Glu Val His Asn Ala Lys Thr Lys Pro Arg Glu Glu
     50                  55                  60

CAG TAC AAC AGC ACG TAC CGG GTG GTC AGC GTC CTC ACC GTC CTG CAC
Gln Tyr Asn Ser Thr Tyr Arg Val Val Ser Val Leu Thr Val Leu His
 65              70                  75                      80

CAG GAC TGG CTG AAT GGC AAG GAG TAC AAG TGC AAG GTC TCC AAC AAA
Gln Asp Trp Leu Asn Gly Lys Glu Tyr Lys Cys Lys Val Ser Asn Lys
                 85                  90                      95

GCC CTC CCA GCC CCC ATC GAG AAA ACC ATC TCC AAA GCC AAA
Ala Leu Pro Ala Pro Ile Glu Lys Thr Ile Ser Lys Ala Lys
             100             105             110
```

FIG. 11K

```
                                    GGG CAG CCC CGA GAA CCA
                                    Gly Gln Pro Arg Glu Pro
                                     1                5

CAG GTG TAC ACC CTG CCC CCA TCC CGG GAT GAG CTG ACC AAG AAC CAG
Gln Val Tyr Thr Leu Pro Pro Ser Arg Asp Glu Leu Thr Lys Asn Gln
            10              15                  20

GTC AGC CTG ACC TGC CTG GTC AAA GGC TTC TAT CCC AGC GAC ATC GCC
Val Ser Leu Thr Cys Leu Val Lys Gly Phe Tyr Pro Ser Asp Ile Ala
        25              30                  35

GTG GAG TGG GAG AGC AAT GGG CAG CCG GAG AAC AAC TAC AAG ACC ACG
Val Glu Trp Glu Ser Asn Gly Gln Pro Glu Asn Asn Tyr Lys Thr Thr
    40              45                  50

CCT CCC GTG CTG GAC TCC GAC GGC TCC TTC TTC CTC TAC AGC AAG CTC
Pro Pro Val Leu Asp Ser Asp Gly Ser Phe Phe Leu Tyr Ser Lys Leu
55              60                  65                      70

ACC GTG GAC AAG AGC AGG TGG CAG CAG GGG AAC GTC TTC TCA TGC TCC
Thr Val Asp Lys Ser Arg Trp Gln Gln Gly Asn Val Phe Ser Cys Ser
                75              80                  85

GTG ATG CAT GAG GCT CTG CAC AAC CAC TAC ACG CAG AAG AGC CTC TCC
Val Met His Glu Ala Leu His Asn His Tyr Thr Gln Lys Ser Leu Ser
            90              95                  100

CTG TCT CCG GGT AAA
Leu Ser Pro Gly Lys
        105
```

FIG. 11L

```
Met Ser Phe Asn Thr Ile Ile Asp Trp Asn Ser Cys Thr Ala Val Gln
 1            5                10                15

Gln Arg Gln Leu Leu Thr Arg Pro Ala Ile Ser Ala Ser Glu Ser Ile
            20                25                30

Thr Arg Thr Val Asn Asp Ile Leu Asp Asn Val Lys Ala Arg Gly Asp
        35                40                45

Glu Ala Leu Arg Glu Tyr Ser Ala Lys Phe Asp Lys Thr Thr Val Thr
    50                55                60

Ala Leu Lys Val Ser Ala Glu Glu Ile Ala Ala Ala Ser Glu Arg Leu
65                70                75                        80

Ser Asp Glu Leu Lys Gln Ala Met Ala Val Ala Val Lys Asn Ile Glu
            85                90                95

Thr Phe His Thr Ala Gln Lys Leu Pro Pro Val Asp Val Glu Thr Gln
            100               105               110

Pro Gly Val Arg Cys Gln Gln Val Thr Arg Pro Val Ala Ser Val Gly
            115               120               125

Leu Tyr Ile Pro Gly Gly Ser Ala Pro Leu Phe Ser Thr Val Leu Met
    130               135               140

Leu Ala Thr Pro Ala Arg Ile Ala Gly Cys Lys Lys Val Val Leu Cys
145               150               155                       160

Ser Pro Pro Pro Ile Ala Asp Glu Ile Leu Tyr Ala Ala Gln Leu Cys
                165               170               175

Gly Val Gln Asp Val Phe Asn Val Gly Gly Ala Gln Ala Ile Ala Ala
            180               185               190

Leu Ala Phe Gly Thr Glu Ser Val Pro Lys Val Asp Lys Ile Phe Gly
        195               200               205

Pro Gly Asn Ala Phe Val Thr Glu Ala Lys Arg Gln Val Ser Gln Arg
        210               215               220

Leu Asp Gly Ala Glu Ile Asp Met Pro Ala Gly Pro Ser Glu Val Leu
225               230               235               240

Val Ile Ala Asp Ser Gly Ala Thr Pro Asp Phe Val Ala Ser Asp Leu
                245               250               255

Leu Ser Gln Ala Glu His Gly Pro Asp Ser Gln Val Ile Leu Leu Thr
            260               265               270
```

FIG. 11M

Pro Ala Ala Asp Met Ala Arg Arg Val Ala Glu Ala Val Glu Arg Gln
    275                 280                 285

Leu Ala Glu Leu Pro Arg Ala Glu Thr Ala Arg Gln Ala Leu Asn Ala
    290                 295                 300

Ser Arg Leu Ile Val Thr Lys Asp Ser Ala Gln Cys Val Glu Ile Ser
305                 310                 315                 320

Asn Gln Tyr Gly Pro Glu His Leu Ile Ile Gln Thr Arg Asn Ala Arg
            325                 330                 335

Glu Leu Val Asp Ser Ile Thr Ser Ala Gly Ser Val Phe Leu Gly Asp
        340                 345                 350

Trp Ser Pro Glu Ser Ala Gly Asp Tyr Ala Ser Gly Thr Asn His Val
        355                 360                 365

Leu Pro Thr Tyr Gly Tyr Thr Ala Thr Cys Ser Ser Leu Gly Leu Ala
    370                 375                 380

Asp Phe Gln Lys Arg Met Thr Val Gln Glu Leu Ser Lys Glu Gly Phe
385                 390                 395                 400

Ser Ala Val Ala Ser Thr Ile Glu Thr Leu Ala Ala Glu Arg Leu
                405                 410                 415

Thr Ala His Lys Asn Ala Val Thr Leu Arg Val Asn Ala Leu Lys Glu
            420                 425                 430

Gln Ala

FIG. 11N

```
HindIII
TTGCAAGCTTTTTGCAAAAGCCTAGGCCTCCCAAAAAGCCTCCTCACTACTTCTGGAATAGCTCAGAGAGGCCGAGGCGCCT
CGGCCTCTGCATAAATAAAAAAATTAGTCAGCCATGGGGCGGAGAATGGGCGGAACTGGGCGGAGTTAGGGCGGGATG
GGCGGAGTTAGGGCGGGACTATGGTTGCTGACTAATTGAGATGCATGCTTTGCATACTTCTGCATACTTCTGCCTGGGAGCCTGG
GGACTTTCCACACCTGGTTGCTGACTAATTGAGATGCATGCTTTGCATACTTCTGCCTGGGAGCCTGGGACTTTC
CACAC
                PvuII
CCTAACTGACACACATTCCACAGCTGCCTCGCGCCGTTTCGGTGTGATGACGGTGAAAACCCTGACACAGCTCCCGGA
GACGGTCACAGCTTGTCTGTAAGCGGATGCCGGGAGCAGACAAGCCCGTCAGGCGCGTCAGGCGGGTGTTGGCGGTGTC
GGGGCGCAGCCATGACCCAGTCACCTAGCGATAGCGGAGTGTATACTGGCTTAACTGCGCATCAGAGCAGATTGTAC
TGAGAGTGCACCATATGCGGTGTGAAATACCGCACAGATGCGTAAGGAGAAAATACCGCATCAGGCGCTCTTCCGTTCC
TCGCTCACTGACTCGCTGCCGCTCGGTCGCTCGGGCTGCGCCGTTCGGCGGGTATCAGCTCACTCAAAGGCGGTAATACGGTTATC
CACAGAATCAGGGGATAACGCAGGAAAGAACATGTGAGCAAGAACCAGCAAAAGGCCAGGAACCGTAAAAAGGCCGCGT
TGCTGGCGTTTTTCCATAGGCTCCGCCCCCCCTGACGAGCATCACAAAAATCGACGCTCAAGTCAGAGGTGGCGAAACCCG
ACAGGACTATAAAGATACCAGGCGTTTCCCCCTGGAAGCGTGGCGCTTTCTCAATGCTCACGCTGTAGGTATCTCAGTTCGGTGTAGG
ATACCTGTCCGCCTTTCTCCCTTCGGGCTGTGTGCACGAACCCCCCGTTCAGCCCGACCGCTGCGCCTTATCCGGTAACTATCGTCTT
TCGTTCCGACTCCAAGCTGGGCTGTGTGCACGAACCGACTTATCGCCACTGGCAGCAGCCACTGGTAACAGGATTAGCAGAGCGAGGTATGTAGG
GAGTCCAACCCGGTAAGACACGACTTATCGCCACTGGCAGCAGCCACTACTAGAAGAACAAACCACCGCTGGTAGCGGTGGTTTTTTTGTT
CGGTGCTACAGAGTTCTTGAAGTGGTGGCCTAACTACGGCTACACTAGAAGAACAAACCACCGCTGGTAGCGGTGGTTTTTTTGTT
AGCCAGTTACCTTCGGAAAAAGAGTTGGTAGCTCTTGATCCGGCAAACAAACCACCGCTGGTAGCGGTGGTTTTTTTGTT
TGCAAGCAGCAGATTACGCGCAGAAAAAAAGGATCTCAAGAAGATCCTTTGATCTTTTCTACGGGGTCTGACGCTCAGTG
GAACGAAAACTCACGTTAAGGGATTTTGGTCATGAGATTATCAAAAAGGATCTTCACCTAGATCCTTTTAAATTAAAAAT
GAAGTTTTAAATCAATCTAAAGTATATATGAGTAAACTTGGTCTGACAGTTACCAATGCTTAATCAGTGAGGCACCTATC
TCAGCGATCTGTCTATTTCGTTCATCCATAGTTGCCTGACTCCCCGTCGTGTAGATAACTACGATACGGGAGGGCTTACC
ATCTGGCCCCAGTGCTGCAATGATACCGCGAGACCCACGCTCACCGGCTCCAGATTTATCAGCAATAAACCAGCCAGCCG
GAAGGGCCGAGCGCAGAAGTGGTCCTGCAACTTTATCCGCCTCCATCCAGTCTATTAATTGTTGCCGGGAAGCTAGAGTA
AGTAGTTCGCCAGTTAATAGTTTGCGCAACGTTGTTGCCATTGCTGCAGGCATCGTGGTGTCACGCTCGTCGTTTGGTAT
GGCTTCATTCAGCTCCGGTTCCCAA
                                                    PvuI
CGATCAAGGCGAGTTACATGATCCCCCATGTTGTGCAAAAAAGCGGTTAGCTCCTTCGGTCCTCCGATCGTTGTCAGAAGT
AAGTTGGCCGCAGTGTTATCACTCATGGTTATGGCAGCACTGCATAATTCTCTTACTGTCATGCCATCCGTAAGATGCTT
TTCTGTGACTGGTGAGTACTCAACCAAGTCATTCTGAGAATAGTGTATGCGGCGACCGAGTTGCTCTTGCCCGGCGTCAA
```

FIG. 13A

```
CACGGGATAATACCGCGCCACATAGCAGAACTTTAAAAGTGCTCATCATTGGAAAACGTTCTTCGGGGCGAAAACTCTCA
AGGATCTTACCGCTGTTGAGATCCAGTTCGATGTAACCCACTCGTGCACCCAACTGATCTTCAGCATCTTTTACTTTCAC
CAGCGTTTCTGGGTGAGCAAAAACAGGAAGGCAAAATGCCGCAAAAAAGGGAATAAGGCGACACGGAAATGTTGAATAC
TCATACTCTTCCTTTTTCAATATTATTGAAGCATTATCAGGGTTATTGTCTCATGAGCGGATACATATTTGAATGTATT
TAGAAAAATAAACAAATAGGGGTTCCGCGCACATTTCCCCGAAAAGTGCCACCTGACGTCTAAGAAACCATTATTATCAT
GACATTAACC
                    EcoRI
TATAAAAATAGGCCTATCACGAGGCCCTTTCGTCTTCAAGAATTCCTTTGCCTAATATTAATGAGGACTTAACCTGTGGA
AATATTTGATGTGGAAGCTGTTACTGTTAAAACTGAGGTTATTGGGGTAACTGCTATGTTAAACTTGCATTCAGGGAC
ACAAAAACTCATGAAATGTGCTGGAAAACCATTCAAGGTCAAATTTTCATTTTTTTGCTGTTGGTGGGAACCTT
TGGAGCTGCAGGTGTGTTAGCAACTACAGACCAAATATCCTCAAACTGTAACCCCAAAAATGCTACAGTTGAC
AGTCAGCAGATGAACACTGACCACAAGGCTGTTTTGGATAAGGATAATGCTTATCCAGTGCAGTGCTGGGTTCCTGATCC
AAGTAAAAATGAAAACACTAGATATTTTGAACCTACACAGGTGGGGAAAATGCCTCCTGTTTTGCACATTACTAACA
CAGCAACCACAGTCGCTGCTTACCAACACTTCTGGAACACAGCAGTGGAAGGACTTCCCAGATATTTAAAATTACCCTTAGAAA
ATTTGTGGGCTGTTGAAAAACCCTACCCAATTTCCTTTTGTTAAGTGACCTAATTAACAGGAGGACACAGAGGGTGGATGGGC
GCGGTCTGTGAAAACCCCTACCCAATTTCCTTTTGTTAAGTGACCTAATTAACAGGAGGACACAGAGGGTGGATGGGC
AGCCTATGATTGGAA
                        BamHI
TGTCCTCTCAAGTAGTAGAGGAGGTTAGGGTTTATGAGGACACAGAGGAGCTTCCTGGGATCCNNNNNNNNNNN...
```

FIG. 13B

```
NNNNNNNNNNNNNNNNNNNNNNNNNNNNNNNNNNNNNNNNNNNNNNNNNNNNNNNNNNNNNNNNNNNNNNNNNN
NNNNNNNNNNNNNNNNNNNNNNNNNNNNNNNNNNNNNNNNNNNNNNNNNNNNNNNNNNNNNNNNNNNNNNNNNN
NNNNNNNNNNNNNNNNNNNNNNNNNNNNNNNNNNNNNNNNNNNNNNNNNNNNNNNNNNNNNNNNNNNNNNNNNN
NNNNNNNNNNNNNNNNNNNNNNNNNNNNNNNNNNNNNNNNNNNNNNNNNNNNNNNNNNNNNNNNNNNNNNNNNN
NNNNNNNNNNNNNNNNNNNNNNNNNNNNNNNNNNNNNNNNNNNNNNNNNNNNNNNNNNNNNNNNNNNNNNNNNN
NNNNNNNNNNNNNNNNNNNNNNNNNNNNNNNNNNNNNNNNNNNNNNNNNNNNNNNNNNNNNNNNNNNNNNNNNN
NNNNNNNNNNNNNNNNNNNNNNNNNNNNNNNNNNNNNNNNNNNNNNNNNNNNNNNNNNNNNNNNNNNNNNNNNN
ATATAGCACAAAGACATGCAAATAATATTCCCTATGCTCATAAAACAGCCCTGACCATGAAGCTTTGACAGACGCACA
ACCCTGGACTCCCAAGTCTTTCTCTTCAGTGACAAACACAGACAT
      EcoRV
AGGATATCCACCATGGATTTTCAAGTGCAGATTTTCAGCTTCCTGCTAATCAGTGCCTCAGTCATACTGTCCAGAGACA
AATTGTTCTCACCCAGTCTCCAGCAATCATGTCTGCATCTCCAGGGGAGAAGGTCACCATGACCTGCAGTGCCAGCTCAA
GTATAGATTACATTCACTGGTACCAGCAGAAGTCAGGCACCTCCCCCAAAAGATGATTTATGACACATCCAAACTGGCT
TCTGGAGTCCCTGCTCGCTTCAGTGGCAGTGGGTCTGGGACCTCTTATTCTCTCACAATCAGCAGCAGCCTGAAGA
TGCTG  CCACTTATTACTGCCATCAGCGGAATAGTTACCCATGGACGTTCGGTGGAGGGACCAAGCTGGAA
     SalI
ATCAGACGTAAGTCGACTTTCTCATCTTTTTTATGTGTAAGACACAGGTTTCATGTTAGGAGTTAAAGTCAGTTCAGA
AAATCTTGAGAAAATGGAGAGGGCTCATTATCAGTGACGTGGCATACAGTGTCAGATTTTCTGTTTATCAAGCTAGTGA
GATTAGGGCAAAAAGAGGCTTTAGTTGAGAGGAAAGTAATTAATACTATGTCACCATCCAAGAGATTGGATCGGAGAA
TAAGCATGAGTAGTTATTGA
                    XbaI
GATCTGGGTCTGACTCGCAGGTAGCGTGGTCTTCTAGACGTTAAGTGGGACGTTTAAGTGGGAGATTTGGAGGGATGAAGGAACT
TCAGGATAGAAAGGGCTGAAGTCAAGTTCAGCTTCCTAAAATGGATGTGGGAGCAAACTTGAAGATAAACTGAATGACC
CAGAGGATGAAACAGCGCAGATCAAAGAGGGCCTAGAGCTCTGAGAAGAGAAGGAGACTCATCCGTGTTGAGTTTCCAC
AAGTACTGTCTCTTGAGTTTTGCAATAAAATCAGTAGTATGTCCTGAAATAATCATTAAGCTGTTTGAAAGTATGACTGCTTGCCAT
TAAGATTTTTATGACTACAAAATCAGTAGTGACTTCTAAAATTTGTCACAAAATGTCAAAA
GTAGATACCATGGCCTTGCTGAATGATCAGAAGAGTGTGACTCTTATTCTACACATTTGGGA
                       PvuII
TGAGAGACTCTGTAGGAACGAGTCCCTTGACAGACAGCTGCAAGGGGTTTTTTTCCTTGTCTCATTTCTACATGAAAGT
AAATTTGAAATGATCNTTTTTTATTATAAGAGTAGAAATACAGTTGGGTTTGAACTATATATGTTTTAATNGGCCNCACGGT
TTTGTAAGACATTTGGTCCTTTGTTTCCCAGTTATTACTCGATTGTAATTTTATATCGCCAGCANTGGTCTGAAACGGT
NNNNNCGCAACCTCTTCGTTTACTAACTGGGTGACCTTCGGCTGTGCCAGCCATTGGCGTTCACCCTGCCGCNGGCCN
ATGAGAACCCCCGCGGTAGNNCCCTTGCTGGACCACTTCCTGAGGACACAGTGATAGGAACAGAGCCACTAAT
CTGAAGAACAGAGATGTGACAGACTACACTAATGTGAGAAAAACAAGGAAAGGTGACTTATTGGAGATTTCAGAAAT
AAAATGCATTTATTATTATTATTCCCTTATTTAATTTTCT
```

FIG. 13C

```
                                          HindIII
ATTAGGGAATTAGAAAGGGCATAAACTGCTTTATCCAGTGTTATATTAAAAGCTTNNNNNNNNNNNNNNNNNN
NNNNNNNNNNNNNNNNNNNNNNNNNNNNNNNNNNNNNNNNNNNNNNNNNNNNNNNNNNNNNNNNNNNNNNNN
NNNNNNNNNNNNNNNNNNNNNNNNNNNNNNNNNNNNNNNNNNNNNNNNNNNNNNNNNNNNNNNNNNNNNNNN
NNNNNNNNNNNNNNNNNNNNNNNNNNNNNNNNNAATCATTTCAAAATGATTTTAGAGAGCCTTTGAAAACTCTTTTAA
ACACTTTTAAACTCTTATTAAAACTAATAAGATAAACTTGAAATAATTTCATGTCAAATACATTAACTGTTTAATGTTTA
AATGCCAGATGAAAAATGTAAAGCTATCAAGAATTCACCCAGATAGAGTATCTTCATAGCATGTTTTCCCTGCTTATT
TTCCAGTGATCACATTATTTGCTACCATGTTATTTTATACAATTATCTGAAAAAAAATTAGTTATGAAGATTAAAAGAG
AAGAAAATATTAAACATAAGAGATTTCAGTCTTTCTGTTGAACTGCTTGGTTAACAGTGAAGTTAGTTTTAAAAA
                 PvuII
AAAAAAAAACTATTTCTGTTATCAGCTGACTTCTCCCTATCTGTTGACTTCTCTCCCAGCAAAAGATTCTTACTTATTTTAC
ATTTTAACCTACTGCTCTCCCACCCAACGGGTGGAATCCCCCAGAGGGGATTTCAAGAGGCCACCTGGCAGTTGCTGA
GGGTCAGAAGTGAAGCTAGCCACTTCCTCTTAGGCAGTGGCCAAGATTACAGTTGACCTCTCCTGGTATGCCTGAAAAT
TGCTGCATATGGTTACAGGCCTTGAGGCTTTGGGAGGCTTAGAGAGAGTTGCTGAACAGTCAGAAGTGAGGGCTG
ACACCACCAGGCGCAGAGGCAGGGCTCAGGGTCTGCTCTGCAGGGGAAATAAAAGCGACGGAGGCTTTCCTTGACTCAGCCGC
GGAGCCCTGTTATCCCAGCACAGTCCTGGAAGAGCACAGGGGGAAATCTAAACTCTGAGGGGTCGGATGACGACGTGGCCATTCTTTGCCTAAAGCAT
TGCCTGGTCTCTTCTGCAAGTCAGAAAAGCATGCAAAAGCTAGGAAGAAGAGCCAAAGCCCTCAGAATGGCTGCAAAGAGCTCCAACAACAATTAGAACTT
TGAGTTTACTGCAAGTCAGAAAAGCATGCAAAAGCTAGGAAGAAGAGCCAAAGCCCTCAGAATGGCTGCAAAGAGCTCCAACAACAATTTAAATACGCTTCTTGTCTTGCTATAAT
TATTAAGAATAGGGGAAGCTAGGAAGAAGAACATGCAAAGAACTCAAAACTCAAAACATCAAGAATTTAAATACGCTTCTTGTCTTGCTATAAT
TATCTGGATAAGCATGCTGTTTTCTGTCTGCTTCTCTGTGTTTGCTTCTTCTGTTGCTCCTCTGTTTGCTCCTGTGCTGAACTGTGGCTGCAATAACTTCTATCCAGAGAGGCCAAAGTACA
ACTTTGTTACTTAACACCATCTGTTTGAAATCTGAACTGCTCCCTCCAATCGGGTAACTCGGGTAACTCGAGCAGAGTGTCACAGAGCAGGACAGCAGCAGCACCTACA
TCTGATGAGCAGTTGAAATCTGAACTGCTCCCTCCAATCGGGTAACTCGAGCAGACTACGAGAAACACAAAGTCTACGCCTGCAAGTCACCATCAGGCC
GTGGAAGGTGGATAACGCCCCTGACGCTGACAAAGACTGAGCGAAGCTTCAACAGGGGAGAGTGTTAGAGGGAGACCACCCCCCCTATTGCGGTCCTCCAGCTCATCTT
CTGAGCTCGCCCGTCACAAAGAGCTTCAACAGGGGAGAGTGTTAGAGGGAGACCACCCCCCCTATTGCGGTCCTCCAGCTCATCTT
CCTGACCCCTCCCATCCTTTGGCCTCTTGCCTTTAATTGCTAATTGTTGGAGGAGAATGAATAAATAAAGTGAATCTTTGCA
TCACCTCACCCCCCTCCTCTCTTCCTCAATTAATTATTATATCGTTGTTGTTACCAACTACTCATTTCTCTTATAAGGACTA
CCTGTGGTTTCTCTTCTCTAAGGCCATAACCCACAAGCCTTCTGCCTCCACAGTCCCCTGGCCGTGTAGGAGAGTCCCGTGTAGGAGAGATCCTTGTAGGAGAGACTGCTTCCTTGTTTTC
AATATGTAGTCATCCTAAGGCGCATAACCCACAAGCCTTCTGCCTCCACAGTCCCCTGGCCGTGTAGGAGAGATCCTTGTAGGAGAGACTGCTTCCTTGTTTTC
CAGTCCTCCCTCAGCAAGCCCTCATAGTCCTTTTTCAAAAGAAGAAACCTGCANANNNNNNNNNNNNNNNNNNNN
CCCTCCTCAGCAAGCCCTCATAGTCCTTTTTCAAAAGAAGAAACCTGCANANNNNNNNNNNNNNNNNNNNN
AATCAACCAAGGCAAATTTTCAAAAGAAGAAACCTGCANANNNNNNNNNNNNNNNNNNNNNN
NNNNNNNNNNNNNNNNNNNNNNNNNNNNNNNNNNNNNNNNNNNNNNNNNNNNNNNNNNNNNNN
```

FIG. 13D

```
                                                                    BamHI
NNNNNNNNNNNNNNNNNNNNNNNNNNNNNNNNNNNNNNNNNNNNNNNNNNNGGATCCAGACATGATAAGATACATT
GATGAGTTTGGACAAACCACAACTAGAATGCAGTGAATAAAAATGCTTTATTTGTGAAATTTGTGATGCTATTGCTTTATT
TGTAACCATTATAAGCTGCAATAAACAAGTTAACAACAACAAGTTCATTCATTTTATGTTTCAGGTTCAGGGGAGGTGT
GGGAGGTTTTTAAAGCAAGTAAAACCTCTAGTTGGTATGGCTGATTATGATCTCTAGTCAAGGCACTATACATCA
AATATTCCTTATTAACCCTTTACAAGAAAAAACAGTATGTTATGATTATAACTGTTATGCCTACTTATAAAGGTTACAGAATATTT
CTATGCCTGTGTGGAGTAAGAAAAAACAGTATGTTATGATTATAACTGTTATGCCTACTTATAAAGGTTACAGAATATTT
TTCCATAATTTCTTGTATAGCAGTGCAGCTTTTTCTCCTTTGTGTGTAAATAGCAAAGCAAGAGTTCTATTACTAA
ACACAGCATGACTCAAAAACTTAGCAATTCTGAAGAAAGTCCTTGGGTCTTCTACCTTTCTCTTCTTTTTGAGGA
GTAGAATGTGAGAGTCAGCAGTAGCCTCATCAGTTCCATAGGTTGGAATCTAAATACACAAACAATTAGAATCAGTAGTTTAA
GGCATTCCACCACTGCTCCCATTCATCAGTTCCATAGGTTGGAATCTAAATCTCGTAGTAGTTTGTCCAATTATGTCACACCA
CACATTATACACTTAAAAATTTTATATTTACCTTATAGCTTAAATCTCGTAGTAGTTTGTCCAATTATGTCACACCGTA
CAGAAGTAAGGTTCCTTCACAAAGATCGATCCGGGCCTCATCACAACAGTGCCTGACGTCGAGGATTTCGCGTGGGTCAAT
TCGTATAAATCATGCGGTACGTTCGGCATCGCTCATCATGCGATACCAGTGAGGATGGTTTTACCATCAAGGGCCGACTGCACAG
GCCGCCCAGATCCACATCAGACGGTTAATCATCAGACGGTTAAAGCGGGGTTTAAAGCGGGGTTTGAACAGGTTTCG
GCGGTTGTGCCCCGTGATTAAAGCGGCGATCAGCAGCCTCCAGAGTTTCAGGATGTTAACCTGAAACTATTGTAACCCGCCTGAAGTTAAAAAGAA
CTCAGGTTTGCCTGTCTGTCATGGATGCAGCAGCCTCCAGAGTTTCAGGATGTTAACCTGAAACTATTGTAACCCGCCTGAAGTTAAAAAGAA
CAACGCCCGGCCAGTGCCAAGCCGTTGAAAAGATTGAAAAGATTGCGGGACGAATACGACCGCCATATCCCACGGC
TGTTC
              EcoRV
AATCCAGTATCTTGCGGGATATCAACAACAACATAGTCATCAACAGCGGACGACCAGCCGGTTTGCGAAGATGGTGACAA
AGTGCGCTTTTGGATACATTTCACGAATGCAACCGCAGTACCACCGGTATCCACCAGGTCATCAATAACGATGAAGCCT
TCGCCATCGCCTTCTGCCGTTTCAGCACTTAAGCTGCACTTAAGCTCGCGCTGCTGTCGTAGCTGCTGGAAATACAAACGGTATC
GACATGACGAATACCCAGTTCACGCGCCAGTAACGCCACCCGGTACCAGACCGCCAACATGTCCCAGGTGACGATGTATTTTCG
ATTGTTCAGAAGGCATCAGTCGGCTTGCGAGTTTACGTGCATGAGATCTGCAACATGTCCCAGGTGACGATGTATTTTCG
CTCATGTGAAGTGTCCCAGCCAGCCTGTTTATCTACGGCTTAAAAAGTGTTCGAGGGGAAAAATAGGTTGCGCGAGATTATAGAG
ATCTGGCGCACTAAAAAACCAGTATTTCACATGAGTCCGGTCTTTTTTACGCACTGCCTCCGCCTCCTCCCTGACGCGGATAAAGTG
GTATTCTCAAACATATCTCGCAAGCCTTGTCTTGTGTCC
```

FIG. 13F

```
ATG
Met
 1

GAT TTT CAA GTG CAG ATT TTC AGC TTC CTG CTA ATC AGT GCC TCA GTC
Asp Phe Gln Val Gln Ile Phe Ser Phe Leu Leu Ile Ser Ala Ser Val
         5               10              15

ATA CTG TCC AGA GGA CAA ATT GTT CTC ACC CAG TCT CCA GCA ATC ATG
Ile Leu Ser Arg Gly Gln Ile Val Leu Thr Gln Ser Pro Ala Ile Met
         20              25              30

TCT GCA TCT CCA GGG GAG AAG GTC ACC ATG ACC TGC AGT GCC AGC TCA
Ser Ala Ser Pro Gly Glu Lys Val Thr Met Thr Cys Ser Ala Ser Ser
     35              40              45

AGT ATA GAT TAC ATT CAC TGG TAC CAG CAG AAG TCA GGC ACC TCC CCC
Ser Ile Asp Tyr Ile His Trp Tyr Gln Gln Lys Ser Gly Thr Ser Pro
 50              55              60              65

AAA AGA TGG ATT TAT GAC ACA TCC AAA CTG GCT TCT GGA GTC CCT GCT
Lys Arg Trp Ile Tyr Asp Thr Ser Lys Leu Ala Ser Gly Val Pro Ala
             70              75              80

CGC TTC AGT GGC AGT GGG TCT GGG ACC TCT TAT TCT CTC ACA ATC AGC
Arg Phe Ser Gly Ser Gly Ser Gly Thr Ser Tyr Ser Leu Thr Ile Ser
             85              90              95

AGC ATG GAG CCT GAA GAT GCT GCC ACT TAT TAC TGC CAT CAG CGG AAT
Ser Met Glu Pro Glu Asp Ala Ala Thr Tyr Tyr Cys His Gln Arg Asn
         100             105             110

AGT TAC CCA TGG ACG TTC GGT GGA GGG ACC AGG CTG GAA ATC AGA
Ser Tyr Pro Trp Thr Phe Gly Gly Gly Thr Arg Leu Glu Ile Arg
     115             120             125
```

FIG. 13G

```
                                        ACT GTG GCT GCA CCA TCT GTC
                                        Thr Val Ala Ala Pro Ser Val
                                         1               5

TTC ATC TTC CCG CCA TCT GAT GAG CAG TTG AAA TCT GGA ACT GCC TCT
Phe Ile Phe Pro Pro Ser Asp Glu Gln Leu Lys Ser Gly Thr Ala Ser
         10              15              20

GTT GTG TGC CTG CTG AAT AAC TTC TAT CCC AGA GAG GCC AAA GTA CAG
Val Val Cys Leu Leu Asn Asn Phe Tyr Pro Arg Glu Ala Lys Val Gln
     25              30              35

TGG AAG GTG GAT AAC GCC CTC CAA TCG GGT AAC TCC CAG GAG AGT GTC
Trp Lys Val Asp Asn Ala Leu Gln Ser Gly Asn Ser Gln Glu Ser Val
 40              45              50                          55

ACA GAG CAG GAC AGC AAG GAC AGC ACC TAC AGC CTC AGC AGC ACC CTG
Thr Glu Gln Asp Ser Lys Asp Ser Thr Tyr Ser Leu Ser Ser Thr Leu
                 60              65                      70

ACG CTG AGC AAA GCA GAC TAC GAG AAA CAC AAA GTC TAC GCC TGC GAA
Thr Leu Ser Lys Ala Asp Tyr Glu Lys His Lys Val Tyr Ala Cys Glu
             75              80              85

GTC ACC CAT CAG GGC CTG AGC TCG CCC GTC ACA AAG AGC TTC AAC AGG
Val Thr His Gln Gly Leu Ser Ser Pro Val Thr Lys Ser Phe Asn Arg
         90              95              100

GGA GAG TGT
Gly Glu Cys
     105
```

FIG. 13H

GATCCGATCCNNNNNNNNNNNNNNNNNNNNNNNNNNNNNNNNNNNNNNNNNNNNNNNNNNN
NNNNNNNNNNNNNNNNNNNNNNNNNNNNNNNNNNNNNNNNNNNNNNNNNNNNNNNNNNNN
NNNNNNNNNNNNNNNNNNNNNNNNNNNNNNNNNNNNNNNNNNNNNNNNNNNNNNNNNNNN
NNNNNNNNNNNNNNNNNNNNNNNNNNNNNNNNNNNNNNNNNNNNNNNNNNNNNNNNNNNN
NNNNNNNNNNNNNNNNNNNNNNNNNNNNNNNNNNNNNNNNNNNNNNNNNNNNNNNNNNNN
NNNNNNNNNNNNNNNNNNNNNNNNNNNNNNNNNNNNNNNNNNNNNNNNNNNNNNNNNNNN
NNNNNNNNNNNNNNNNNNNNNNNNNNNNNNNNNNNNNNNNNNNNNNNNNNNNNNNNNNNN
NNNNNNNNNNNNNNNNNNNNNNNNNNNNNNNNNNNNNNNNNNNNNNNNNNNNNNNNNNNN
NNNNNNNNNNNNNNNNNNNNNNNNNNNNNNNNNNNNNNNNNNNNNNNNNNNNNNNNNNNN
NNNNNNNNNNNNNNNNNNNNNNNNNNNNNNNNNNNNNNNNNNNNNNNNNNNNNNNNNNNN
NNNNNNNNNNNNNNNNNNNNNNNNNNNNNNNNNNNNNNNNNNNNNNNNNNNNNNNNNNNN
NNNNNNNNNNNNNNNNNNNNNNNNNNNNNNNNNNNNNNNNNNNNNNNNNNNNNNNNNNNN
NNNNNNNNNNNNNNNNNNNNNNNNNNNNNNNNNNNNNNNNNNNNNNNNNNNNNNNNNNNN
NNNNNNNNNNNNNNNNNNNNNNNNNNNNNNNNNNNNNNNNNNNNNNNNNNNNNNNNNNNN
NNNNNNNNNNNNNNNNNNNNNNNNNNNNNNNNNNNNNNNNNNNNNNNNNNNNNNNNNNNN
NNNNNNNNNNNNNNNNNNNNNNNNNNNNNNNNNNNNNNNNNNNNNNNNNNNNNNNNNNNN
NNNNNNNNNNNNNNNNNNNNNNNNNNNNNNNNNNNNNNNNNNNNNNNNNNNNNNNNNNNN
NNNNNNNNNNNNNNNNNNNNNNNNNNNNNNNNNNNNNNNNNNNNNNNNNNNNNNNNNNNN
NNNNNNNNNNNNNNNNNNNNNNNNNNNNNNNNNNNNNNNNNNNNNNNNNNNNNNNNNNNN
NNNNNNNNNNNNNNNNNNNNNNNNNNNNNNNNNNNNNNNNNNNNNNNNNNNNNNNNNNNN
NNNNNNNNNNNNNNNNNNNNNNNNNNNNNNNNNNNNNNNNNNNNNNNNNNNNNNNNNNNN
NNNNNNNNNNNNNNNNNNNNNNNNNNNNNNNNNNNNNNNNNNNNNNNNNNNNNNNNNNNN
NNNNNNNNNNNNNNNNNNNNNNNNNNNNNNNNNNNNNNNNNNNNNNNNNNNNNNNNNNNN
NNNNNNNNNNNNNNNNNNNNNNNNNNNNNNNNNNNNNNNNNNNNNNNNNNNNNNNNNNNN
NNNNNNNNNNNNNNNNNNNNNNNNNNNNNNNNNNNNNNNNNNNNNNNNNNNNNNNNNNNN
NNNNNNNNNNNNNNNNNNNNNNNNNNNNNNNNNNNNNNNNNNNNNNNNNNNNNNNNNNNN
NNNNNNNNNNNNNNNNNNNNNNNNNNNNNNNNNNNNNNNNNNNNNNNNNNNNNNNNNNNN
NNNNNNNNNNNNNNNNNNNNNNNNNNNNNNNNNNNNNNNNNNNNNNNNNNNNNNNNNNNN
NNNNNNNNNNNNNNNNNNNNNNNNNNNNNNNNNNNNNNNNNNNNNNNNNNNNNNNNNNNN
NNNNNNNNNNNNNNNNNNNNNNNNNNNNNNATAGCACAAAGACATGCAAATAATATTCCCTATGCTCATAAAAACAG
CCCTGACCATGAAGCTTTGACAGAACGCACAACCCTGGACTCCCAAGTCTTTCTCTTCCTCCTGTCAGTGA
       EcoRV
CAAACACAGACATAGGATATCCACCATGGAATGGAGCTGGTAATGCTCTTCCTCCTGTCAGGAA
                 PvuII
CTGCAGGTGTCCGCTCTGAGTCCAGTCGACCTGAACTGGTGAAGCCTGGAGCTTCAATGAAGATTTCC
TGCAAGGCTTCTGGTTACTCATTCACTGGCTACACCATGAACTGGTGAAGCAGAGCCATGGAGAACCTTGAGTGGAT
TGGACGTATTAATCCTCACAATGGTGGTACTACTGACTACAACCAGAAGTTCAAGGACAAGGCCCCTTAACTGTAGACAAGT
CATCCAACACAGCCTACATGGAGCTCCGCAGTCTGACATCTGAGGACTCTGCAGTCTATTACTGTGCAAGAGGCTACTAT
TACTA

FIG. 17A

```
                                              NheI
TTCTTTGGACTACTGGGGTCAAGGAACCTCAGTCACCGTGTCTCCTCAGCTAGCACCAAGGGCCCATCGGTCTTCCCCCTGG
CGCCCTGCTCCAGGAGCACCTCCGAGAGCACAGCGGCCCTGGGCTGCCTGGTCAAGGACTACTTCCCCGAACCGGTGACG
GTGTCGTGGAACTCAGGCGCTCTGACCAGCGGCGT
       PvuII
GCACACCTTCCCAGCTGTCCTACAGTCCTCAGGACTCTACTCCCTCAGCAGCGTGGTGACCGTGCCCTCCAGCAACTTCG
GCACCCAGACCTACACCTGCAACGTAGATCACAAGCCCAGCAACACCAAGGTGGACAAGACAGTTGAGAGGCCAGCT
CAGGGAGGAGGGTGTCTGCTGGAAGCCAGGCTCAGCCCTCGGAACGCACCCCGGCTGCAGCCCGTGCAGCCCCAGCCCAGG
GCAGCAAGGCAGGCCCCATC
           StuI
TGTCTCCTCACCCGGAGGCCTCTGCCCGCCCCACTCATGCTCAGGGAGAGGTCTTCTGGCTTTTCCACCAGGCTCCAG
GCAGGCACAGGCTGGGTGGTGCCTACCCCAGGCCCCTTCACACACAGGGCAGGTGCAGGTGCTCAGACCTGCCAAAGCCAT
ATCGGGAGGACCCTGCCCCTGACCTAAGCCGAACCCCCCAAACTGTCCACTCCCCTCAGCTCTCGGACACCTTCTCTC
CTCCCAGATCCGAGTAACTC

CCAATCTCTCTGCAGAGCGCAAATGTTGTGTCGAGTGCCCACCGTGCCCAGGTAAGCCAGCCCCTGCCCCTCC
AGC
                                            PvuII
TCAAGGCGGGACAGGTGCCCTAGAGTAGCCTGCATCCAGGACAGGCCCCAGCTGGGTGCTGACACGTCCACCTCCATCT
CTTCCTCAGCACCACCTGTGCCAGGACGACCTGTCAGTCTTCCTCTTCCCCCAAAACCCAAGGACACCCTCATGATCTCCGG
ACCCCTGAGGTCACGTGCGTGGTGGTGGACGTGAGCCACGAAGACCCCGAGGTCCAGTTCAACTGGTACGTGGACGGCGT
GGAGGTGCATAATGCCAAGACAAAGCCACGGGAGGAGCAGTTCAACAGCACGTTCCGTGTGGTCAGCGTCCTCACCGTTG
TGCAC
                  StuI
CAGGACTGGCTGAACGGCAAGGAGTACAAGTGCAAGGTCTCCAACAAAGGCCTCCCAGCCCCCAT
                                     BglI
CGAGAAAACCATCTCCAAAACCAAAGGGCAGCCCCGGGAGCCACAGGTGTATACCCTGCCCCCATCCCGGGAGGAGATGACCAAGAACCAGGTCAGCCTGACCTGC
CTGGTCAAAGGCTTCTACCCCAGCGACATCGCCGTGGAGTGGGAGAGCAATGGGCAGCCGGAGAACAACTACAAGACCAC
CCCTCCCATGCTGGACTCCGATGGCTCCTTCTTCCTCTACAGCAAGCTCACCGTGGACAAGAGCAGGTGGCAGCAGGGGA
ACGTCTTCTCATGCTCCGTGATGCATGAGGCTCTGCACAACCACTACACGCAGAAGAGCCTCTCCCTGTCTCCGGGTAAA
TGAGTGCCACGGCCGGCAACCCCGCCTCCCCAGGCTCTCGGGGTCGCGTGAGGATGCTTGGCACGTACCCCGTGTACAT
ACTTCCCAGGCACCCCAGCATGGAAATAAAGCACCCGC
```

FIG. 17B

```
                                                            BglI
                                                            StuI
TGCCCTGGGGCCCCTGCGAGACTGTGATGGTTCTTTCCGTGGGTCAGGCCCGAGTCTCAGGCCCTGAGTGGCATGAGGGAGGC
AGAGTGGGTCANNNNNNNNNNNNNNNNNNNNNNNNNNNNNNNNNNNNNNNNNNNNNNNNNNNNNNNNNNNNNNNNNNNNNNN
NNNNNNNNNNNNNNNNNNNNNNNNNNNNNNNNNNNNNNNNNNNNNNNNNNNNNNNNNNNNNNNNNNNNNNNNNNNNNNNNNN
NNNNNNNNNNNNNNNNNNNNNNNNNNNNNNNNNNNNNNNNNNNNNNNNNN
  PvuII
NCAGCTGNNNNNNNNNNNNNNNNNNNNNNNNNNNNNNNNNNNNNNNNNNNNNNNNNNNNNNNNNNNNNNNNNNNNNNNNNNN
NNNNNNNNNNNNNNNNNNNNNNNNNNNNNNNNNNNNNNNNNNNNNNNNNNNNNNNNNNNNNNNNNNNNNNNNNNNNNNNNNN
NNNNNNNNNNNNNNNNNNNNNNNNNNNNNNNNNNNN
  BamHI
NNNNNNNNNNNGGATCCAGACATGATAAGATACATTGATGAGTTTGGACAAACCACAACTAGAATGCAGTGAAAAAAT
GCTTTATTTGTGAAATTTGTGATGCTATTGCTTTATTTGTAACCATTATA
  HpaI
AGCTGCAATAAACAAGTTAACAACAACAAGTTCATTCATTTTATGTTCAGGGGAGGTGTGGGAGGTTTTTA
AAGCAAGTAAAACCCTCTACACAAATGTGGTATGCTCTAGTCAAGGCACTATACATCAAATATTCCTTATT
AACCCCTTTACAAATTAAAAAGCTAAAGTTATTAATAGCAGACACTCTATGCCTGTG
GAGTAAGAAAAACAGTATGTTATGATTATAACTGTTATGCCTACTTATAAGGTTACAGAATATTTTCCATAATTTTC
TTGTATAGCAGTGCAGCTTTTCCTTTGTGGTGTAAATAGCAAGCAAGAGTTCTATTACTAAACACAGCATGACT
CAAAAACTTAGCAATTCTGAAGGAAAGTCCTGGGTCTCTTCTACCTTTCTCTTTTTGGAGGAGTAGAATGTTGAG
AGTCAGCAGTAGCCTCATCATCACTAGAGTTGGAATCTAAAATCACAAACAATTAGAATCAGTAGTTTAACACATTATACACT
TGCTCCCATTCAGTTCAGTAGCTTTATAGCTTTAAATCTCGTAGGTAGTTTGTCCAATTATGTCACACCACAGAAGTAAGGTT
TAAAAATTTTATATTTACCTTATATTTCCGGNNNNNNNNNNNNNNNNTCATGCTTGTCCTTGAG
CCTTCACAAAGATCCGGNNNNNNNNNNNNNNNNNTCATGCTTGTCCTTGAG
  HpaI
GGCGTTAACGCGCAAGGTAACGGCATTTTTATGGGCGGTTCGGGCGGTTCCGGCGGGGCCCAGTGTTTCTATGGTTGAAGCCA
CCGGGAGAACCCCTCTTTCGACAGTTCCTGTACGGTCATACGCTTCTGAAATCTGCCAGCCCGAGGCTGGAACAGGTG
GCGGTGTAACCGTAAGTCGGTAGAACGTGGTTGGTTCCGGAGGCGGTAATCACCTGCCGATTCCGGTGACCAGTCACCAAG
AAATACCGAACCGGCGGCTGGTGGTCTATCGACCAGTTCACGGGCGGTTGCGGGTCTGAATGATCAGGTGCTCCGGCCGT
ACTGATTAGAGATCTCCACGCACTGGTCATGCCACTCTTTAGTCACGATCAGGCGGTTCAGTGCCTGGGCGGGTT
TCGGCACGCGGCCAGTTCCGCCAGTTGCGGCCCCAGTTGCGGTTGGCGGTTGGCGCGACGCGCCATATCCAGCAGGGGTCAGTAA
AATCACCTGTGAGTCCGGGCCCGTGTTCAGCCTGTTCAGCCTGTTCAGCCCTGAGAGAGCAAATCAGAAGCCACGAAAT
```

FIG. 17C

```
                                                                        ClaI
CCGGCGTTGCGCCGCTGTCAGCAATCACCAGCACTTCCGACGGCACTTCCGACGGCCTGCGGGCATATGATCTCCGCACCGTCCAGACGC
TGGCTCACCTGACGTTTCGCTTCGGTGACAAGGCGTTACCCGGCCCGGCGTTACCCGGCCGAAGATTTTGTCCACTTTGCACGATTCCGT
ACCAAACGCCAGTGCGGCAATGGCCTGTGCGCCGC
                       PvuII
CGACGTTGAACACGTCCTGCACACCGCACAGCTGCGCCCACCGGCACATCGGCCGGTGAGCACAGC
ACCACTTTTTACAGCCCCGCAATACCGCCGGAGTCGCCCAGCATTAATACCGTTGAGAAGAGCGGGAGCGCCAGG
AATATACAACCCAACTGAAGCTACCGGACGCGTGACCTGCTGGCAACGCACGCCTGCGTTCTACATCTACCGGCG
GCAGTTTTGCGCAGTGTGGAAGGTTTCAATATTCTTACTGCCACCGCCATGCCCTGTTTATCAAACTTCGCGCTGTATTCCCG
TCGCTGGCGGCGGGCGATCTCCTCTGCAGACACACCTTGGTTTTATCAAACTTCGCGCTGTATTCCCG
CAGGGCCTCATCGCCCGTGCTTTCACGTTATCGAGAATATCGTTAACAGTGCGGGTAATGCTTTCAGAGGCGAAATCG
CCGGGCGCGTTAA
PvuII
CAGCTGGCGTTGTGCACCGCAGTACAGCTATTCCAGTCAATGATTGTGTTAAAGCTCATNNNNCCGGATCAGCTTTTG
CAAAGCCTAGGCCTCCAAAAAGCTCCTCCACTACTTCTGAATAGCTCAGAGCCCGAGGCGCCTCGGCCTCTGCATAA
ATAAAAAAATTAGTCAGCCATGGGGCGAATGCCATGGGGCGGAACTGGGCGGAGTTAGGGCGCGGATGGGCGGAGTTAGGGG
CGGGACTATGGTTGCTGACTAATTGAGATGCATGCTTTGCATACTTCTGCCTGCTGGGAGCCTGGGACTTTCCACACC
TGGTTGCTGACTAATTGAGATGCATGCTTTGC
                                                                   PvuII
ATACTTCTGCCTGCTGGGAGCCTGGGACTTTCCACACCATTCCACAGCTGCCTCCGCCGCGTTTCGG
TGATGACGGTGAAAACCTCTGACACATGCAGCTCAGCTTGGCGGATGCCGGGAGCGGAGCAGAC
AAGCCCGTCAGGGCGCAGCACATGCGTGTTGGCGGGCGGCGCGCCCAGTCACGTAGCGATAGCGGAGTG
TATACTGGCTTAACTATACCGGCTCACTATGCGGTGTGAAATACCGCACAGATGC
GTAAGGAGAAAATACCGCATCAGGCGCTCTTCCGCTTCCTCGCGCGTCGTTCGGCTGCGGCCG
AGCGGTATCAGCTCACTCAAAGGCGGTAATACGGTTATCCACAGAATCAGGGGATAACGCAGGAAAGAACATGTGAGCAA
AAGGCCAGCAAAAGGCCAGGAACCGTAAAAAGGCCGCGTTGCTGGCGTTTTTCCATAGGCTCCGCCCCCCTGACGAGCAT
CACAAAAATCGACGCTCAAGTCAGAGGTGGCGAAACCCGACAGGACTATAAAGATACCAGGCGTTTCCCCCTGGAAGCTC
CCTCGTGCGCTCTCCTGTTCCGACCCTGCCGCTTACCGGATATCTGTCGTTCCTCCAAGCTGGGCTGTGTGCACGAACCCCCCGTT
CTCAATGCTCACGCTGTAGGTATCTCAGTTCGGTGTAGGTCGTTCGCTCCAAGCTGGGCTGTGTGCACGAACCCCCCGTT
CAGCCCGACCCCGCTGCGCCTTATCCGGTAACTATCGTCTTGAGTCCAACCCGGTAAGACACGACTTATCGCCACTGGCAGC
AGCCACTGGTAACAGGATTAGCAGAGCGAGGTATGTAGGCGGTGCTACAGAGTTCTTGAAGTGGTGGCCTAACTACGGCT
ACACTAGAAGGACAGTATTTGGTATCTGCGCTCTGCTGAAGCCAGTTACCTTCGGAAAAAGAGTTGGTAGCTCTTGATCC
GGCAAACAAACCACCGCTGGTAGCGGTGGTTTTTTGTTTGCAAGCAGCAGATTACGCGCAGAAAAAAGGATCTCAAGA
AGATCCTTTGATCTTTTCTACGGGGTCTGACGCTCAGTGGAACGAAAACTCACGTTAAGGGATTTTGGTCATGAGATTAT
```

FIG. 17D

```
TCTGACAGTTACCAATGCTTAATCAGTGAGGCACCTATCTCAGCGATCTGTCTATTTCGTTCATCCATAGTTGCCTGACT
CCCGTCGTGTAGATAACTACGATACGGGAGGGCTTACCATCTGGCCCCAGTCTGCCTGCAATGATACCGCGAGACCACGCT
CACCGGCTCCAGATTTATCAGCAATAAACCAGCCAGCCGGAAGGGCCGAGCGCAGAAGTGGTCCTGCAACTTTATCCGCC
TCCATCCAGTCTATTAATTGTTGCCGGGAAGCTAGAGTAA
                                       PstI
GTAGTTCGCCAGTTAATAGTTTGCGCAACGTTGTTGCCATTGCTGCAGGCATCGTGGTGTCACGCTCGTCGTTTGGTATG
GCTTCATTCAGCTCCGGTTCCCAACGATCAAGGCGAGTTACATGATCCCC
                         PvuI
CATGTTGTGCAAAAAAGCGGTTAGCTCCTTCGGTCCTCCTCCGATCGTTGTCAGAAGTAAGTTGGCCGCAGTGTTATCACTCA
TGGTTATGGCAGCACTGCATAATTCTCTTACTGTCATGCCATCCGTAAGATGCTTTTCTGTGACTGGTGAGTACTCAACC
AAGTCATTCTGAGAATAGTGTATGCGGCGACCGAGTTGCTCTTGCCCGGCGTCAACACGGATAATACCGCGCCACATAG
CAGAACTTTAAAAGTGCTCATCATTGGAAAACGTTCTTCGGGGCGAAAACTCTCAAGGATCTTACCGCTGTTGAGATCCA
GTTCGATGTAACCCACTCGTGCACCCAACTGATCTTCAGCATCTTTTACTTTCACCAGCGTTTCTGGGTGAGCAAAAACA
GGAAGGCAAAATGCCGCAAAAAAGGGAATAAGGGCGACACGGAAATGTTGAATACTCATACTCTTCCTTTTTCAATATTA
TTGAAGCATTTATCAGGGTTATTGTCTCATGAGCGGATACATATTTGAATGTATTTAGAAAAATAAACAAATAGGGGTTC
CGCGCACATTTCCCCGAAAAGTGCCACCTGACGTCTAAGAAACC
                              EcoRI
ATTATTATCATGACATTAACCTATAAAAATAGGCGTATCACGAGGCCCTTTCGTCTTCAAGAATTCAGAGAGGTCTGGTG
GAGCCTGCAAAAGTCCAGCTTCAGTTCGTATGGAATATTGTATGGAATATTAGAAGATGTTGCTTTACTCTTAAG
TTGGTTCCTAGGAAAAGTCAGCTTTAAATACTGTGACTTTAAAATGTGAGAGGGTTTTCAAGTACTCATTTTTAAATGTCC
AAAATTTTGTCAATCAATTTCAGAGTCTTGTGTAGAACTGACATTAAATTAAGTTTAAAATATTTTAAATGAA
GCTCTCTATACCCTATTCAGAACTGACTTTTAACCAATAATAAAGTTTAAAATATTTTAGCTT
                                                 PvuII
TTGAGCAATGTTGAGTGAGTTGAGTGAAGGAAAATAAAACCACTAGGTAAACTTGTAGCTGTGGTTTGAAGAAGTGGTTTTGAAACACTC
CAAGGCTATTTGGGAGGAAGGAAAATAAAACCGAAGTCCAGGCTGAGCAAAACCACCTGGGTAATTTGCATTTCTAAAATAAGTTGAGGA
TGTCCAGCCGCCACCAAACCGAAAGTCCTCCTCTTTATTGAGTTCAACCTTTTAATTTGAGTTAGCTTGAGTAGTTCTAGTTTCCC
TTCAGCCGCGAAACTGGAGAGGTCCTCCTCTTTATTGAGTTCAACCTTTTAATTTGAGTTAGCTTGAGTAGTTCTAGTTTCCC
CAAAC
                               EcoRI
TTAAGTTTATCGACTTCTAAAATGTATTTAGAATTCCTTTGCCTAATATTAATGAGGACTTAACCTGTGGAAATATTTTG
ATGTGGAAGCTGTTACTGTTAAACTGAGGTTATTGGGTAACTGCTATGTTAAACTTGCATTCAGGGACACAAAAAAC
TCATGAAAATGGTGCTGGAAAACCCATTCAAGGGTCAAATTTCATTTTTTGCTGTTGGGGAACCTTTGGAGCTGC
AGGGTGTGTTAGCAAACTACAGGACCAAATATCCTGCTCAAACTGTAACCCAAAAATGCTACAGTTGACAGTCAGCAG
ATGAACACTGACCACCAAGGCTGTTTGGATAAGGATAATGCTTATCCAGTGGAGTGCTGGTTCCTGATCCAAGTAAAAA
```

FIG. 17E

```
TGAAAACACTAGATATTTGGAACCTACACAGGTGGGAAAATGTGCCTCCTGTTTGCACATTACTAACACAGCAACCA
CAGTGCTGCTTGATGAGCAGGTGTTGGGCCCTTGTGCAAAGCTGACAGCTTGTGTTCTGCTGTTGACATTTGTGGG
CTGTTTACCACACTTCTGGAACACAGCAGTGGAAGGACTTCCCAGATATTTAAAATTACCCTTAGAAAGCGGTCTGT
GAAAACCCCTACCCAATTTCCTTTTGTTAAGTGACCTAATTAACAGGAGACACAGAGGGTGGATGGGCAGCC
                                                              BamHI
TATGATTGGAATGTCCCTCTCAAGTAGAGGAGTTAGGGTTTATGAGGACACAGAGGAGCTTCCTGGG
```

FIG. 17F

|     |     |     |     |     |     |     | ATG | GAA | TGG | AGC | TGG | GTA | ATG | CTC |
|-----|-----|-----|-----|-----|-----|-----|-----|-----|-----|-----|-----|-----|-----|-----|
|     |     |     |     |     |     |     | Met | Glu | Trp | Ser | Trp | Val | Met | Leu |
|     |     |     |     |     |     |     | 1   |     |     |     | 5   |     |     |     |

TTC CTC CTG TCA GGA ACT GCA GGT GTC CGC TCT GAG GTC CAG CTG CAA
Phe Leu Leu Ser Gly Thr Ala Gly Val Arg Ser Glu Val Gln Leu Gln
    10                  15                    20

CAG TCT GGA CCT GAA CTG GTG AAG CCT GGA GCT TCA ATG AAG ATT TCC
Gln Ser Gly Pro Glu Leu Val Lys Pro Gly Ala Ser Met Lys Ile Ser
25                 30                   35                  40

TGC AAG GCT TCT GGT TAC TCA TTC ACT GGC TAC ACC ATG AAC TGG GTG
Cys Lys Ala Ser Gly Tyr Ser Phe Thr Gly Tyr Thr Met Asn Trp Val
                        45                   50                    55

AAG CAG AGC CAT GGA GAG AAC CTT GAG TGG ATT GGA CGT ATT AAT CCT
Lys Gln Ser His Gly Glu Asn Leu Glu Trp Ile Gly Arg Ile Asn Pro
         60                        65                    70

CAC AAT GGT GGT ACT GAC TAC AAC CAG AAG TTC AAG GAC AAG GCC CCT
His Asn Gly Gly Thr Asp Tyr Asn Gln Lys Phe Lys Asp Lys Ala Pro
              75                    80                   85

TTA ACT GTA GAC AAG TCA TCC AAC ACA GCC TAC ATG GAG CTC CTC AGT
Leu Thr Val Asp Lys Ser Ser Asn Thr Ala Tyr Met Glu Leu Leu Ser
    90                          95                     100

CTG ACA TCT GAG GAC TCT GCA GTC TAT TAC TGT GCA AGA GGC TAC TAT
Leu Thr Ser Glu Asp Ser Ala Val Tyr Tyr Cys Ala Arg Gly Tyr Tyr
105                  110                  115              120

TAC TAT TCT TTG GAC TAC TGG GGT CAA GGA ACC TCA GTC ACC GTC TCC
Tyr Tyr Ser Leu Asp Tyr Trp Gly Gln Gly Thr Ser Val Thr Val Ser
                     125                  130              135

TCA GCT AGC ACC AAG GGC CCA TCG GTC TTC CCC CTG GCG CCC TGC TCC
Ser Ala Ser Thr Lys Gly Pro Ser Val Phe Pro Leu Ala Pro Cys Ser
              140                   145              150

AGG AGC ACC TCC GAG AGC ACA GCG GCC CTG GGC TGC CTG GTC AAG GAC
Arg Ser Thr Ser Glu Ser Thr Ala Ala Leu Gly Cys Leu Val Lys Asp
          155                  160              165

TAC TTC CCC GAA CCG GTG ACG GTG TCG TGG AAC TCA GGC GCT CTG ACC
Tyr Phe Pro Glu Pro Val Thr Val Ser Trp Asn Ser Gly Ala Leu Thr
170                  175                  180

AGC GGC GTG CAC ACC TTC CCA GCT GTC CTA CAG TCC TCA GGA CTC TAC
Ser Gly Val His Thr Phe Pro Ala Val Leu Gln Ser Ser Gly Leu Tyr
185                 190                  195              200

FIG. 17G

```
TCC CTC AGC AGC GTG GTG ACC GTG CCC TCC AGC AAC TTC GGC ACC CAG
Ser Leu Ser Ser Val Val Thr Val Pro Ser Ser Asn Phe Gly Thr Gln
            205                 210                 215

ACC TAC ACC TGC AAC GTA GAT CAC AAG CCC AGC AAC ACC AAG GTG GAC
Thr Tyr Thr Cys Asn Val Asp His Lys Pro Ser Asn Thr Lys Val Asp
            220                 225                 230

AAG ACA GTT
Lys Thr Val
        235
```

FIG. 17H

```
GAG CGC AAA TGT TGT GTC GAG TGC CCA CCG TGC CCA
Glu Arg Lys Cys Cys Val Glu Cys Pro Pro Cys Pro
 1           5                    10
```

FIG. 17I

```
                                            GCA CCA CCT GTG GCA
                                            Ala Pro Pro Val Ala
                                             1               5

GGA CCG TCA GTC TTC CTC TTC CCC CCA AAA CCC AAG GAC ACC CTC ATG
Gly Pro Ser Val Phe Leu Phe Pro Pro Lys Pro Lys Asp Thr Leu Met
             10                  15                      20

ATC TCC CGG ACC CCT GAG GTC ACG TGC GTG GTG GTG GAC GTG AGC CAC
Ile Ser Arg Thr Pro Glu Val Thr Cys Val Val Val Asp Val Ser His
         25                      30                  35

GAA GAC CCC GAG GTC CAG TTC AAC TGG TAC GTG GAC GGC GTG GAG GTG
Glu Asp Pro Glu Val Gln Phe Asn Trp Tyr Val Asp Gly Val Glu Val
             40                  45                  50

CAT AAT GCC AAG ACA AAG CCA CGG GAG GAG CAG TTC AAC AGC ACG TTC
His Asn Ala Lys Thr Lys Pro Arg Glu Glu Gln Phe Asn Ser Thr Phe
     55                      60                  65

CGT GTG GTC AGC GTC CTC ACC GTT GTG CAC CAG GAC TGG CTG AAC GGC
Arg Val Val Ser Val Leu Thr Val Val His Gln Asp Trp Leu Asn Gly
 70                      75                  80                  85

AAG GAG TAC AAG TGC AAG GTC TCC AAC AAA GGC CTC CCA GCC CCC ATC
Lys Glu Tyr Lys Cys Lys Val Ser Asn Lys Gly Leu Pro Ala Pro Ile
                 90                  95                      100

GAG AAA ACC ATC TCC AAA ACC AAA
Glu Lys Thr Ile Ser Lys Thr Lys
             105
```

FIG. 17J

```
Met Ser Phe Asn Thr Ile Ile Asp Trp Asn Ser Cys Thr Ala Val Gln
 1           5                  10                  15

Gln Arg Gln Leu Leu Thr Arg Pro Ala Ile Ser Ala Ser Glu Ser Ile
            20                  25                  30

Thr Arg Thr Val Asn Asp Ile Leu Asp Asn Val Lys Ala Arg Gly Asp
        35                  40                  45

Glu Ala Leu Arg Glu Tyr Ser Ala Lys Phe Asp Lys Thr Thr Val Thr
    50                  55                  60

Ala Leu Lys Val Ser Ala Glu Glu Ile Ala Ala Ala Ser Glu Arg Leu
65                  70                  75                      80

Ser Asp Glu Leu Lys Gln Ala Met Ala Val Ala Val Lys Asn Ile Glu
            85                  90                  95

Thr Phe His Thr Ala Gln Lys Leu Pro Pro Val Asp Val Glu Thr Gln
        100                 105                 110

Pro Gly Val Arg Cys Gln Gln Val Thr Arg Pro Val Ala Ser Val Gly
            115                 120                 125

Leu Tyr Ile Pro Gly Gly Ser Ala Pro Leu Phe Ser Thr Val Leu Met
    130                 135                 140

Leu Ala Thr Pro Ala Arg Ile Ala Gly Cys Lys Lys Val Val Leu Cys
145                 150                 155                 160

Ser Pro Pro Pro Ile Ala Asp Glu Ile Leu Tyr Ala Ala Gln Leu Cys
            165                 170                 175

Gly Val Gln Asp Val Phe Asn Val Gly Gly Ala Gln Ala Ile Ala Ala
            180                 185                 190

Leu Ala Phe Gly Thr Glu Ser Val Pro Lys Val Asp Lys Ile Phe Gly
        195                 200                 205

Pro Gly Asn Ala Phe Val Thr Glu Ala Lys Arg Gln Val Ser Gln Arg
    210                 215                 220

Leu Asp Gly Ala Glu Ile Asp Met Pro Ala Gly Pro Ser Glu Val Leu
225                 230                 235                 240

Val Ile Ala Asp Ser Gly Ala Thr Pro Asp Phe Val Ala Ser Asp Leu
            245                 250                 255

Leu Ser Gln Ala Glu His Gly Pro Asp Ser Gln Val Ile Leu Leu Thr
            260                 265                 270
```

FIG. 17K

Pro Ala Ala Asp Met Ala Arg Arg Val Ala Glu Ala Val Glu Arg Gln
        275                 280                 285

Leu Ala Glu Leu Pro Arg Ala Glu Thr Ala Arg Gln Ala Leu Asn Ala
    290                 295                 300

Ser Arg Leu Ile Val Thr Lys Asp Ser Ala Gln Cys Val Glu Ile Ser
305                 310                 315                 320

Asn Gln Tyr Gly Pro Glu His Leu Ile Ile Gln Thr Arg Asn Ala Arg
            325                 330                 335

Glu Leu Val Asp Ser Ile Thr Ser Ala Gly Ser Val Phe Leu Gly Asp
        340                 345                 350

Trp Ser Pro Glu Ser Ala Gly Asp Tyr Ala Ser Gly Thr Asn His Val
    355                 360                 365

Leu Pro Thr Tyr Gly Tyr Thr Ala Thr Cys Ser Ser Leu Gly Leu Ala
    370                 375                 380

Asp Phe Gln Lys Arg Met Thr Val Gln Glu Leu Ser Lys Glu Gly Phe
385                 390                 395                 400

Ser Ala Val Ala Ser Thr Ile Glu Thr Leu Ala Ala Ala Glu Arg Leu
                405                 410                 415

Thr Ala His Lys Asn Ala Val Thr Leu Arg Val Asn Ala Leu Lys Glu
            420                 425                 430

Gln Ala

FIG. 17L

```
GATCCGATCCNNNNNNNNNNNNNNNNNNNNNNNNNNNNNNNNNNNNNNNNNNNNNNNNNNN
NNNNNNNNNNNNNNNNNNNNNNNNNNNNNNNNNNNNNNNNNNNNNNNNNNNNNNNNNNNN
NNNNNNNNNNNNNNNNNNNNNNNNNNNNNNNNNNNNNNNNNNNNNNNNNNNNNNNNNNNN
NNNNNNNNNNNNNNNNNNNNNNNNNNNNNNNNNNNNNNNNNNNNNNNNNNNNNNNNNNNN
NNNNNNNNNNNNNNNNNNNNNNNNNNNNNNNNNNNNNNNNNNNNNNNNNNNNNNNNNNNN
NNNNNNNNNNNNNNNNNNNNNNNNNNNNNNNNNNNNNNNNNNNNNNNNNNNNNNNNNNNN
NNNNNNNNNNNNNNNNNNNNNNNNNNNNNNNNNNNNNNNNNNNNNNNNNNNNNNNNNNNN
NNNNNNNNNNNNNNNNNNNNNNNNNNNNNNNNNNNNNNNNNNNNNNNNNNNNNNNNNNNN
NNNNNNNNNNNNNNNNNNNNNNNNNNNNNNNNNNNNNNNNNNNNNNNNNNNNNNNNNNNN
NNNNNNNNNNNNNNNNNNNNNNNNNNNNNNNNNNNNNNNNNNNNNNNNNNNNNNNNNNNN
NNNNNNNNNNNNNNNNNNNNNNNNNNNNNNNNNNNNNNNNNNNNNNNNNNNNNNNNNNNN
NNNNNNNNNNNNNNNNNNNNNNNNNNNNNNNNNNNNNNNNNNNNNNNNNNNNNNNNNNNN
NNNNNNNNNNNNNNNNNNNNNNNNNNNNNNNNNNNNNNNNNNNNNNNNNNNNNNNNNNNN
NNNNNNNNNNNNNNNNNNNNNNNNNNNNNNNNNNNNNNNNNNNNNNNNNNNNNNNNNNNN
NNNNNNNNNNNNNNNNNNNNNNNNNNNNNNNNNNNNNNNNNNNNNNNNNNNNNNNNNNNN
NNNNNNNNNNNNNNNNNNNNNNNNNNNNNNNNNNNNNNNATATAGCACAAAGACATGCAAATAATATTCCCTATGCTCATAAAACAG
CCCTGACCATGAAGCTTTGACAGACGCACAACCCTGACTCCCAAGTCTTTCTTCTTCAGTGA
        EcoRV
CAAACACAGACATAGGATATCCACCATGGAATGGAGCTGGGTAATGCTCTTCCTCCTGTCAGGAACTGCAGGTGTCCGCT
CTGAGGTCCAGTCCAGTCTGCAACAGTCTGACCATGAACTGGTGAAGCCTGGAGCTTCCTGCAAGATTCCTGCAAGGCTTCTGT
TACTCATTCACTGGCTACACCATGAACTGGGTGAAGCAGAGCCATGGAGAGAACCTTGAGTGGATTGGACGTATTAATCC
TCACAATGGTGGTACTGACTACAACCAGAAGTTCAAGGACAAGGCCCCCTTTAACTGTGACAAGGCTCATCCAACACAGCCT
ACATGGAGCTCCTCAGTCTGACATCTGAGGACTCTGCAGTCTATTACTGTGCAAGAGGCTACTACTATTACTTTGAC
TACTGGGGTCAAGGAACCTCAGTCACCGTCTCCTCAGGCCCATCCGGTCTTCCCCCTGGCGCCCTGCTCCAGGAG
CACCTCTGGGGCACAGCGGCCCTGGGCTGCCTGGTCAAGGACTACTTCCCCGAACCGGTGACGGTGTCGTGGAACTCAG
GCGCCCTGACCAGCAGCGGCGTGCACAC
```

FIG. 18A

```
                                          BstEII
CTTCCCGGCTGTGTCCTACAGTCCTCAGGACTCTACTCCCTCAGCAGCCGTGCCCTGCCCTCCAGCAGCTTGGGCACCC
AGACCTACACCTGCAACGTGAATCACAAGCCCAGCAACACCAAGGTGGACAAGAGAGTTGGTGAGAGGCCAGGCAGGGA
GGAGGGTGTCTGCTGGAAGCCAGGCTCCTCACCCGGAGGCCTCTGCCCGCCCACTCATGCTCAGGGAGAGGGTCTTCTGGCTTTTT
AGGCAGGCCCCGTCTGACTCCTGCAGGCACAGGCTGATGCCCCCAGGCCCTTCACACACAGGGCAGGTGCTGCCTCAGAG
CCACCAGGCTCCGGCAGCAGCCATATCCAGGAGGACCCCTGCCCCCTGACCTAAGCCACCCCAAAG
                Bg1II
GCCAAACTCTCTACTCACTCAGCTCAGACACCTTCTCTTCCCAGATCTGAGTAACTCCCAATCTTCTCTCTGCAGAGC
TCAAAACCCACTTGGTGACACAACTCACACATGCCCAGCACCCAGGCTGCCCAGGTAAGCCAGCCCAGGTCTGCCCAGCTCA
AGGCGGGACAAGAGCCCTAGAGTGGCCTGAGCCAGGGACAGGCCCCAGCAGGGTGCTGACGCATCCACCTCCATCCCAG
ATCCCCGTAACTCTCTACTCTTCTCTGCAGAGCCCAAATCTTGTGACACACCTCCCCGTGCCTGAGTCCAGGACAGGCCCCAGTAA
GCCAGCCCAGGCCCTCGCCCTCCAGCTCAAGGCAGGAGACAGGTGCCTAGAGCTCTCTGCAGCCCAAATCTTGTGACAC
GGTGCTGACGCATCCACCTCCAGTAACTCCCAGGCCTCGCCCCAGTCCCAGATCTCAAGGCAGGAGGTGCCTAGAGTG
CTCCCCGTGCCAAGGTGCCCAGGCAGGCCCCAGAGTGCTGACGCATCCCAGATCCCCGTAACTCCCAATCTTCTC
GCCTGAGTCCAGGACAGGCCCAAATCTTGTGACACAGTCCCCTGCCCAGCCCAGCCCTGCTGCCCTCCAG
TCTGCAGAGGCAGGACAGGCCCTGAACTCTGGTGCCTGGAGGACCAGGTCCCAGTCCGGTCTGACACATCCTCCATC
CTCAAGGCAGGAGACAGGTGCCTGAACTCCTGGCGTGCTGTGGACAACAAAGCCCGAGGTCCAGTTCAAGTTGGTACGTGGACG
TCTTCCTCAGCACCTGAGTCACGTGCTGTGGACAACAAAGCTGCGGAGAAGACAGTAGAACAAGTGCTCCTCACC
CGGACCCTGAGTCACGTGCATAATGCCAAGACAAACTGCGGAGAAGACAGTACAACAAAGCCCTTCCTCAC
GCGTGGAGGTGCATAATGCCAAGACAAACTGCGGAGAAGACAGTACAAGTGGTCAAGGTCTCCAACAAGCCCTCACC
GTCCTGCAGGACTGGCTGAACGGCAAGGAGTACAAGTGCAAGGTCTCCAACAAGCCCCCCATGAGAA
AAC
                      SacII
CATCTCCAAAGCCAAAGGTGGGACCCCGGGTATGAGGGCCACGTGGACAGAGGCCAGCTTGACCCACCCTCTGCCCTG
GGAGTGACCGCTGTGCCAACCTCTGTCCTACAGGACCAGCCGAGAACACAGGTGTACACCCTGCCCCCATCCCGGGA
GGAGATGACCAAGAACCAGGTCAGCCTGACCTGCCTGGTCAAAGGCTTCTACCCCAGCGACATCGCCGTGGAGTGGGAGA
GCAATGGGCAGCCGGAGAACAACTACAACACCACGCCTCCCATGCTGGACTCCGACGGCTCCTTCTTCCTCTACAGCAAG
CTCAC
                                                       NsiI
CGTGGACAAGAGAGCAGGTGGCAGCAGGGAACATCTTCATGTCCGTGATGCATGAGGCTCTGCACAACCGCTACACCCC
AGAAGAGCCTCTCCCTGTCTCCGGGTAAATGAGTGCGACAGCCGGCAAGCCCCGCTCCCGGGCTCTCGGCGTCGGCGG
AGGATGCTTGGCACGTACCCCGTGTACATATCTTCCCGGGCCCAGTCTGAGGCCTCAGGGTCAGCGGTGCACATTGAAATAAAGCACCAGCCTGCCCTGGCC
CCTGTGAGACTGTGATGGTTCTTTCCACGGGTCAGGGTGAGGCCTGAGCCTGAGCCTGAGCATGAGGTACCTGCACATGAGGAGGAGGCAGAGCGGGTCN
```

FIG. 18B

```
NNNNNNNNNNNNNNNNNNNNNNNNNNNNNNNNNNNNNNNNNNNNNNNNNNNNNNNNNNNNNNNNNNNNNNNNNNNNNNNNNNNNNNNNNNNNNNN
NNNNNNNNNNNNNNNNNNNNNNNNNNNNNNNNNNNNNNNNNNNNNNNNNNNNNNNNNNNNNNNNNNNNNNNNNNNNNNNNNNNNNNNNNNNNNNN
NNNNNNNNNNNNNNNNNNNNNNNNNNNNNNNNNNNNNNNNNNNNNNNNNNNNNNNNNNNNNNNNNNNNNNNNNNNNNNNNNNNNNNNNNNNNNNN
NNNNNNNNNNNNNNNNNNNNNNNNNNNNNNNNNNNNNNNNNNNNNNNNNNNNNNNNNNNNNNNNNNNNNNNNNNNNNNNNNNNNNNNNNNNNNNN
NNNNNNNNNNNNNNNNNNNNNNNNNNNNNNNNNNNNNNNNNNNNNNNNNNNNNNNNNNNNNNNNNNNNNNNNNNNNNNNNNNNNNNNNNNNNNNN
NNNNNNNNNNNNNNNNNNNNNNNNNNNNNNNNNNNNNNNNNNNNNNNNNNNNNNNNNNNNNNNNNNNNNNNNNNNNNNNNNNNNNNNNNNNNNNN
NNNNNNNNNNNNNNNNNNNNNNNNNNNNNNNNNNNNNNNNNNNNNNNNNNNNNNNNNNNNNNNNNNNNNNNNNNNNNNNNNNNNNNNNNNNNNNN
NNNNNNNNNNNNNNNNNNNNNNNNNNNNNNNNNNNNNNNNNNNNNNNNNNNNNNNNNNNNNNNNNNNNNNNNNNNNNNNNNNNNNNNNNNNNNNN
NNNNNNNNNNNNNNNNNNNNNNNNNNNNNNNNNNNNNNNNNNNNNNNNNNNNCAGCTGNNNNNNNNNNNNNNNNNNNNNNNNNNNNNNNNNNN
NNNNNNNNNNNNNNNNNNNNNNNNNNNNNNNNNNNNNNNNNNNNNNNNNNN
NNNNNNNNNNNNNNNNNNNNNNNNNNNNNNNNNNNNNNNNNNNNNNNNNNNNNNNNNNGGATCCAGACATGATAAGATACATTG
                                                  BamHI
ATGAGTTTGGACAAACCAACCACCACTAGAATAGCAGTGAATGCAGTGAAAAAATGCTTTATTTGTGAAATTTGTGATGCTA
                                                  HpaI
TTGCTTTATTTGTAACCATTATAAGCTGCAATAACAAGTTAACAACAACAATTGCATTCATTTATGTTTCAGGTTCAG
GGGGAGGTGTGGGAGGTTTTAAAGCAAGTAAAACCTCTACAAATGTGGCTATGGCTGATTATGATCTCTAGTCAAGCA
CTATACATCAAATATTCCTTATTAACCCCCTTACAAATTAAAAAACAGTATGTTATGATTATAACTGTTATGCCTACTTATAAAGTTA
AGCAGACACTCTATGCCTG: 'GTGGAGTAAGAAAAACAGTATGTTATGATTATAACTGTTATGCCTACTTATAAGCAAGAGTT
CAGAATATTTTTCCATAATTTCTTGTATAGCAGTGCAGCTTTTCCTTGTGGTGTAAATAGCAAGCAAGCAAGAGTT
CTATTACTAAACACAGCATGACTCAAAAAACTTAGCAATTCTGAAGGAAAGTCCTTGGGGTCTTCTTCTCTGAGCCAAACAGGTTTT
TTTGGAGGAGTAGAATGTTGAGAGTCAGCAGTAGCCTCATCATCCATAGTGGTTGAATCTAAAATACACAAACAATTAGAATC
CCTCATTAAAGGCATTCCACCACTGCTCCCATTCATCAGTTCCATAGTTGAATCTAAAATCTCTGTAGGTAGTTTGTCCAATTA
AGTAGTTTAACACATTATACACATTAAAAATTTTATATTTACCTTATAGCTTTAAATCTCTGTAGGTAGTTTGTCCAATTA
TGTCACACCAGAAGTTCCTTCACAAGATCCGNNNNNNNNNNNNNNN
                    HpaI
NNNNNTCATGCTTGCTCCTTGAGGCGTTAACGCGCAAGTAACGGCATTTTTATGGGCGGTCAGACGTTCGGCGGCGGC
CAGTGTTTCTATGGTTGAAGCCACCCGGAGAACCCCTCTTTCGACAGTTCCTGTACGGTCATACGCTTCTGGAAATCTG
CCAGCCCGAGGCTGGAACAGGTGGCGGTGTAACCGTAAGTCGGTAGAACGTGGTTGGTTCCGAGGCGTAATCACCTGCC
GATTCCGGTGACCAGTCACCAAGAAATACCGAACCGGCCGCTGGTCGTATCGACTCGACCAGTTCACGGGCGTTGCGGGTCTG
```

FIG. 18C

AATGATCAGGTGCTCCGGGCCGTACTGATTAGAGATCTCCACGCCACTGCCGCTGAATCTTTAGTCACGATCAGGCGGCTGG
CGTTCAGTGCCTGGCCGCTGGCGGGCGCGGTTCGGCACGCGGCCAGTTCCGCCAGTTGGCGTTCGACGGCCTCGGCAACGGCGACGCCC
ATATCAGCAGCGGGGCGTCAGTAAATCACCTGTGAGTCCGGGCCCGTGTTCAGCCTGAGAGAGCAAATCAGAAGCCACGAA
ATCCGGGCGTTGCGCCCGCTGTCAGCA
                       ClaI
ATCACCAGCACTTCCGACGGCCTGCGCGGGCCATATCGATCTCCGCACCCGTCCAGACGCTGGCTCCAGGCGCTGCCTTC
GGTGACAAAGGCGTTACCCGCCGAAGATTTTGTCCACTTTGGCACGGATTCCGTACCAAACGCCAGTGCGGCAATGG
CCTGTGCCGCCGACGTTGAACACGTCCTGCACA
      PvuII
CCGCACAGCTGCCGCCGCATAAAGGATCTCATCGGCAATCGGCGGCCGGTGAGCACAGACACCACTTTTTACAGCCCCGCAAT
ACGCGCGGAGTCGCCAGCATTAATACCGTTGAGAAGAGACGGGGCGGAGCCGCCAGAATATACAACCCAACTGAAGCTA
CCGGACGCCGTGACCTGCTGGCAACGCCTGGCGTTCTACATCTACCGGCGGCAGTTTTGCGCAGTGTGAAG
GTTTCAATATTCTTACTGCCACCGCCATGCCCTGTTTTAGCTCGTCGCTCAGCGTTCGCTGGCGGCGGATCTCCTC
TGCAGACACCTTCAGCGCGGGTAACCGTGGTTTTATCAAACTTCGCGCTGTATTCCCGCAGGCCTCATCGCCGCGTGCTT
TCACGTTATCGAGAATATCGTTAACAGTGCGGGTAATGCTTTCAGAGGCGAAAT
              PvuII
CGCCGGGGCCGTTAACAGCTGGCCGTTGTGCACCGCAGTACAGCTATTCCAGTCAATGATTGTGTTAAAGCTCATNNNC
CGGATCAGCTTTTGCAAAAGCCTAGCCTCCAAAAAGCTCCTCACTACTTCTGAATAGCTCAGAGGCCGAGGCGCC
TCGGCCTCTGCATAATAAAAAAATTAGTCAGCATGGGCGAACCATGGCGAGAATGCGGCGGAGTGGGCGGAGGGGGAT
GGGCGAGTTAGGGCGGGACTATGGTTGCTGACTATGGTTGCTGACTAATTGAGATGCATGCTTTGCATACTTCTGCCTGCTGGGAGCC
GGGACTTTCCACACCTGGTTGCTGACTAATTGAGATGCTTTGCATACTTCTGCCTGCTGGGAGCC
            PvuII
TGGGGACTTTCCACACCCTAACTGACACATTCCACAGCTGCCTCGCCGCGTTTCGGTGATGACGGTGAAAACCTCTGAC
ACATGCAGCTCCCGGAGACGTCACAGTTGTCTGTAAGCGGATGCCGGAGCAGACAAGCCCGTCAGGGCGCGTCAGCG
GGTGTTGCGGGGTGTCGGGGCGCAGCCATGACCCAGTCACGTCACGTGGAGTGTATACTGGCTTAACTATGCGGCA
TCAGAGCAGATTGTACTGAGAGTTGCACCATATGCGGTGTGAAATACCGCACAGATGCGTAAGGAGAGAAATACCGCATCAG
GCGCTCTTCCGCTTCCGCTTCACAGATCAGGGGATAACGCAGGAAAGAACATGTGAGCAGAACATGTGAGCAAAAGGCCAGAAC
CGTAATACGGTTATCCACAGAATCAGGGGATAACGCAGGAAAGAACATGTGAGCAAAAGGCCAGCAACAAAATGACGCTCAAGTCA
GAGGTGGCGAAACCCGACAGGACTATAAAGATACCAGGCGTTTCCCCCTGGAAGCGTGGCGCTTTCTCAATGCTCACGCTGTAGTAT
CCCTGCCGCTTACCGGATACCTGTCGCCTTCAAGCTGGGCTGTGTGCACGAACCCCCCGTTCAGCCCGACCGCTGCGCCTTATC
CTCAGTTCGGTGTAGGTCGTTCGCTCCAAGCTGGGCTGTGTGCACGAACCCCCCGTTCAGCCCGACCGCTGCGCCTTATC
CGGTAACTATCGTCTTGAGTCCAACCCGGTAAGACAGACTTATGCCAGCAGCCACTGGTAACAGGATTAGCA
GAGCGAGGTATGTAGGCGGTGCTACAGAGTTCTTGAAGTGGTGGCCTAACTACGGCTACACTAGAAGGACAGTATTTGGT

```
ATCTGCGCTCTGCTGAAGCCAGTTACCTTCGAAAAAGAGTTGGTAGCTCTTGATCCGGCAAACAACCACCGCTGGTAG
CGGTGGTTTTTGTTGTTGCAAGCAGCAGATTACGCCAGCAGATTATCAAGAAGATCTCAAAAAGGATCTCAAGAAGATCCTTGATCTTTTCTACGG
GGTCTGACGCTCAGTGGAACGAAACTCACGTTAAGGGATTTTGGTCATGAGATTATCAAAAAGGATCTCAAAAAGGATCTTCACCTAGATC
CTTTAAATTAAAAATGAAGTTTAAATCAATCTAAAGTATATATGAGTAAACTTGGTCTGACAGTTACCAATGCTTAAT
CAGTGAGGCACCTATCTCAGCGATCTGTCTATTTCGTTCATCCATAGTTGCCTGACTCCCCGTCGTGTAGATAACTACGA
TACGGGAGGGCTTACCATCTGGCCCCAGTGCTGCAATGATACCGCGAGACCCACGCTCACCGGCTCCAGATTTATCAGCA
ATAAACCAGCCAGCGGAAGGGCCGAGCGCAGAAGTGGTCCTGCAACTTTATCCGCCTCCATCCAGTCTATTAATTGTTG
CCGGGAAGCTAGAGTAAGTAGTTCGCCAGTTAATAGTTTGCGCAACGTTGTTGCCATTG
PstI
CTGCAGGCCATCGTCGTGTCACGCTCGTCGTTTGGTATGGCTTCATTCAGCTCCGGTTCCCAACGA
                                                    PvuI
TCAAGGCGAGTTACATGATCCCCCATGTTGTGCAAAAAAGCGGTTAGCTCCTTCGGTTCCTCCGATCGTTGTCAGAAGTAA
GTTGGCCCGCAGTGTTATCACTCATGGTTATGGCAGCACTGCATAATTCTCTTACTGTCATGCCATCCGTAAGATGCTTTT
CTGTGACTGGTGAGTACTCAACCAAGTCATTCTGAGAATAGTGTATGCGGCGACCGAGTTGCTCTTGCCCGGCGTCAACA
CGGGATAATACCGCGCCACATAGCAGAACTTTAAAAGTGCTCATCATTGGAAAACGTTCTTCGGGGCGAAAACTCTCAAG
GATCTTACCGCTGTTGAGATCCAGTTCGATGTAACCCACTCGTGCACCCAATTCTGGCGACCATCTTTTACTTTCACCA
GCGTTTCTGGGTGAGCAAAAACAGGAAGGCAAAATGCCGCAAAAAAGGGAATAAGGGCGACACGGATACATATTTGAATACTC
ATACTCTTCCTTTTTCAATATTATTGAAGCATTTATCAGGGTTATTGTCTCATGAGCGGATACATATTTGAAATGTATTTA
GAAAAATAAACAAATAGGGGTTCCGCGCACATTTCCCCGAAAAGTGCCACCTGACGTCTAAGAAACCATTATTATCATGA
CATTAACCTA
                                                            EcoRI
TAAAAATAGGCGTATCACGAGGCCCTTTCGTCTCTTCAAGAATTCAGAGAGGTCTGGTGGAGCCTGCAAAAGTCCAGCTTTC
AAAGGAACACAGAAGTATGTGATGGAATATTAGAAGATGTTGCTTTTACTCTTAAGTTGGTTCCTAGGAAAAATAGTTA
AATACTGTGACTTTGACTTTAAAATGTGAGAGGTTTCAAGTACCTCATTTTTTAAATGTCCAAAATTTTTGTCAATCAATTGA
GGTCTGTTGTTGTGTAGAACTGACATTACTTAAAGTTTAACCGAGAATGGAGTGAGGCTTCTCATACCCTATTCAGAA
CTGACTTTACAATAATAAATTAAGTTTAAAATATTTTTAAATGAATTGAGCAATGTTGAGTTGAGTCA
         PvuII
AGATGGCCGATCAGAACCGGAACACCTGCAGCAGCTGGCAGGAAGCAGGTCATGTGGCAAGGCTATTTGGGAAGGCAAA
ATAAAACCACTAGTAAACTTGTAGCTGTGGTTTGAAGAAGTGGTTTGAAACACTCTGTCCAGCCCCACCAAACCGAAA
GTCCAGGCTGAGCAAAACCACCACCTGGTAATTTGCATTTCTAAAATAAGTTGAGATTCAGCGCCGAAACTGGAGAGGTCC
TCTTTTAACTTATTGAGTTCAACCTTTCAACCTTTAATTTAGCTTGAGTAGTTCTAGTTCCCAAACTTAAGTTTATCGACTTCT
AAAAT
```

FIG. 18E

EcoRI
GTATTTAGAATTCCTTTGCCTAATATTAATGAGGACTTAACCTGTGGAAATATTTGATGTGGGAAGCTGTTACTGTTAA
AACTGAGGTTATTGGGGTAACTGCTATGTTAAACTTGCATTCAGGGACACAAAAACTCATGAAATGGTGCTGGAAAAC
CCATTCAAGGGTCAAATTTCATTTTTTGCTGTGTTGGGGAACCTTTGAGCTGCAGGTGTGTTAGCAACTGACAAACTACAGG
ACCAAATATCCTGCTCAAACTGTAACCCCAAAAAATGCTACAGTTGACAGTCAGCAGATGAACACTGACCACAAGGCTGT
TTTGGATAAGGATAATGCTTATCCAGTGGAGTGCTGGGTTCCTGATCCAAGTAAAACACTAGATATTTGAA
CCTACACAGGTGGGAAAATGCCTCCTGTTTGTGCACATTAAACAGCAACCACAGTGCTGCTTGATGAGCAGGT
GTTGGGCCCTGTGCAAAGCTGACAGCTTGTATGTTTCTGCTGTTGACATTTGGGCTGTGTTTACCAACACTTCTGGAAC
ACAGCAGTGGAAGGACTTCCCAGATATTTAAAATTACCCTTAGAAAAGCGGTCTGTGAAAAACCCTACCCAATTTCCT
TTTTGTTAAGTGACCTAATTAACAGGAGGACACAGAGGGTGGATGGGCAGCCTATGATTGGAATGTCCTCTCAAGTAGAG
                                                                        BamHI

GAGGTTAGGGTTTATGAGGACACAGAGGAGCTTCCTGGG

FIG. 18F

```
                                    ATG GAA TGG AGC TGG GTA ATG CTC
                                    Met Glu Trp Ser Trp Val Met Leu
                                     1                   5

TTC CTC CTG TCA GGA ACT GCA GGT GTC CGC TCT GAG GTC CAG CTG CAA
Phe Leu Leu Ser Gly Thr Ala Gly Val Arg Ser Glu Val Gln Leu Gln
    10              15                  20

CAG TCT GGA CCT GAA CTG GTG AAG CCT GGA GCT TCA ATG AAG ATT TCC
Gln Ser Gly Pro Glu Leu Val Lys Pro Gly Ala Ser Met Lys Ile Ser
 25              30                  35                      40

TGC AAG GCT TCT GGT TAC TCA TTC ACT GGC TAC ACC ATG AAC TGG GTG
Cys Lys Ala Ser Gly Tyr Ser Phe Thr Gly Tyr Thr Met Asn Trp Val
                 45                  50                      55

AAG CAG AGC CAT GGA GAG AAC CTT GAG TGG ATT GGA CGT ATT AAT CCT
Lys Gln Ser His Gly Glu Asn Leu Glu Trp Ile Gly Arg Ile Asn Pro
             60                  65                  70

CAC AAT GGT GGT ACT GAC TAC AAC CAG AAG TTC AAG GAC AAG GCC CCT
His Asn Gly Gly Thr Asp Tyr Asn Gln Lys Phe Lys Asp Lys Ala Pro
         75                  80                  85

TTA ACT GTA GAC AAG TCA TCC AAC ACA GCC TAC ATG GAG CTC CTC AGT
Leu Thr Val Asp Lys Ser Ser Asn Thr Ala Tyr Met Glu Leu Leu Ser
     90                  95                 100

CTG ACA TCT GAG GAC TCT GCA GTC TAT TAC TGT GCA AGA GGC TAC TAT
Leu Thr Ser Glu Asp Ser Ala Val Tyr Tyr Cys Ala Arg Gly Tyr Tyr
105                 110                 115                 120

TAC TAT TCT TTG GAC TAC TGG GGT CAA GGA ACC TCA GTC ACC GTC TCC
Tyr Tyr Ser Leu Asp Tyr Trp Gly Gln Gly Thr Ser Val Thr Val Ser
                125                 130                 135

TCA ACC AAG GGC CCA TCG GTC TTC CCC CTG GCG CCC TGC TCC AGG AGC
Ser Thr Lys Gly Pro Ser Val Phe Pro Leu Ala Pro Cys Ser Arg Ser
            140                 145                 150

ACC TCT GGG GGC ACA GCG GCC CTG GGC TGC CTG GTC AAG GAC TAC TTC
Thr Ser Gly Gly Thr Ala Ala Leu Gly Cys Leu Val Lys Asp Tyr Phe
        155                 160                 165

CCC GAA CCG GTG ACG GTG TCG TGG AAC TCA GGC GCC CTG ACC AGC GGC
Pro Glu Pro Val Thr Val Ser Trp Asn Ser Gly Ala Leu Thr Ser Gly
    170                 175                 180
```

FIG. 18G

```
GTG CAC ACC TTC CCG GCT GTC CTA CAG TCC TCA GGA CTC TAC TCC CTC
Val His Thr Phe Pro Ala Val Leu Gln Ser Ser Gly Leu Tyr Ser Leu
185             190                 195                     200

AGC AGC GTG GTG ACC GTG CCC TCC AGC AGC TTG GGC ACC CAG ACC TAC
Ser Ser Val Val Thr Val Pro Ser Ser Ser Leu Gly Thr Gln Thr Tyr
            205                 210                     215

ACC TGC AAC GTG AAT CAC AAG CCC AGC AAC ACC AAG GTG GAC AAG AGA
Thr Cys Asn Val Asn His Lys Pro Ser Asn Thr Lys Val Asp Lys Arg
            220                 225                     230

GTT
Val
```

FIG. 18H

```
                                            GAG CTC AAA ACC
                                            Glu Leu Lys Thr
                                                 1

CCA CTT GGT GAC ACA ACT CAC ACA TGC CCA CGG TGC CCA
Pro Leu Gly Asp Thr Thr His Thr Cys Pro Arg Cys Pro
 5            10                15
```

FIG. 18I

```
            GAG CCC AAA TCT TGT GAC ACA CCT CCC CCG TGC CCA
            Glu Pro Lys Ser Cys Asp Thr Pro Pro Pro Cys Pro
             1           5                        10
AGG TGC CCA
Arg Cys Pro
       15
```

FIG. 18J

```
                                              GAG CCC AAA TCT
                                              Glu Pro Lys Ser
                                                1

TGT GAC ACA CCT CCC CCG TGC CCA AGG TGC CCA
Cys Asp Thr Pro Pro Pro Cys Pro Arg Cys Pro
  5               10                  15
```

FIG. 18K

```
GAG CCC AAA TCT TGT GAC ACA CCT CCC CCG TGC CCA AGG TGC CCA
Glu Pro Lys Ser Cys Asp Thr Pro Pro Pro Cys Pro Arg Cys Pro
 1           5                   10                      15
```

FIG. 18L

```
GCA CCT GAA CTC CTG GGA GGA CCG TCA GTC TTC CTC TTC CCC CCA AAA
Ala Pro Glu Leu Leu Gly Gly Pro Ser Val Phe Leu Phe Pro Pro Lys
 1           5                   10                  15

CCC AAG GAT ACC CTT ATG ATT TCC CGG ACC CCT GAG GTC ACG TGC GTG
Pro Lys Asp Thr Leu Met Ile Ser Arg Thr Pro Glu Val Thr Cys Val
            20                  25                  30

GTG GTG GAC GTG AGC CAC GAA GAC CCC GAG GTC CAG TTC AAG TGG TAC
Val Val Asp Val Ser His Glu Asp Pro Glu Val Gln Phe Lys Trp Tyr
            35                  40                  45

GTG GAC GGC GTG GAG GTG CAT AAT GCC AAG ACA AAG CTG CGG GAG GAG
Val Asp Gly Val Glu Val His Asn Ala Lys Thr Lys Leu Arg Glu Glu
            50                  55                  60

CAG TAC AAC AGC ACG TTC CGT GTG GTC AGC GTC CTC ACC GTC CTG CAC
Gln Tyr Asn Ser Thr Phe Arg Val Val Ser Val Leu Thr Val Leu His
65              70                  75                       80

CAG GAC TGG CTG AAC GGC AAG GAG TAC AAG TGC AAG GTC TCC AAC AAA
Gln Asp Trp Leu Asn Gly Lys Glu Tyr Lys Cys Lys Val Ser Asn Lys
                85                  90                  95

GCC CTC CCA GCC CCC ATC GAG AAA ACC ATC TCC AAA GCC AAA
Ala Leu Pro Ala Pro Ile Glu Lys Thr Ile Ser Lys Ala Lys
            100                 105                 110
```

FIG. 18M

```
                                    GGA CAG CCC CGA GAA CCA
                                    Gly Gln Pro Arg Glu Pro
                                     1                   5

CAG GTG TAC ACC CTG CCC CCA TCC CGG GAG GAG ATG ACC AAG AAC CAG
Gln Val Tyr Thr Leu Pro Pro Ser Arg Glu Glu Met Thr Lys Asn Gln
             10              15                  20

GTC AGC CTG ACC TGC CTG GTC AAA GGC TTC TAC CCC AGC GAC ATC GCC
Val Ser Leu Thr Cys Leu Val Lys Gly Phe Tyr Pro Ser Asp Ile Ala
             25              30              35

GTG GAG TGG GAG AGC AAT GGG CAG CCG GAG AAC AAC TAC AAC ACC ACG
Val Glu Trp Glu Ser Asn Gly Gln Pro Glu Asn Asn Tyr Asn Thr Thr
             40              45              50

CCT CCC ATG CTG GAC TCC GAC GGC TCC TTC TTC CTC TAC AGC AAG CTC
Pro Pro Met Leu Asp Ser Asp Gly Ser Phe Phe Leu Tyr Ser Lys Leu
 55              60              65                          70

ACC GTG GAC AAG AGC AGG TGG CAG CAG GGG AAC ATC TTC TCA TGC TCC
Thr Val Asp Lys Ser Arg Trp Gln Gln Gly Asn Ile Phe Ser Cys Ser
                 75              80                      85

GTG ATG CAT GAG GCT CTG CAC AAC CGC TAC ACC CAG AAG AGC CTC TCC
Val Met His Glu Ala Leu His Asn Arg Tyr Thr Gln Lys Ser Leu Ser
             90              95                 100

CTG TCT CCG GGT AAA
Leu Ser Pro Gly Lys
         105
```

FIG. 18N

```
Met Ser Phe Asn Thr Ile Ile Asp Trp Asn Ser Cys Thr Ala Val Gln
 1           5               10              15
Gln Arg Gln Leu Leu Thr Arg Pro Ala Ile Ser Ala Ser Glu Ser Ile
             20              25              30
Thr Arg Thr Val Asn Asp Ile Leu Asp Asn Val Lys Ala Arg Gly Asp
         35              40              45
Glu Ala Leu Arg Glu Tyr Ser Ala Lys Phe Asp Lys Thr Thr Val Thr
     50              55              60
Ala Leu Lys Val Ser Ala Glu Glu Ile Ala Ala Ala Ser Glu Arg Leu
65              70              75              80
Ser Asp Glu Leu Lys Gln Ala Met Ala Val Ala Val Lys Asn Ile Glu
             85              90              95
Thr Phe His Thr Ala Gln Lys Leu Pro Pro Val Asp Val Glu Thr Gln
             100             105             110
Pro Gly Val Arg Cys Gln Gln Val Thr Arg Pro Val Ala Ser Val Gly
         115             120             125
Leu Tyr Ile Pro Gly Gly Ser Ala Pro Leu Phe Ser Thr Val Leu Met
     130             135             140
Leu Ala Thr Pro Ala Arg Ile Ala Gly Cys Lys Lys Val Val Leu Cys
145             150             155             160
Ser Pro Pro Pro Ile Ala Asp Glu Ile Leu Tyr Ala Ala Gln Leu Cys
             165             170             175
Gly Val Gln Asp Val Phe Asn Val Gly Gly Ala Gln Ala Ile Ala Ala
             180             185             190
Leu Ala Phe Gly Thr Glu Ser Val Pro Lys Val Asp Lys Ile Phe Gly
         195             200             205
Pro Gly Asn Ala Phe Val Thr Glu Ala Lys Arg Gln Val Ser Gln Arg
     210             215             220
Leu Asp Gly Ala Glu Ile Asp Met Pro Ala Gly Pro Ser Glu Val Leu
225             230             235             240
Val Ile Ala Asp Ser Gly Ala Thr Pro Asp Phe Val Ala Ser Asp Leu
             245             250             255
Leu Ser Gln Ala Glu His Gly Pro Asp Ser Gln Val Ile Leu Leu Thr
             260             265             270
```

FIG. 18O

```
Pro Ala Ala Asp Met Ala Arg Arg Val Ala Glu Ala Val Glu Arg Gln
        275                 280                 285
Leu Ala Glu Leu Pro Arg Ala Glu Thr Ala Arg Gln Ala Leu Asn Ala
        290                 295                 300
Ser Arg Leu Ile Val Thr Lys Asp Ser Ala Gln Cys Val Glu Ile Ser
305                 310                 315                 320
Asn Gln Tyr Gly Pro Glu His Leu Ile Ile Gln Thr Arg Asn Ala Arg
                325                 330                 335
Glu Leu Val Asp Ser Ile Thr Ser Ala Gly Ser Val Phe Leu Gly Asp
                340                 345                 350
Trp Ser Pro Glu Ser Ala Gly Asp Tyr Ala Ser Gly Thr Asn His Val
        355                 360                 365
Leu Pro Thr Tyr Gly Tyr Thr Ala Thr Cys Ser Ser Leu Gly Leu Ala
    370                 375                 380
Asp Phe Gln Lys Arg Met Thr Val Gln Glu Leu Ser Lys Glu Gly Phe
385                 390                 395                 400
Ser Ala Val Ala Ser Thr Ile Glu Thr Leu Ala Ala Glu Arg Leu
                405                 410                 415
Thr Ala His Lys Asn Ala Val Thr Leu Arg Val Asn Ala Leu Lys Glu
            420                 425                 430
Gln Ala
```

FIG. 18P

```
CGTTGTCAGAAGTAAGTTGGCCGCAGTGTTATCACTCATGGTTATGGCAGCACTGCATAATTCTCTTACTGTCATGCCAT
CCGTAAGATGCTTTCTGTGACTGGTGAGTACTCAACCAAGTCATTCTGAGAATAGTGCTATGCGGCGACCGAGTTGCTCT
TGCCCGGCGTCAACACGGGATCTACCGCGCTGTTGAGATCCAGTTCGATGTAACCACTCGTGCACCAACTGATCTTCAGCAT
GCGAAACTCAAGGATCTTACCGCGTTTGGGTGAGCAAAACAGGAAGGCAAAATGCCGCAAAAAAGGAATAAGGGCGACACGG
CTTTACTTCACCAGCGTTTCTGGGTGAGCAAAAACAGGAAGGCAAAATGCCGCAAAAAAGGAATAAGGGCGACACGG
AAATGTGAATACTCATACTCTTCCTTTTCAATATTATTGAAGCATTTATCAGGTTATTGTCTCATGAGCGGATACAT
ATTTGAATGTATTTAGAAAAATAAACAAATAGGGGTTCCGCGCACATTTCCCGAAAAGTGCCACCTGACGTCTAAGAAA
CCATTATTATCATGACATTAACCTA
                         EcoRI
TAAAATAGGCGTATCACGAGGCCCTTTCGTCTCTTCAAGAATTCAGAGAGGTCTGGTGGACCTGCAAAAGTCCAGCTTTC
AAGGAACACAGAAGTGTATGGAATATTAGAAGATGTTGCTTTACTCTTAAGTTGGTTCCTAGGAAAATAGTTA
AATACTGTGACTTTAAAATGTGAGAGGGTTTCAAGTACTCATTTTTTAAATGTCAAAATTTTGTCAATCAATTGA
GGTCTTGTGTAGAACTGACATTAAGTTAACGGAATGGGAGTGAGGCTCTCATACCCTATTCAGAA
CTGACTTTTAACAATAATAAGTTTAAAATATTTTAAATGAATTGAGCAATGTTGAGTGAGTTGAGTCAAGATGGCCGA
           PvuII
TCAGAACCCGAACACCTGCAGCAGCTGGGCAGGAAGCAGGTCATGTGGCAAGGCTATTTGGGAAGGGAAATAAACCAC
TAGGTAAACTTGTAGCTGTGGTTTGAAGAAGTGGTTTCTAAAATAAGTTGAGAGATTCAGCAGCCCGAAACTGGCTG
AGCAAACACCACCTGGGTAATTGCATTTGCATTTCTAAAATAAGTTGAGATTCAGCAGCCCGAAACTTCAGCGGGTCCTCTTTAACT
TATTGAGTTCAACCTTTTAATTTTAGCTTGAGTAGTTCTAGTTTCCCAAACTTAAGTTTATCGACTTCTAAAATGTATT
EcoRI
TAGAATTCCTTTGCCTAATATTAATGAGGACTTAACCTGTGTGAAATATTTGATGTGGAAGCTGTTACTGTTAAAACTG
AGGTTATTGGGTAACTGCTATGTTAAACTTGCATTCAGGGACCACAAAAAACTCATGAAAATGGTGCTGGAAACCCATT
CAAGGGTCAAATTTCATTTTTGTGTTGGTGGGAACCTTTGGAGCTGCAGGGTGTTAGCAAACTACAGGACCAA
ATATCCTGCTCAAACTGTAACCCAAAAAAATGCTACAGTTGACAGTCAGCAGATGAACACTAGATATTTGGAACCTAC
ATAAGGATAATGCTTATCCAGTGCGAGTGCTGGGTTCCTGATCCAAGTAAACAGCAACCACAGTGCTCTTGATGAGCAGGTGTTGG
ACAGGTGGGGAAAATGCCTCCTGTTTGTATGTTTCTGCTGTTGACATTGTGGGCGTCTGTGAAAAACCCCTACCACTTCTGGAACACAGC
GCCCTGTCCAAAGCTGACAGCTTGTGTATTTTAAATTACCCTAGAAAAGCGGTTCTGTGAAAACCCTACCCAATTTCCTTTTG
AGTGGAAGGGACTTCCCAGATTAACAGGAGGACACAGAGGGTGATGGGCAGCCTATGATTGGAATGTCCTCTCAAG
TTAAGTGACCTAATTAACAGGAGGACACAGAGGGTGATGGGCAGCCTATGATTGGAATGTCCTCTCAAG
```

FIG. 19A

```
                              BamHI
TAGAGGAGGTTAGGGTTTATGAGGACACAGAGGAGCTTCCTGGGGATCCGATCCNNNNNNNNNNNNNNNNNNNNN
NNNNNNNNNNNNNNNNNNNNNNNNNNNNNNNNNNNNNNNNNNNNNNNNNNNNNNNNNNNNNNNNNNNNNNNNNNN
NNNNNNNNNNNNNNNNNNNNNNNNNNNNNNNNNNNNNNNNNNNNNNNNNNNNNNNNNNNNNNNNNNNNNNNNNNN
NNNNNNNNNNNNNNNNNNNNNNNNNNNNNNNNNNNNNNNNNNNNNNNNNNNNNNNNNNNNNNNNNNNNNNNNNNN
NNNNNNNNNNNNNNNNNNNNNNNNNNNNNNNNNNNNNNNNNNNNNNNNNNNNNNNNNNNNNNNNNNNNNNNNNNN
NNNNNNNNNNNNNNNNNNNNNNNNNNNNNNNNNNNNNNNNNNNNNNNNNNNNNNNNNNNNNNNNNNNNNNNNNNN
NNNNNNNNNNNNNNNNNNNNNNNNNNNNNNNNNNNNNNNNNNNNNNNNNNNNNNNNNNNNNNNNNNNNNNNNNNN
NNNNNNNNNNNNNNNNNNNNNNNNNNNNNNNNNNNNNNNNNNNNNNNNNNNNNNNNNNNNNNNNNNNNNNNNNNN
NNNNNNNNNNNNNNNNNNNNNNNNNNNNNNNNNNNNNNNNNNNNNNNNNNNNNNNNNNNNNNNNNNNNNNNNNNN
NNNNNNNNNNNNNNNNNNNNNNNNNNNNNNNNNNNNNNNNNNNNNNNNNNNNNNNNNNNNNNNNNNNNNNNNNNN
NNNNNNNNNNNNNNNNNNNNNNNNNNNNNNNNNNNNNNNNNNNNNNNNNNNNNNNNNNNNNNNNNNNNNNNNNNN
NNNNNNNNNNNNNNNNNNNNNNNNNNNNNNNNNNNNNNNNNNNNNNNNNNNNNNNNNNNNNNNNNNNNNNNNNNN
NNNNNNNNNNNNNNNNNNNNNNNNNNNNNNNNNNNNNNNNNNNNNNNNNNNNNNNNNNNNNNNNNNATATAG
CACAAAGACATGCAA
                              HindIII
ATAATATTTCCCTATGCTCATAAAACAGCCCTGACCATGAAGCTTTGACAGACGCCACAACCCTG
                              EcoRV
GACTCCCAAGTCTTTCTCCTTCAGTGACAAACACAGACATAGGATATCCACCATGAATGGAGCTGGTAATGCTCTTCCT
CCTGTCAGGAACTGCAGGTGTCCGCTCGAGGTCCAGCTCTGGACCTGAACCAGTCTGGACCTGAAGCCTGGAGCTTCAA
TGAAGATTCCTGCAAGGCTTCTGGTTACTCCATTCACTGGGTACACCATGAACTGGGTGAAGCAGAGCCATGGAGAGAAC
CTTGAGTGGATTGGACGTATTAATCCTCACAATGGTGGTACTGACTACAACCAGAAGTTCAAGGACAAGGCCCCTTTAAC
TGTAGACAAGTCATCCAACACAGCCTACATGGAGCTCCTCAGTCTGACATCTGAGGACTCTGCAGTCTATTACTGTGCAA
GAGGCTACTATTACTATTCTTTGGACTACTGGGGTCAAGGAACCTCAGTCACCGT
```

FIG. 19B

NheI
CTCCCTCAGCTAGCACCAAGGGCCCCATCCGTCTTCCCCCTGGCGCCCTGCTCCAGGAGGACCTCCGAGAGACACAGCCGCCC
TGGGCTGCCTGGTCAAGGACTACTTCCCCGAACCGGTGACGGTGTCGTGGAACTCAGGCGCCCTGACCAGCGGCGTGCAC
ACCTTCCCGGCTGTCCTACAGTCCTCACTCCCTCAGGACTCTACTCCCTCAGCAGCGTGGTGACCGTGCCCTCCAGCAGCTTGGGCAC
GAAGACCTACACCTGCAACGTAGATCACAAGCCCAGCAACACCAAGGTGGACAAGAGAGTTGGTGAGAGGCCAGCACAGG
GAGGGAGGGTGTCTGTGTTCTCCTACCCGGAGTCCTCAGCCCGGGAGGCCTTCAGCCACCACCACTCATGCTCAGGGAGAGGTGTTCTCTGATTTTTC
CAAGGCCCCCATCTGTCTATCCTGGAGGAGGGCACCACAGGCTGGATGCCCCTACCCCAGGCCCTGCGCATACAGGGCAGTGCTGCGCTCAGACCTG
CACCAGGCTCCCGGCACCACAGGCTGGATGCCCCCTACCCCAGGCCCTGCGCATACAGGGCAGTGCTGCGCTCAGACCTG
CCAAGAGCCATATCCGGGAGGACCCTGCCCCTGACCTAAGCCCACCCCAAAGCCCAAACTCTCCACTCCCTCAGCTCAGA
CACCTTCTCT
        BglII                  PstI
CCTCCCAGATCTGAGTAACTCCCCAATCTTCTCTGCAGAGTCCAAATATGGTCCCCCATGCCCATCATGCCCAGTAAG
CCAACCCAGCCTCGCCCTCCAGGCTCAAGGCGGACAGGTGCCCTAGAGTAGCCTGCATCCAGGACAGCCCCAGCCGG
GTGCTGACGCGCATCCACCTCCATCTCTTCCCCGAGTTCCTGGGGGACCATCAGTCTTCCTGTTCCCCAAAA
CCCAAGGACAACTCTCATGATCTCCCGGACCCCCTGAGGTCACGTGCGTGGTGGACGTGAGCGTGAGCGTGAGCCAGGAAGACCCGAGGT
CCAGT
                              SstII
TCAACTGGTACGTGGATGCCGTGGAGGTGCATAATGCCAAGACAAAGCCCGGGAGGAGCAGTCAACAGCACGTACCGT
GTGGTCAGCGTCCTGACCGTCCTGCACCAGGACTGGCTGAATGGCCAAGGAGTACAAGTGCAAGGTCTCCAACAAAGGCCT
CCCGTCCTCCATCGAGAAAACCATCTCCAAAGCCA
    DraIII                 BglI
AAGGTGGGACCCACGGGGTGCGAGGGCCAGCTCCCCAGCTCGGCCAGCTCGGCCCTCTGCCCTGGGAGTGACCGCTGT
GCCAACCTCTGTCCTACAGGGCAGCCCGAGAGCCACAGTGTACACCCTGCCCCCATCCGGGATGAAGGCAGCAAGA
ACCAGGTCAGCTGACCTGCCTGGTCAAAGGCTTCTACCCCAGCGACATCGCCGTGGAGTGGGAGAGCAATGGGCAGCCG
GAGAACAACTACAAGACCACGCCTCCCGTGCTGGACTCCGATGGCTCCTTCTTCCTCTACAGCAAGCTAACCGTGGACAA
GAGCAGGTGGCAGCAGGGGAATGTCTTCTCATGCTCCGTGATGCATGAGGCTCTGCACAACCACTACACG
                                                SmaI
CAGAAGAGCCTCTCCCTGTCTCCGGGTAAATGAGTGAGTGCCAGGGCCCGGCAAGCCCCCGGCTCTCGGGTCGCGC
GAGGATGCTTGGCACGTACCCCGTCTACATACTTCCCAGGCACCCAGCATGAAAGCACCCACCACTGCCCCTGGGC
CCCTGTGAGACTGTGATGGTTCTTCCACGGGTCAGGCCGAGTCTGAGGCCTGAGTGACATGAGGCCTGACATGAGGCAGAGCGGGTC
CCACTGTCCCCACACTGGNNNNNNNNNNNNNNNNNNNNNNNNNNNNNNNNNNNNNNNNNNNNNNNNNNNNNNNN
NNNNNNNNNNNNNNNNNNNNNNNNNNNNNNNNNNNNNNNNNNNNNNNNCAGCTGNNNNNNNNNNNNNNNNNNN
NNNNNNNNNNNNNNNNNNNNNNNNNNNNNNNNNNNNNNNNNNNNNNNNNNNNNNNNNNNNNNNNNNNNNNNN

FIG. 19C

```
NNNNNNNNNNNNNNNNNNNNNNNNNNNNNNNNNNNNNNNNNNNNNNNNNNNNNNNNNNNNNNNNNNNNNNNNNN
NNNNNNNNNNNNNNNNNNNNNNNNNNNNNNNNNNNNNNNNNNNNNNNNNNNNNNNNNNNNNNNNNNNNNNNNNN
NNNNNNNNNNNNNN
                BamHI
NNNNNNNNNNNNNNNNNNNNNNNNNNNGGATCCAGACATGATAAGATACATTGATGAGTTTGACAAACCACAACT
AGAATGCAGTGAAAAAAATGCTTTATTTGTGAAATTTGTGATGCTATTGC
                                                 HpaI
TTTATTTGTAACCATTATAAGCTGCAATAAACAAGTTAACAACAACAAGTTCATTCATTTTATGTTTCAGGTTCAGGGGG
AGGTGTGGGAGGTTTTTAAAGCAAGTAAAACCTCTACAAATGTGGCTATTATGATCTCTAGTCAAGGCACTAT
ACATCAAATATTCCTTATTAACCCCTTTACAAATTAAAAAGCTACACAATTTTGAGCATAGTTATTAATAGCA
GACACTCTATGCCTGTGTGGAGTAAGAAAAAAACAGTATGTTATGATTATAACTGTTATGCCTACTTATAAAGTTACAGA
ATATTTTCCATAATTTCTTGTATAGCAGTGCAGTTTTTCCTTGTGGTGTAAATAGCAAAGCAAGAGAGTTCTAT
TACTAAACACAGCATGACTCAAAAAACTTAGCAATTCTGAAGGAAAGTCCTTGGGGTCTTCTACCTTTCTCTTTTTT
GGAGGAGTAGAATGTTGAGAGTCAGCAGTAGCCTCATCATCAGTTCCATAGTGGCATTTCTTCTGAGCAAAACAGGTTTTCCTC
ATTAAAGGCATTCCACCACTGCTCCCATTCAGTTCCATAGTTGAATCTAAAATCACAAATTAGAATCAGTA
GTTAACACATTATACACTTAAAATTTTATATTTACCTTATAGCTTTAAATCTCTGTAGTAGTTTGTCCAATTATGTC
ACACCACAGAAGTAAGGTTCCTTCACAAGATCCGGNNNNNNNNNNNNNNNNNNN
                                     HpaI
NTCATGCTTGCTCTCCTTGAGGGGTTAACGCGCGAAGTAACGGCATTTTTATGGGCGGTCAGACGTTCGGCGGCGGCCAGT
GTTTCTATGGTTGAAGCCACCGCGAGAACCCCTCTTTCGACAGTTCCTGTACGTCATACGCTTCTGAAATCTGCCAG
CCCGAGGCTGAACAGGTGGCGGTGTAACGGAACCGAACCGGCGTAAGTCGGTAACGTGGTTGGTTCCGAGGCGTAATCACCTGCCGATT
CCGGTGACCAGTCACCAAGAAATACCGAACCGGCGTGGTATCGACAGCTGATGCTATCGACCAGTTCACGGCGTCACGGCGTTCGGCGTCGGCGTT
ATCAGGTGCTCCGGCCGTCTCCGGCCGTTCGCACGCGGATCTGATTAGAGATCTCCACGCGCCAGTTCCGCCACTGCCGTCGAATCTTTAGTCACGATCAGGCGCCATAT
CAGTGCCTGCTCCGGCCGGTTTCGCACGCGGATCTGATTAGAGATCTCCACGCGCCAGTTCCGCCACTGCCGTCGAATCTTTAGTCACGATCAGGCGCCATAT
CAGCAGCGGGCGTCAGTAAAATCACCTGTGAGTCCGGCCGTGTTCAGCCTGAGAGAGCAAATCAGAAGCCACGAAATCC
GGCGTTGCGCCGCTGTCAGCAATCA
                         ClaI
CCAGCACTTCCGACGGGCCTGCGGGCCATATCGATCTCCGCACCGTCGGCTGCCTCACCTGACGTTCGCTTCGGTG
ACAAAGGCGTACCCGGCGTACCCGGCCCGAAGATTTTGTCCACTTTTGGCACGGATTCCGTACGCCAGTGCGGGCAATGGCCTG
TGCGCCGACGTTGAACACGTCCTGCCACCGC
  PvuII
ACAGCTGCGCCGCCGCCATAAAGGATCTCATCGCGCCGCAATCGGCGGCGGCGGTGAGCACAGCAGCACCACCACTTTTTACAGCCCGCAATACGC
GCCGGAGTCGCCAGCATTAATACCGTTGAGAAGAGCGGGCCCCAGGAATATACAACCCAACTGAAGCTACCGG
ACGCGTGACCTGCTGGCAACGCCACGCCCTGCTCTACATCTACCGGGCGGCAGTTTTGCGGCAGTGTGCCAGTGGAAGGTTT
```

FIG. 19D

```
CAATATTCTTTACTGCTGCCACCGCCATCGCCCTGTTTAGCTCGTCGTCGCTCAGGCGGTTCGCTGGCGGGCGGCGATCTCCTCTGCA
GACACCTTCAGCGCGGGTAACCGTGGTTTTATCAAACTTCGCCGTGTATTCCCGCAGGCCTCATCGCCGCCGTGCTTTCAC
GTTATCGAGAATATCGTTAACAGTGCGGGTAATGCTTTCAGAGGCGGAAATCGCC
          PvuII
GGGCGCGTTAACAGTGCCGTTGTTGCACCGCAGTACAGCTATTCCAGTCAATGATTGTGTTAAAGCTCATNNNCCGGA
TCAGCTTTTTGCAAAAGCCTAGGCCTCCAAAAAGCCTCCTACTACTTCTGAATAGCTCAGAGGCCGAGGCGCCTCGG
CCTCTGCATAAATAAAAAAAATTAGTCAGCCATGGGCGGAGAATGGGCGAACTGGGCGGCGGAGTAGGGCGGGATGGGC
GGAGTTAGGGCGGGACTATGGTTGCTGACTATGTTGCTTTGCATACTTCTGCCTGCTGGGGAGCCTGGGA
CTTTCCACACCTGGTTGCTGACTAATTGAGATGCATGCTTTGCATACTTCTGCCTGCTGGGAGCCTGGGACTTTCCAC
ACCCTAACT    PvuII
GACACACATTCCACAGCTGCCTCCGCGCGTTTCGGTGATGACGGTGAAAACCTCTGACACATGCAGCTCCCGGAGACGGTC
ACAGCTTGTCTGTAAGCGGATGCCGGGAGCAGCAGACAAGCCCCGTCAGGCGCGTCAGGGCGTGTTGGCGGGTGTGCGGGCGC
AGCCATGACCCAGTCACGTCACGTAGCGGATAGCGGAGTGTATACTGGCTTAACTATGCCGCATCAGAGCAGATTGTACTGAGAGT
GCACCATGCGGTTGCGACTCACGTGTGAAATACCGCACAGATGCGTAAGGAGAGAAAATACCGCTCCTCTTCCGCTCTTCCGCTCTCA
CTGACTCGCTGCTCGGTCGTTCCGCTCGGGCGAGCGGTATCAGCTCACTCAAAGGCGGTAATACGGTTATCCACAGAA
TCAGGGGATAACGCAGGAAAGAACATGTGAGCAAAAGGCCAGCAACCGTAAAAAGGCCGCGTTGCTGGC
GTTTTCCATAGGCTCCGCCCCCCTGACGAGCATCACAAAATCGACGCTCAAGTCAGAGGTGGCGAAACCCGACAGGAC
TATAAAGATACCAGGCGTTTCCCCCTGGAAGCTCCCTCGTGCGCTCTCCTGTTCCGACCCTGCCGCTTACCGGATACCTG
TCCGCCTTTCTCCCTTCGGGAAGCGTGGCGCTTTCTCATGCTCACGCTGTAGGTATCTCAGTTCGGTGTAGTCGTTCG
CTCCAAGCTGGGCTGTGTGCACGAACCCCCCGTTCAGCCCGACCGCTGCGCCTTATCCGGTAACTATCGTCTTGAGTCCA
ACCCGGTAAGACACGACTTATCGCCACTGGCAGCAGCCACTGGTAACAGGATTAGCAGAGCGAGGTATGTAGGCGGTGCT
ACAGAGTTCTTGAAGTGGTGGCCTAACTACGGCTACACTAGAAGGACAGTATTTGGTATCTGCGCTCTGCTGAAGCCAGT
TACCTTCGGAAAAAGAGTTGGTAGCTCTTGATCCGGCAAACAAACCACCGCTGGTAGCGGTGGTTTTTTTGTTTGCAAGC
AGCAGATTACGCGCAGAAAAAAAGGATCTCAAGAAGATCTTCACCTAGATCCTTTTAAATTAAAAATGAAGTTT
AACTCACGTTAAGGGATTTTGGTCATGAGATTATCAAAAAGGATCTTCACCTAGATCGTTTAATTAAAAATGAAGTTT
TAAATCAATCTAAAGTATATATGAGTAAACTTGGTCTGACAGTTACCAATGCTTAATCAGTGAGGCACCTATCTCAGCGA
TCTGTCTATTTCGTTCATCCATAGTTGCCTGACTCCCCGTCGTGTAGATAACTACGATACGGGAGGGCTTACCATCTGGC
CCCAGTGCTGCAATGATACCGCGAGACCCACGCTCACCGGCTCCAGATTTATCAGCAATAAACCAGCCAGCCGGAAGGGC
CGAGCGCAGAAGTGGTCCTGCAACTTTATCCGCCTCCATCCAGTCTATTAATTGT
```

FIG. 19E

```
                                              PstI
TGCCGGGAAGCTAGAGTAAGTAGTTCGCCAGTTAATAGTTTGCCGCAACGTTGTTGCCATTGCTGCAGGCATCGTGGTGTC
ACGCTCGTCGTTTGGTATGGCTTCATTCAGCTCCGGTTCCCAACGATCAA
                        PvuI
GGCGAGTTACATGATCCCCCATGTTGTGCAAAAAGCGGTTAGCTCCTTCGGTCCTCCGAT
```

FIG. 19F

```
                                              ATG GAA TGG
                                              Met Glu Trp
                                                   1

AGC TGG GTA ATG CTC TTC CTC CTG TCA GGA ACT GCA GGT GTC CGC TCT
Ser Trp Val Met Leu Phe Leu Leu Ser Gly Thr Ala Gly Val Arg Ser
     5               10                      15

GAG GTC CAG CTG CAA CAG TCT GGA CCT GAA CTG GTG AAG CCT GGA GCT
Glu Val Gln Leu Gln Gln Ser Gly Pro Glu Leu Val Lys Pro Gly Ala
 20              25                  30                      35

TCA ATG AAG ATT TCC TGC AAG GCT TCT GGT TAC TCA TTC ACT GGC TAC
Ser Met Lys Ile Ser Cys Lys Ala Ser Gly Tyr Ser Phe Thr Gly Tyr
             40                  45                      50

ACC ATG AAC TGG GTG AAG CAG AGC CAT GGA GAG AAC CTT GAG TGG ATT
Thr Met Asn Trp Val Lys Gln Ser His Gly Glu Asn Leu Glu Trp Ile
                 55                  60                  65

GGA CGT ATT AAT CCT CAC AAT GGT GGT ACT GAC TAC AAC CAG AAG TTC
Gly Arg Ile Asn Pro His Asn Gly Gly Thr Asp Tyr Asn Gln Lys Phe
             70                  75                  80

AAG GAC AAG GCC CCT TTA ACT GTA GAC AAG TCA TCC AAC ACA GCC TAC
Lys Asp Lys Ala Pro Leu Thr Val Asp Lys Ser Ser Asn Thr Ala Tyr
 85                      90                  95

ATG GAG CTC CTC AGT CTG ACA TCT GAG GAC TCT GCA GTC TAT TAC TGT
Met Glu Leu Leu Ser Leu Thr Ser Glu Asp Ser Ala Val Tyr Tyr Cys
100                 105                 110                 115

GCA AGA GGC TAC TAT TAC TAT TCT TTG GAC TAC TGG GGT CAA GGA ACC
Ala Arg Gly Tyr Tyr Tyr Tyr Ser Leu Asp Tyr Trp Gly Gln Gly Thr
                120                 125                 130

TCA GTC ACC GTC TCC TCA GCT AGC ACC AAG GGC CCA TCC GTC TTC CCC
Ser Val Thr Val Ser Ser Ala Ser Thr Lys Gly Pro Ser Val Phe Pro
             135                 140                 145

CTG GCG CCC TGC TCC AGG AGG ACC TCC GAG AGC ACA GCC GCC CTG GGC
Leu Ala Pro Cys Ser Arg Arg Thr Ser Glu Ser Thr Ala Ala Leu Gly
         150                 155                 160

TGC CTG GTC AAG GAC TAC TTC CCC GAA CCG GTG ACG GTG TCG TGG AAC
Cys Leu Val Lys Asp Tyr Phe Pro Glu Pro Val Thr Val Ser Trp Asn
165                 170                 175
```

FIG. 19G

```
TCA GGC GCC CTG ACC AGC GGC GTG CAC ACC TTC CCG GCT GTC CTA CAG
Ser Gly Ala Leu Thr Ser Gly Val His Thr Phe Pro Ala Val Leu Gln
180             185             190             195

TCC TCA GGA CTC TAC TCC CTC AGC AGC GTG GTG ACC GTG CCC TCC AGC
Ser Ser Gly Leu Tyr Ser Leu Ser Ser Val Val Thr Val Pro Ser Ser
            200             205             210

AGC TTG GGC ACG AAG ACC TAC ACC TGC AAC GTA GAT CAC AAG CCC AGC
Ser Leu Gly Thr Lys Thr Tyr Thr Cys Asn Val Asp His Lys Pro Ser
            215             220             225

AAC ACC AAG GTG GAC AAG AGA GTT
Asn Thr Lys Val Asp Lys Arg Val
        230             235
```

FIG. 19H

```
GAG TCC AAA TAT GGT CCC CCA TGC CCA TCA TGC CCA
Glu Ser Lys Tyr Gly Pro Pro Cys Pro Ser Cys Pro
 1           5                       10
```

FIG. 19I

```
                                                    GCA CCT GAG
                                                    Ala Pro Glu
                                                         1

TTC CTG GGG GGA CCA TCA GTC TTC CTG TTC CCC CCA AAA CCC AAG GAC
Phe Leu Gly Gly Pro Ser Val Phe Leu Phe Pro Pro Lys Pro Lys Asp
     5                  10                  15

ACT CTC ATG ATC TCC CGG ACC CCT GAG GTC ACG TGC GTG GTG GTG GAC
Thr Leu Met Ile Ser Arg Thr Pro Glu Val Thr Cys Val Val Val Asp
 20              25                  30                      35

GTG AGC CAG GAA GAC CCC GAG GTC CAG TTC AAC TGG TAC GTG GAT GGC
Val Ser Gln Glu Asp Pro Glu Val Gln Phe Asn Trp Tyr Val Asp Gly
                 40                  45                  50

GTG GAG GTG CAT AAT GCC AAG ACA AAG CCG CGG GAG GAG CAG TTC AAC
Val Glu Val His Asn Ala Lys Thr Lys Pro Arg Glu Glu Gln Phe Asn
             55                  60                  65

AGC ACG TAC CGT GTG GTC AGC GTC CTC ACC GTC CTG CAC CAG GAC TGG
Ser Thr Tyr Arg Val Val Ser Val Leu Thr Val Leu His Gln Asp Trp
         70                  75                  80

CTG AAC GGC AAG GAG TAC AAG TGC AAG GTC TCC AAC AAA GGC CTC CCG
Leu Asn Gly Lys Glu Tyr Lys Cys Lys Val Ser Asn Lys Gly Leu Pro
     85                  90                  95

TCC TCC ATC GAG AAA ACC ATC TCC AAA GCC AAA
Ser Ser Ile Glu Lys Thr Ile Ser Lys Ala Lys
100             105                 110
```

FIG. 19J

```
                    GGG CAG CCC CGA GAG CCA CAG GTG TAC ACC CTG
                    Gly Gln Pro Arg Glu Pro Gln Val Tyr Thr Leu
                     1               5                      10

CCC CCA TCC CAG GAG GAG ATG ACC AAG AAC CAG GTC AGC CTG ACC TGC
Pro Pro Ser Gln Glu Glu Met Thr Lys Asn Gln Val Ser Leu Thr Cys
            15                  20                  25

CTG GTC AAA GGC TTC TAC CCC AGC GAC ATC GCC GTG GAG TGG GAG AGC
Leu Val Lys Gly Phe Tyr Pro Ser Asp Ile Ala Val Glu Trp Glu Ser
        30                  35                  40

AAT GGG CAG CCG GAG AAC AAC TAC AAG ACC ACG CCT CCC GTG CTG GAC
Asn Gly Gln Pro Glu Asn Asn Tyr Lys Thr Thr Pro Pro Val Leu Asp
    45                  50                  55

TCC GAC GGC TCC TTC TTC CTC TAC AGC AGG CTA ACC GTG GAC AAG AGC
Ser Asp Gly Ser Phe Phe Leu Tyr Ser Arg Leu Thr Val Asp Lys Ser
60                  65                  70                  75

AGG TGG CAG GAG GGG AAT GTC TTC TCA TGC TCC GTG ATG CAT GAG GCT
Arg Trp Gln Glu Gly Asn Val Phe Ser Cys Ser Val Met His Glu Ala
                80                  85                  90

CTG CAC AAC CAC TAC ACG CAG AAG AGC CTC TCC CTG TCT CCG GGT AAA
Leu His Asn His Tyr Thr Gln Lys Ser Leu Ser Leu Ser Pro Gly Lys
            95                  100                 105
```

FIG. 19K

```
Met Ser Phe Asn Thr Ile Ile Asp Trp Asn Ser Cys Thr Ala Val Gln
 1           5                   10                  15

Gln Arg Gln Leu Leu Thr Arg Pro Ala Ile Ser Ala Ser Glu Ser Ile
            20                  25              30

Thr Arg Thr Val Asn Asp Ile Leu Asp Asn Val Lys Ala Arg Gly Asp
        35                  40                  45

Glu Ala Leu Arg Glu Tyr Ser Ala Lys Phe Asp Lys Thr Thr Val Thr
    50                  55                  60

Ala Leu Lys Val Ser Ala Glu Glu Ile Ala Ala Ala Ser Glu Arg Leu
65                  70                  75                  80

Ser Asp Glu Leu Lys Gln Ala Met Ala Val Ala Val Lys Asn Ile Glu
                85                  90                  95

Thr Phe His Thr Ala Gln Lys Leu Pro Pro Val Asp Val Glu Thr Gln
            100                 105                 110

Pro Gly Val Arg Cys Gln Gln Val Thr Arg Pro Val Ala Ser Val Gly
            115                 120                 125

Leu Tyr Ile Pro Gly Gly Ser Ala Pro Leu Phe Ser Thr Val Leu Met
    130                 135                 140

Leu Ala Thr Pro Ala Arg Ile Ala Gly Cys Lys Lys Val Val Leu Cys
145                 150                 155                 160

Ser Pro Pro Pro Ile Ala Asp Glu Ile Leu Tyr Ala Ala Gln Leu Cys
                165                 170                 175

Gly Val Gln Asp Val Phe Asn Val Gly Gly Ala Gln Ala Ile Ala Ala
            180                 185                 190

Leu Ala Phe Gly Thr Glu Ser Val Pro Lys Val Asp Lys Ile Phe Gly
        195                 200                 205

Pro Gly Asn Ala Phe Val Thr Glu Ala Lys Arg Gln Val Ser Gln Arg
    210                 215                 220

Leu Asp Gly Ala Glu Ile Asp Met Pro Ala Gly Pro Ser Glu Val Leu
225                 230                 235                 240

Val Ile Ala Asp Ser Gly Ala Thr Pro Asp Phe Val Ala Ser Asp Leu
            245                 250                 255

Leu Ser Gln Ala Glu His Gly Pro Asp Ser Gln Val Ile Leu Leu Thr
            260                 265                 270
```

FIG. 19L

Pro Ala Ala Asp Met Ala Arg Arg Val Ala Glu Ala Val Glu Arg Gln
        275                 280                 285

Leu Ala Glu Leu Pro Arg Ala Glu Thr Ala Arg Gln Ala Leu Asn Ala
        290                 295                 300

Ser Arg Leu Ile Val Thr Lys Asp Ser Ala Gln Cys Val Glu Ile Ser
305                 310                 315                 320

Asn Gln Tyr Gly Pro Glu His Leu Ile Ile Gln Thr Arg Asn Ala Arg
                325                 330                 335

Glu Leu Val Asp Ser Ile Thr Ser Ala Gly Ser Val Phe Leu Gly Asp
            340                 345                 350

Trp Ser Pro Glu Ser Ala Gly Asp Tyr Ala Ser Gly Thr Asn His Val
        355                 360                 365

Leu Pro Thr Tyr Gly Tyr Thr Ala Thr Cys Ser Ser Leu Gly Leu Ala
    370                 375                 380

Asp Phe Gln Lys Arg Met Thr Val Gln Glu Leu Ser Lys Glu Gly Phe
385                 390                 395                 400

Ser Ala Val Ala Ser Thr Ile Glu Thr Leu Ala Ala Ala Glu Arg Leu
                405                 410                 415

Thr Ala His Lys Asn Ala Val Thr Leu Arg Val Asn Ala Leu Lys Glu
            420                 425                 430

Gln Ala

FIG. 19M

TRANSFERRIN RECEPTOR SPECIFIC ANTIBODY-NEUROPHARMACEUTICAL OR DIAGNOSTIC AGENT CONJUGATES

RELATED APPLICATIONS

This application is a division of co-pending application Ser. No. 08/232,246, filed Jul. 5, 1994, which is the 371 U.S. National Phase of PCT/US92/10206, filed Nov. 24, 1992, which is a Continuation-in-Part of Ser. No. 07/800,458, filed Nov. 26, 1991 (now abandoned), which is a Continuation-in-Part and the 371 U.S. National Phase Filing of PCT/US90/05077, filed Sep. 7, 1990, designating the U.S., which is a Continuation-in-Part of Ser. No. 07/404,089, filed Sep. 7, 1989 (now U.S. Pat. No. 5,154,924, issued Oct. 13, 1992).

BACKGROUND

The capillaries that supply blood to the tissues of the brain constitute the blood brain barrier (Goldstein et al. (1986) Scientific American 255:74–83; Pardridge, W. M. (1986) Endocrin. Rev. 7:314–330). The endothelial cells which form the brain capillaries are different from those found in other tissues in the body. Brain capillary endothelial cells are joined together by tight intercellular junctions which form a continuous wall against the passive movement of substances from the blood to the brain. These cells are also different in that they have few pinocytic vesicles which in other tissues allow somewhat unselective transport across the capillary wall. Also lacking are continuous gaps or channels running through the cells which would allow unrestricted passage.

The blood-brain barrier functions to ensure that the environment of the brain is constantly controlled. The levels of various substances in the blood, such as hormones, amino acids and ions, undergo frequent small fluctuations which can be brought about by activities such as eating and exercise (Goldstein et al, cited supra). If the brain were not protected by the blood brain barrier from these variations in serum composition, the result could be uncontrolled neural activity.

The isolation of the brain from the bloodstream is not complete. If this were the case, the brain would be unable to function properly due to a lack of nutrients and because of the need to exchange chemicals with the rest of the body. The presence of specific transport systems within the capillary endothelial cells assures that the brain receives, in a controlled manner, all of the compounds required for normal growth and function. In many instances, these transport systems consist of membrane-associated receptors which, upon binding of their respective ligand, are internalized by the cell (Pardridge, W. M., cited supra). Vesicles containing the receptor-ligand complex then migrate to the abluminal surface of the endothelial cell where the ligand is released.

The problem posed by the blood-brain barrier is that, in the process of protecting the brain, it excludes many potentially useful therapeutic agents. Presently, only substances which are sufficiently lipophilic can penetrate the blood-brain barrier (Goldstein et al, cited supra; Pardridge, W. M., cited supra). Some drugs can be modified to make them more lipophilic and thereby increase their ability to cross the blood brain barrier. However, each modification has to be tested individually on each drug and the modification can alter the activity of the drug. The modification can also have a very general effect in that it will increase the ability of the compound to cross all cellular membranes, not only those of brain capillary endothelial cells.

SUMMARY OF THE INVENTION

The present invention pertains to a method for delivering a neuropharmaceutical or diagnostic agent across the blood brain barrier to the brain of a host. The method comprises administering to the host a therapeutically effective amount of an antibody-neuropharmaceutical or diagnostic agent conjugate wherein the antibody is reactive with a transferrin receptor and the antibody is a chimera between the variable region from one animal source and the constant region from a different animal source. The conjugate is administered under conditions whereby binding of the antibody to a transferrin receptor on a brain capillary endothelial cell occurs and the neuropharmaceutical agent is transferred across the blood brain barrier in a pharmaceutically active form. Other aspects of this invention include a delivery system comprising an antibody reactive with a transferrin receptor linked to a neuropharmaceutical agent and methods for treating hosts afflicted with a disease associated with a neurological disorder.

In embodiments of the present invention, the antibody that is reactive with a transferrin receptor is a chimeric antibody. This antibody is composed of a variable region, immunologically reactive with the transferrin receptor, that is derived from one animal source and a constant region that is derived from an animal source other than the one which provided the variable region. The chimeric antibodies of this invention can exist either as isolated entities or as conjugates with a neuropharmaceutical agent for transferal across the blood brain barrier. In the latter mode, the chimeric antibody-neuropharmaceutical agent conjugate forms a delivery system for delivering the neuropharmaceutical agent across the blood brain barrier.

Presently available means for delivering therapeutic agents to the brain are limited in that they are invasive. The delivery system of the present invention is non-invasive and can utilize readily available antibodies reactive with a transferrin receptor as carriers for neuropharmaceutical agents. The delivery system is advantageous in that the antibodies are capable of transporting neuropharmaceutical agents across the blood brain barrier without being susceptible to premature release of the neuropharmaceutical agent prior to reaching the brain-side of the blood brain barrier. Further, if the therapeutic activity of the agent to be delivered to the brain is not altered by the addition of a linker, a noncleavable linker can be used to link the neuropharmaceutical agent to the antibody.

DESCRIPTION OF THE DRAWINGS

FIGS. 11A–11G (SEQ ID NO: 18) is the antibody coding sequence of heavy chain expression vector pAH4602 containing the γ-1 isotype constant region; FIGS. 11H–11I (SEQ ID NO: 19), FIG. 11J (SEQ ID NO: 20) FIG. 11K (SEQ ID NO: 21), FIG. 11L (SEQ ID NO; 22), and FIGS. 11M–11N (SEQ ID NO: 23) are amino acid sequences of polypeptides which are encoded within the pAH4602 coding sequence (the polypeptide of FIGS. 11M–11N is encoded within the complementary polynucleotide sequence).

FIGS. 13A–13F (SEQ ID NO: 25) is the antibody coding sequence of light chain expression vector pAG4611; FIG. 13G (SEQ ID NO: 25) and FIG. 13H (SEQ ID NO: 26) are amino acid sequences of polypeptides which are encoded within the pAG4611 coding sequence.

FIGS. 17A–17F (SEQ ID NO: 27) is the antibody coding sequence of heavy chain expression vector pAH4625 containing the γ-2 isotype constant region; FIGS. 17G–17H (SEQ ID NO: 28), FIG. 17I (SEQ ID NO: 29), FIG. 17J (SEQ ID NO: 30), and FIGS. 17K–17L (SEQ ID NO: 31) are amino acid sequences of polypeptides which are encoded within the pAH4625 coding sequence (the polypeptide of FIGS. 17K–17L is encoded within the complementary polynucleotide sequence).

FIGS. 18A–18F (SEQ ID NO: 32) is the antibody coding sequence of heavy chain expression vector pAH4807 containing the γ-3 isotype constant region; FIGS. 18G–18H (SEQ ID NO: 33), FIG. 18I (SEQ ID NO: 34), FIG. 18J (SEQ ID NO: 35), FIG. 18K (SEQ ID NO: 36), FIG. 18L (SEQ ID NO: 37), FIG. 18M (SEQ ID NO: 38), FIG. 18N (SEQ ID NO: 39), and FIGS. 18O–18P (SEQ ID NO: 40) are amino acid sequences of polypeptides which are encoded within the pAH4807 coding sequence (the polypeptide of FIGS. 18O–18P is encoded within the complementary polynucleotide sequence).

FIGS. 19A–19F (SEQ ID NO: 41) is the antibody coding sequence of heavy chain expression vector pAH4808 containing the γ-4 isotype constant region; FIGS. 19G–19H, (SEQ ID NO: 42), FIG. 19I (SEQ ID NO: 43), FIG. 19J (SEQ ID NO: 44), FIG. 19K (SEQ ID NO: 45), and FIGS. 19L–19M (SEQ ID NO: 46) are amino acid sequences of polypeptides which are encoded within the pAH4808 coding sequence (the polypeptide of FIGS. 19L–19M is encoded within the complementary polynucleotide sequence).

DETAILED DESCRIPTION

Figure 1:
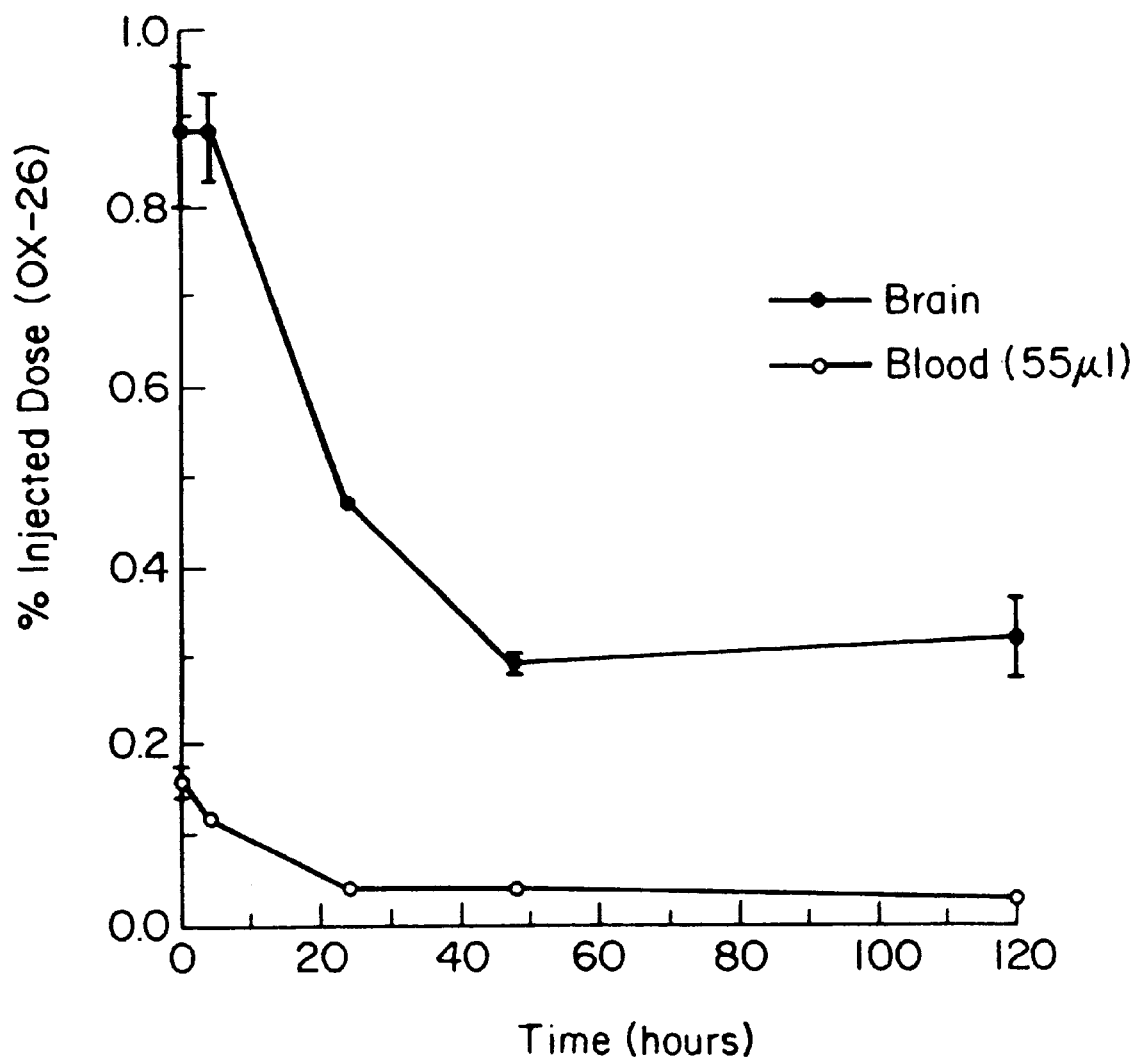
FIG. 1 is a graphic representation of rat brain uptake of $^{14}C$-labelled murine monoclonal antibody (OX-26) to rat transferrin receptor in rats where the percent injected dose of radiolabelled antibody per brain and per 55 $\mu$l of blood is plotted versus time post-injection.

The method for delivering a neuropharmaceutical agent across the blood brain barrier to the brain of a host comprises administering to the host a therapeutically effective amount of an antibody-neuropharmaceutical agent conjugate wherein the antibody is reactive with a transferrin receptor present on a brain capillary endothelial cell. The method is conducted under conditions whereby the antibody binds to the transferrin receptor on the brain capillary endothelial cell and the neuropharmaceutical agent is transferred across the blood brain barrier in a pharmaceutically active form.

The host can be an animal susceptible to a neurological disorder (i.e., an animal having a brain). Examples of hosts include mammals such as humans, domestic animals (e.g., dog, cat, cow or horse), mice and rats.

The neuropharmaceutical agent can be an agent having a therapeutic or prophylactic effect on a neurological disorder or any condition which affects biological functioning of the central nervous system. Examples of neurological disorders include cancer (e.g. brain tumors), Autoimmune Deficiency Syndrome (AIDS), stroke, epilepsy, Parkinson's disease, multiple sclerosis, neurodegenerative disease, trauma, depression, Alzheimer's disease, migraine, pain, or a seizure disorder. Classes of neuropharmaceutical agents which can be used in this invention include proteins, antibiotics, adrenergic agents, anticonvulsants, small molecules, nucleotide analogs, chemotherapeutic agents, anti-trauma agents, peptides and other classes of agents used to treat or prevent a neurological disorder. Examples of proteins include CD4 (including soluble portions thereof), growth factors (e.g. nerve growth factor and interferon), dopamine decarboxylase and tricosanthin. Examples of antibiotics include amphotericin B, gentamycin sulfate, and pyrimethamine. Examples of adrenergic agents (including blockers) include dopamine and atenolol. Examples of chemotherapeutic agents include adriamycin, methotrexate, cyclophosphamide, etoposide, and carboplatin. An example of an anticonvulsant which can be used is valproate and an anti-trauma agent which can be used is superoxide dismutase. Examples of peptides would be somatostatin analogues and enkephalinase inhibitors. Nucleotide analogs which can be used include azido thymidine (hereinafter AZT), dideoxy Inosine (ddI) and dideoxy cytodine (ddc).

The antibody, which is reactive with a transferrin receptor present on a brain capillary endothelial cell, may also be conjugated to a diagnostic agent. In this method and delivery system, the neuropharmaceutical agent of the neuropharmaceutical agent—anti-transferrin receptor conjugate has been replaced with a diagnostic agent. The diagnostic agent is then delivered across the blood brain barrier to the brain of the host. The diagnostic agent is then detected as indicative of the presence of a physiological condition for which the diagnostic agent is intended. For example, the diagnostic agent may be an antibody to amyloid plaques. When conjugated to an antibody reactive with a transferrin receptor present on a brain capillary endothelial cell, this diagnostic agent antibody can be transferred across the blood brain barrier and can then subsequently immunoreact with amyloid plaques. Such an immunoreaction is indicative of Alzheimer's Disease.

Serum transferrin is a monomeric glycoprotein with a molecular weight of 80,000 daltons that binds iron in the circulation and transports it to the various tissues(Aisen et al. (1980) *Ann. Rev. Biochem.* 49:357–393; MacGillivray et al. (1981) *J. Biol. Chem.* 258:3543–3553). The uptake of iron by individual cells is mediated by the transferrin receptor, an integral membrane glycoprotein consisting of two identical 95,000 dalton subunits that are linked by a disulfide bond. The number of receptors on the surface of a cell appears to correlate with cellular proliferation, with the highest number being on actively growing cells and the lowest being on resting and terminally differentiated cells. Jeffries et al (*Nature* Vol. 312 (November 1984) pp. 167–168) used monoclonal antibodies to show that brain capillary endothelial cells have a high density of transferrin receptors on their cell surface.

Antibodies which can be used within this invention are reactive with a transferrin receptor. The term antibody is intended to encompass both polyclonal and monoclonal antibodies. The preferred antibody is a monoclonal antibody reactive with a transferrin receptor. The term antibody is also intended to encompass mixtures of more than one antibody reactive with a transferrin receptor (e.g., a cocktail of different types of monoclonal antibodies reactive with a transferrin receptor). The term antibody is further intended to encompass whole antibodies, biologically functional fragments thereof, and chimeric antibodies comprising portions from more than one species, bifunctional antibodies, etc. Biologically functional antibody fragments which can be used are those fragments sufficient for binding of the antibody fragment to the transferrin receptor to occur.

The antibodies, chimeric or otherwise, are not to be considered as being restricted to a specific isotype. Any of the antibody isotypes are within the present invention. For example, antibodies with identical light chains but different heavy chains are intended. In addition, mutations of certain regions of the antibodies, e.g., in the γ chains, are also intended. These mutations, particularly point mutations, may occur anywhere provided functionality of the antibodies as reactive with a transferrin receptor is still maintained.

The chimeric antibodies can comprise portions derived from two different species (e.g., human constant region and murine variable or binding region). The portions derived from two different species can be joined together chemically by conventional techniques or can be prepared as single contiguous proteins using genetic engineering techniques. DNA encoding the proteins of both the light chain and heavy chain portions of the chimeric antibody can be expressed as contiguous proteins.

One genetic engineering approach that can be used to produce or clone chimeric antibodies reactive with a transferrin receptor is to prime the DNAs encoding the variable region of functional antibodies for amplification by PCR using specific oligonucleotides. The variable region of functional antibodies is that portion of the antibody that immunologically reacts with the transferrin receptor antigen. Both the heavy chain and light chain of antibodies contribute to the variable region. Thus, the DNA encoding the variable region has two portions: a polynucleotide sequence encoding the variable region heavy chain and a polynucleotide sequence encoding the variable region light chain. The primed variable regions can then be cloned into vectors which contain the DNA encoding the constant region of antibodies. A particularly useful vector is one which contains DNA encoding the constant region of human antibodies that has been designed to also express immunoglobulin variable regions from other sources. The DNA encoding the constant region is usually from a separate source than the one whose DNA encodes the variable region. Although different animals from the same species may be the sources of the DNA encoding the variable region and the constant region, the usual situation is where the animal species are different (e.g., human constant region and murine variable region). Following the cloning of the primed variable regions into vectors containing the constant region, chimeric antibodies can be expressed from such vectors.

A general strategy that can be used to amplify immunoglobulin variable regions has been previously described (Orlandi et al., *Proc. Natl. Acad. Sci.*, 86: 3833–3837 (1989); Larrick et al., *Bio/technology*, 7: 934–938 (1989); Gavilondo et al., Hybridoma, 9(5): 407–417 (1990)). Two approaches have been used in the general strategy. In one approach, 5' primers are designed to prime the first framework region of the variable region. The 3' primers are designed to prime either the J region or the constant region. Priming in the frameworks (Orlandi) takes advantage of the conserved nature of these sequences. This makes it feasible to use relatively few degenerate primers to clone the majority of the variable regions. The disadvantage of this approach is that it may introduce amino acid substitutions into the framework regions which affect antibody affinity.

In the second approach (Larrick, Gavilondo), 5' primers are designed to prime some portion of the leader sequence. The 3' primers are designed to prime either the J region or the constant region, as in the first approach. The second approach takes advantage of the relatively conserved nature of the leader sequences and uses a set of redundant oligonucleotides to prime this site. Priming in the leader sequences is generally the more powerful approach since this (leader) peptide is removed from the mature antibody molecule and variations in its sequence will have no effect on antibody affinity. Many different leader peptide sequences are effective in targeting the immature antibody molecule to the endoplasmic reticulum. This second approach is the preferred embodiment in this disclosure.

The term transferrin receptor is intended to encompass the entire receptor or portions thereof. Portions of the transferrin receptor include those portions sufficient for binding of the receptor to an anti-transferrin receptor antibody to occur.

Monoclonal antibodies reactive with at least a portion of the transferrin receptor can be obtained (e.g., OX-26, B3/25 (Omary et al. (1980) *Nature* 286,888–891), T56/14 (Gatter et al. (1983) *J. Clin. Path.* 36 539–545; Jefferies et al. *Immunology* (1985) 54:333–341), OKT-9 (Sutherland et al. (1981) *Proc. Natl. Acad. Sci. USA* 78:4515–4519), L5.1 (Rovera, C. (1982) *Blood* 59:671–678), 5E-9 (Haynes et al.(1981) *J. Immunol.* 127:347–351), RI7 217 (Trowbridge et al. *Proc. Natl. Acad. Sci. USA* 78:3039 (1981) and T58/30 (Omary et al. cited supra)or can be produced using conventional somatic cell hybridization techniques (Kohler and Milstein (1975) *Nature* 256, 495–497). A crude or purified protein or peptide comprising at least a portion of the transferrin receptor can be used as the immunogen. An animal is vaccinated with the immunogen to obtain an anti-transferrin receptor antibody-producing spleen cells. The species of animal immunized will vary depending on the species of monoclonal antibody desired. The antibody producing cell is fused with an immortalizing cell (e.g. myeloma cell) to create a hybridoma capable of secreting anti-transferrin receptor antibodies. The unfused residual antibody-producing cells and immortalizing cells are eliminated. Hybridomas producing the anti-transferrin receptor antibodies are selected using conventional techniques and the selected anti-tranferrin receptor antibody producing hybridomas are cloned and cultured.

Polyclonal antibodies can be prepared by immunizing an animal with a crude or purified protein or peptide comprising at least a portion of a transferrin receptor. The animal is maintained under conditions whereby antibodies reactive with a transferrin receptor are produced. Blood is collected from the animal upon reaching a desired titer of antibodies. The serum containing the polyclonal antibodies (antisera) is separated from the other blood components. The polyclonal antibody-containing serum can optionally be further separated into fractions of particular types of antibodies (e.g. IgG, IgM).

The neuropharmaceutical agent can be linked to the antibody using standard chemical conjugation techniques. Generally, the link is made via an amine or a sulfhydryl group. The link can be a cleavable link or non-cleavable link depending upon whether the neuropharmaceutical agent is more effective when released in its native form or whether the pharmaceutical activity of the agent can be maintained while linked to the antibody. The determination of whether to use a cleavable or non-cleavable linker can be made without undue experimentation by measuring the activity of the drug in both native and linked forms or for some drugs can be determined based on known activities of the drug in both the native and linked form.

For some cases involving the delivery of proteins or peptides to the brain, release of the free protein or peptide may not be necessary if the biologically active portion of the protein or peptide is uneffected by the link. As a result, antibody-protein or antibody peptide conjugates can be constructed using noncleavable linkers. Examples of such proteins or peptides include CD4, superoxide dismutase, interferon, nerve growth factor, tricosanthin, dopamine decarboxylase, somatostatin analogues and enkephalinase inhibitors. Terms such as "CD4" are used herein to include modified versions of the natural molecule, such as soluble CD4, truncated CD4, etc. Examples of non-cleavable linker systems which can be used in this invention include the carbodiimide (EDC), the sulfhydryl-maleimide, the N-succinimidyl-3-(2-pyridyldithio) propionate (SPDP; Pharmacia), and the periodate systems. In the carbodiimide system, a water soluble carbodiimide reacts with carboxylic acid groups on proteins and activates the carboxyl group. The carboxyl group is coupled to an amino group of the second protein. The result of this reaction is a noncleavable amide bond between two proteins.

In the sulfhydryl-maleimide system, a sulfhydryl group is introduced onto an amine group of one of the proteins using a compound such as Traut's reagent. The other protein is reacted with an NHS ester (such as gamma-maleimidobutyric acid NHS ester (GMBS)) to form a maleimide derivative that is reactive with sulfhydryl groups. The two modified proteins are then reacted to form a covalent linkage that is noncleavable.

SPDP is a heterobifunctional crosslinking reagent that introduces thiol-reactive groups into either the monoclonal antibody or the neuropharmaceutical agent. The thiol-reactive group reacts with a free sulfhydryl group forming a disulfide bond.

Periodate coupling requires the presence of oligosaccharide groups on either the carrier or the protein to be delivered. If these groups are available on the protein to be delivered (as in the case of horseradish peroxidase (HRP)), an active aldehyde is formed on the protein to be delivered which can react with an amino group on the carrier. It is also possible to form active aldehyde groups from the carbohydrate groups present on antibody molecules. These groups can then be reacted with amino groups on the protein to be delivered generating a stable conjugate. Alternatively, the periodate oxidized antibody can be reacted with a hydrazide derivative of a protein to be delivered which will also yield a stable conjugate.

Cleavable linkers can be used to link neuropharmaceutical agents which are to be deposited in the brain or when a non-cleavable linker alters the activity of a neuropharmaceutical agent. Examples of cleavable linkers include the acid labile linkers described in copending patent application Ser. No. 07/308,960 filed Feb. 6, 1989 and issued as U.S. Pat. No. 5,144,011 on Sep. 1, 1992, the contents of which are hereby incorporated by reference. Acid labile linkers include cis-aconitic acid, cis-carboxylic alkadienes, cis-carboxylic alkatrienes, and poly-maleic anhydrides. Other cleavable linkers are linkers capable of attaching to primary alcohol groups. Examples of neuropharmaceutical agents which can be linked via a cleavable link include AZT, ddI, ddc, adriamycin, amphotericin B, pyrimethamine, valproate, methotrexate, cyclophosphamide, carboplatin and superoxide dimutase. The noncleavable linkers used generally to link proteins to the antibody can also be used to link other neuropharmaceutical agents to the antibody.

The antibody-neuropharmaceutical agent conjugates can be administered orally, by subcutaneous or other injection, intravenously, intramuscularly, parenternally, transdermally, nasally or rectally. The form in which the conjugate is administered (e.g., capsule, tablet, solution, emulsion) will depend at least in part on the route by which it is administered.

A therapeutically effective amount of an antibody-neuropharmaceutical agent conjugate is that amount necessary to significantly reduce or eliminate symptoms associated with a particular neurological disorder. The therapeutically effective amount will be determined on an individual basis and will be based, at least in part, on consideration of the individuals's size, the severity of symptoms to be treated, the result sought, the specific antibody, etc. Thus, the therapeutically effective amount can be determined by one of ordinary skill in the art employing such factors and using no more than routine experimentation.

Although the description above focuses on antibodies, any protein which interacts with the extracellular domain of the transferrin receptor, including the ligand binding site, could potentially serve as a vehicle for the delivery of drugs across the blood-brain barrier. In addition to anti-transferrin receptor antibodies, this would include transferrin, the ligand which binds to the receptor, and any transferrin derivatives which retain receptor-binding activity. In fact, any ligand which binds to the transferrin receptors could potentially be employed.

Figure 8:
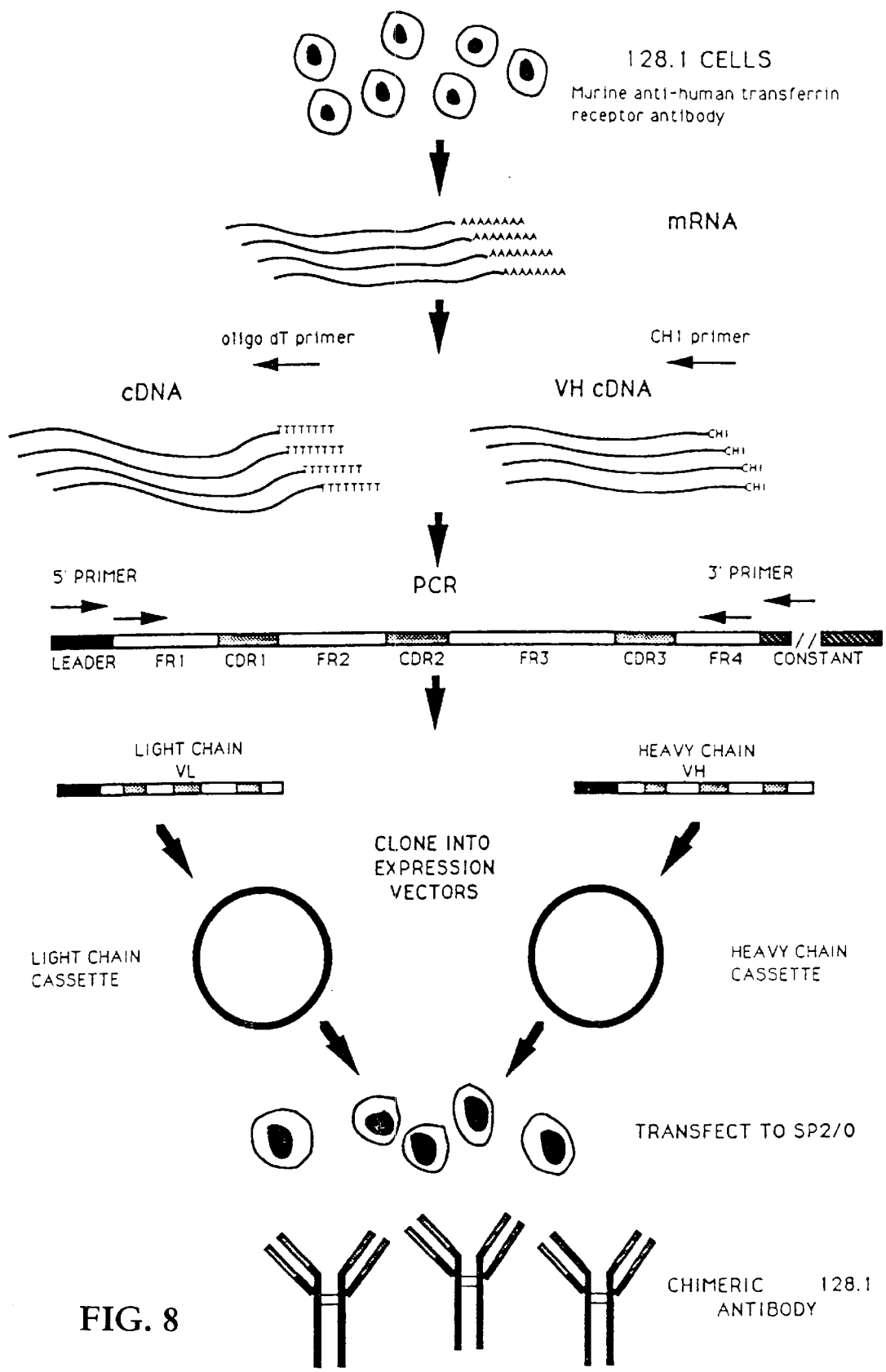
FIG. 8 is a flow diagram of the general strategy for the expression of immunoglobulin variable region genes obtained by PCR.

A procedure for producing chimeric antibodies reactive with a transferrin receptor may be performed as follows: cDNA is synthesized from mRNA purified from a small number of cells producing the antibody of interest. A PCR reaction is performed in order to obtain the antibody heavy and light chain variable regions which are then cloned and sequenced. After a second PCR reaction to modify the ends of these regions to make them compatible with the expression cassettes, they are cloned into novel expression vectors which contain human constant regions, immunoglobulin promoter and enhancers, and selection markers. In these vectors, a murine heavy chain promoter has been provided with restriction sites so that the leader sequences primed and expanded can be directly cloned into a functional promoter. Restriction sites have also been provided for the direct cloning of the 3' end of the variable region into a constant region. In the heavy chain vector, a novel restriction site has been engineered into the CH1domain of the human γ1 heavy chain gene. VH can then be joined at this site to provide a complete heavy chain protein. For VL, a restriction site has been engineered just 3' of the splice site so that the cloned will then splice the kappa to produce a complete κ light chain protein. The final constructs are then transfected into non-producer hybridoma cell lines as SP2/0 or P3.X63.Ag8653 and the supernatants tested for antibody production (FIG. 8).

Further procedures and materials, such as expression cassettes, for producing chimeric antibodies reactive with a transferrin receptor can be found in the patent application: Ser. No. 07/798,696, filed on the same date as the present application. Such teachings of this co-filed application are herein incorporated by reference.

The present invention will be illustrated by the following examples.

EXAMPLE 1

In Vitro Binding of Murine Monoclonal Antibodies to Human Brain Endothelial Cells Two murine monoclonal antibodies, B3/25 and T58/30, described by Trowbridge (U.S. Pat. No. 4,434,156 issued Feb. 28, 1984, and Nature Vol. 294, pp. 171–173 (1981)), the contents of both are hereby incorporated by reference, which recognize the human transferrin receptor were tested for their ability to bind to human brain capillary endothelial cells. Hybridoma cell lines which produce B3/25 and T58/30 antibodies were obtained from the American Type Culture Collection (ATTC) in Rockville, Md., and grown in DMEM medium supplemented with 2.0 mM glutamine, 10.0 mM HEPES (pH 7.2), 100 µM non-essential amino acids and 10% heat-inactivated fetal calf serum. The hybridoma cultures were scaled-up in 225 $cm^2$ T-flasks for the production of milligram quantities of IgG antibody. The hybridoma supernatants were concentrated 50× using vacuum dialysis and applied to a protein-A sepharose column using the BioRad MAPS buffer system. Purified antibody was eluted from the column, dialyzed against 0.1 M sodium phosphate (pH 8.0), concentrated and stored in aliquots at −20° C.

Primary cultures of human brain endothelial cells were grown in flat-bottom 96-well plates until five days post-confluency. The cells were then fixed using 3.0% buffered formalin and the plate blocked with 1.0% bovine serum albumin (BSA) in Dulbecco's phosphate buffered saline (DPBS). Aliquots (100 µl) of the B3/25 or T58/30 antibodies, either in the form of culture supernatants or purified protein, were then added to the wells (antibody concentrations were in the range of 1–50 µg/ml). Antibody which had specifically bound to the fixed cells was detected using a biotin-labeled polyclonal goat-anti-mouse IgG anti-sera followed by a biotinylated horseradish peroxidase (HRP)/avidin mixture (Avidin Biotin Complex technique). Positive wells were determined using a Titertek Multiscan Enzyme Linked Immunosorbent Assay (ELISA) plate reader. The results showed that both antibodies bind to human brain capillary endothelial cells with the T58/30 antibody exhibiting a higher level of binding.

These same antibodies were also tested for binding to human brain capillaries using sections of human brain tissue that were fresh frozen (without fixation), sectioned on a cryostat (section thickness was 5–20 µm), placed on glass slides and fixed in acetone (10 minutes at room temperature). These sections were then stored at −20° C. prior to use.

The slides containing the human brain sections were allowed to come to room temperature prior to use. The sections were then rehydrated in DPBS and incubated in methanol containing 0.3% $H_2O_2$ to block endogenous peroxidate activity. The sections were blocked for fifteen minutes in a solution containing 0.2% non-fat dry milk and 0.2% methylmannopyranoside. B3/25 and T58/30 antibodies, purified as discussed above, were applied to the sections at a concentration of 5–50 µg/ml and incubated at room temperature for one to two hours. Antibody that specifically bound to the tissue was detected using the Avidin-Biotin Complex (ABC) technique as described above for the ELISA assay. Staining of capillaries in the human brain sections was observed with both the B3/25 and T58/30 antibodies. The T58/30 antibody also displayed some binding to the white matter of the brain cortex.

EXAMPLE 2

In-Vitro Binding of Murine Monoclonal Antibody OX-26 to Rat Transferrin Receptor The OX-26 murine antibody, which recognizes the rat transferrin receptor, has been shown in vivo to bind to brain capillary endothelial cells (Jeffries et al., cited supra). The murine hybridoma line which produces the OX-26 murine antibody was obtained and the hybridoma cell line was grown in RPMI 1640 medium supplemented with 2.0 mM glutamine and 10% heat-inactivated fetal calf serum. The OX-26 antibody was purified using the affinity chromatography technique described in Example 1.

The purified antibody was tested in vitro as described for the anti-human transferrin receptor antibodies in Example 1 to determine whether it would bind to brain capillaries in fresh frozen, acetone-fixed rat brain sections. The results showed that the OX-26 anti-transferrin receptor antibody did bind to capillaries in rat brain sections in vitro.

EXAMPLE 3

In-Vivo Binding of OX-26 Murine Monoclonal Antibody to Rat Transferrin Receptor

Dose Range

The rat anti-transferrin receptor antibody OX-26 was tested in vivo by injecting purified antibody (purification as described in Example 1) into female Sprague-Dawley rats (100–150 gm) via the tail vein. Prior to injection, the rats were anesthetized with halothane. The samples, ranging from 2.0 mg to 0.05 mg of antibody/rat were injected into the tail vein in 400 µl aliquots. All doses were tested in duplicate animals. One hour post-injection, the animals were sacrificed and perfused through the heart with DPBS to clear the blood from the organs. Immediately after the perfusion was completed, the brain was removed and quick frozen in liquid nitrogen. The frozen brain was then sectioned (30–50 µm) on a cryostat and the sections placed on glass microscope slides. The brain sections were air dried at room temperature one to two hours before fixation in acetone (10 minutes at room temperature). After this treatment the sections could be stored at −20° C.

The OX-26 antibody was localized in the brain sections using immunohistochemistry as-described above for the in vitro experiments in Example 1. The addition of the primary antibody was unnecessary in that it is present in the brain sections. The results indicated that the OX-26 antibody binds to rat brain capillary endothelial cells and that doses of as little as 50 µg result in detectable levels of antibody in the brain using the methods described herein. Doses above 0.5 µg did not appear to show significantly more antibody binding to the endothelial cells, suggesting that the sites for antibody binding may be saturated. No specific binding to capillary endothelium was detected in the liver, kidney, heart, spleen or lung.

A non-specific antibody of the same subclass as OX-26 (IgG 2a) was also tested in vivo to show that the binding of OX-26 to rat brain endothelial cells that has been observed is specific to the OX-26 antibody. 0.5 mg of the control antibody was injected per rat as described above. The results indicate that the staining pattern observed with the OX-26 antibody is specific to that antibody.

Time Course

After establishing that the OX-26 antibody is detectable in the rat brain capillaries after in vivo administration, the time frame in which this binding occurred was determined. Using 0.5 mg of purified OX-26 antibody as the standard dose, brain sections taken from animals sacrificed 5 minutes, 15 minutes, 1 hour, 2 hours, 4 hours, 8 hours and 24 hours post-injection were examined for the presence of OX-26 antibody. All doses were administered in 400 μl aliquots and each time point was tested in duplicate animals. Samples were injected and the rats were processed at the various times post-injection as described above in the dose range section.

The results showed that the OX-26 antibody can be detected in or on the rat brain capillary endothelial cells as early as five minutes and as late as 24 hours post-injection. At 4 and 8 hours post-injection, the staining pattern of the antibody is very punctate suggesting that the antibody has accumulated in vesicular compartments either in endothelial or perivascular cells.

EXAMPLE 4

The Use of a Conjugate of OX-26 Murine Monoclonal Antibody for Tranferring Horseradish Peroxidase Across the Blood Brain Barrier Horseradish Peroxidase (HRP; 40 kD) was chosen as a compound to be delivered to the brain because it is similar in size to several therapeutic agents and it can be easily detected in the brain using an enzymatic assay. HRP was conjugated to the OX-26 antibody using a non-cleavable periodate linkage and the ability of the antibody to function as a carrier of compounds to the brain was examined. The antibody conjugate was tested in vivo to determine if the antibody could deliver HRP to the brain.

The antibody (10 mg) was first dialyzed overnight against 0.01 M sodium bicarbonate (pH 9.0). The HRP (10 mg) was dissolved in 2.5 μl deionized water, 0.1 M sodium periodate (160 μl) was added and the mixture was incubated for five minutes at room temperature. Ethylene glycol (250 μl) was added to the HRP solution followed by an additional five minute incubation. This solution was then dialyzed overnight against 1.0 mM sodium acetate buffer (pH 4.4). To the dialyzed OX-26 antibody (2.0 μl, 5.08 mg/ml) was added 200 μl of 1.0 M sodium bicarbonate buffer, pH 9.5 and 1.25 μl of the dialyzed HRP solution. This mixture was incubated in the dark for two hours followed by the addition of 100 μl of 10 mg/ml sodium borohydride. The resulting mixture was incubated two additional hours in the dark at 4° C. The protein was precipitated from the solution by the addition of an equal volume of saturated ammonium sulfate and resuspended in a minimal volume of water. Free antibody was removed from the mixture by chromatography on a concanavalin A-sepharose column (a column which binds HRP and the HRP-antibody conjugate and allows the free antibody to pass through). The free HRP was removed by chromatography on a protein A-sepharose column which retains the antibody-HRP conjugate. The final product had an HRP/antibody ratio of 4/1.

A time course experiment identical to that described in Example 3 was performed using the antibody-HRP conjugate. The antibody-HRP conjugate (0.5 mg) was injected in a 400 μl aliquot/rat. The animals were sacrificed at the various times post-injection and the brains processed as described above in Example 3. The antibody HRP conjugate was localized in the brain either by staining for antibody immunohistochemically as described in Example 1 or by directly staining the brain sections for the presence of HRP. To detect HRP, the slides were first allowed to come to room temperature before incubating in methanol for thirty minutes. The brain sections were then washed in DPBS and reacted with 3,3'-diamino benzidine (DAB), the substrate for HRP. The results showed that the OX-26 antibody HRP conjugate binds to rat brain capillary endothelial cells in a manner identical to that of the unconjugated antibody. The punctate staining 4–8 hours after injection which was seen with the antibody alone is also seen with the antibody conjugate, suggesting that the conjugate can also be going into the pericytes on the abluminal side of the blood brain barrier. Taken together, these results indicate that the OX-26 antibody can deliver a protein molecule of at least 40 KD to the brain.

EXAMPLE 5

The In-Vivo Delivery of Adriamycin to the Brain by Murine Monoclonal Antibody OX-26

A non-cleavable linker system similar to that used in Example 4, was used to couple the chemotherapeutic drug adriamycin to the OX-26 antibody. The availability of antibodies that can detect adriamycin as well as the system previously described in Example 1 for detecting the antibody carrier allowed the use of immunohistochemical techniques for monitoring the localization of the antibody carrier as well as the delivery of adriamycin to the brain.

To conjugate adriamycin to the antibody, the drug (10 mg in 0.5 ml DPBS) was oxidized by the addition of 200 μl of 0.1 M sodium periodate. This mixture was incubated for one hour at room temperature in the dark. The reaction was quenched by the addition of 200 μl of ethylene glycol followed by a five minute incubation. The OX-26 antibody (5.0 mg in 0.5 ml of carbonate buffer (pH 9.5)) was added to the oxidized adriamycin and incubated at room temperature for one hour. Sodium borohydride (100 μl of 10 mg/ml) was added and the mixture was incubated for an additional two hours at room temperature. The free adriamycin was separated from the OX-26 antibody-adriamycin conjugate by chromatography on a PD-10 column. The adriamycin/OX-26 antibody ratio within the conjugate was 2/1. for this particular batch of conjugate.

The effectiveness of the OX-26 antibody as a carrier for delivering adriamycin to the brain was determined by administering 0.5 mg of the antibody-adriamycin conjugate in a 400 μl aliquot per rat by injection via the tail vein. One hour post-injection, the rat was sacrificed and the brain processed as described in Example 1. All injections were performed in duplicate. As a control, 400 μg of free adriamycin in a 400 μl aliquot was also injected into a rat. Immunohistochemistry was used to detect both the carrier OX-26 antibody and the adriamycin in the rat brain sections. In the case of adriamycin, polyclonal rabbit anti-adriamycin antisera was applied to the sections followed by a biotinylated goat anti-rabbit IgG antisera. This was then followed by the addition of a biotinylated HRP/avidin mixture and enzymatic detection of HRP.

The results indicate that both the OX-26 antibody and the conjugated adriamycin localized to the rat brain capillary endothelial cells after in vivo administration. There is no evidence that free adriamycin binds to brain capillary endothelial cells or enters the brain.

An adriamycin-OX-26 conjugate coupled via a carbodiimide linkage was also synthesized (drug/antibody ratio of 10/1) and tested in vivo. The results of this experiment were essentially identical to that obtained with the periodate-linked antibody-drug conjugate. In both cases, staining for the antibody carrier was quite strong and was visualized in the capillaries in all areas of the brain. This staining was evenly distributed along the capillaries. Staining for adriamycin was less intense but again was seen in capillaries throughout the brain. Some punctate staining was observed which suggests accumulation in pericytes which lie on the brain side of the blood-brain barrier.

EXAMPLE 6

In Vivo Delivery of Methotrexate to the Brain by Murine Monoclonal Antibody OX-26.

A noncleavable carbodiimide linkage was used to couple methotrexate to the OX-26 murine monoclonal antibody. A system analogous to that described in Example 5 was used to monitor the delivery of both the methotrexate and the carrier antibody to the brain capillary endothelial cells.

Methotrexate was coupled to murine monoclonal antibody OX-26 via its active ester. Briefly, 81 mg (0.178 mM) of methotrexate (Aldrich) was stirred with 21 mg (0.182 mM) of N-hydroxysuccinimide (Aldrich) in 3 ml of dimethylformamide (DMF) at 4° C. Ethyl-3-dimethylaminopropyl-carbodiimide (180 mg;EDC;0.52 mM) was added to this solution and the reaction mixture was stirred overnight. The crude ester was purified from the reaction by-products by flash chromatography over silica gel 60 (Merck) using a solution of 10% methanol in chloroform as an eluant. The purified active ester fractions were pooled and concentrated to dryness. The ester was dissolved in 1 ml of DMF and stored at −20° C. until use. 50 mg (50%) of active ester was recovered as determined by $A_{372}(\epsilon_{372}=7200)$.

A solution of OX-26 containing 2.1 mg (14 nmoles) of antibody in 0.9 ml of 0.1 M phosphate (pH 8.0) was thawed to 4° C. To this stirred antibody solution was added 1.4 μL (140 nmoles) of the active ester prepared as described above. After 16 hours at 4° C., the mixture was chromatographed over Sephadex PD-10 column (Pharmacia) using phosphate buffered saline (PBS) to separate conjugate from free drug. The fractions containing the antibody-methotrexate conjugate were pooled. Antibody and drug concentration were determined spectrophotometrically as described by Endo et al. (*Cancer Research* (1988) 48:3330–3335). The final conjugate contained 7 methotrexates/antibody.

The ability of the OX-26 monoclonal antibody to deliver methotrexate to the rat brain capillary endothelial cells was tested in vivo by injecting 0.2 mg of conjugate (in 400 μl) into each of two rats via the tail vein. The animals were sacrificed one hour post-injection and the brains processed for immunohistochemistry as described in Example 1. To detect methotrexate in the brain, a rabbit antisera raised against methotrexate was used as the primary antibody. A biotinylated goat-anti-rabbit antisera in conjunction with a mixture of biotinylated HRP and avidin was then used to visualize methotrexate in the rat brain. The carrier antibody was detected as described previously.

The results of these experiments indicate that methotrexate in the form of a conjugate with OX-26 does accumulate along or in the capillary endothelial cells of the brain. The staining observed for methotrexate is comparable in intensity to that seen for the carrier. The staining appears to be in all areas of the brain and is evenly distributed along the capillaries.

EXAMPLE 7

Antibody Derivatives

The Fc portion of the OX-26 murine monoclonal antibody was removed to determine whether this would alter its localization to or uptake by the rat brain capillary endothelial cells. F(ab)$_2$ fragments of OX-26 were produced from intact IgG's via digestion with pepsin. A kit available from Pierce Chemical Co. contains the reagents and protocols for cleaving the antibody to obtain the fragments. The F(ab')$_2$ fragment (0.2 mg doses) in 400 μl aliquots were injected into rats via the tail vein. A time course experiment identical to that done with the intact antibody (Example 2) was then performed. F(ab')$_2$ fragment was detected immunohistochemically using a goat anti-mouse F(ab')$_2$ antisera followed by a biotinylated rabbit anti-goat IgG antisera. A biotinylated HRP/avidin mixture was added and the antibody complex was visualized using an HRP enzymatic assay. The results indicate that the F(ab)$_2$ fragment of the OX-26 antibody binds to the capillary endothelial cells of the rat brain.

EXAMPLE 8

Measurement of OX-26 in Brain Tissue

To quantitate the amount of OX-26 which accumulates in the brain, radioactively-labelled antibody was injected into rats via the tail vein. Antibodies were labelled with either $^{14}$C-acetic anhydride or $^{3}$H-succinimidyl proprionate essentially as described in Kummer, U., *Methods in Enzymology*, 121: 670–678 (1986), Mondelaro, R. C., and Rueckert, R. R., *J. of Biological Chemistry*, 250: 1413–1421 (1975), hereby incorporated by reference. For all experiments, the radiolabelled compounds were injected as a 400 μl bolus into the tail vein of female Sprague-Dawley rats (100–125 gms) under Halothane anesthesia and the animals were sacrificed at the appropriate time post-injection using a lethal dose of anesthetic. A $^{3}$H-labelled IgC2a control antibody was co-injected with the $^{14}$C-labelled OX-26 to serve as a control for non-specific radioactivity in the brain due to residual blood. At the appropriate time post-injection, animals were sacrificed and the brains were removed immediately and homogenized in 5 ml of 0.5% sodium dodecysulfate using an Omni-mixer. An aliquot of the homogenate was incubated overnight with 2 ml of Soluene 350 tissue solubilizer prior to liquid scintillation counting. All data were collected as disintegrations per minute (dpm). Blood samples were centrifuged to pellet red blood cells (which do not display significant binding of radiolabelled materials) and the radioactivity in an aliquot of serum determined using liquid scintillation counting.

The amount of antibody associated with the brain was determined at various times post-injection to examine the pharmacokinetics of brain uptake. In addition, the amount of labelled antibody in the blood was measured so that the rate of clearance from the bloodstream could be determined. This information was also used to calculate the amount of radioactivity in the brain due to blood contamination, which was then subtracted from the total to give the amount of antibody that is specifically associated with the brain.

A peak level of $^{14}$C-labelled OX-26 corresponding to approximately 0.9% of the injected dose was reached in the brain between 1 and 4 hours post-injection as illustrated in FIG. 1 (with the values shown as means plus or minus standard error of measurement (SEM) and N=3 rats per time point). The amount of radioactivity associated with the brain decreased steadily from 4 to 48 hours post-injection, at which point it leveled off at approximately 0.3% of the injected dose. The accumulation of OX-26 in the brain was significantly reduced by the addition of unlabelled monoclonal antibody (0.5 or 2.0 mg in the bolus injection). As an additional control, a $^{3}$H-IgG2a control antibody was co-injected with the $^{14}$C-OX-26. The control antibody did not accumulate in the brain and represented the blood contamination of the brain.

In contrast to the levels in the brain, the blood level of OX-26 dropped quite dramatically immediately after injection such that by 1 hour post-injection, the percent of injected dose in 55 μl of blood (the volume of blood associated with the brain) was approximately 0.16% as illustrated in FIG. 1. This corresponds to a value of approximately 20% of the injected dose in the total blood volume of the rat. Extraction of total IgG from serum followed by polyacrylamide gel electrophoresis (PAGE) and autoradiography did not reveal detectable levels of OX-26 degradation indicating that the antibody remains intact in the blood as long as 48 hours after injection.

EXAMPLE 9

Distribution of OX-26 in Brain Parenchyma and Capillaries

To demonstrate that anti-transferrin receptor antibody accumulates in the brain parenchyma, homogenates of brains taken from animals injected with labelled OX-26 were depleted of capillaries by centrifugation through dextran to yield a brain tissue supernatant and a capillary pellet. Capillary depletion experiments followed the procedure of Triguero, et al., *J. of Neurochemistry*, 54: 1882–1888 (1990), hereby incorporated by reference. As for the brain uptake experiments of Example 8, the radiolabelled compounds were injected as a 400 μl bolus into the tail vein of females Sprague-Dawley rats (100–125 gm) under Halothane anesthesia and the animals were sacrificed at the appropriate time post-injection using a lethal dose of anesthetic. A $^3$H-labelled IgG 2a control antibody was co-injected with the $^{14}$C-labelled OX-26 to serve as a control for non-specific radioactivity in the brain due to residual blood. After sacrifice, the brains were removed and kept on ice. After an initial mincing, the brains were homogenized by hand (8–10 strokes) in 3.5 ml of ice cold physiologic buffer (100 mM NaCl, 4.7 mM KCl, 2.5 mM CaCl$_2$, 1.2 mM KH$_2$PO$_4$, 1.2 mM MgSO$_4$, 14.5 mM HEPES, 10 mM D-glucose, pH 7.4). Four ml of 26% dextran solution in buffer was added and homogenization was continued (3 strokes). After removing an aliquot of the homogenate, the remainder was spun at 7200 rpm in a swinging bucket rotor. The resulting supernatant was carefully removed from the capillary pellet. The entire capillary pellet and aliquots of of the homogenate and supernatant were incubated overnight with 2 ml of Soluene 350 prior to liquid scintillation counting. This method removes greater than 90% of the vasculature from the brain homogenate (Triguero et al., cited supra).

Figure 2:
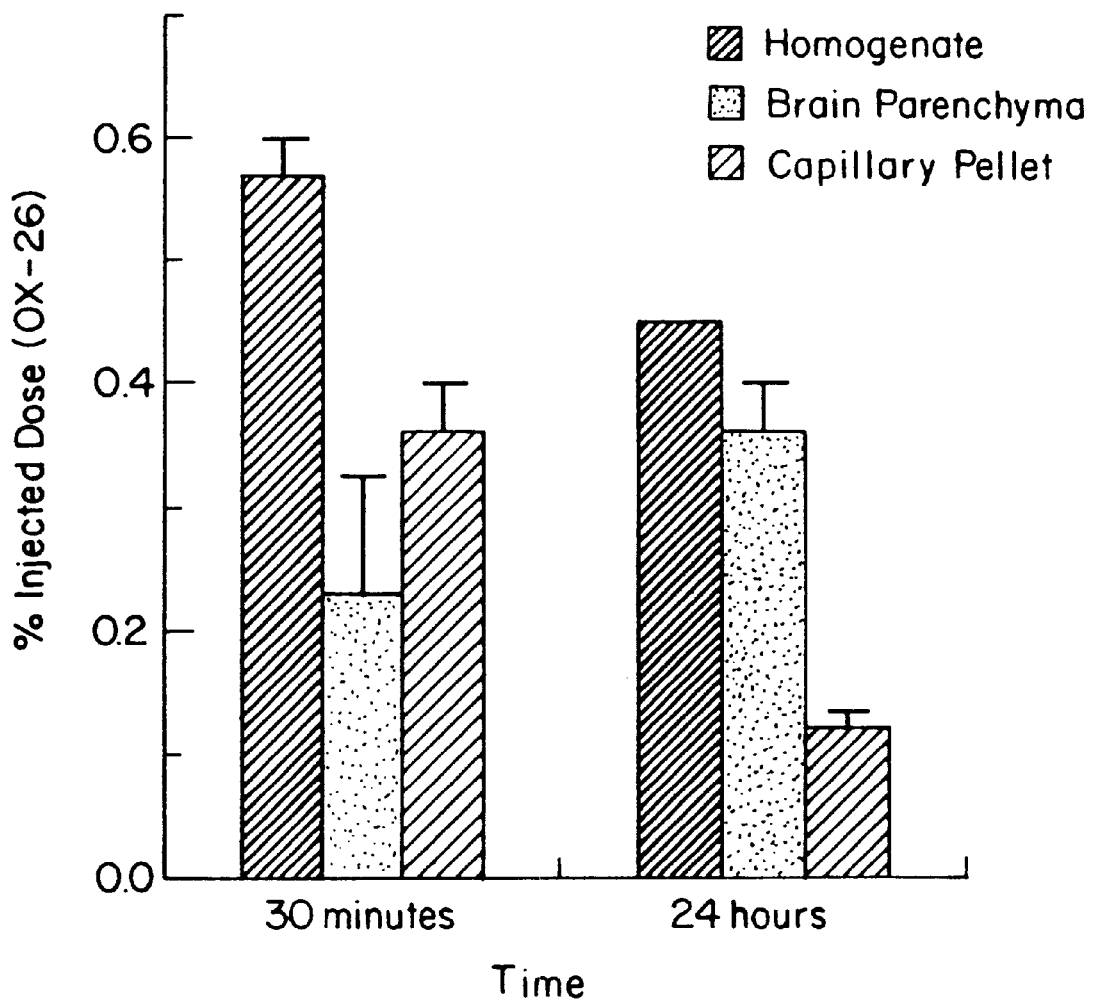
FIG. 2 is a histogram illustrating time dependent changes in the disposition of radiolabelled OX-26 between brain parenchyma and vasculature.

A comparison of the relative amounts of radioactivity in the different brain fractions as a function of time indicates whether transcytosis of the labelled antibody has occurred. The amount of OX-26 in total brain homogenate, the brain parenchyma fraction and the brain capillary fraction at an early time (30 minutes) and a later time (24 hours) post-injection is illustrated in FIG. 2. The values in FIG. 2 are shown as means±SEM with N=3 rats per time point. At the 30 minute time point, more of the radiolabelled antibody is associated with the capillary fraction than with the brain parenchyma fraction (0.36% of the injected dose (%ID) and 0.23% ID, respectively). By 24 hours post-injection, the distribution is reversed and the majority of the radioactivity (0.36% ID) is in the parenchymal fraction as compared to the capillary fraction (0.12% ID). The redistribution of the radiolabelled OX-26 from the capillary fraction to the parenchyma fraction is consistent with the time dependent migration of the anti-transferrin receptor antibody across the blood-brain barrier.

EXAMPLE 10

Figure 3:
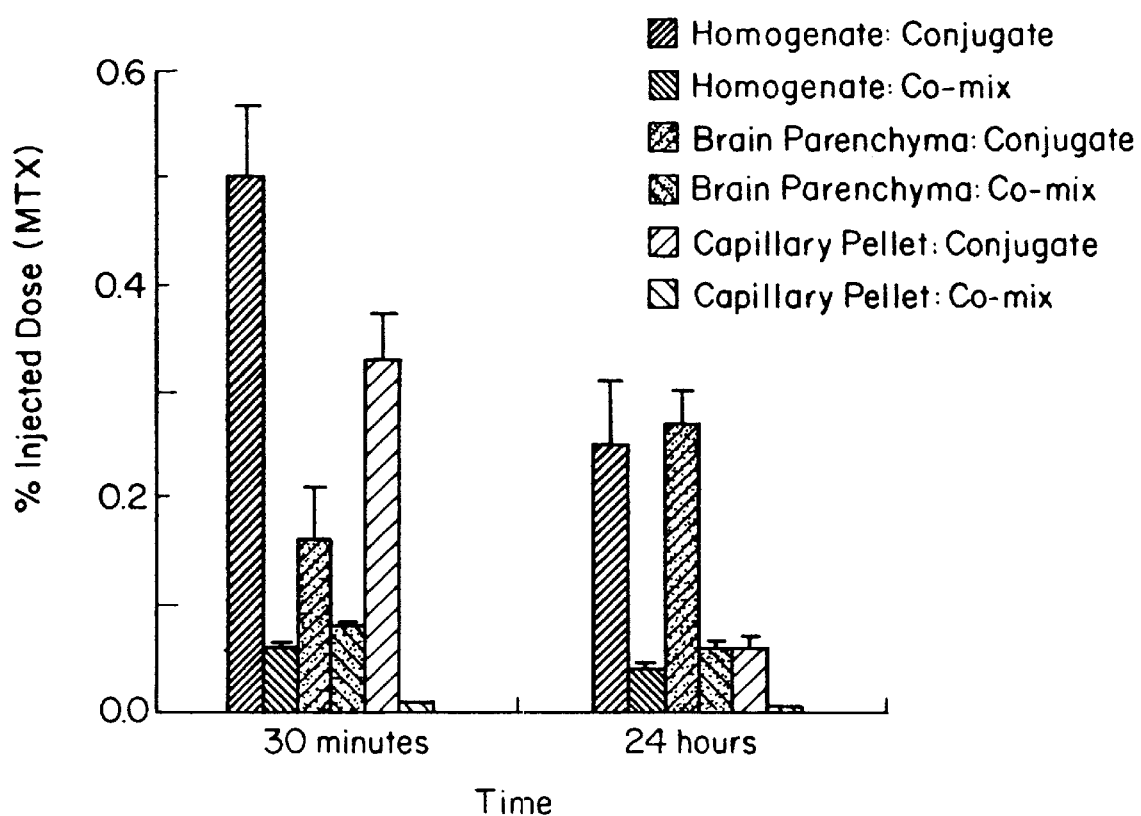
FIG. 3 is a histogram illustrating the enhanced delivery of methotrexate across the blood-brain barrier when administered as a conjugate with OX-26.

Distribution of an OX-26-methotrexate Conjugate in Brain Parenchyma and Capillaries Capillary depletion studies following the procedures described in Example 9 were performed with an OX-26-methotrexate (MTX) conjugate linked via a gamma-hydrazid as described in Kralovec, et al., *J. of Medicinal Chem.*, 32: 2426–2431 (1989), hereby incorporated by reference, in which the MTX moiety was labelled with $^3$H. As with unconjugated antibody, the amount of label in the capillary fraction at 30 minutes post-injection is greater than the parenchyma fraction (approximately 2-fold as illustrated in FIG. 3, with the data expressed as means±SEM and N=3 rats per time point). This distribution changes over time such that by 24 hours post-injection, approximately 4.5-fold more of the labelled MTX is in the brain parenchyma than in the capillaries. These results are consistent to those obtained with unconjugated antibody and, again, suggest that these compounds cross the blood-brain barrier.

To ensure that these results were not due to contaminating amounts of free $^3$H-MTX or $^3$H-MTX that had been cleaved from the conjugate after injection, a co-mix of labelled drug and antibody was injected into rats and a capillary depletion experiment performed. The amount of $^3$H-MTX in the different brain fraction is significantly lower for the co-mix as compared to the conjugate (as much as 47 fold in the case of the capillary fraction at 30 minutes post-injection as illustrated in FIG. 3). The $^3$H-MTX and the co-mix also does not show the change in distribution of the label between the different brain fractions over time as was seen with the antibody-MTX conjugate or antibody alone. These results demonstrate that delivery of $^3$H-MTX across the blood-brain barrier to the brain parenchyma is greatly enhanced by the conjugation of the drug to the anti-transferrin receptor antibody OX-26.

EXAMPLE 11

Distribution of OX-26-AZT in Brain Parenchyma and Capillaries

Capillary depletion studies following the procedures of Example 9 were performed with an OX-26-AZT conjugate using a pH-sensitive succinate linker. These studies employed a dual-labelled conjugate in which the AZT was $^{14}$C-labelled and the antibody carrier was $^3$H-labelled. The use of such a conjugate allowed independent monitoring of the disposition of both the antibody and AZT within the brain.

The linker was synthesized as follows. Succinic anhydride was used to acylate the AZT by reacting equimolar amounts of these two compounds for 3 hours at room temperature under argon in the presence of dimethylaminopyridine and sodium bisulfate in freshly distilled pyridine. The product was isolated by chromatography on a DEAE sephadex A50 column run with a triethylammonium bicarbonate buffer. The succinate derivative of AZT was activated at the carboxyl group as the NHS ester by reaction with equimolar amounts of N-hydroxysuccinimide and dicyclohexylcarbodiimide (DCC) in freshly distilled THF at 4° C. for 2 hours. The product was purified by flash charomatography on silica gel. The resulting NHS-ester of AZT-succinate was used to acylate amine groups on OX-26, resulting in an AZT-OX-26 conjugate. A 15-fold molar excess of AZT-NHS ester was reacted with OX-26 in HEPES buffer overnight at 4° C. The antibody-drug conjugate was isolated from free drug on a PD-10 column. The molar ratio of drug to antibody was 7:1. These studies employed a dual-labelled conjugate in which the AZT was $^{14}C$-labelled and the antibody carrier was $^3H$-labelled.

Figure 4A:
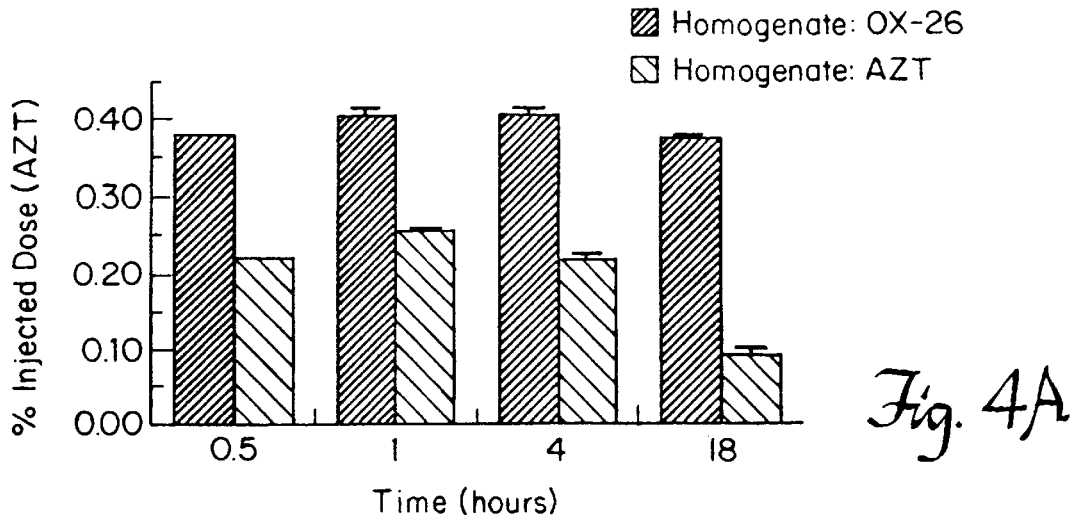
FIGS. 4A–4C is a set of histograms illustrating the distribution in the brain of both the antibody and AZT components of an OX-26-AZT conjugate. Panel A shows the distribution of components in the brain homogenate; panel B shows the distribution of components in the brain parenchyma fraction; and panel C shows the distribution of components in the capillary pellet.
Figure 4B:
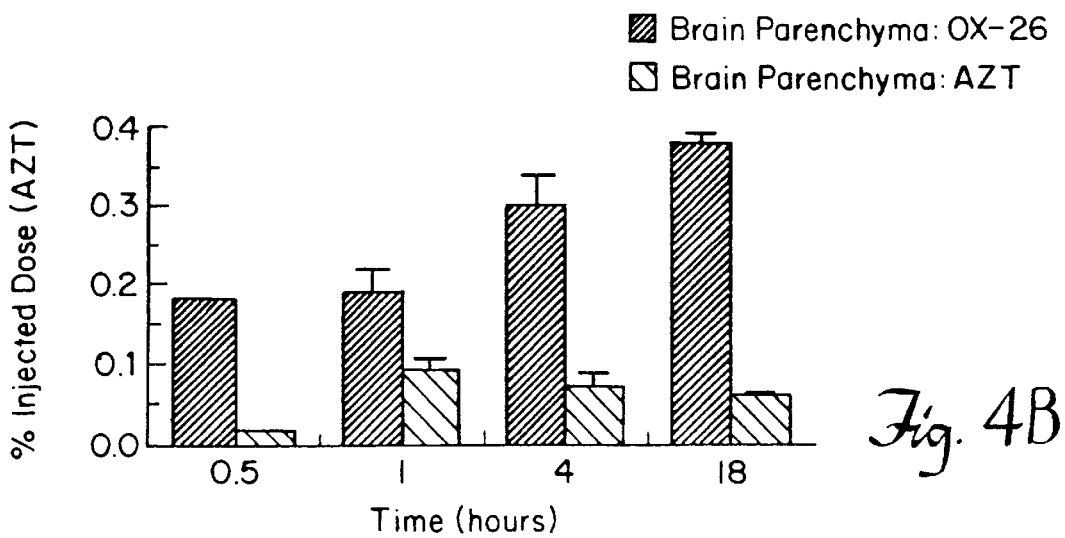
Figure 4C:
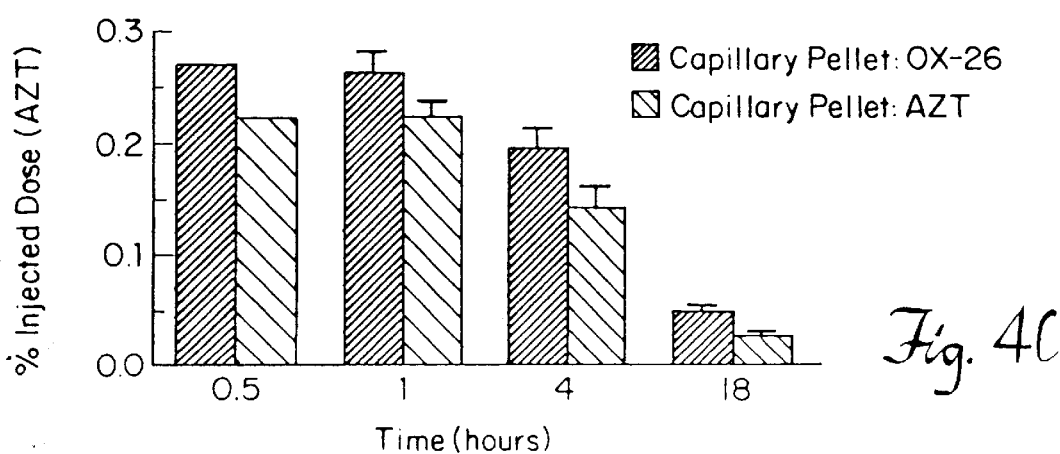

Similar levels of OX-26 and AZT are seen in the capillary fraction of the brain and these levels decrease with time, suggesting that the materials are not being retained by the capillary endothelial cells as illustrated in FIG. 4c. As the levels of OX-26 in the capillary fraction decrease, the levels in the parenchyma fraction increase, indicating that the antibody is migrating from the capillaries to the parenchyma in a time-dependent manner as illustrated in FIG. 4b. In contrast, the levels of AZT in the brain parenchyma do not rise significantly, suggesting that the majority of the drug is released in the endothelial cells and is not transported across the blood-brain barrier. The levels of OX-26 and AZT remained similar in unfractionated homogenates over time as illustrated in FIG. 4a. The data in FIG. 4 are expressed as means±SEM with N=3 rats per time point. These results indicate that the linker is cleaved within the endothelial cells and may represent a method for delivering compounds to those cells.

EXAMPLE 12

Figure 5:
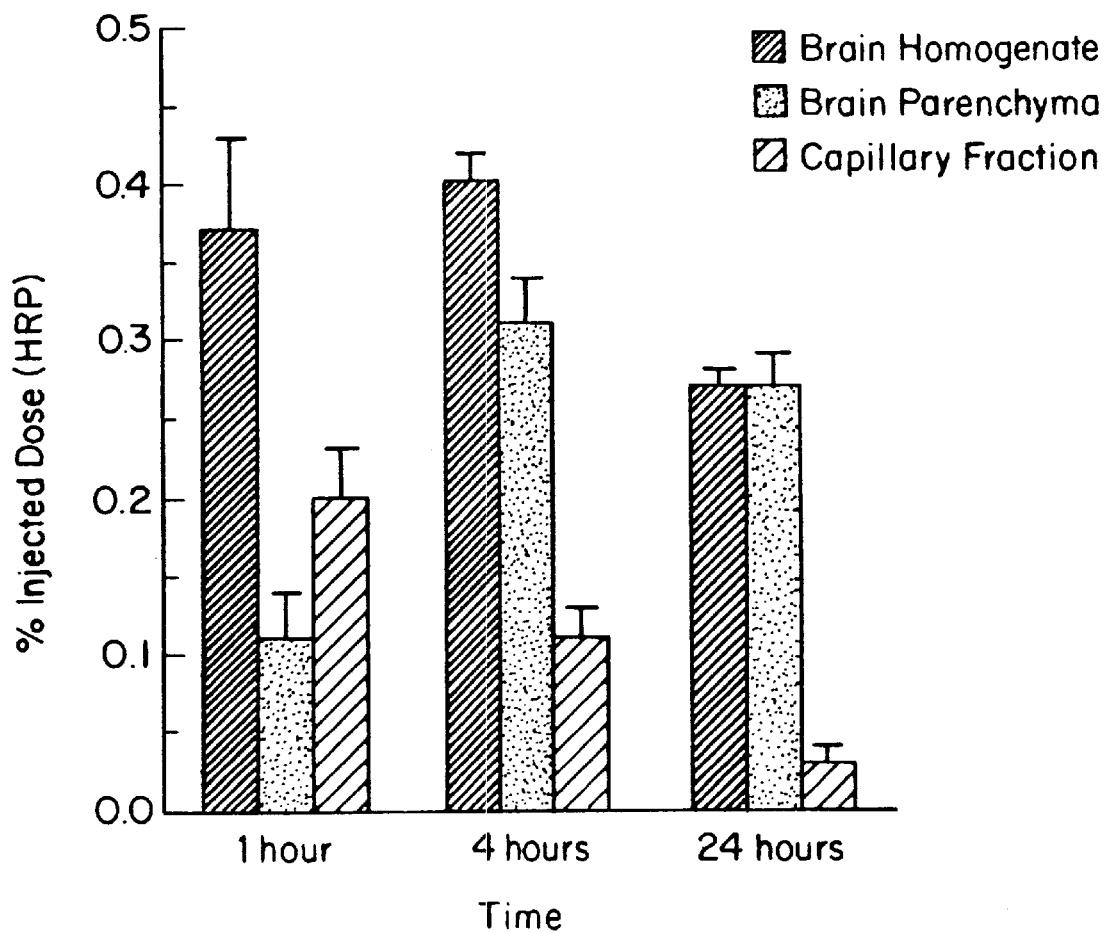
FIG. 5 is a histogram illustrating the experimental results of delivery of a protein, horseradish peroxidase, across the blood-brain barrier in rat brains in the form of a conjugate with OX-26.

Distribution of OX-26-Horseradish Peroxidase (HRP) in Brain Perenchyma and Capillaries Capillary depletion studies following the procedures described for OX-26 in Example 9 were performed with a $^3H$-labelled OX-26-HRP conjugate that was prepared using a non-cleavable periodate linkage as described in Example 4. The tritium label was distributed between the antibody and the HRP portion of the conjugate. At 1 hour post-injection, the majority of the radioactivity associated with the brain is in the capillary fraction as illustrated in FIG. 5. The data in FIG. 5 are expressed as means±SEM with N=3 rats per time point. By 4 hours post-injection, the distribution of radioactivity associated with the brain changed such that the majority is in the fraction which represents the brain parenchyma. At 24 hours post-injection, essentially all of the $^3H$-labelled OX-26-HRP conjugate is in the parenchyma fraction of the brain indicating that the material has crossed the blood-brain barrier. Similar results were obtained in experiments in which only the HRP portion of the conjugate was radiolabelled.

The percent of injected dose of the OX-26-HRP conjugate that reaches the brain is somewhat lower than that for antibody alone or the OX-26-HRP conjugate. This is most likely due to the presence of 2 to 3 40 kD HRP molecules attached to each carrier and that these "passenger" molecules are randomly attached to the carrier. Due to this, many of the HRP passengers may be attached to the antibody in such a way as to interfere with antigen recognition. This problem can be alleviated by directing the attachment of the passenger to regions of the carrier removed from critical functional domains.

EXAMPLE 13

Distribution of OX-26-CD4 in Brain Parenchyma and Capillaries

A soluble form of CD4, consisting of amino acids 1–368, was conjugated to OX-26 using a linkage that directed the attachment of the CD4 to the carbohydrate groups located in the Fc portion of the antibody. By directing the site of attachment in this way, the chance that the passenger molecules will interfere with antibody-antigen recongition is lessened. The linkage between the proteins was achieved by first introducing a sulfhydryl group onto CD4 using SATA (N-Succinimidyl S-acetylthioacetate), a commerically available compound. A hydrizid derivative of SDPD, another commercial cross-linking agent, was attached to OX-26 via carbohydrate groups on the antibody. Reaction of the two modified proteins gives rise to a disulfide-linked conjugate.

More specificallyk the linkage between the proteins was achieved by first introducing a sulfhydryl group onto CD4 using N-succinimidyl S-acetylthioacetate (SATA), a commercially available compound. A 4-fold molar excess of SATA was added to 5 mg of CD4 in 0.1 M sodium phosphate buffer containing 3 mM EDTA (pH 7.5). This mixture was reacted at room temperature in the dark for 30 minutes. Unreacted starting materials were removed by passage over a PD-10 column. A hydrizid derivative of SPDP, another commercially available cross-linking agent, was attached to OX-26 via carbohydrate groups on the antibody. Ten milligrams of OX-26 in 2.0 ml of 0.1 M sodium acetate, 0.15 M sodium chloride (pH 5.0) was reacted with a 1000-fold molar excess of sodium periodate for 1 hour at 4° C. in the dark. Unreacted starting materials were removed by passage over a PD-10 column. The oxidized antibody was reacted with a 30-fold molar excess of hydrazido-SPDP overnight at 4° C. with stirring. Reaction of the two modified proteins gives rise to a disulfide-linked conjugate. One tenth volume of 0.5 M hydroxylamine was added to the thioacetylated CD4 (CD4-DATA) and derivatized antibody was then added such that the ratio of CD4 to antibody was 7.5:1. This mixture was reacted at room temperature in the dark for 2 hours. conjugate was purified by running the reaction mixture over a protein A column followed by a CD4 affinity column.

Figure 6:
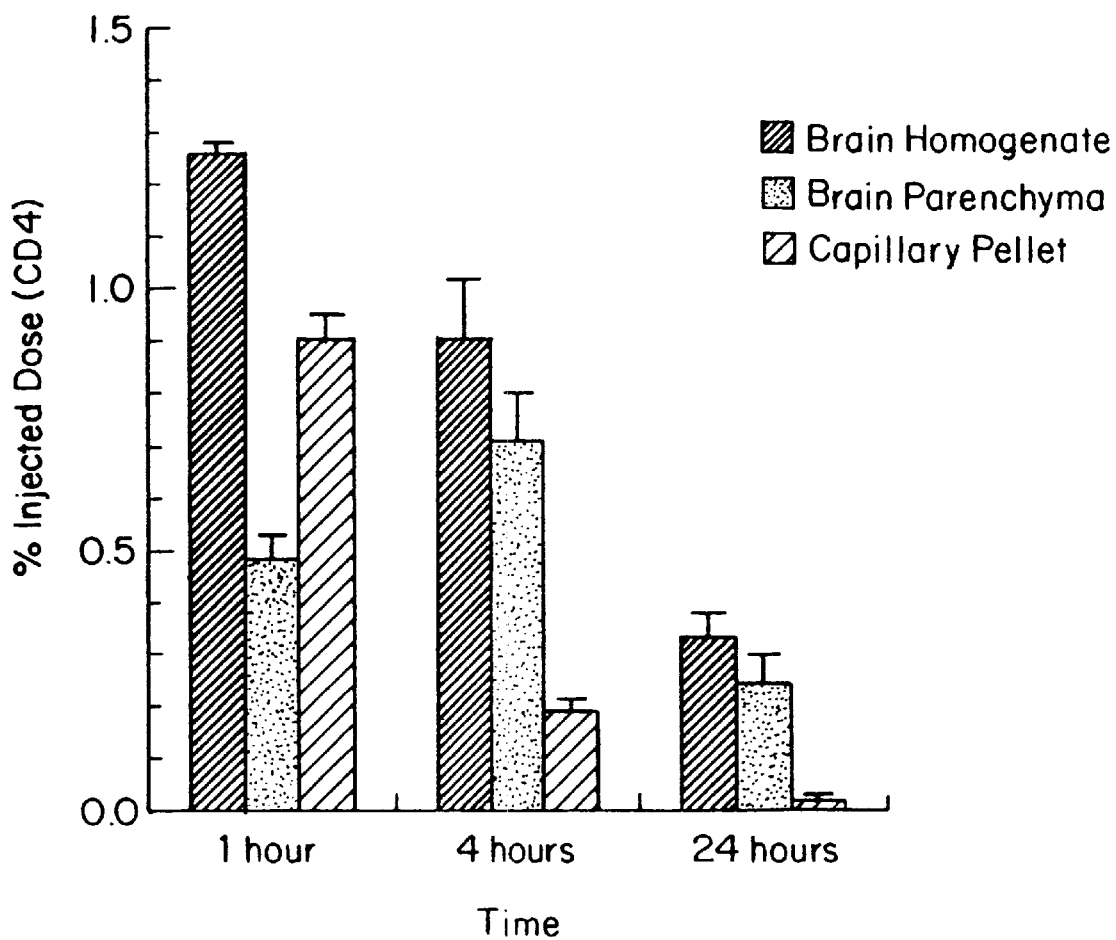
FIG. 6 is a histogram illustrating the experimental results of delivering soluble CD4 to rat brain parenchyma using CD4 in the form of a conjugate with OX-26.

Capillary depletion experiments following the procedures described in Example 9 with OX-26 were performed with an OX-26-CD4 conjugate in which only the CD4 portion was $^3H$-labelled. Time dependent changes in the distribution of the labelled conjugate between the capillary and parenchyma fractions of the brain which are consistent with transcytosis across the blood-brain barrier were observed as illustrated in FIG. 6. The data in FIG. 6 are expressed as means±SEM with N=3 rats per time point.

EXAMPLE 14

Biodistribution and Brain Uptake of Anti-Human Transferrin Receptor Antibodies in Cynomolgous Monkeys A collection of 32 murine monoclonal antibodies which recognize various epitopes on the human transferrin receptor were examined for reactivity with brain capillary endothelial cells in sections from human, monkey (cynomolgous), rat and rabbit brain samples by the immunohistochemical methods described in Example 1. These antibodies were obtained from Dr. Ian Trowbridge of the Salk Institute, LaJolla, Calif. All 32 antibodies displayed some reactivity with human brain endothelial cells. Two antibodies reacted very weakly with rabbit brain capillaries and none reacted with rat. While 21 of the antibodies reacted with monkey brain capillaries, only 2 displayed strong reactivity comparable to that seen with human brain capillaries. These 2 antibodies are herewithin referred to as 128.1 and Z35.2.

Figure 7:
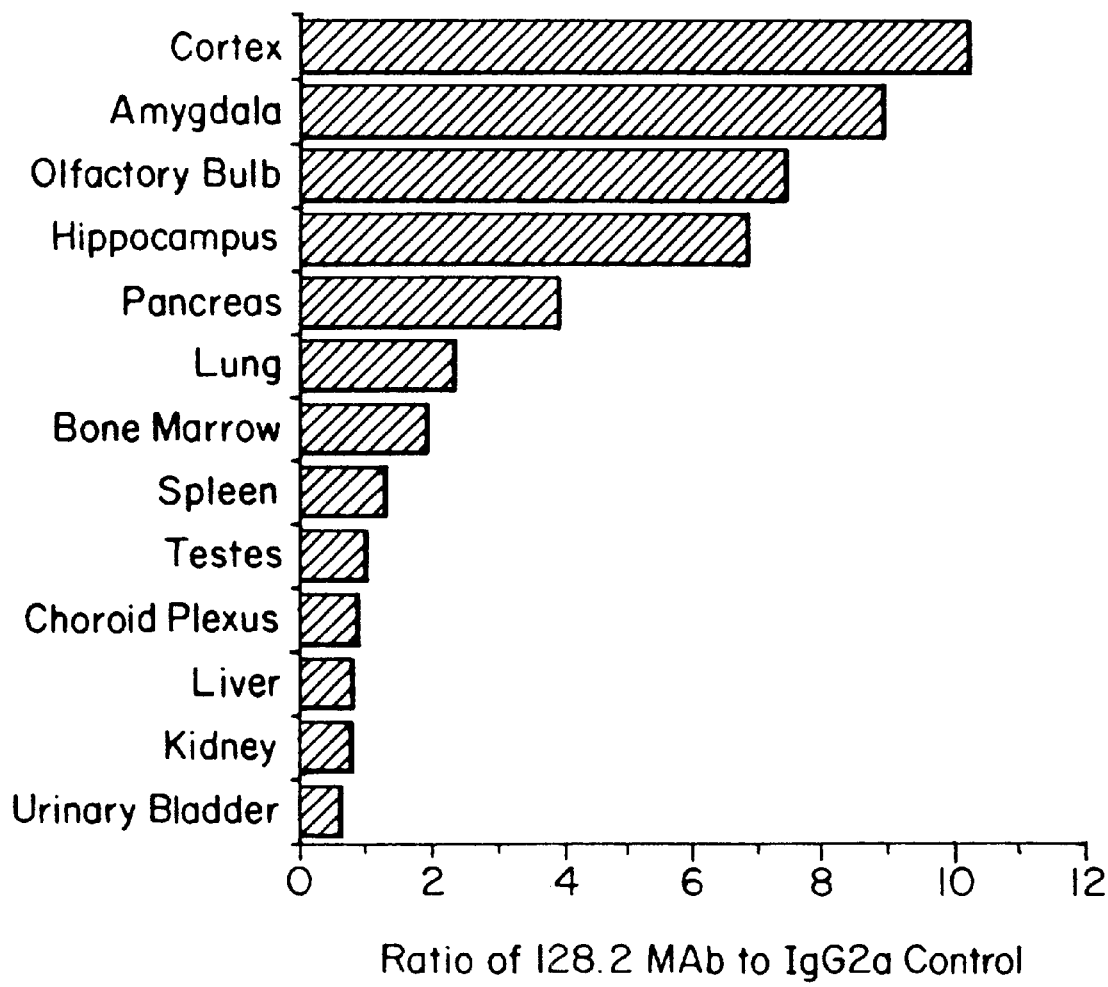
FIG. 7 is a histogram illustrating the biodistribution of antibody 128.1 and control IgG in a cynomolgous monkey.

These antibodies were used to determine the tissue distribution and blood clearance of the $^{14}C$-labelled anti-human transferrin receptor antibodies 128.1 and Z35.2 in 2 male cynomolgous monkeys. 128.1 or Z35.2 was administered concurrently with a $^3$H-labelled control IgG to one of the monkeys with an intravenous catheter. During the course of the study, blood samples were collected to determine the clearance of the antibodies from the circulation. At 24 hours post-injection, the animals were euthanized and selected organs and representative tissues were collected for the determination of isotope distribution and clearance by combustion. In addition, samples from different regions of the brain were processed as described for the capillary depletion experiments in Example 9 to determine whether the antibodies had crossed the blood-brain barrier. The results of the capillary depletion experiments were performed on samples from the cortex, frontal cortex, cerebellum and striatum. All samples had greater than 90% of the 128.1 or Z35.2 in the brain parenchyma, suggesting that the antibodies crossed the blood-brain barrier. The levels of the control antibody in the same samples were from 5 to 10-fold lower. Using the average brain homogenate value for dpm/G tissue, the percent injected dose of 128.1 in the whole brain is approximately 0.2–0.3%. This compares to a value of 0.3–0.5% for OX-26 in the rat at 24 hours post-injection. A comparison of the ratios of 128.1 to the control antibody for various organs is illustrated in FIG. 7. Similar results were obtained for Z35.2. These results suggest that 128.1 is preferentially taken up by the brain as compared to control antibody. For the majority of organs and tissues tested, the ratio of 128.1 to control is less than 2.

EXAMPLE 15

Cloning and Expressing of ALK 128.1: An Anti-Human Transferrin Receptor Chimeric Antibody

RNA EXTRACTION

RNA was extracted following the single step guanidinium/phenol method (P.Chomczynski and S. Sacchi. 1987, Anal. Bioch. 162:156–259). All the instruments and containers used were previously autoclaved and rinsed with diethyl pyrocarbonate (depc) treated water to avoid degradation due to RNAases. Several samples each containing 5×10$^5$ cells from the 128.1 hybridoma which secretes a murine anti human transferrin receptor monoclonal antibody, were washed twice with PBS. The pellets were quick frozen in liquid nitrogen and either kept at –70° C. for later use or extracted immediately.

For the extraction, in a RNase free microfuge tube, ½ml of solution D (Solution D:36 μl 2-mercaptoethanol per 5 ml of 1X GITC [1×GITC: 250 g guanidinium thiocyanate, 17.6 ml 0.75 M Na citrate pH7, 26.4 ml 10% sarcosyl, 293 ml dH20]), 50 μl of 2M Na acetate pH 4, 0.5 ml phenol (dH20 equilibrated) and 100 μl of chloroform:isoamylalcohol (49:1) were added to the cell pellet mixing by inversion after each addition. The extraction was left on ice for 15 minutes and centrifuged at 13000g for 20 min at 4° C.

The upper aqueous phase containing the RNA was removed to a new tube and precipitated with 2 volumes of cold absolute ethanol for 2 hr. at –70° C. After two 70% depc-ethanol washes the RNA pellet was dried briefly and resuspended in dH20 0.5% SDS.

First Strand cDNA Synthesis

Total RNA from 5×10$^5$ cells was resuspended in 18 μl of 0.5% SDS. 9 μl of RNA were annealed with 2 μof 3' primer (1 mg/ml) at 60° C. for 10 minutes. For light chain V region amplifications, an oligo dT primer was used, whereas for the amplification of heavy chain V regions a γ CH1 antisense primer, containing an XbaI site (underlined in Table 1), with degeneracies introduced so that it will prime all isotypes of murine heavy chains except γ3 was used (Table 1).

After annealing, the samples were cooled on ice, 4 μl of first strand cDNA buffer (50 mM Tris pH 8.3, 50 mM KCl, 10 mM MgCl$_2$, 1 mM DTT, 1 mM EDTA, 0.5 mM spermidine), 1 μl of RNAse inhibitor (Promega), 2 μl of 10 mM dNTP's and 2 μl of prediluted 1:10 Promega AMV Reverse Transcriptase were added and the reaction incubated for 1 hour at 42° C. The cDNA was kept at –20° C. until used for PCR.

TABLE 1

PRIMERS FOR cDNA SYNTHESIS

PRIMER FOR SYNTHESIS OF LIGHT CHAIN V REGION cDNA

OLIGO dT.R1.XBA.H3
5' GCCGGAATTCTAGAAGC(T)$_{17}$ (SEQ ID NO: 1)

PRIMER FOR SYNTHESIS OF HEAVY CHAIN V REGION cDNA

| MγC.CHI AS | (Degeneracies at a single position are shown in parenthesis.) |
|---|---|

5' AGG TCTAGA A(CT)C TCC ACA CAC AGG (AG) (AG)C CAG TGG ATA GAC (SEQ ID NO: 2)

PRIMERS AND PCR REACTION:

A first PCR reaction was performed in order to amplify the variable regions and determine their sequence. To achieve this the PCR primers were designed to hybridize to the leader sequence (5' primer) and to the constant region immediately downstream of the V-J region (3' primer).

The oligonucleotides were synthesized in an Applied Biosystem 391 DNA Synthesizer, eluted without purification, diluted to 20 μM and kept at 4° C.

All primers were designed with a restriction site with three additional bases upstream to protect the site and facilitate enzyme digestion. The sites were chosen to make possible the cloning of the PCR product into a subcloning vector and into the final expression cassett vectors.

For the leader region, the primers contain a ribosome recognition site (Kozak's sequence CACC; Kozak M. 1981, Nucl. Acid. Res., 9:20, 5233–5252) 5' of the start codon, and an EcoR V site (underlined in Tables 2 and 3) protected by three 5' G's. A set of 4 universal 5' sense primers was used simultaneously in the light variable region amplification, and a set of 3 universal 5' sense primers in the case of heavy variable regions (Coloma et al. 1991, Biotechniques 11,2, 152–156). An equimolar amount of each primer was used in the PCR reaction. These primers contain degeneracies in order to hybridize with all the families of murine leader sequences reported in Kabat's database. (Kabat E. 1987, Sequences of Proteins of Immunological Interest, NIH). The 3' primers were designed in the constant region 20 bases downstream of the V-J region and contain an XbaI site (underlined in Tables 2 and 3) for subcloning purposes (Tables 2 and 3).

TABLE 2

PRIMERS FOR MURINE HEAVY CHAIN VARIABLE REGION AMPLIFICATION.
(Degeneracies at a single position are shown in parenthesis.)

LEADER REGION PRIMERS (5' SENSE)

MHALT1.RV    #085
Leader Murine Heavy IgV
5' GGG GATATC CACC ATG G(AG)A TG(CG) AGC TG(TG) GT(CA) AT(CG) CTC TT (SEQ ID NO: 3)
MHALT2.RV    #086
Leader Murine Heavy IgV

TABLE 2-continued

PRIMERS FOR MURINE HEAVY CHAIN VARIABLE
REGION AMPLIFICATION.
(Degeneracies at a single position are shown
in parenthesis.)

5' GGG <u>GATATC</u> CACC ATG (AG)AC TTC GGG (TC)TG
AGC T(TG)G GTT TT (SEQ ID NO: 4
MHALT3.RV    #087
Leader Murine Heavy IgV
5' GGG GATATC CACC ATG GCT GTC TTG GGG CTG
CTC TTC T (SEQ ID NO: 5)
    CONSTANT REGION PRIMER (3' ANTISENSE)
Primer designed to hybridize at amino acids 130–120 in
CH1 of Igγ. This primer is identical to the primer used
for heavy chain first strand cDNA synthesis.

MCγ CH1AS.XBA    #097
CH1 antisense primer for murine Igγ, except Igγ3
5' AGG <u>TCTAGA</u> A(CT)C TCC ACA CAC AGG (AG)(AG)C
CAG TGG ATA GAC (SEQ ID NO: 6)

TABLE 3

PRIMERS FOR MURINE LIGHT CHAIN VARIABLE
REGION AMPLIFICATION. (Degeneracies at a single
positino are shown in parenthesis.)

LEADER REGION PRIMERS (5' SENSE)

MLALT1.RV    #088
Leader Murine Light IgV
5' GGG <u>GATATC</u> CAC ATG GAG ACA GAC ACA CTC CTG
CTA T (SEQ ID NO: 7)
MLALT2.RV    #089
Leader Murine Light IgV
5' GGG <u>GATATC</u> CACC ATG GAT TTT CAA GTG CAG
ATT TTC AG (SEQ ID NO: 8)
MLALT3.RV    #090
Leader Murine Light IgV
5' GGG <u>GATATC</u> CACC ATG GAG (TA)CA CA (GT)
(TA)CT CAG GTC TTT (GA)TA (SEQ ID NO: 9)
MLALT4.RV    #091
Leader Murine Light IgV
5' GGG <u>GATATC</u> CACC ATG (GT)CC CC(AT) (GA)CT CAG
(CT)T(CT) CT(TG) GT (SEQ ID NO: 10)
    CONSTANT REGION PRIMER (3' ANTISENSE)
Primer designed to hybridize to amino acids 122–116
of kappa constant region.

MCκ AS.XBA    #096
Constant Murine Light
5' GCG <u>TCTAGA</u> ACT GGA TGG TGG GAA GAT GGA
(SEQ ID NO: 11)

Figure 9:
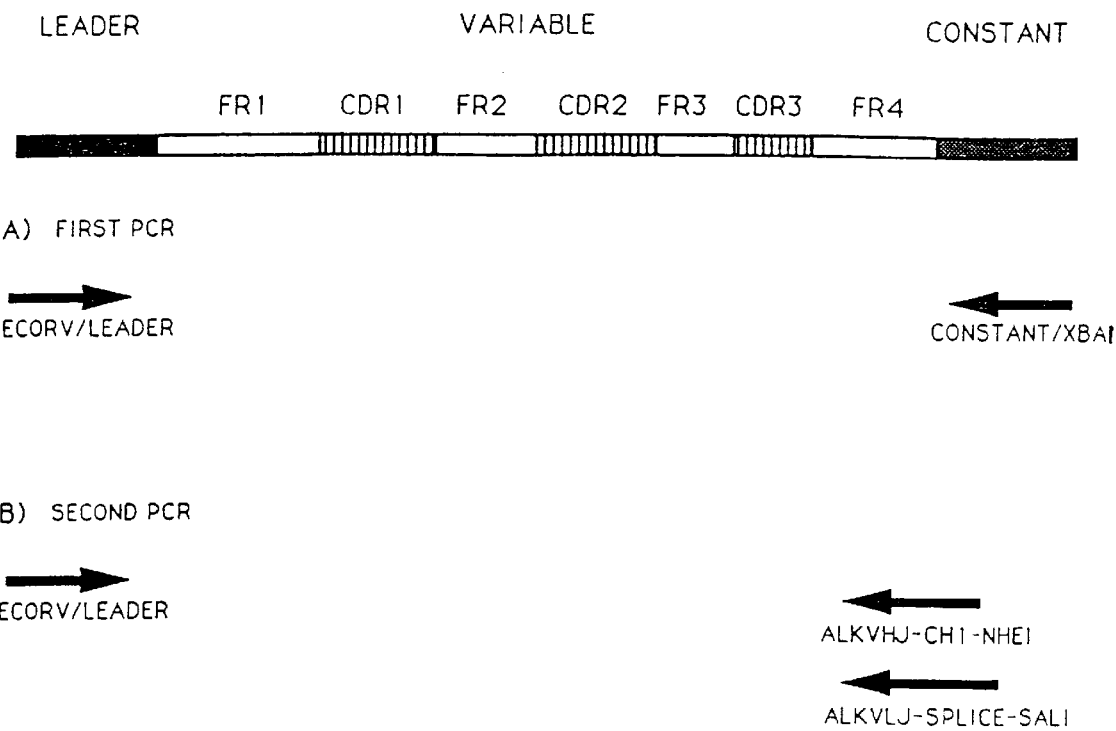
FIG. 9 illustrates the primers used for variable region amplification, both for first cloning and sequencing the V region and then for cloning into the final expression vector.

The primers for the second PCR reaction (Table 4) have the actual sequence of the V-J regions, determined by sequencing of the subcloned products (FIG. 9). These primers have a Nhe I site in the case of the VH primer and Sal I for the VL primer, which permits the cloning into the expression vectors. (The restriction enzyme sites are underlined in Table 4). The Nhe I site in the 3' primer for the VH allows the direct ligation of the VH-J region to the first two amino acids of the CH1 of the γ1 constant region. The VL 3' primer has a donor splice sequence before its Sal I site which is necessary to splice the VL to C κ in the expression vector.

TABLE 4

PRIMERS FOR 128.1 V-J REGION MODIFICATION
BY SECOND PCR PRIOR TO THE CLONING INTO
EXPRESSION VECTORS

HEAVY CHAIN PRIMER (3' ANTISENSE):
Primer designed to hybridize to amino acids 111–113
in J4 region of 128.1 heavy chain V region. It includes
a Nhe I site for cloning into the expression vector
(links J4 to CHI) and Sal I for subcloning (upstream Nhe I).

ALKJR AS.NHE.SAL1    #098
Antisnese of JHJ4 + γ1 CH1
5' TGG <u>GTCGAC</u> AGA TGG GGG TGT TGT <u>GCTAGC</u> TGA
GGA GAC (SEQ ID NO: 12).
    LIGHT CHAIN PRIMER (3' ANTISENSE):
Primer designed to hybridize to amino acids 101–107
in J4 region of 128.1 light chain V region. It includes a donor
splicing sequence which is highlighted.

ALKκ-J4AS.SAL1    #101
Antisense of Vl J4 + splicing donor
5' AGC <u>GTCGAC</u> TTACG TCT GAT TTC CAG CCT
GGT CCCT (SEQ ID NO: 13)

PCR reactions were performed in a volume of 100 μl with the following final conditions: 2 μl of cDNA, 0.5 μl Taq polymerase (Cetus Corporation), 1×buffer (10 mM Tris pH8, 1.5 mM MgCl$_2$, 50 mM KCl, 100 μg BSA), 200 μM each dNTP, 1 μM of each primer and 50 μl of mineral oil. PCR was carried out for 30 cycles in a PTC 100 Thermal Controller (M.J. Research Inc.) with 1 min. denaturing (94° C.), 1 min. annealing (55° C.), 1.5 min. extension (72° C.), and a final extension of 10 min.

The size of the PCR products was verified by agarose gel electrophoresis in a 2% TAE gel stained with ethidium bromide. The correct products were approximately 380 base pairs for the light chain and 420 base pairs for the heavy chain variable region.

SUBCLONING AND SEQUENCING:

After the PCR reaction the oil was removed by chloroform extraction and the samples kept at 40° C. For subcloning, the products were either directly cloned into Bluescript KS T-A (blunt ended by digestion at EcoR V site and tailed with dideoxythymidine triphosphate using terminal transferase) prepared following the procedure by Holton (T. A. Holton and M. W. Graham. 1990 Nucl. Acid. Res., 19:5, 1156), or gel isolated, cut with the appropriate restriction enzymes (EcoR V and Sal I) and cloned into Bluescript KS previously cut with the same enzymes.

For TA cloning 3 μl of the PCR product was directly ligated with 50 ng of T-A vector in a 15 μl reaction for 4–12 hours at 16° C. For sticky end ligations 200 ng of cut Bluescript was ligated with 200–400 ng of cut product in 20 μl ligation reactions. 5 μl of the ligation was used for transformation of E. Coli. XL1-blue (Stratagene) competent cells prepared by calcium chloride treatment. White colonies, containing inserts were picked above a blue colony background. Miniprep DNA was restriction digested, analyzed and the apparently correct clones sequenced.

Dideoxynucleotide chain termination sequencing was carried out using T7 DNA polymerase (Pharmacia, Uppsala, Sweden or Sequenase, U.S. Biochemical Corp., Cleveland, Ohio) according to the manufacturer's protocol. Four independent clones from different PCR reactions were sequenced in both directions, to obtain the concensus sequence.

The obtained sequences were compared against other murine sequences in Genbank and aligned with reported V regions in Kabat's database to identify their family and conserved amino acids. (See Tables 5 and 6.)

TABLE 5

COMPLETE SEQUENCE OF CHIMERIC 128.1
(Anti-Human Transferrin Receptor)
LIGHT CHAIN VARIABLE REGION, MOUSE KAPPA SUBGROUP VI

```
                       -22          LEADER
                       ATG GAT TTT CAA GTG CAG ATT    (SEQ ID NO: 14)
                       Met Asp Phe Gln Val Gln Ile    (SEQ ID NO: 15)

TTC AGC TTC CTG CTA ATC AGT GCC TCA GTC ATA CTG TCC AGA
Phe Ser Phe Leu Leu Ile Ser Ala Ser Val Ile Leu Ser Arg

-1       1                    FR1
GGA --- CAA ATT GTT CTC ACC CAG TCT CCA GCA ATC ATG TCT
Gly --- Gln Ile VAL LEU Thr GLN SER PRO ALA ILE Met Ser

FR1                     24      CDR1
GTA TCT CCA GGG GAG AAG GTC ACC ATG ACC TGC AGT GCC AGC
VAL SER Pro GLY Glu LYS VAL THR Met THR CYS Ser ALA SER 27-29   *   CDR1        35           FR2
TCA AGT ATA CGT TAC ATT CAC TGG TAC CAG CAG AGG CCA GGC
SER SER Ile Arg TYR Ile His TRP Tyr-
GLN GLN ARG Pro Ser Gly

FR2              50    CDR2
ACC TCC CCC AAA AGA TGG ATT TAT GAC ACA TCC AAC CTG GCT
Thr SER PRO LYS Arg Trp ILE TYR Asp Thr SER Asn LEU Ala

57             FR3
TCT GGA GTC CCT GCT CGC TTC AGT GGC AGT GGG TCT GGG ACC
SER GLY VAL PRO Ala ARG PHE SER GLY SER GLY SER GLY Thr

FR3
TCT TAT TCT CTC ACA ATC AGC AGC ATG GAG GCT GAA GAT GCT
Ser Tyr Ser LEU Thr ILE Ser Ser Met GLU Ala GLU ASP Ala

89           CDR3                97
GCC ACT TAT TAC TGC CAT CAG CGG AAT AGT TAC CCA TGG ACG
ALA THR TYR TYR CYS His GLN Arg Asn Ser Tyr Pro Trp THR

98           FR4   *           107      CONST.
TTC GGT GGA GGC ACC AGG CTG GAA ATC AGA --> CGG GCT
PHE GLY GLY GLY THR Arg LEU GLU Ile ARG --> ARG ALA
                                J4
```

Conserved amino acids are capitalized and bold.
*NOTE:
Amino acid #30 is a conserved Val and amino acid #103 and #107 a conserved Lys in 98% of the sequences reported in Kabat's database for this family.

TABLE 6

COMPLETE SEQUENCE OF CHIMERIC 128.1
(Anti-Human Transferrin Receptor)
HEAVY CHAIN VARIABLE REGION.
MOUSE GAMMA SUBGROUP IIB.

```
                       -19          LEADER
                       ATG GAA TGG AGC TGG GTA    (SEQ ID NO: 16)
                       Met Glu Trp Ser Trp Val    (SEQ ID NO: 17)

LEADER                    -1
ATC CTC TTC CTC CTG TCA GGA ACT GCA GGT GTC CGC TCT ---
Met Leu Phe LEU Leu Ser Gly Thr Ala Gly Val Arg Ser ---

1                  FR1
GAG GTC CAG CTG CAA CAG TCT GGA CCT GAA CTG GTG AAG CCT
Glu VAL GLN LEU Gln GLN Ser GLY Pro Glu LEU VAL Lys PRO

*18          FR1
GGA GCT TCA ATG AAG ATT TCC TGC AAG GCT TCT GGT TAC TCA
GLY Ala SER Met LYS Ile SER CYS LYS ALA SER GLY TYR Ser

31    CDR1       36         FR2
```

TABLE 6-continued

COMPLETE SEQUENCE OF CHIMERIC 128.1
(Anti-Human Transferrin Receptor)
HEAVY CHAIN VARIABLE REGION.
MOUSE GAMMA SUBGROUP IIB.

```
TTC ACT GGC TAC ACC ATG AAC TGG GTG AAG CAG AGC CAT GGA
Phe Thr Gly Tyr Thr Met Asn TRP VAL Lys GLN Ser His Gly

FR2              50       52--a- 53   CDR2
GAG AAC CTT GAG TGG ATT GGA CGT ATT AAT CCT CAC AAT GGT
Glu Asn Leu Glu Trp Ile Gly Arg Ile Asn PRO His Asn Gly

CDR2                      66     *68
GGT ACT GAC TAC AAC CAG AAG TTC AAG GAC AAG GCC CCT TTA
Gly Thr Asp TYR Asn Gln LYS PHE Lys Asp LYS Ala Pro LEU

FR3                      82--a-
ACT GTA GAC AAG TCA TCC AAC ACA GCC TAC ATG GAG CTC CTC
THR Val Asp Lys SER Ser Asn THR Ala TYR Met Gly LEU Leu 82b-c-   83               FR3
AGT CTG ACA TCT GCG GAC TCT GCA GTC TAT TAC TGT GCA AGA
Ser Leu THR SER GLY ASP Ser ALA Val TYR Tyr CYS Ala Arg

95           CFR3   100--a-        103         FR4
GGC TAC TAT TAC TAT TCT TTG GAC TAC TGG GGT CAA GGA ACC
Gly Tyr Tyr Tyr Tyr Ser Leu Asp Tyr TRP GLY Gln GLY THR

FR4         113         CH1
TCA GTC ACC GTC TCC TCA --> GCC AAA
Ser Val THR VAL SER Ser --> Ala Lys
              J4
```

Conserved amino acids are capitalized and bold. Amino acid #18 is a conserved
Val and amino acid #68 a conserved Thr in 98% of the sequences reported in
Kabat's data base for this family.

The final clones were named pBKS4600 for the VH region and pBKS4601 for the VL region.

CLONING INTO EXPRESSION VECTORS:

Plasmid pAH4274 is the vector for expression of heavy chain variable regions obtained by PCR with leader/J region priming. V region cloning into this cassette is performed by a complete digestion of vector and product with EcoR V and Nhe I. This vector has a human γ1 constant region whose CH1 is directly linked with the 3' end of the VH-J region by means of a Nhe I site. This 11 kb vector contains an ampicillin resistance gene for procaryotic selection, a heavy chain immunoglobulin enhancer and a histidine (histidinol) selection marker for selection of transfectants (Hartman, S., R. Mulligan, Proc. Natl. Acad. Sci. 85, 8047–8051); transcription is from the VH promoter of the murine 27.44 gene.

Figure 10:
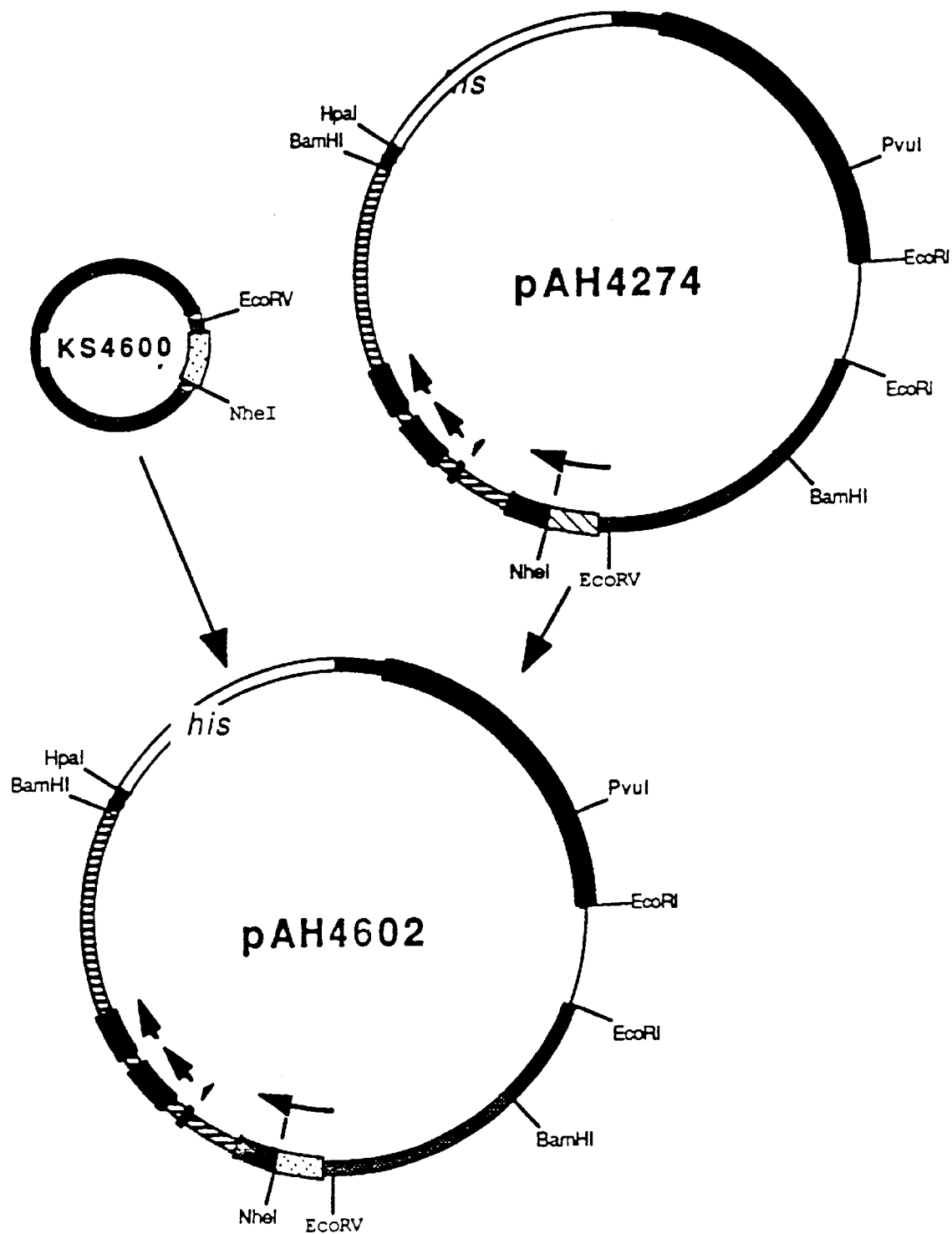
FIG. 10 illustrates the cloning of the 128.1 heavy chain variable region.

The 400 bp. EcoR V-Nhe I fragment (VH of 128.1) from pBKS4600 was used to replace the EcoR V-Nhe I fragment in plasmid pAH 4274. HB101 competent cells were transformed and plated on LB plates with 50 μg/ml of ampicillin. Colonies were screened by colony hybridization with a $^{32}$P end labelled leader region oligonucleotide. Positive clones were restriction mapped and maxi plasmid preps prepared using the QIAGEN maxi prep kit (QIAGEN Inc., Studio City, Calif.). The final expression vector with the VH of 128.1 joined to human γ1 constant region was named pAH4602 (FIG. 10). The coding sequence for this expression vector is given in (SEQ ID NO: 18), (SEQ ID NO: 19), (SEQ ID NO: 20), (SEQ ID NO: 21), (SEQ ID NO: 22), and (SEQ ID NO: 23).

Plasmid pAG4270 is the expression vector for light chain variable regions obtained by PCR with leader/J region priming. The 14 kb vector has an ampicillin resistance gene, a gpt (mycophenolic acid resistance) selected marker, an immunoglobulin H enhancer and an introl for V-Constant region splicing; transcription is from the murine VH promoter from the 27.44 gene.

Figure 12:
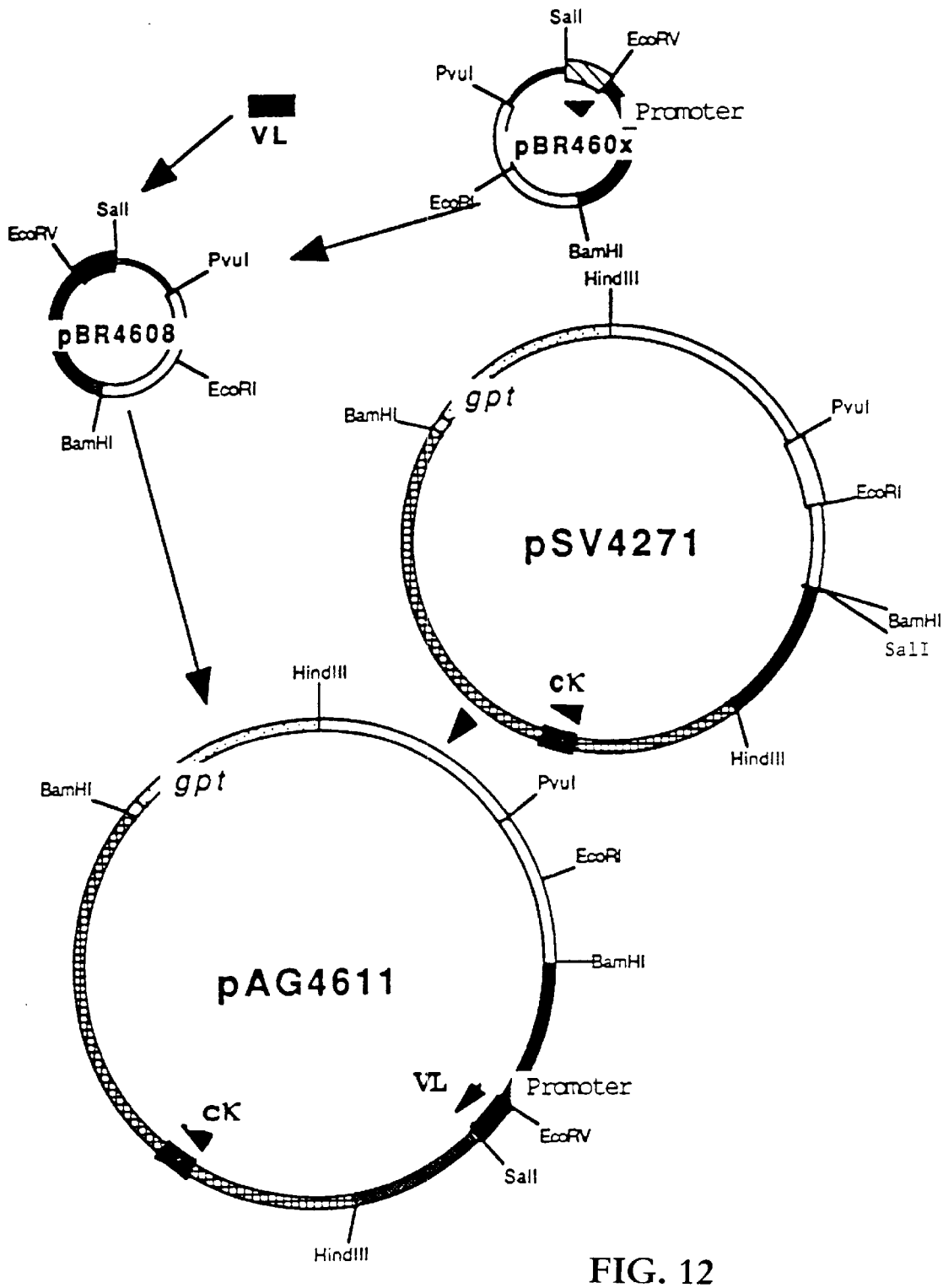
FIG. 12 illustrates the cloning of the 128.1 light chain variable region.
Figure 13E:
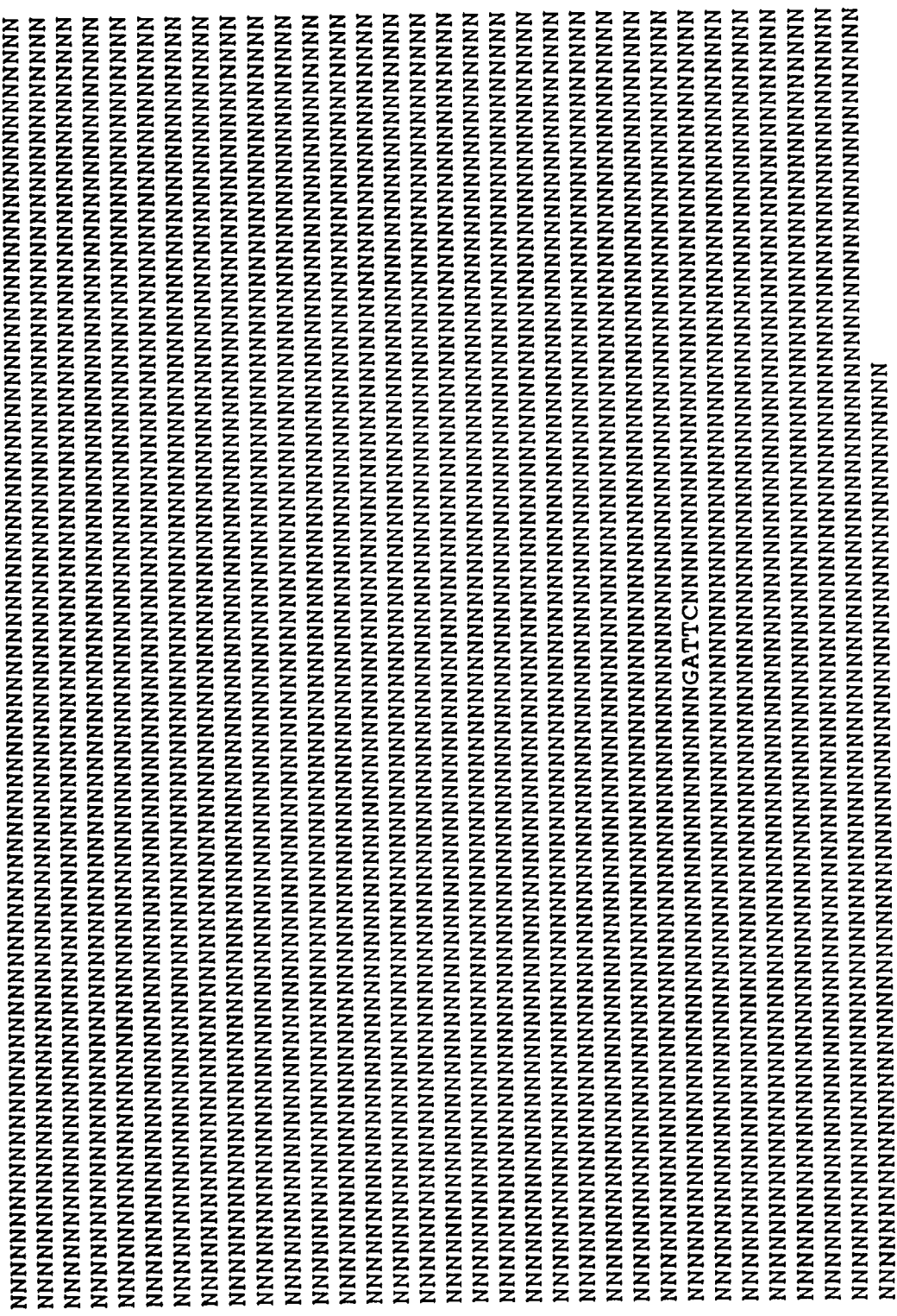

Due to the presence of an EcoR V within the gpt gene in the vector, the cloning of the anti-transferrin receptor VL was performed in two steps to avoid inefficient partial digestions. The 380 bp EcoR V-Sal I fragment (VL) from pBKS4601 was cloned into pBR460x (6.9 kb), a subcloning vector with the VH promoter, previously cut with the same enzymes. The resulting construct (pBR4608) was then cut with Pvu I-Sal I and the 4 kb fragment containing the promoter, the V region and part of the ampicillin resistance gene was ligated to the 9.7 kb Pvu I-Sal I fragment of pSV4271 an intermediate vector which lacks the promoter. HB101 competent cells were transformed and positives screened by colony hybridization and restriction digestion. Maxipreps were prepared as described above. The final expression vector was named pAG4611 (FIG. 12). The coding sequence of this expression vector is shown in FIGS. 13A–13F (SEQ ID NO: 24), (SEQ ID NO: 25), and (SEQ ID NO: 26).

TRANSFECTION AND SELECTION:

Ten μg of maxiprep DNA from each final expression vector was linearized by BSPC1 (Stratagene, Pvu I isochizomer) digestion and 1×10$^7$ SP2/0 cells were cotransfected by electroporation. Prior to transfection the cells were washed with cold PBS, then resuspended in 0.9 ml of the same cold buffer and placed in a 0.4 cm electrode gap electroporation cuvette (Bio-Rad) with the DNA. For the electrical pulse, the Gene Pulser from Bio-Rad (Bio-Rad, Richmond, Calif.) was set at a capacitance of 960 μF and 200 V. After the pulse the cells were incubated on ice for 10 minutes then washed once in IMDM with 10% calf serum and resuspended in IMDM with 10% calf serum at a concentration of 105 cells/ml.

The transfected cells were plated into five 96 well plates at a concentration of 10$^4$ cells/well. Selection was started after 48 hours. Two plates were selected with 5 mM histidinol (heavy chain selection), 2 plates were selected with 1 μl/ml mycophenolic acid (light chain selection) and 1 plate was selected with histidinol and mycophenolic acid (heavy and light chain selection).

Twelve days post selection supernatants were screened by ELISA to test for the secretion of both chains. Immulon II 96 well plates were coated with 5 μg/ml of goat anti human γ1 in carbonate buffer at pH9.6, and blocked with 3% BSA. Supernatants from the transfectants were added and the plates were incubated overnight at 4° C. After washing, plates were developed with goat anti-human k conjugated with alkaline phosphatase and wells secreting H and L chains identified (Table 7).

TABLE 7

RESULTS OF TRANSFECTIONS
Results of cotransfection with vectors pAH4602 and pAG4611 in SP2/0 cells. 2 plates were selected with 5 mM histidinol (HIS), 2 plates with 1 μg/ml mycophenolic acid (HXM) and 1 plate selected with both (HIS + HXM). Wells containing clones were analyzed by ELISA to determine those containing secreted antibody (# positive wells).

|  | SELECTION | | |
| --- | --- | --- | --- |
|  | HIS | HXM | HIS + HXM |
| #WELLS WITH CLONES | 78/96 83/96 | 76/96 64/96 | 13/96 |
| #POSITIVE WELLS | 20/78 25/83 | 28/76 20/64 | 10/13 |

High producers were expanded for further analysis; selected transfectants were subcloned.
ANTIBODY ANALYSIS:

To determine the nature of the protein being produced, transfectants were biosynthetically labelled with $^{35}S$ methionine, cytoplasmic and secreted antibodies immunoprecipitated with rabbit anti-human Ig and protein-A and the immunoprecipitates fractioned on SDS polyacrylamide gels.

Clones with the highest production identified by ELISA were expanded to 5 ml petri dishes and removed from selection. $1 \times 10^6$ cells were pelleted at 220×g for 5 minutes at 4° C. and washed twice with labelling medium (high glucose DME deficient in methionine: GIBCO). Cells were finally resuspended in 1 ml labeling medium containing 25 μCi$^{35}$S-Methionine (Amersham Corp.) and allowed to incorporate label for 3 hours at 37° C. under tissue culture atmospheric conditions.

Cells were pelleted and supernatants drawn off for immunoprecipitation of secreted IgG. Cell pellets were lysed in NDET (1% NP-40, 0.4% deoxycholate, 66 mM EDTA, 10 mM Tris, pH 7.4), centrifuged, and the supernatants removed and incubated 1 hour at 4° C. with rabbit anti-human IgG Fc polyclonal antiserum (5 μl/ml). To the labelled supernatants, 100 μl/ml of protein A (10% in NDET, IgG Sorb) was added and mixed by rotation at 4° C. for 15 minutes. Protein-A bound IgG was washed by centrifuging through 1 ml 30% sucrose in 100 μl NDET+0.3% SDS. The protein A pellet was then resuspended in 100 μl NDET/3% SDS, transferred to a 1.5 ml polypropylene tube with 100 μl of the same buffer, and the previous tube rinsed with 100 μl. The 300 μl suspension was centrifuged and washed with deionized water. Finally, the protein A pellet was resuspended in 50 μl of loading buffer (25 mMTris pH 6.7, 0.2% SDS, 10% glycerol, 8% μg/100 ml bromophenol blue) and boiled for two minutes prior to gel loading. Antibodies were analyzed by SDS-PAGE (5% acrylamide gels, 0.1% sodium phosphate buffered) to confirm proper assembly of H and L chains. In addition, a portion of the labelled sample was reduced by treatment with 0.15 M 2-mercaptoethanol, 37° C. for 1 hour and analyzed on 12% acrylamide gels to confirm the size of the unassembled H and L chains. The gels were stained, dried and exposed for autoradiograms.

The resultant autoradiograms revealed the expected patterns for fully functional antibodies. The secreted antibodies that were in the cell supernatant exhibited the expected molecular weight pattern of free light chain, light chain dimer and the tetramer formed from two light chains and two heavy chains for fully expressed and assembled functional antibodies. The pattern for antibody parts in the cell cytoplasm was also as expected for fully expressed antibody constitutents.

EXAMPLE 16

Further Mouse/Human Chimeras of the Anti-Human Transferrin Receptor Antibody 128.1.

Figure 14:
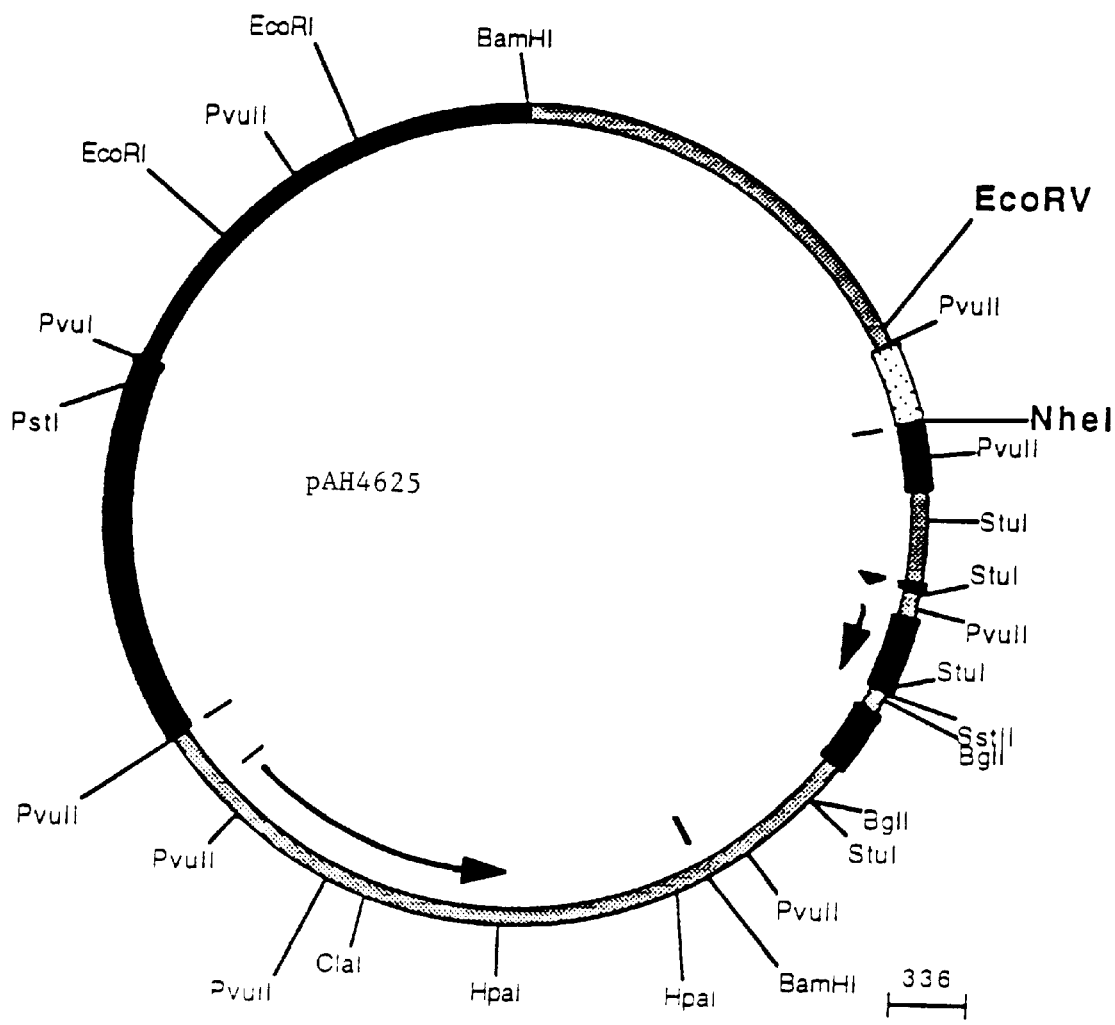
FIG. 14 illustrates the plasmid map of the heavy chain expression vector pAH4625 containing the γ-2 isotype.
Figure 15:
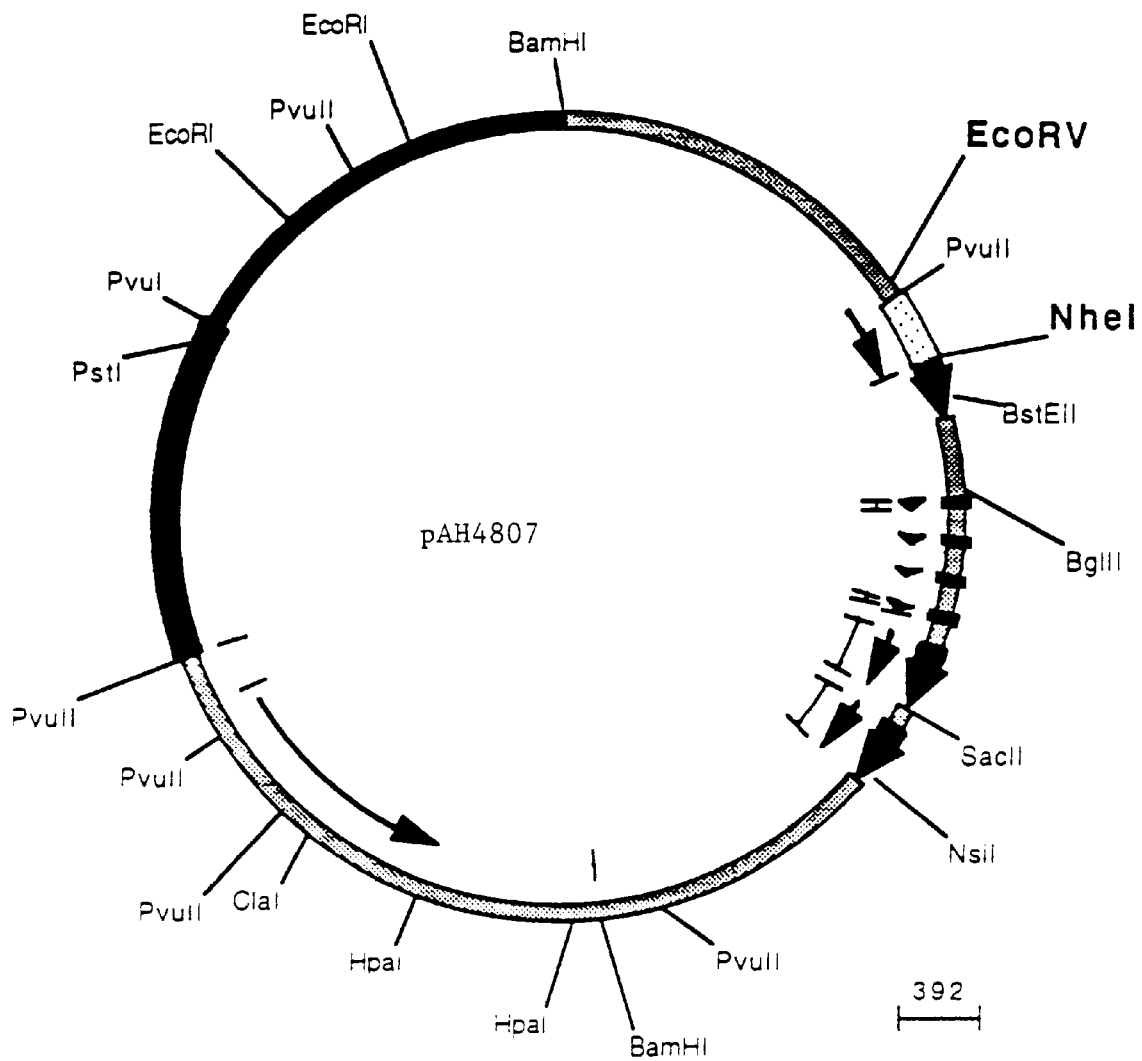
FIG. 15 illustrates the plasmid map of the heavy chain expression vector pAH4807 containing the γ-3 isotype.
Figure 16:
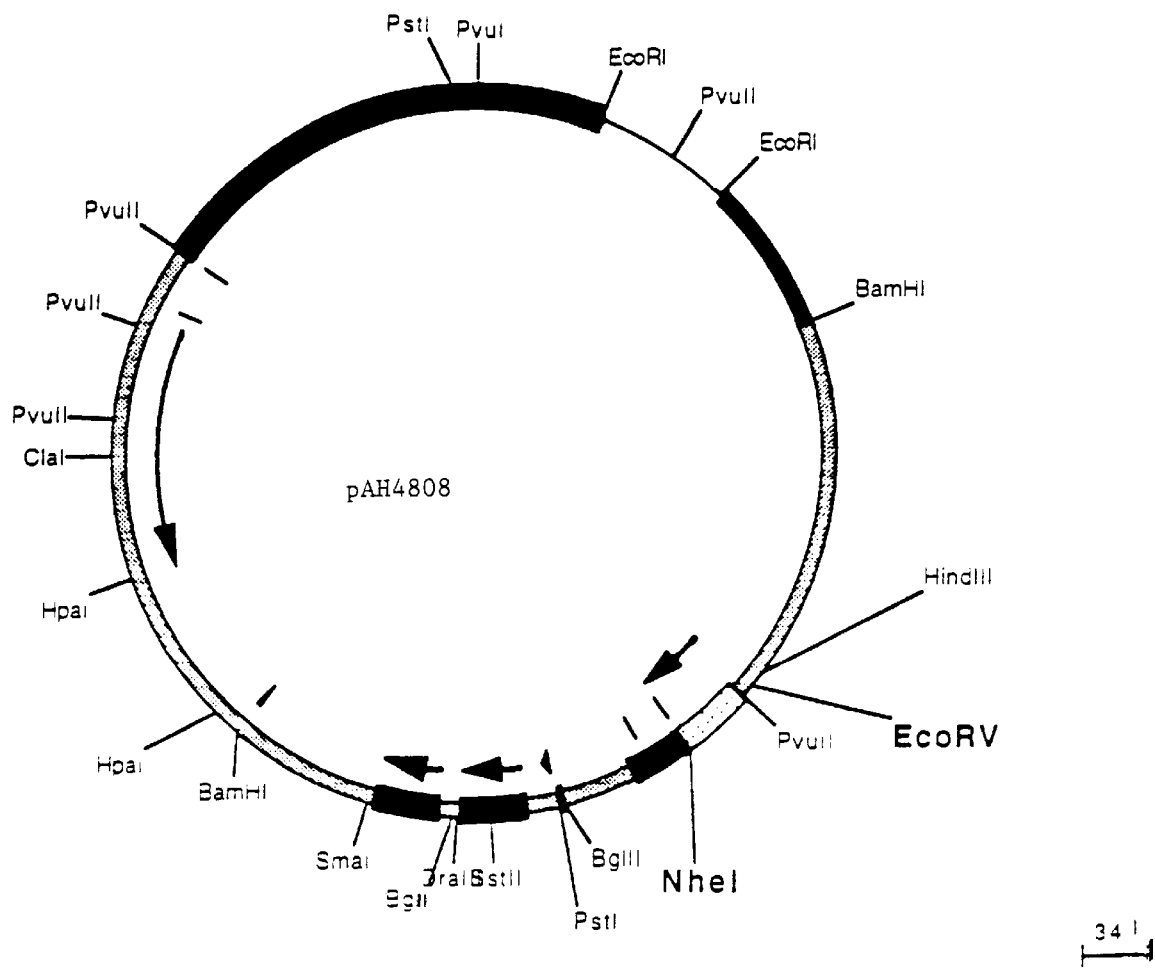
FIG. 16 illustrates the plasmid map of the heavy chain expression vector pAH4808 containing the γ-4 isotype.

As described in Example 15, the initial cloning of the gene encoding the heavy chain of the murine monoclonal antibody 128.1, which binds the human transferrin receptor, involved placing the sequences encoding the variable region of the heavy chain into an expression vector containing the human γ1 constant region framework. This created a mouse/human chimera in which the sequences encoding the variable region of the antibody heavy chain (VH) were derived from a murine source and the sequences encoding $CH_1$, $CH_2$ and $CH_3$ were derived from a human source. Because the different human gamma isotypes (γ-1, -2, -3 and -4) have different biological properties, it was necessary to create chimeric antibodies with constant region sequences from each isotype in order to obtain mouse/human chimeras for each of these isotypes. The production of these chimeras was accomplished by cloning the 400 bp Eco RV-Nhe 1 fragment containing the VH region of antibody 128.1 from plasmid pBSK4600 into expression vectors containing the γ-2, γ-3 and γ-4 constant regions in a fashion similar to that previously described in Example 15 for the cloning of the VH region of antibody 128.1 into the expression vector containing the γ-1 constant region. These clonings with the γ-2, γ-3 and γ-4 constant regions resulted in respective plasmids pAH4625, pAH4807 and pAH4808 whose plasmid maps are shown in FIG. 14, FIG. 15 and FIG. 16, respectively. The antibody coding sequences of the heavy chain expression vectors pAH4625, pAH4807 and pAH4808 are shown in FIGS. 17A–17F (SEQ ID NO: 27), (SEQ ID NO: 28), (SEQ ID NO: 29), (SEQ ID NO: 30), and (SEQ ID NO: 31), FIGS. 18A–18F (SEQ ID NO: 32), (SEQ ID NO: 33), (SEQ ID NO: 34), (SEQ ID NO: 35), (SEQ ID NO: 36), (SEQ ID NO: 37), (SEQ ID NO: 38), and (SEQ ID NO: 40) and FIGS. 19A-19F (SEQ ID NO: 41), (SEQ ID NO: 42), (SEQ ID NO: 43), (SEQ ID NO: 44), (SEQ ID NO: 45) and (SEQ ID NO: 46), respectively.

These vectors, in combination with the chimeric light chain vector pAG4611, were transfected into SP2/0 cells and clones selected as described in Example 15. Initial antibody analysis using biosynthetically labeled proteins, immunoprecipitation and SDS-PAGE as previously described gave rise to the appropriate bands for the heavy and light chains as well as the assembled antibody for the γ-3 and γ-4 chimeras. No detectable protein was made by the γ-2 transfectants.

EXAMPLE 17

Antibody Production by Transfectants

Antibody production by selected transfectants was assessed by ELISA. Cells were diluted in fresh aliquoted into each of 3 wells on a 24-well culture plate. The plates were then incubated for 24 hours at 37° C. with 5% $CO_2$. The media was then collected from the wells and the cells and debris were spun down to give a clarified supernatant. For the ELISA, a 96-well microtiter dish was coated with a goat antisera against human IgG. After blocking with 3% BSA, the plate was washed and a series of dilutions of both the cell supernatants and human IgG standard of known concentration were applied to the plate and incubated for 1 hour at room temperature. The plate was then washed and biotinylated goat antisera against human IgG was added, followed by a mixture of avidin and biotinylated horseradish peroxidase (HRP). The amount of antibody present in the samples was then determined, based on the amount of substrate converted by the HRP.

Three clones resulting from the γ-1 chimera transfection were tested for antibody production. The average values from three experiments were 39, 21 and 24 μg/ml IgG/$10^6$ cells/24 hours, respectively, for the different clones. One γ-3 clone has been tested and it was found to produce approximately 1 μg/ml IgG/$10^6$ cells/24 hours. Two different clones of the γ-4 chimera have been tested and were found to produce 2.8 and 0.2 ng/ml IgG/$10^6$ cells/24 hours, respectively.

Equivalents

Those skilled in the art will know, or be able to ascertain using no more than routine experimentation, many equivalents to the specific embodiments expressly described herein. These are intended to be within the scope of the invention as described by the claims herein.

I claim:

1. A method for delivering a neuropharmceutical or diagnostic agent across the blood brain barrier to type brain of a host, wherein the method comprises administering to a host a chimeric antibody, capable of binding to a transferrin receptor present on brain capillary cells, covalenty linked to a neuropharmaceutical or agent, whereby the neuropharmaceutical or agent is transferred across the blood brain barrier when administered in vivo, wherein the chimeric antibody comprises a variable region from one antibody and a constant region from a different antibody.

2. The method according to claim 1 wherein the chimeric antibody comprises a chimera between the variable region of a murine antibody and the constant region of an antibody from a mammalian species other than murine, wherein said chimera is selected from the group consisting of the light chain, the heavy chain and both the light chain and the heavy chain.

3. The method system according to claim 2 wherein the mammalian source is human.

4. A method for delivering a neuropharmaceutical or diagnostic agent across the blood brain barrier to the brain of a host which comprises administering to the host an antibody-neuropharmaceutical agent conjugate or an antibody-diagnostic agent conjugate under conditions whereby binding of the antibody to a transferrin receptor present on brain capillary cells occurs and the neuropharmaceutical or diagnostic agent is transferred across the blood brain barrier in a pharmaceutically or diagnostically active form, wherein the antibody is a chimeric antibody that specifically binds said transferrin receptor, wherein the chimeric antibody comprises a variable region from one antibody and a constant region from a different antibody.

5. The method for delivering a neuropharmaceutical or diagnostic agent across the blood brain barrier according to claim 4 wherein the chimeric antibody comprises a chimera between the variable region of a murine antibody and the constant region of an antibody from a mammalian species other than murine, wherein said chimera is selected from the group consisting of the light chain, the heavy chain and both the light chain and the heavy chain.

6. The method for delivering a neuropharmaceutical or diagnostic agent across the blood-brain barrier of claim 5, wherein the mammalian species is human.

* * * * *

UNITED STATES PATENT AND TRADEMARK OFFICE
CERTIFICATE OF CORRECTION

PATENT NO. : 6,015,555
DATED : January 18, 2000
INVENTOR(S) : Phillip M. Friden

It is certified that error appears in the above-indentified patent and that said Letters Patent is hereby corrected as shown below:

Claim 1, line 2: After the words "blood brain barrier", delete "to type brain" and insert therefor --to the brain--.

Signed and Sealed this

Twenty-fourth Day of October, 2000

Attest:

Q. TODD DICKINSON

*Attesting Officer*      *Director of Patents and Trademarks*

SEQUENCE LISTING (1) GENERAL INFORMATION:

(iii) NUMBER OF SEQUENCES: 46

(2) INFORMATION FOR SEQ ID NO:1:

(i) SEQUENCE CHARACTERISTICS:
       (A) LENGTH: 34 base pairs
       (B) TYPE: nucleic acid
       (C) STRANDEDNESS: single
       (D) TOPOLOGY: linear (ii) MOLECULE TYPE: DNA (genomic)

(iii) HYPOTHETICAL: NO (iv) ANTI-SENSE: NO (vi) ORIGINAL SOURCE:
       (C) INDIVIDUAL ISOLATE: synthesized (ix) FEATURE:
       (A) NAME/KEY: misc_feature
       (B) LOCATION: 1..34
       (D) OTHER INFORMATION: /function= "Light Chain V Region"

(xi) SEQUENCE DESCRIPTION: SEQ ID NO:1:

GCCGGAATTC TAGAAGCTTT TTTTTTTTTT TTTT                          34

(2) INFORMATION FOR SEQ ID NO:2:

(i) SEQUENCE CHARACTERISTICS:
       (A) LENGTH: 39 base pairs
       (B) TYPE: nucleic acid
       (C) STRANDEDNESS: single
       (D) TOPOLOGY: linear (ii) MOLECULE TYPE: DNA (genomic)

(iii) HYPOTHETICAL: NO (iv) ANTI-SENSE: NO (vi) ORIGINAL SOURCE:
       (C) INDIVIDUAL ISOLATE: synthesized (ix) FEATURE:
       (A) NAME/KEY: misc_feature
       (B) LOCATION: 1..39
       (D) OTHER INFORMATION: /function= "Heavy Chain V Region"

(xi) SEQUENCE DESCRIPTION: SEQ ID NO:2:

AGGTCTAGAA YCTCCACACA CAGGRRCCAG TGGATAGAC                     39

(2) INFORMATION FOR SEQ ID NO:3:

(i) SEQUENCE CHARACTERISTICS:
        (A) LENGTH: 39 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iv) ANTI-SENSE: NO (vi) ORIGINAL SOURCE:
        (C) INDIVIDUAL ISOLATE: synthesized (ix) FEATURE:
        (A) NAME/KEY: misc_feature
        (B) LOCATION: 1..39
        (D) OTHER INFORMATION: /function= "Heavy Chain V Region"

(xi) SEQUENCE DESCRIPTION: SEQ ID NO:3:

GGGGATATCC ACCATGGRAT GSAGCTGKGT MATSCTCTT                39

(2) INFORMATION FOR SEQ ID NO:4:

(i) SEQUENCE CHARACTERISTICS:
        (A) LENGTH: 39 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iv) ANTI-SENSE: NO (vi) ORIGINAL SOURCE:
        (C) INDIVIDUAL ISOLATE: synthesized (ix) FEATURE:
        (A) NAME/KEY: misc_feature
        (B) LOCATION: 1..39
        (D) OTHER INFORMATION: /function= "Heavy Chain V Region"

(xi) SEQUENCE DESCRIPTION: SEQ ID NO:4:

GGGGATATCC ACCATGRACT TCGGGYTGAG CTKGGTTTT                39

(2) INFORMATION FOR SEQ ID NO:5:

(i) SEQUENCE CHARACTERISTICS:
        (A) LENGTH: 38 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iv) ANTI-SENSE: NO (vi) ORIGINAL SOURCE:
        (C) INDIVIDUAL ISOLATE: synthesized (ix) FEATURE:
        (A) NAME/KEY: misc_feature
        (B) LOCATION: 1..38
        (D) OTHER INFORMATION: /function= "Heavy Chain V Region"

(xi) SEQUENCE DESCRIPTION: SEQ ID NO:5:

```
GGGGATATCC ACCATGGCTG TCTTGGGGCT GCTCTTCT                                   38

(2) INFORMATION FOR SEQ ID NO:6:

(i) SEQUENCE CHARACTERISTICS:
        (A) LENGTH: 39 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iv) ANTI-SENSE: YES (vi) ORIGINAL SOURCE:
        (C) INDIVIDUAL ISOLATE: synthesized (ix) FEATURE:
        (A) NAME/KEY: misc_feature
        (B) LOCATION: 1..39
        (D) OTHER INFORMATION: /function= "Heavy Chain C Region"

(xi) SEQUENCE DESCRIPTION: SEQ ID NO:6:

AGGTCTAGAA YCTCCACACA CAGGRRCCAG TGGATAGAC                                  39

(2) INFORMATION FOR SEQ ID NO:7:

(i) SEQUENCE CHARACTERISTICS:
        (A) LENGTH: 37 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iv) ANTI-SENSE: NO (vi) ORIGINAL SOURCE:
        (C) INDIVIDUAL ISOLATE: synthesized (ix) FEATURE:
        (A) NAME/KEY: misc_feature
        (B) LOCATION: 1..37
        (D) OTHER INFORMATION: /function= "Light Chain V Region"

(xi) SEQUENCE DESCRIPTION: SEQ ID NO:7:

GGGGATATCC ACATGGAGAC AGACACACTC CTGCTAT                                    37

(2) INFORMATION FOR SEQ ID NO:8:

(i) SEQUENCE CHARACTERISTICS:
        (A) LENGTH: 39 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iv) ANTI-SENSE: NO (vi) ORIGINAL SOURCE:
        (C) INDIVIDUAL ISOLATE: synthesized (ix) FEATURE:
        (A) NAME/KEY: misc_feature
        (B) LOCATION: 1..39
        (D) OTHER INFORMATION: /function= "Light Chain V Region"

(xi) SEQUENCE DESCRIPTION: SEQ ID NO:8:
```

```
GGGGATATCC ACCATGGATT TTCAAGTGCA GATTTTCAG                                   39
```

(2) INFORMATION FOR SEQ ID NO:9:

(i) SEQUENCE CHARACTERISTICS:
        (A) LENGTH: 37 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iv) ANTI-SENSE: NO (vi) ORIGINAL SOURCE:
        (C) INDIVIDUAL ISOLATE: symthesized (ix) FEATURE:
        (A) NAME/KEY: misc_feature
        (B) LOCATION: 1..37
        (D) OTHER INFORMATION: /function= "Light Chain V Region"

(xi) SEQUENCE DESCRIPTION: SEQ ID NO:9:

```
GGGGATATCC ACCATGGAGW CACAKWCTCA GGTCTTT                                    37
```

(2) INFORMATION FOR SEQ ID NO:10:

(i) SEQUENCE CHARACTERISTICS:
        (A) LENGTH: 36 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iv) ANTI-SENSE: NO (vi) ORIGINAL SOURCE:
        (C) INDIVIDUAL ISOLATE: synthesized (ix) FEATURE:
        (A) NAME/KEY: misc_feature
        (B) LOCATION: 1..36
        (D) OTHER INFORMATION: /function= "Light Chain V Region"

(xi) SEQUENCE DESCRIPTION: SEQ ID NO:10:

```
GGGGATATCC ACCATGKCCC CWRCTCAGYT YCTKGT                                     36
```

(2) INFORMATION FOR SEQ ID NO:11:

(i) SEQUENCE CHARACTERISTICS:
        (A) LENGTH: 30 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iv) ANTI-SENSE: YES (vi) ORIGINAL SOURCE:
        (C) INDIVIDUAL ISOLATE: synthesized (ix) FEATURE:
        (A) NAME/KEY: misc_feature
        (B) LOCATION: 1..30
        (D) OTHER INFORMATION: /function= "Light Chain C Region"

(xi) SEQUENCE DESCRIPTION: SEQ ID NO:11:

GCGTCTAGAA CTGGATGGTG GGAAGATGGA                                          30

(2) INFORMATION FOR SEQ ID NO:12:

(i) SEQUENCE CHARACTERISTICS:
        (A) LENGTH: 39 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iv) ANTI-SENSE: YES (vi) ORIGINAL SOURCE:
        (C) INDIVIDUAL ISOLATE: synthesized (ix) FEATURE:
        (A) NAME/KEY: misc_feature
        (B) LOCATION: 1..39
        (D) OTHER INFORMATION: /function= "Heavy Chain V-J Region"

(xi) SEQUENCE DESCRIPTION: SEQ ID NO:12:

TGGGTCGACA GATGGGGGTG TTGTGCTAGC TGAGGAGAC                                 39

(2) INFORMATION FOR SEQ ID NO:13:

(i) SEQUENCE CHARACTERISTICS:
        (A) LENGTH: 36 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iv) ANTI-SENSE: YES (vi) ORIGINAL SOURCE:
        (C) INDIVIDUAL ISOLATE: synthesized (ix) FEATURE:
        (A) NAME/KEY: misc_feature
        (B) LOCATION: 1..36
        (D) OTHER INFORMATION: /function= "Light Chain V-J Region"

(xi) SEQUENCE DESCRIPTION: SEQ ID NO:13:

AGCGTCGACT TACGTCTGAT TTCCAGCCTG GTCCCT                                    36

(2) INFORMATION FOR SEQ ID NO:14:

(i) SEQUENCE CHARACTERISTICS:
        (A) LENGTH: 384 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (ix) FEATURE:
        (A) NAME/KEY: misc_feature
        (B) LOCATION: 1..384
        (D) OTHER INFORMATION: /function= "Chimeric 128.1 Light
            Chain V Region"

(xi) SEQUENCE DESCRIPTION: SEQ ID NO:14:

ATGGATTTTC AAGTGCAGAT TTTCAGCTTC CTGCTAATCA GTGCCTCAGT CATACTGTCC          60

| AGAGGACAAA TTGTTCTCAC CCAGTCTCCA GCAATCATGT CTGTATCTCC AGGGGAGAAG | 120 |
| GTCACCATGA CCTGCAGTGC CAGCTCAAGT ATACGTTACA TTCACTGGTA CCAGCAGAGG | 180 |
| CCAGGCACCT CCCCCAAAAG ATGGATTTAT GACACATCCA ACCTGGCTTC TGGAGTCCCT | 240 |
| GCTCGCTTCA GTGGCAGTGG GTCTGGGACC TCTTATTCTC TCACAATCAG CAGCATGGAG | 300 |
| GCTGAAGATG CTGCCACTTA TTACTGCCAT CAGCGGAATA GTTACCCATG GACGTTCGGT | 360 |
| GGAGGCACCA GGCTGGAAAT CAGA | 384 |

(2) INFORMATION FOR SEQ ID NO:15:

(i) SEQUENCE CHARACTERISTICS:
        (A) LENGTH: 128 amino acids
        (B) TYPE: amino acid
        (D) TOPOLOGY: linear (ii) MOLECULE TYPE: peptide (v) FRAGMENT TYPE: N-terminal (ix) FEATURE:
        (A) NAME/KEY: Peptide
        (B) LOCATION: 1..128
        (D) OTHER INFORMATION: /note= "Chimeric 128.1 Light Chain
           V Region"

(xi) SEQUENCE DESCRIPTION: SEQ ID NO:15:

Met Asp Phe Gln Val Gln Ile Phe Ser Phe Leu Leu Ile Ser Ala Ser
1               5                   10              15

Val Ile Leu Ser Arg Gly Gln Ile Val Leu Thr Gln Ser Pro Ala Ile
           20                  25              30

Met Ser Val Ser Pro Gly Glu Lys Val Thr Met Thr Cys Ser Ala Ser
        35                  40              45

Ser Ser Ile Arg Tyr Ile His Trp Tyr Gln Gln Arg Pro Gly Thr Ser
    50                  55              60

Pro Lys Arg Trp Ile Tyr Asp Thr Ser Asn Leu Ala Ser Gly Val Pro
65              70                  75              80

Ala Arg Phe Ser Gly Ser Gly Ser Gly Thr Ser Tyr Ser Leu Thr Ile
        85                  90              95

Ser Ser Met Glu Ala Glu Asp Ala Ala Thr Tyr Tyr Cys His Gln Arg
        100                105            110

Asn Ser Tyr Pro Trp Thr Phe Gly Gly Gly Thr Arg Leu Glu Ile Arg
        115                120            125

(2) INFORMATION FOR SEQ ID NO:16:

(i) SEQUENCE CHARACTERISTICS:
        (A) LENGTH: 411 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (ix) FEATURE:
        (A) NAME/KEY: misc_feature
        (B) LOCATION: 1..411
        (D) OTHER INFORMATION: /function= "Chimeric 128.1 Heavy
           Chain V Region"

(xi) SEQUENCE DESCRIPTION: SEQ ID NO:16:

| ATGGAATGGA GCTGGGTAAT GCTCTTCCTC CTGTCAGGAA CTGCAGGTGT CCGCTCTGAG | 60 |

```
GTCCAGCTGC AACAGTCTGG ACCTGAACTG GTGAAGCCTG GAGCTTCAAT GAAGATTTCC      120

TGCAAGGCTT CTGGTTACTC ATTCACTGGC TACACCATGA ACTGGGTGAA GCAGAGCCAT      180

GGAGAGAACC TTGAGTGGAT TGGACGTATT AATCCTCACA ATGGTGGTAC TGACTACAAC      240

CAGAAGTTCA AGGACAAGGC CCCTTTAACT GTAGACAAGT CATCCAACAC AGCCTACATG      300

GAGCTCCTCA GTCTGACATC TGGGGACTCT GCAGTCTATT ACTGTGCAAG AGGCTACTAT      360

TACTATTCTT TGGACTACTG GGGTCAAGGA ACCTCAGTCA CCGTCTCCTC A               411
```

(2) INFORMATION FOR SEQ ID NO:17:

(i) SEQUENCE CHARACTERISTICS:
        (A) LENGTH: 137 amino acids
        (B) TYPE: amino acid
        (D) TOPOLOGY: linear (ii) MOLECULE TYPE: peptide (v) FRAGMENT TYPE: N-terminal (ix) FEATURE:
        (A) NAME/KEY: Peptide
        (B) LOCATION: 1..137
        (D) OTHER INFORMATION: /note= "Chimeric 128.1 Heavy Chain
           V-Region"

(xi) SEQUENCE DESCRIPTION: SEQ ID NO:17:

```
Met Glu Trp Ser Trp Val Met Leu Phe Leu Leu Ser Gly Thr Ala Gly
1               5                   10                  15

Val Arg Ser Glu Val Gln Leu Gln Gln Ser Gly Pro Glu Leu Val Lys
            20                  25                  30

Pro Gly Ala Ser Met Lys Ile Ser Cys Lys Ala Ser Gly Tyr Ser Phe
        35                  40                  45

Thr Gly Tyr Thr Met Asn Trp Val Lys Gln Ser His Gly Glu Asn Leu
    50                  55                  60

Glu Trp Ile Gly Arg Ile Asn Pro His Asn Gly Gly Thr Asp Tyr Asn
65                  70                  75                  80

Gln Lys Phe Lys Asp Lys Ala Pro Leu Thr Val Asp Lys Ser Ser Asn
                85                  90                  95

Thr Ala Tyr Met Glu Leu Leu Ser Leu Thr Ser Gly Asp Ser Ala Val
            100                 105                 110

Tyr Tyr Cys Ala Arg Gly Tyr Tyr Tyr Ser Leu Asp Tyr Trp Gly
        115                 120                 125

Gln Gly Thr Ser Val Thr Val Ser Ser
    130                 135
```

(2) INFORMATION FOR SEQ ID NO:18:

(i) SEQUENCE CHARACTERISTICS:
        (A) LENGTH: 11528 base pairs
        (B) TYPE: nucleic acid
        (C) STRANDEDNESS: double
        (D) TOPOLOGY: circular (ii) MOLECULE TYPE: DNA (genomic)

(iii) HYPOTHETICAL: NO (iv) ANTI-SENSE: NO (vii) IMMEDIATE SOURCE:
        (B) CLONE: pAH4602

(ix) FEATURE:
        (A) NAME/KEY: misc_feature
        (B) LOCATION: 1..11528

(D) OTHER INFORMATION: /note= "Function="Expression Vector Coding Sequence""

(xi) SEQUENCE DESCRIPTION: SEQ ID NO:18:

```
CGTTGTCAGA AGTAAGTTGG CCGCAGTGTT ATCACTCATG GTTATGGCAG CACTGCATAA      60
TTCTCTTACT GTCATGCCAT CCGTAAGATG CTTTTCTGTG ACTGGTGAGT ACTCAACCAA     120
GTCATTCTGA GAATAGTGTA TGCGGCGACC GAGTTGCTCT TGCCCGGCGT CAACACGGGA     180
TAATACCGCG CCACATAGCA GAACTTTAAA AGTGCTCATC ATTGGAAAAC GTTCTTCGGG     240
GCGAAAACTC TCAAGGATCT TACCGCTGTT GAGATCCAGT TCGATGTAAC CCACTCGTGC     300
ACCCAACTGA TCTTCAGCAT CTTTTACTTT CACCAGCGTT TCTGGGTGAG CAAAAACAGG     360
AAGGCAAAAT GCCGCAAAAA AGGGAATAAG GGCGACACGG AAATGTTGAA TACTCATACT     420
CTTCCTTTTT CAATATTATT GAAGCATTTA TCAGGGTTAT TGTCTCATGA GCGGATACAT     480
ATTTGAATGT ATTTAGAAAA ATAAACAAAT AGGGGTTCCG CGCACATTTC CCCGAAAAGT     540
GCCACCTGAC GTCTAAGAAA CCATTATTAT CATGACATTA ACCTATAAAA ATAGGCGTAT     600
CACGAGGCCC TTTCGTCTTC AAGAATTCAG AGAGGTCTGG TGGAGCCTGC AAAAGTCCAG     660
CTTTCAAAGG AACACAGAAG TATGTGTATG GAATATTAGA AGATGTTGCT TTTACTCTTA     720
AGTTGGTTCC TAGGAAAAAT AGTTAAATAC TGTGACTTTA AAATGTGAGA GGGTTTTCAA     780
GTACTCATTT TTTTAAATGT CCAAAATTTT TGTCAATCAA TTTGAGGTCT TGTTTGTGTA     840
GAACTGACAT TACTTAAAGT TTAACCGAGG AATGGGAGTG AGGCTCTCTC ATACCCTATT     900
CAGAACTGAC TTTTAACAAT AATAAATTAA GTTTAAAATA TTTTTAAATG AATTGAGCAA     960
TGTTGAGTTG AGTCAAGATG GCCGATCAGA ACCGGAACAC CTGCAGCAGC TGGCAGGAAG    1020
CAGGTCATGT GGCAAGGCTA TTTGGGGAAG GGAAAATAAA ACCACTAGGT AAACTTGTAG    1080
CTGTGGTTTG AAGAAGTGGT TTTGAAACAC TCTGTCCAGC CCCACCAAAC CGAAAGTCCA    1140
GGCTGAGCAA ACACCACCT GGGTAATTTG CATTTCTAAA ATAAGTTGAG GATTCAGCCG    1200
AAACTGGAGA GGTCCTCTTT TAACTTATTG AGTTCAACCT TTTAATTTTA GCTTGAGTAG    1260
TTCTAGTTTC CCCAAACTTA AGTTTATCGA CTTCTAAAAT GTATTTAGAA TTCCTTTGCC    1320
TAATATTAAT GAGGACTTAA CCTGTGGAAA TATTTTGATG TGGGAAGCTG TTACTGTTAA    1380
AACTGAGGTT ATTGGGGTAA CTGCTATGTT AAACTTGCAT TCAGGACAC AAAAAACTCA    1440
TGAAAATGGT GCTGGAAAAC CCATTCAAGG GTCAAATTTT CATTTTTTTG CTGTTGGTGG    1500
GGAACCTTTG GAGCTGCAGG GTGTGTTAGC AAACTACAGG ACCAAATATC CTGCTCAAAC    1560
TGTAACCCCA AAAATGCTA CAGTTGACAG TCAGCAGATG AACACTGACC ACAAGGCTGT    1620
TTTGGATAAG GATAATGCTT ATCCAGTGGA GTGCTGGGTT CCTGATCCAA GTAAAAATGA    1680
AAACACTAGA TATTTTGGAA CCTACACAGG TGGGGAAAAT GTGCCTCCTG TTTTGCACAT    1740
TACTAACACA GCAACCACAG TGCTGCTTGA TGAGCAGGGT GTTGGGCCCT TGTGCAAAGC    1800
TGACAGCTTG TATGTTTCTG CTGTTGACAT TTGTGGGCTG TTTACCAACA CTTCTGGAAC    1860
ACAGCAGTGG AAGGGACTTC CCAGATATTT TAAAATTACC CTTAGAAAGC GGTCTGTGAA    1920
AAACCCCTAC CCAATTTCCT TTTTGTTAAG TGACCTAATT AACAGGAGGA CACAGAGGGT    1980
GGATGGGCAG CCTATGATTG GAATGTCCTC TCAAGTAGAG GAGGTTAGGG TTTATGAGGA    2040
CACAGAGGAG CTTCCTGGGG ATCCGATCCN NNNNNNNNNN NNNNNNNNNN NNNNNNNNNN    2100
NNNNNNNNNN NNNNNNNNNN NNNNNNNNNN NNNNNNNNNN NNNNNNNNNN NNNNNNNNNN    2160
NNNNNNNNNN NNNNNNNNNN NNNNNNNNNN NNNNNNNNNN NNNNNNNNNN NNNNNNNNNN    2220
NNNNNNNNNN NNNNNNNNNN NNNNNNNNNN NNNNNNNNNN NNNNNNNNNN NNNNNNNNNN    2280
```

| | | | | | | |
|---|---|---|---|---|---|---|
| NNNNNNNNNN | NNNNNNNNNN | NNNNNNNNNN | NNNNNNNNNN | NNNNNNNNNN | NNNNNNNNNN | 2340 |
| NNNNNNNNNN | NNNNNNNNNN | NNNNNNNNNN | NNNNNNNNNN | NNNNNNNNNN | NNNNNNNNNN | 2400 |
| NNNNNNNNNN | NNNNNNNNNN | NNNNNNNNNN | NNNNNNNNNN | NNNNNNNNNN | NNNNNNNNNN | 2460 |
| NNNNNNNNNN | NNNNNNNNNN | NNNNNNNNNN | NNNNNNNNNN | NNNNNNNNNN | NNNNNNNNNN | 2520 |
| NNNNNNNNNN | NNNNNNNNNN | NNNNNNNNNN | NNNNNNNNNN | NNNNNNNNNN | NNNNNNNNNN | 2580 |
| NNNNNNNNNN | NNNNNNNNNN | NNNNNNNNNN | NNNNNNNNNN | NNNNNNNNNN | NNNNNNNNNN | 2640 |
| NNNNNNNNNN | NNNNNNNNNN | NNNNNNNNNN | NNNNNNNNNN | NNNNNNNNNN | NNNNNNNNNN | 2700 |
| NNNNNNNNNN | NNNNNNNNNN | NNNNNNNNNN | NNNNNNNNNN | NNNNNNNNNN | NNNNNNNNNN | 2760 |
| NNNNNNNNNN | NNNNNNNNNN | NNNNNNNNNN | NNNNNNNNNN | NNNNNNNNNN | NNNNNNNNNN | 2820 |
| NNNNNNNNNN | NNNNNNNNNN | NNNNNNNNNN | NNNNNNNNNN | NNNNNNNNNN | NNNNNNNNNN | 2880 |
| NNNNNNNNNN | NNNNNNNNNN | NNNNNNNNNN | NNNNNNNNNN | NNNNNNNNNN | NNNNNNNNNN | 2940 |
| NNNNNNNNNN | NNNNNNNNNN | NNNNNNNNNN | NNNNNNNNNN | NNNNNNNNNN | NNNNNNNNNN | 3000 |
| NNNNNNNNNN | NNNNNNNNNN | NNNNNNNNNN | NNNNNNNNNN | NNNNNNNNNN | NNNNNNNNNN | 3060 |
| NNNNNNNNNN | NNNNNNNNNN | NNNNNNNNNN | NNNNNNNNNN | NNNNNNNNNN | NNNNNNNNNN | 3120 |
| NNNNNNNNNN | NNNNNNNNNN | NNNNNNNNNN | NNNNNNNNNN | NNNNNNNNNN | NNNNNNNNNN | 3180 |
| NNNNNNNNNN | NNNNNNNNNN | NNNNNNNNNN | NNNNNNNNNN | NNNNNNNNNN | NNNNNNNNNN | 3240 |
| NNNNNNNNNN | NNNNNNNNNN | NNNNNNNNNN | NNNNNNNNNN | NNNNNNNNNN | NNNNNNNNNN | 3300 |
| NNNNNNNNNN | NNNNNNNNNN | NNNNNNNNNN | NNNNNNNNNN | NNNNNNNNNN | NNNNNNNNNN | 3360 |
| NNNNNNNNNN | NNNNNNNNNN | NNNNNNNNNN | NNNNNNNNNN | NNNNNNNNNN | NNNNNNNNNN | 3420 |
| NNNNNNNNNN | NNNNNNNNNN | NNNNNNNNNN | NNNNNNNNNN | NNNNNNNNNN | NNNNNNNNNN | 3480 |
| NNNNNNNNNN | NNNNNNNNNN | NNNNNNNNNN | NNNNNNNNNN | NNNNNNNNNN | NNNNNNNNNN | 3540 |
| NNNNNNNNNN | NNNNNNNNNN | NNNNNNNNNN | NNNNNNNNNN | NNNNNNNNNN | NNNNNNNNNN | 3600 |
| NNNNNNNNNN | NNNNNNNNNN | NNNNNNNNNN | NNNNNNNNNN | NNNNNNNNNN | NNNNNNNNNN | 3660 |
| NNNNNNNNNN | NNNNNNNNNN | NNNNNNNNNN | NNNNNNNNNN | NNNNNNNNNN | NNNNNNNNNN | 3720 |
| NNNNNNNNNN | NNNNNNNNNN | NNNNNNNNNN | NNNNNNNNNN | NNNNNNNNNA | TATAGCACAA | 3780 |
| AGACATGCAA | ATAATATTTC | CCTATGCTCA | TAAAAACAGC | CCTGACCATG | AAGCTTTGAC | 3840 |
| AGACGCACAA | CCCTGGACTC | CCAAGTCTTT | CTCTTCAGTG | ACAAACACAG | ACATAGGATA | 3900 |
| TCCACCATGG | AATGGAGCTG | GGTAATGCTC | TTCCTCCTGT | CAGGAACTGC | AGGTGTCCGC | 3960 |
| TCTGAGGTCC | AGCTGCAACA | GTCTGGACCT | GAACTGGTGA | AGCCTGGAGC | TTCAATGAAG | 4020 |
| ATTTCCTGCA | AGGCTTCTGG | TTACTCATTC | ACTGGCTACA | CCATGAACTG | GGTGAAGCAG | 4080 |
| AGCCATGGAG | AGAACCTTGA | GTGGATTGGA | CGTATTAATC | CTCACAATGG | TGGTACTGAC | 4140 |
| TACAACCAGA | AGTTCAAGGA | CAAGGCCCCT | TTAACTGTAG | ACAAGTCATC | CAACACAGCC | 4200 |
| TACATGGAGC | TCCTCAGTCT | GACATCTGAG | GACTCTGCAG | TCTATTACTG | TGCAAGAGGC | 4260 |
| TACTATTACT | ATTCTTTGGA | CTACTGGGGT | CAAGGAACCT | CAGTCACCGT | CTCCTCAGCT | 4320 |
| AGCACCAAGG | GCCCATCGGT | CTTCCCCCTG | GCACCCTCCT | CCAAGAGCAC | CTCTGGGGGC | 4380 |
| ACAGCGGCCC | TGGGCTGCCT | GGTCAAGGAC | TACTTCCCCG | AACCGGTGAC | GGTGTCGTGG | 4440 |
| AACTCAGGCG | CCCTGACCAG | CGGCGTGCAC | ACCTTCCCGG | CTGTCCTACA | GTCCTCAGGA | 4500 |
| CTCTACTCCC | TCAGCAGCGT | GGTGACCGTG | CCCTCCAGCA | GCTTGGGCAC | CCAGACCTAC | 4560 |
| ATCTGCAACG | TGAATCACAA | GCCCAGCAAC | ACCAAGGTGG | ACAAGAAAGT | TGGTGAGAGG | 4620 |
| CCAGCACAGG | GAGGGAGGGT | GTCTGCTGGA | AGCAGGCTCA | GCGCTCCTGC | CTGGACGCAT | 4680 |

```
CCCGGCTATG CAGCCCCAGT CCAGGGCAGC AAGGCAGGCC CCGTCTGCCT CTTCACCCGG    4740

AGCCTCTGCC CGCCCCACTC ATGCTCAGGG AGAGGGTCTT CTGGCTTTTT CCCAGGCTCT    4800

GGGCAGGCAC AGGCTAGGTG CCCCTAACCC AGGCCCTGCA CACAAAGGGG CAGGTGCTGG    4860

GCTCAGACCT GCCAAGAGCC ATATCCGGGA GGACCCTGCC CCTGACCTAA GCCCACCCCA    4920

AAGGCCAAAC TCTCCACTCC CTCAGCTCGG ACACCTTCTC TCCTCCCAGA TTCCAGTAAC    4980

TCCCAATCTT CTCTCTGCAG AGCCCAAATC TTGTGACAAA ACTCACACAT GCCCACCGTG    5040

CCCAGGTAAG CCAGCCCAGG CCTCGCCCTC CAGCTCAAGG CGGGACAGGT GCCCTAGAGT    5100

AGCCTGCATC CAGGGACAGG CCCCAGCCGG GTGCTGACAC GTCCACCTCC ATCTCTTCCT    5160

CAGCACCTGA ACTCCTGGGG GGACCGTCAG TCTTCCTCTT CCCCCCAAAA CCCAAGGACA    5220

CCCTCATGAT CTCCCGGACC CCTGAGGTCA CATGCGTGGT GGTGGACGTG AGCCACGAAG    5280

ACCCTGAGGT CAAGTTCAAC TGGTACGTGG ACGGCGTGGA GGTGCATAAT GCCAAGACAA    5340

AGCCGCGGGA GGAGCAGTAC AACAGCACGT ACCGGGTGGT CAGCGTCCTC ACCGTCCTGC    5400

ACCAGGACTG GCTGAATGGC AAGGAGTACA AGTGCAAGGT CTCCAACAAA GCCCTCCCAG    5460

CCCCCATCGA GAAAACCATC TCCAAAGCCA AAGGTGGGAC CCGTGGGGTG CGAGGGCCAC    5520

ATGGACAGAG GCCGGCTCGG CCCACCCTCT GCCCTGAGAG TGACCGCTGT ACCAACCTCT    5580

GTCCTACAGG GCAGCCCCGA GAACCACAGG TGTACACCCT GCCCCCATCC CGGGATGAGC    5640

TGACCAAGAA CCAGGTCAGC CTGACCTGCC TGGTCAAAGG CTTCTATCCC AGCGACATCG    5700

CCGTGGAGTG GGAGAGCAAT GGGCAGCCGG AGAACAACTA CAAGACCACG CCTCCCGTGC    5760

TGGACTCCGA CGGCTCCTTC TTCCTCTACA GCAAGCTCAC CGTGGACAAG AGCAGGTGGC    5820

AGCAGGGGAA CGTCTTCTCA TGCTCCGTGA TGCATGAGGC TCTGCACAAC CACTACACGC    5880

AGAAGAGCCT CTCCCTGTCT CCGGGTAAAT GAGTGCGACG GCCGGCAAGC CCCGCTCCCC    5940

GGGCTCTCGC GGTCGCACGA GGATGCTTGG CACGTACCCC CTGTACATAC TTCCCGGGCG    6000

CCCAGCATGG AAATAAAGCA CCCAGCGCTG CCCTGGGCCC CTGCGAGACT GTGATGGTTC    6060

TTTCCACGGG TCAGGCCGAG TCTGAGGCCT GAGTGGCATG AGGGAGGCAG AGCGGGTCNA    6120

ANNNNNNNNN NNNNNNNNNN NNNNNNNNNN NNNNNNNNNN NNNNNNNNNN NNNNNNNNNN    6180

NNNNNNNNNN NNNNNNNNNN NNNNNNNNNN NNNNNNNNNN NNNNNNNNNN NNNNNNNNNN    6240

NNNNNNNNNN NNNNNNNNNN NNNNNNNNNN NNNNNNNNNN NNNNNNNNNN NNNNNNNNNN    6300

NNNNNNNNNN NNNNNNNNNN NNNNNNNNNN NNNNNNNNNN NNNNNNNNNN NNNNNNNNNN    6360

NNNNNNNNNN NNNNNNNNNN NNNNNNNNNN NNNNNNNNNN NNNNNNNNNN NNNNNNNNNN    6420

NNNNNNNNNN NNNNNNNNNN NNNNNNNNNN NNNNNNNNNN NNNNNNNNNN NNNNNNNNNN    6480

NNNNNNNNNN NNNNNNNNNN NNNNNNNNNN NNNNNNNNNN NNNNNNNNNN NNNNNNNNNN    6540

NNNNNNNNNN NNNNNNNNNN NNNNNNNNNN NNNNNNNNNN NNNNNNNNNN NNNNNNNNNN    6600

NNNNNNNNNN NNNNNNNNNN NNNNNNNNNN NNNNNNNNNN NNNNNNNNNN NNNNNNNNNN    6660

NNNNNNNNNN NNNNNNNNNN NNNNNNNNNN NNNNNNNNNN NNNNNNNNNN NNNNNNNNNN    6720

NNNNNNNNNN NNNNNNNNNN NNNNNNNNNN NNNNNNNNNN NNNNNNNNNN NNNNNNNNNN    6780

NNNNNNNNNN NNNNNNNNNN NNNNNNNNNN NNNNNNNNNN NNNNNNNNNN NNNNNNNNNN    6840

NNNNNNNNNN NNNNNNNNNN NNNNNNNNNN NNNNNNNNNN NNNNNNNNNN NNNNNNNNNN    6900

NNNNNNNNNN NNNNNNNNNN NNNNNNNNNN NNNNNNNNNN NNNNNNNNNN NNNNNNNNNN    6960

NNNNNNNNNN NNNNNNNNNN NNNNNNNNNN NNNNNNNNNN NNNNNNNNNN NNNNNNNNNN    7020

NNNNNNNNNN NNNNNNNNNN NNNNNNNNNN NNNNNNNNNN NNNNNNNNNN NNNNNNNNNN    7080
```

-continued

```
NNNNNNNNNN NNNNNNNNNN NNNNNNNNNN NNNNNNNNNN NNNNNNNNNN NNNNNNNNNN    7140

NNNNNNNNNN NNNNNNNNNN NNNNNNNNNN NNNNNNNNNN NNNNNNNNNN NNNNNNNNNN    7200

NNNNNNNNNN NNNNNNNNNN NNNNNNNNNN NNNNNNNNNN NNNNNNNNNN NNNNNNNNNN    7260

NNNNNNNNNN NNNNNNNNNN NNNNNNNNNN NNNNNNNNNN NNNNNNNNNN NNNNNNNNNN    7320

NGGATCCAGA CATGATAAGA TACATTGATG AGTTTGGACA AACCACAACT AGAATGCAGT    7380

GAAAAAAATG CTTTATTTGT GAAATTTGTG ATGCTATTGC TTTATTTGTA ACCATTATAA    7440

GCTGCAATAA ACAAGTTAAC AACAACAATT GCATTCATTT TATGTTTCAG GTTCAGGGGG    7500

AGGTGTGGGA GGTTTTTTAA AGCAAGTAAA ACCTCTACAA ATGTGGTATG GCTGATTATG    7560

ATCTCTAGTC AAGGCACTAT ACATCAAATA TTCCTTATTA ACCCCTTTAC AAATTAAAAA    7620

GCTAAAGGTA CACAATTTTT GAGCATAGTT ATTAATAGCA GACACTCTAT GCCTGTGTGG    7680

AGTAAGAAAA AACAGTATGT TATGATTATA ACTGTTATGC CTACTTATAA AGGTTACAGA    7740

ATATTTTTCC ATAATTTTCT TGTATAGCAG TGCAGCTTTT TCCTTTGTGG TGTAAATAGC    7800

AAAGCAAGCA AGAGTTCTAT TACTAAACAC AGCATGACTC AAAAAACTTA GCAATTCTGA    7860

AGGAAAGTCC TTGGGGTCTT CTACCTTTCT CTTCTTTTTT GGAGGAGTAG AATGTTGAGA    7920

GTCAGCAGTA GCCTCATCAT CACTAGATGG CATTTCTTCT GAGCAAAACA GGTTTTCCTC    7980

ATTAAAGGCA TTCCACCACT GCTCCCATTC ATCAGTTCCA TAGGTTGGAA TCTAAAATAC    8040

ACAAACAATT AGAATCAGTA GTTAACACA TTATACACTT AAAAATTTTA TATTTACCTT    8100

ATAGCTTTAA ATCTCTGTAG GTAGTTTGTC CAATTATGTC ACACCACAGA AGTAAGGTTC    8160

CTTCACAAAG ATCCGGNNNN NNNNNNNNNN NNNNNNNNNN NTCATGCTTG CTCCTTGAGG    8220

GCGTTAACGC GCAAGGTAAC GGCATTTTTA TGGGCGGTCA GACGTTCGGC GGCGGCCAGT    8280

GTTTCTATGG TTGAAGCCAC CGCGGAGAAC CCCTCTTTCG ACAGTTCCTG TACGGTCATA    8340

CGCTTCTGGA AATCTGCCAG CCCGAGGCTG GAACAGGTGG CGGTGTAACC GTAAGTCGGT    8400

AGAACGTGGT TGGTTCCGGA GGCGTAATCA CCTGCCGATT CCGGTGACCA GTCACCAAGA    8460

AATACCGAAC CGGCGCTGGT GATGCTATCG ACCAGTTCAC GGGCGTTGCG GGTCTGAATG    8520

ATCAGGTGCT CCGGGCCGTA CTGATTAGAG ATCTCCACGC ACTGCGCTGA ATCTTTAGTC    8580

ACGATCAGGC GGCTGGCGTT CAGTGCCTGG CGGGCGGTTT CGGCACGCGG CAGTTCCGCC    8640

AGTTGGCGTT CGACGGCCTC GGCAACGCGA CGCGCCATAT CAGCAGCGGG CGTCAGTAAA    8700

ATCACCTGTG AGTCCGGGCC GTGTTCAGCC TGAGAGAGCA AATCAGAAGC CACGAAATCC    8760

GGCGTTGCGC CGCTGTCAGC AATCACCAGC ACTTCCGACG GGCCTGCGGG CATATCGATC    8820

TCCGCACCGT CCAGACGCTG GCTCACCTGA CGTTTCGCTT CGGTGACAAA GGCGTTACCC    8880

GGCCCGAAGA TTTTGTCCAC TTTTGGCACG GATTCCGTAC CAAACGCCAG TGCGGCAATG    8940

GCCTGTGCGC CGCCGACGTT GAACACGTCC TGCACACCGC ACAGCTGCGC CGCATAAAGG    9000

ATCTCATCGG CAATCGGCGG CGGTGAGCAC AGCACCACTT TTTTACAGCC CGCAATACGC    9060

GCCGGAGTCG CCAGCATTAA TACCGTTGAG AAGAGCGGGG CGGAGCCGCC AGGAATATAC    9120

AACCCAACTG AAGCTACCGG ACGCGTGACC TGCTGGCAAC GCACGCCTGG CTGCGTTTCT    9180

ACATCTACCG GCGGCAGTTT TTGCGCAGTG TGGAAGGTTT CAATATTCTT TACTGCCACC    9240

GCCATCGCCT GTTTTAGCTC GTCGCTCAGG CGTTCGCTGG CGGCGGCGAT CTCCTCTGCA    9300

GACACCTTCA GCGCGGTAAC CGTGGTTTTA TCAAACTTCG CGCTGTATTC CCGCAGGGCC    9360

TCATCGCCGC GTGCTTTCAC GTTATCGAGA ATATCGTTAA CAGTGCGGGT AATGCTTTCA    9420

GAGGCGGAAA TCGCCGGGCG CGTTAACAGC TGGCGTTGTT GCACCGCAGT ACAGCTATTC    9480
```

```
CAGTCAATGA TTGTGTTAAA GCTCATNNNN CCGGATCAGC TTTTTGCAAA AGCCTAGGCC    9540

TCCAAAAAAG CCTCCTCACT ACTTCTGGAA TAGCTCAGAG GCCGAGGCGC CTCGGCCTCT    9600

GCATAAATAA AAAAAATTAG TCAGCCATGG GGCGGAGAAT GGGCGGAACT GGGCGGAGTT    9660

AGGGGCGGGA TGGGCGGAGT TAGGGGCGGG ACTATGGTTG CTGACTAATT GAGATGCATG    9720

CTTTGCATAC TTCTGCCTGC TGGGGAGCCT GGGGACTTTC CACACCTGGT TGCTGACTAA    9780

TTGAGATGCA TGCTTTGCAT ACTTCTGCCT GCTGGGGAGC CTGGGGACTT CCACACCCT     9840

AACTGACACA CATTCCACAG CTGCCTCGCG CGTTTCGGTG ATGACGGTGA AAACCTCTGA    9900

CACATGCAGC TCCCGGAGAC GGTCACAGCT TGTCTGTAAG CGGATGCCGG GAGCAGACAA    9960

GCCCGTCAGG GCGCGTCAGC GGGTGTTGGC GGGTGTCGGG GCGCAGCCAT GACCCAGTCA   10020

CGTAGCGATA GCGGAGTGTA TACTGGCTTA ACTATGCGGC ATCAGAGCAG ATTGTACTGA   10080

GAGTGCACCA TATGCGGTGT GAAATACCGC ACAGATGCGT AAGGAGAAAA TACCGCATCA   10140

GGCGCTCTTC CGCTTCCTCG CTCACTGACT CGCTGCGCTC GGTCGTTCGG CTGCGGCGAG   10200

CGGTATCAGC TCACTCAAAG GCGGTAATAC GGTTATCCAC AGAATCAGGG GATAACGCAG   10260

GAAAGAACAT GTGAGCAAAA GGCCAGCAAA AGGCCAGGAA CCGTAAAAAG GCCGCGTTGC   10320

TGGCGTTTTT CCATAGGCTC CGCCCCCCTG ACGAGCATCA CAAAAATCGA CGCTCAAGTC   10380

AGAGGTGGCG AAACCCGACA GGACTATAAA GATACCAGGC GTTTCCCCCT GGAAGCTCCC   10440

TCGTGCGCTC TCCTGTTCCG ACCCTGCCGC TTACCGGATA CCTGTCCGCC TTTCTCCCTT   10500

CGGGAAGCGT GGCGCTTTCT CAATGCTCAC GCTGTAGGTA TCTCAGTTCG GTGTAGGTCG   10560

TTCGCTCCAA GCTGGGCTGT GTGCACGAAC CCCCCGTTCA GCCCGACCGC TGCGCCTTAT   10620

CCGGTAACTA TCGTCTTGAG TCCAACCCGG TAAGACACGA CTTATCGCCA CTGGCAGCAG   10680

CCACTGGTAA CAGGATTAGC AGAGCGAGGT ATGTAGGCGG TGCTACAGAG TTCTTGAAGT   10740

GGTGGCCTAA CTACGGCTAC ACTAGAAGGA CAGTATTTGG TATCTGCGCT CTGCTGAAGC   10800

CAGTTACCTT CGGAAAAAGA GTTGGTAGCT CTTGATCCGG CAAACAAACC ACCGCTGGTA   10860

GCGGTGGTTT TTTTGTTTGC AAGCAGCAGA TTACGCGCAG AAAAAAAGGA TCTCAAGAAG   10920

ATCCTTTGAT CTTTTCTACG GGGTCTGACG CTCAGTGGAA CGAAAACTCA CGTTAAGGGA   10980

TTTTGGTCAT GAGATTATCA AAAAGGATCT TCACCTAGAT CCTTTTAAAT TAAAAATGAA   11040

GTTTTAAATC AATCTAAAGT ATATATGAGT AAACTTGGTC TGACAGTTAC CAATGCTTAA   11100

TCAGTGAGGC ACCTATCTCA GCGATCTGTC TATTTCGTTC ATCCATAGTT GCCTGACTCC   11160

CCGTCGTGTA GATAACTACG ATACGGGAGG GCTTACCATC TGGCCCCAGT GCTGCAATGA   11220

TACCGCGAGA CCCACGCTCA CCGGCTCCAG ATTTATCAGC AATAAACCAG CCAGCCGGAA   11280

GGGCCGAGCG CAGAAGTGGT CCTGCAACTT TATCCGCCTC CATCCAGTCT ATTAATTGTT   11340

GCCGGGAAGC TAGAGTAAGT AGTTCGCCAG TTAATAGTTT GCGCAACGTT GTTGCCATTG   11400

CTGCAGGCAT CGTGGTGTCA CGCTCGTCGT TTGGTATGGC TTCATTCAGC TCCGGTTCCC   11460

AACGATCAAG GCGAGTTACA TGATCCCCCA TGTTGTGCAA AAAAGCGGTT AGCTCCTTCG   11520

GTCCTCCG                                                            11528
```

(2) INFORMATION FOR SEQ ID NO:19:

(i) SEQUENCE CHARACTERISTICS:
        (A) LENGTH: 235 amino acids
        (B) TYPE: amino acid
        (D) TOPOLOGY: linear (ii) MOLECULE TYPE: protein (iii) HYPOTHETICAL: NO (iv) ANTI-SENSE: NO (v) FRAGMENT TYPE: N-terminal (xi) SEQUENCE DESCRIPTION: SEQ ID NO:19:

```
Met Glu Trp Ser Trp Val Met Leu Phe Leu Leu Ser Gly Thr Ala Gly
1               5                   10                  15

Val Arg Ser Glu Val Gln Leu Gln Gln Ser Gly Pro Glu Leu Val Lys
            20                  25                  30

Pro Gly Ala Ser Met Lys Ile Ser Cys Lys Ala Ser Gly Tyr Ser Phe
        35                  40                  45

Thr Gly Tyr Thr Met Asn Trp Val Lys Gln Ser His Gly Glu Asn Leu
    50                  55                  60

Glu Trp Ile Gly Arg Ile Asn Pro His Asn Gly Gly Thr Asp Tyr Asn
65                  70                  75                  80

Gln Lys Phe Lys Asp Lys Ala Pro Leu Thr Val Asp Lys Ser Ser Asn
            85                  90                  95

Thr Ala Tyr Met Glu Leu Leu Ser Leu Thr Ser Glu Asp Ser Ala Val
            100                 105                 110

Tyr Tyr Cys Ala Arg Gly Tyr Tyr Tyr Ser Leu Asp Tyr Trp Gly
        115                 120                 125

Gln Gly Thr Ser Val Thr Val Ser Ser Ala Ser Thr Lys Gly Pro Ser
    130                 135                 140

Val Phe Pro Leu Ala Pro Ser Ser Lys Ser Thr Ser Gly Gly Thr Ala
145                 150                 155                 160

Ala Leu Gly Cys Leu Val Lys Asp Tyr Phe Pro Glu Pro Val Thr Val
            165                 170                 175

Ser Trp Asn Ser Gly Ala Leu Thr Ser Gly Val His Thr Phe Pro Ala
            180                 185                 190

Val Leu Gln Ser Ser Gly Leu Tyr Ser Leu Ser Ser Val Val Thr Val
            195                 200                 205

Pro Ser Ser Ser Leu Gly Thr Gln Thr Tyr Ile Cys Asn Val Asn His
    210                 215                 220

Lys Pro Ser Asn Thr Lys Val Asp Lys Lys Val
225                 230                 235
```

(2) INFORMATION FOR SEQ ID NO:20:

(i) SEQUENCE CHARACTERISTICS:
        (A) LENGTH: 15 amino acids
        (B) TYPE: amino acid
        (D) TOPOLOGY: linear (ii) MOLECULE TYPE: protein (v) FRAGMENT TYPE: internal (xi) SEQUENCE DESCRIPTION: SEQ ID NO:20:

```
Glu Pro Lys Ser Cys Asp Lys Thr His Thr Cys Pro Pro Cys Pro
1               5                   10                  15
```

(2) INFORMATION FOR SEQ ID NO:21:

(i) SEQUENCE CHARACTERISTICS:
        (A) LENGTH: 110 amino acids
        (B) TYPE: amino acid
        (D) TOPOLOGY: linear (ii) MOLECULE TYPE: protein (v) FRAGMENT TYPE: internal (xi) SEQUENCE DESCRIPTION: SEQ ID NO:21:

```
Ala Pro Glu Leu Leu Gly Gly Pro Ser Val Phe Leu Phe Pro Pro Lys
1               5                   10                  15

Pro Lys Asp Thr Leu Met Ile Ser Arg Thr Pro Glu Val Thr Cys Val
                20                  25                  30

Val Val Asp Val Ser His Glu Asp Pro Glu Val Lys Phe Asn Trp Tyr
            35                  40                  45

Val Asp Gly Val Glu Val His Asn Ala Lys Thr Lys Pro Arg Glu Glu
    50                  55                  60

Gln Tyr Asn Ser Thr Tyr Arg Val Val Ser Val Leu Thr Val Leu His
65                  70                  75                  80

Gln Asp Trp Leu Asn Gly Lys Glu Tyr Lys Cys Lys Val Ser Asn Lys
                85                  90                  95

Ala Leu Pro Ala Pro Ile Glu Lys Thr Ile Ser Lys Ala Lys
                100                 105                 110
```

(2) INFORMATION FOR SEQ ID NO:22:

(i) SEQUENCE CHARACTERISTICS:
        (A) LENGTH: 107 amino acids
        (B) TYPE: amino acid
        (D) TOPOLOGY: linear (ii) MOLECULE TYPE: protein (v) FRAGMENT TYPE: internal (xi) SEQUENCE DESCRIPTION: SEQ ID NO:22:

```
Gly Gln Pro Arg Glu Pro Gln Val Tyr Thr Leu Pro Pro Ser Arg Asp
1               5                   10                  15

Glu Leu Thr Lys Asn Gln Val Ser Leu Thr Cys Leu Val Lys Gly Phe
                20                  25                  30

Tyr Pro Ser Asp Ile Ala Val Glu Trp Glu Ser Asn Gly Gln Pro Glu
            35                  40                  45

Asn Asn Tyr Lys Thr Thr Pro Pro Val Leu Asp Ser Asp Gly Ser Phe
    50                  55                  60

Phe Leu Tyr Ser Lys Leu Thr Val Asp Lys Ser Arg Trp Gln Gln Gly
65                  70                  75                  80

Asn Val Phe Ser Cys Ser Val Met His Glu Ala Leu His Asn His Tyr
                85                  90                  95

Thr Gln Lys Ser Leu Ser Leu Ser Pro Gly Lys
                100                 105
```

(2) INFORMATION FOR SEQ ID NO:23:

(i) SEQUENCE CHARACTERISTICS:
        (A) LENGTH: 434 amino acids
        (B) TYPE: amino acid
        (D) TOPOLOGY: linear (ii) MOLECULE TYPE: protein (ix) FEATURE:
        (A) NAME/KEY: Protein
        (B) LOCATION: 1..434
        (D) OTHER INFORMATION: /note= "Translation from
            complementary DNA."

(xi) SEQUENCE DESCRIPTION: SEQ ID NO:23:

Met Ser Phe Asn Thr Ile Ile Asp Trp Asn Ser Cys Thr Ala Val Gln

```
 1               5                10               15
Gln Arg Gln Leu Leu Thr Arg Pro Ala Ile Ser Ala Ser Glu Ser Ile
                20                25               30

Thr Arg Thr Val Asn Asp Ile Leu Asp Asn Val Lys Ala Arg Gly Asp
        35              40              45

Glu Ala Leu Arg Glu Tyr Ser Ala Lys Phe Asp Lys Thr Thr Val Thr
    50              55              60

Ala Leu Lys Val Ser Ala Glu Glu Ile Ala Ala Ala Ser Glu Arg Leu
65              70              75              80

Ser Asp Glu Leu Lys Gln Ala Met Ala Val Ala Val Lys Asn Ile Glu
                85              90              95

Thr Phe His Thr Ala Gln Lys Leu Pro Pro Val Asp Val Glu Thr Gln
            100             105             110

Pro Gly Val Arg Cys Gln Gln Val Thr Arg Pro Val Ala Ser Val Gly
        115             120             125

Leu Tyr Ile Pro Gly Gly Ser Ala Pro Leu Phe Ser Thr Val Leu Met
    130             135             140

Leu Ala Thr Pro Ala Arg Ile Ala Gly Cys Lys Lys Val Val Leu Cys
145             150             155             160

Ser Pro Pro Pro Ile Ala Asp Glu Ile Leu Tyr Ala Ala Gln Leu Cys
                165             170             175

Gly Val Gln Asp Val Phe Asn Val Gly Gly Ala Gln Ala Ile Ala Ala
            180             185             190

Leu Ala Phe Gly Thr Glu Ser Val Pro Lys Val Asp Lys Ile Phe Gly
        195             200             205

Pro Gly Asn Ala Phe Val Thr Glu Ala Lys Arg Gln Val Ser Gln Arg
    210             215             220

Leu Asp Gly Ala Glu Ile Asp Met Pro Ala Gly Pro Ser Glu Val Leu
225             230             235             240

Val Ile Ala Asp Ser Gly Ala Thr Pro Asp Phe Val Ala Ser Asp Leu
                245             250             255

Leu Ser Gln Ala Glu His Gly Pro Asp Ser Gln Val Ile Leu Leu Thr
            260             265             270

Pro Ala Ala Asp Met Ala Arg Arg Val Ala Glu Ala Val Glu Arg Gln
        275             280             285

Leu Ala Glu Leu Pro Arg Ala Glu Thr Ala Arg Gln Ala Leu Asn Ala
    290             295             300

Ser Arg Leu Ile Val Thr Lys Asp Ser Ala Gln Cys Val Glu Ile Ser
305             310             315             320

Asn Gln Tyr Gly Pro Glu His Leu Ile Ile Gln Thr Arg Asn Ala Arg
                325             330             335

Glu Leu Val Asp Ser Ile Thr Ser Ala Gly Ser Val Phe Leu Gly Asp
            340             345             350

Trp Ser Pro Glu Ser Ala Gly Asp Tyr Ala Ser Gly Thr Asn His Val
        355             360             365

Leu Pro Thr Tyr Gly Tyr Thr Ala Thr Cys Ser Ser Leu Gly Leu Ala
    370             375             380

Asp Phe Gln Lys Arg Met Thr Val Gln Glu Leu Ser Lys Glu Gly Phe
385             390             395             400

Ser Ala Val Ala Ser Thr Ile Glu Thr Leu Ala Ala Ala Glu Arg Leu
                405             410             415

Thr Ala His Lys Asn Ala Val Thr Leu Arg Val Asn Ala Leu Lys Glu
            420             425             430
```

Gln Ala (2) INFORMATION FOR SEQ ID NO:24:

(i) SEQUENCE CHARACTERISTICS:
        (A) LENGTH: 13999 base pairs
        (B) TYPE: nucleic acid
        (C) STRANDEDNESS: double
        (D) TOPOLOGY: circular (ii) MOLECULE TYPE: DNA (genomic)

(vii) IMMEDIATE SOURCE:
        (B) CLONE: pAG4611

(ix) FEATURE:
        (A) NAME/KEY: misc_feature
        (B) LOCATION: 1..13999
        (D) OTHER INFORMATION: /note= "Function = "Expression
            Vector Coding Sequence""

(xi) SEQUENCE DESCRIPTION: SEQ ID NO:24:

```
TTGCAAGCTT TTTGCAAAAG CCTAGGCCTC CAAAAAAGCC TCCTCACTAC TTCTGGAATA      60

GCTCAGAGGC CGAGGCGCCT CGGCCTCTGC ATAAATAAAA AAAATTAGTC AGCCATGGGG     120

CGGAGAATGG GCGGAACTGG GCGGAGTTAG GGGCGGGATG GCGGAGTTA GGGGCGGGAC     180

TATGGTTGCT GACTAATTGA GATGCATGCT TTGCATACTT CTGCCTGCTG GGGAGCCTGG     240

GGACTTTCCA CACCTGGTTG CTGACTAATT GAGATGCATG CTTTGCATAC TTCTGCCTGC     300

TGGGGAGCCT GGGGACTTTC CACACCCTAA CTGACACACA TTCCACAGCT GCCTCGCGCG     360

TTTCGGTGAT GACGGTGAAA ACCTCTGACA CATGCAGCTC CCGGAGACGG TCACAGCTTG     420

TCTGTAAGCG GATGCCGGGA GCAGACAAGC CCGTCAGGGC GCGTCAGCGG GTGTTGGCGG     480

GTGTCGGGGC GCAGCCATGA CCCAGTCACG TAGCGATAGC GGAGTGTATA CTGGCTTAAC     540

TATGCGGCAT CAGAGCAGAT TGTACTGAGA GTGCACCATA TGCGGTGTGA AATACCGCAC     600

AGATGCGTAA GGAGAAAATA CCGCATCAGG CGCTCTTCCG CTTCCTCGCT CACTGACTCG     660

CTGCGCTCGG TCGTTCGGCT GCGGCGAGCG GTATCAGCTC ACTCAAAGGC GGTAATACGG     720

TTATCCACAG AATCAGGGGA TAACGCAGGA AGAACATGT GAGCAAAAGG CCAGCAAAAG     780

GCCAGGAACC GTAAAAAGGC CGCGTTGCTG GCGTTTTTCC ATAGGCTCCG CCCCCCTGAC     840

GAGCATCACA AAAATCGACG CTCAAGTCAG AGGTGGCGAA ACCCGACAGG ACTATAAAGA     900

TACCAGGCGT TTCCCCCTGG AAGCTCCCTC GTGCGCTCTC CTGTTCCGAC CTGCCGCTT     960

ACCGGATACC TGTCCGCCTT TCTCCCTTCG GGAAGCGTGG CGCTTTCTCA ATGCTCACGC    1020

TGTAGGTATC TCAGTTCGGT GTAGGTCGTT CGCTCCAAGC TGGGCTGTGT GCACGAACCC    1080

CCCGTTCAGC CCGACCGCTG CGCCTTATCC GGTAACTATC GTCTTGAGTC AACCCGGTA    1140

AGACACGACT TATCGCCACT GGCAGCAGCC ACTGGTAACA GGATTAGCAG AGCGAGGTAT    1200

GTAGGCGGTG CTACAGAGTT CTTGAAGTGG TGGCCTAACT ACGGCTACAC TAGAAGGACA    1260

GTATTTGGTA TCTGCGCTCT GCTGAAGCCA GTTACCTTCG GAAAAAGAGT TGGTAGCTCT    1320

TGATCCGGCA AACAAACCAC CGCTGGTAGC GGTGGTTTTT TTGTTTGCAA GCAGCAGATT    1380

ACGCGCAGAA AAAAGGATC TCAAGAAGAT CCTTTGATCT TTTCTACGGG GTCTGACGCT    1440

CAGTGGAACG AAAACTCACG TTAAGGGATT TTGGTCATGA GATTATCAAA AAGGATCTTC    1500

ACCTAGATCC TTTTAAATTA AAAATGAAGT TTTAAATCAA TCTAAAGTAT ATATGAGTAA    1560

ACTTGGTCTG ACAGTTACCA ATGCTTAATC AGTGAGGCAC CTATCTCAGC GATCTGTCTA    1620

TTTCGTTCAT CCATAGTTGC CTGACTCCCC GTCGTGTAGA TAACTACGAT ACGGGAGGGC    1680
```

```
TTACCATCTG GCCCCAGTGC TGCAATGATA CCGCGAGACC CACGCTCACC GGCTCCAGAT     1740

TTATCAGCAA TAAACCAGCC AGCCGGAAGG GCCGAGCGCA GAAGTGGTCC TGCAACTTTA     1800

TCCGCCTCCA TCCAGTCTAT TAATTGTTGC CGGGAAGCTA GAGTAAGTAG TTCGCCAGTT     1860

AATAGTTTGC GCAACGTTGT TGCCATTGCT GCAGGCATCG TGGTGTCACG CTCGTCGTTT     1920

GGTATGGCTT CATTCAGCTC CGGTTCCCAA CGATCAAGGC GAGTTACATG ATCCCCCATG     1980

TTGTGCAAAA AAGCGGTTAG CTCCTTCGGT CCTCGATCGT TGTCAGAAGT AAGTTGGCCG     2040

CAGTGTTATC ACTCATGGTT ATGGCAGCAC TGCATAATTC TCTTACTGTC ATGCCATCCG     2100

TAAGATGCTT TTCTGTGACT GGTGAGTACT CAACCAAGTC ATTCTGAGAA TAGTGTATGC     2160

GGCGACCGAG TTGCTCTTGC CCGGCGTCAA CACGGGATAA TACCGCGCCA CATAGCAGAA     2220

CTTTAAAAGT GCTCATCATT GGAAAACGTT CTTCGGGGCG AAAACTCTCA AGGATCTTAC     2280

CGCTGTTGAG ATCCAGTTCG ATGTAACCCA CTCGTGCACC CAACTGATCT TCAGCATCTT     2340

TTACTTTCAC CAGCGTTTCT GGGTGAGCAA AAACAGGAAG GCAAAATGCC GCAAAAAAGG     2400

GAATAAGGGC GACACGGAAA TGTTGAATAC TCATACTCTT CCTTTTTCAA TATTATTGAA     2460

GCATTTATCA GGGTTATTGT CTCATGAGCG GATACATATT TGAATGTATT TAGAAAAATA     2520

AACAAATAGG GGTTCCGCGC ACATTTCCCC GAAAAGTGCC ACCTGACGTC TAAGAAACCA     2580

TTATTATCAT GACATTAACC TATAAAAATA GGCGTATCAC GAGGCCCTTT CGTCTTCAAG     2640

AATTCCTTTG CCTAATATTA ATGAGGACTT AACCTGTGGA ATATTTTGA TGTGGGAAGC      2700

TGTTACTGTT AAAACTGAGG TTATTGGGGT AACTGCTATG TTAAACTTGC ATTCAGGGAC     2760

ACAAAAAACT CATGAAAATG GTGCTGGAAA ACCCATTCAA GGGTCAAATT TTCATTTTTT     2820

TGCTGTTGGT GGGGAACCTT TGGAGCTGCA GGGTGTGTTA GCAAACTACA GGACCAAATA     2880

TCCTGCTCAA ACTGTAACCC CAAAAAATGC TACAGTTGAC AGTCAGCAGA TGAACACTGA     2940

CCACAAGGCT GTTTTGGATA AGGATAATGC TTATCCAGTG GAGTGCTGGG TTCCTGATCC     3000

AAGTAAAAAT GAAAACACTA GATATTTTGG AACCTACACA GGTGGGAAA ATGTGCCTCC      3060

TGTTTTGCAC ATTACTAACA CAGCAACCAC AGTGCTGCTT GATGAGCAGG GTGTTGGGCC     3120

CTTGTGCAAA GCTGACAGCT TGTATGTTTC TGCTGTTGAC ATTTGTGGGC TGTTTACCAA     3180

CACTTCTGGA ACACAGCAGT GGAAGGGACT TCCCAGATAT TTTAAAATTA CCCTTAGAAA     3240

GCGGTCTGTG AAAAACCCCT ACCCAATTTC CTTTTTGTTA AGTGACCTAA TTAACAGGAG     3300

GACACAGAGG GTGGATGGGC AGCCTATGAT TGGAATGTCC TCTCAAGTAG AGGAGGTTAG     3360

GGTTTATGAG GACACAGAGG AGCTTCCTGG GATCCNNNNN NNNNNNNNNN NNNNNNNNNN     3420

NNNNNNNNNN NNNNNNNNNN NNNNNNNNNN NNNNNNNNNN NNNNNNNNNN NNNNNNNNNN     3480

NNNNNNNNNN NNNNNNNNNN NNNNNNNNNN NNNNNNNNNN NNNNNNNNNN NNNNNNNNNN     3540

NNNNNNNNNN NNNNNNNNNN NNNNNNNNNN NNNNNNNNNN NNNNNNNNNN NNNNNNNNNN     3600

NNNNNNNNNN NNNNNNNNNN NNNNNNNNNN NNNNNNNNNN NNNNNNNNNN NNNNNNNNNN     3660

NNNNNNNNNN NNNNNNNNNN NNNNNNNNNN NNNNNNNNNN NNNNNNNNNN NNNNNNNNNN     3720

NNNNNNNNNN NNNNNNNNNN NNNNNNNNNN NNNNNNNNNN NNNNNNNNNN NNNNNNNNNN     3780

NNNNNNNNNN NNNNNNNNNN NNNNNNNNNN NNNNNNNNNN NNNNNNNNNN NNNNNNNNNN     3840

NNNNNNNNNN NNNNNNNNNN NNNNNNNNNN NNNNNNNNNN NNNNNNNNNN NNNNNNNNNN     3900

NNNNNNNNNN NNNNNNNNNN NNNNNNNNNN NNNNNNNNNN NNNNNNNNNN NNNNNNNNNN     3960

NNNNNNNNNN NNNNNNNNNN NNNNNNNNNN NNNNNNNNNN NNNNNNNNNN NNNNNNNNNN     4020

NNNNNNNNNN NNNNNNNNNN NNNNNNNNNN NNNNNNNNNN NNNNNNNNNN NNNNNNNNNN     4080
```

```
NNNNNNNNNN NNNNNNNNNN NNNNNNNNNN NNNNNNNNNN NNNNNNNNNN NNNNNNNNNN      4140

NNNNNNNNNN NNNNNNNNNN NNNNNNNNNN NNNNNNNNNN NNNNNNNNNN NNNNNNNNNN      4200

NNNNNNNNNN NNNNNNNNNN NNNNNNNNNN NNNNNNNNNN NNNNNNNNNN NNNNNNNNNN      4260

NNNNNNNNNN NNNNNNNNNN NNNNNNNNNN NNNNNNNNNN NNNNNNNNNN NNNNNNNNNN      4320

NNNNNNNNNN NNNNNNNNNN NNNNNNNNNN NNNNNNNNNN NNNNNNNNNN NNNNNNNNNN      4380

NNNNNNNNNN NNNNNNNNNN NNNNNNNNNN NNNNNNNNNN NNNNNNNNNN NNNNNNNNNN      4440

NNNNNNNNNN NNNNNNNNNN NNNNNNNNNN NNNNNNNNNN NNNNNNNNNN NNNNNNNNNN      4500

NNNNNNNNNN NNNNNNNNNN NNNNNNNNNN NNNNNNNNNN NNNNNNNNNN NNNNNNNNNN      4560

NNNNNNNNNN NNNNNNNNNN NNNNNNNNNN NNNNNNNNNN NNNNNNNNNN NNNNNNNNNN      4620

NNNNNNNNNN NNNNNNNNNN NNNNNNNNNN NNNNNNNNNN NNNNNNNNNN NNNNNNNNNN      4680

NNNNNNNNNN NNNNNNNNNN NNNNNNNNNN NNNNNNNNNN NNNNNNNNNN NNNNNNNNNN      4740

NNNNNNNNNN NNNNNNNNNN NNNNNNNNNN NNNNNNNNNN NNNNNNNNNN NNNNNNNNNN      4800

NNNNNNNNNN NNNNNNNNNN NNNNNNNNNN NNNNNNNNNN NNNNNNNNNN NNNNNNNNNN      4860

NNNNNNNNNN NNNNNNNNNN NNNNNNNNNN NNNNNNNNNN NNNNNNNNNN NNNNNNNNNN      4920

NNNNNNNNNN NNNNNNNNNN NNNNNNNNNN NNNNNNNNNN NNNNNNNNNN NNNNNNNNNN      4980

NNNNNNNNNN NNNNNNNNNN NNNNNNNNNN NNNNNNNNNN NNNNNNNNNN NNNNNNNNNN      5040

NNNNNNNNNN NNNNNNNNNN NNNNNNNNNN NNNNNNNNNN NNNNNNNNNN NNNNNATATA      5100

GCACAAAGAC ATGCAAATAA TATTTCCCTA TGCTCATAAA AACAGCCCTG ACCATGAAGC      5160

TTTGACAGAC GCACAACCCT GGACTCCCAA GTCTTTCTCT TCAGTGACAA ACACAGACAT      5220

AGGATATCCA CCATGGATTT TCAAGTGCAG ATTTTCAGCT TCCTGCTAAT CAGTGCCTCA      5280

GTCATACTGT CCAGAGGACA AATTGTTCTC ACCCAGTCTC CAGCAATCAT GTCTGCATCT      5340

CCAGGGAGA AGGTCACCAT GACCTGCAGT GCCAGCTCAA GTATAGATTA CATTCACTGG      5400

TACCAGCAGA AGTCAGGCAC CTCCCCCAAA AGATGGATTT ATGACACATC CAAACTGGCT      5460

TCTGGAGTCC CTGCTCGCTT CAGTGGCAGT GGGTCTGGGA CCTCTTATTC TCTCACAATC      5520

AGCAGCATGG AGCCTGAAGA TGCTGCCACT TATTACTGCC ATCAGCGGAA TAGTTACCCA      5580

TGGACGTTCG GTGGAGGGAC CAGGCTGGAA ATCAGACGTA AGTCGACTTT CTCATCTTTT      5640

TTTATGTGTA AGACACAGGT TTTCATGTTA GGAGTTAAAG TCAGTTCAGA AAATCTTGAG      5700

AAAATGGAGA GGGCTCATTA TCAGTTGACG TGGCATACAG TGTCAGATTT TCTGTTTATC      5760

AAGCTAGTGA GATTAGGGGC AAAAAGAGGC TTTAGTTGAG AGGAAAGTAA TTAATACTAT      5820

GGTCACCATC CAAGAGATTG GATCGGAGAA TAAGCATGAG TAGTTATTGA GATCTGGGTC      5880

TGACTGCAGG TAGCGTGGTC TTCTAGACGT TTAAGTGGGA GATTTGGAGG GGATGAGGAA      5940

TGAAGGAACT TCAGGATAGA AAAGGGCTGA AGTCAAGTTC AGCTCCTAAA ATGGATGTGG      6000

GAGCAAACTT TGAAGATAAA CTGAATGACC CAGAGGATGA AACAGCGCAG ATCAAAGAGG      6060

GGCCTAGAGC TCTGAGAAGA GAAGGAGACT CATCCGTGTT GAGTTTCCAC AAGTACTGTC      6120

TTGAGTTTTG CAATAAAAGT GGGATAGCAG AGTTGAGTGT NAGCCGTANA GTATACTCTC      6180

TTTTGTCTCC TAAGATTTTT ATGACTACAA AAATCAGTAG TATGTCCTGA ATAATCATT      6240

AAGCTGTTTG AAAGTATGAC TGCTTGCCAT GTAGATACCA TGGCTTGCTG AATGATCAGA      6300

AGAGGTGTGA CTCTTATTCT AAAATTTGTC ACAAAATGTC AAAATGAGAG ACTCTGTAGG      6360

AACGAGTCCC TTGACAGACA GCTGCAAGGG GTTTTTTTCC TTTGTCTCAT TTCTACATGA      6420

AAGTAAATTT GAAATGATCN TTTTTTATTA TAAGAGTAGA AATACAGTTG GGTTTGAACT      6480
```

```
ATATGTTTTA ATNGGCCNCA CGGTTTTGTA AGACATTTGG TCCTTTGTTT TCCCAGTTAT    6540

TACTCGATTG TAATTTTATA TCGCCAGCAN TGGTCTGAAA CGGTNNNNNN CGCAACCTCT    6600

TCGTTTACTA ACTGGGTGAC CTTCGGCTGT GCCAGCCATT TGGCGTTCAC CCTGCCGCNG    6660

GCCNATGAGA ACCCCCGCGG TAGNNCCCTT GCTCCGCGTG GACCACTTTC CTGAGGACAC    6720

AGTGATAGGA ACAGAGCCAC TAATCTGAAG AGAACAGAGA TGTGACAGAC TACACTAATG    6780

TGAGAAAAAC AAGGAAAGGG TGACTTATTG GAGATTTCAG AAATAAAATG CATTTATTAT    6840

TATATTCCCT TATTTTAATT TTCTATTAGG GAATTAGAAA GGGCATAAAC TGCTTTATCC    6900

AGTGTTATAT TAAAAGCTTN NNNNNNNNNN NNNNNNNNNN NNNNNNNNNN NNNNNNNNNN    6960

NNNNNNNNNN NNNNNNNNNN NNNNNNNNNN NNNNNNNNNN NNNNNNNNNN NNNNNNNNNN    7020

NNNNNNNNNN NNNNNNNNNN NNNNNNNNNN NNNNNNNNNN NNNNNNNNNN NNNNNNNNNN    7080

NNNNNNNNNN NNNNNNNNNN NNNNNNNNNN NNNNNNNNNN NNNNNNNNNN NNNNNNNNNN    7140

NNNNNNNNNN NNNNNNNNNN NNNNNNNNNN NNNNNNNNNN NNNNNNNNNN NNNNNNNNNN    7200

NNNNNNNNNN NNNNNNNNAA TCATTTCAAA ATGATTTTAG AGAGCCTTTT GAAAACTCTT    7260

TTAAACACTT TTTAAACTCT ATTAAAACTA ATAAGATAAC TTGAAATAAT TTTCATGTCA    7320

AATACATTAA CTGTTTAATG TTTAAATGCC AGATGAAAAA TGTAAAGCTA TCAAGAATTC    7380

ACCCAGATAG GAGTATCTTC ATAGCATGTT TTTCCCTGCT TATTTCCAG TGATCACATT     7440

ATTTTGCTAC CATGGTTATT TTATACAATT ATCTGAAAAA AATTAGTTAT GAAGATTAAA    7500

AGAGAAGAAA ATATTAAACA TAAGAGATTC AGTCTTTCAT GTTGAACTGC TTGGTTAACA    7560

GTGAAGTTAG TTTTAAAAAA AAAAAAAACT ATTTCTGTTA TCAGCTGACT TCTCCCTATC    7620

TGTTGACTTC TCCCAGCAAA AGATTCTTAC TTATTTTACA TTTTAACCTA CTGCTCTCCC    7680

ACCCAACGGG TGGAATCCCC CAGAGGGGGA TTTCCAAGAG GCCACCTGGC AGTTGCTGAG    7740

GGTCAGAAGT GAAGCTAGCC ACTTCCTCTT AGGCAGGTGG CCAAGATTAC AGTTGACCTC    7800

TCCTGGTATG GCTGAAAATT GCTGCATATG GTTACAGGCC TTGAGGCTTT GGGAGGGCTT    7860

AGAGAGAGTT GCTGGAACAG TCAGAAGGTG GAGGGGCTGA CACCACCCAG GCGCAGAGGC    7920

AGGGCTCAGG GCCTGCTCTG CAGGGAGGTT TTAGCCCAGC CCAGCCAAAG TAACCCCCGG    7980

GAGCCTGTTA TCCCAGCACA GTCCTGGAAG AGGCACAGGG GAAATAAAAG CGGACGGAGG    8040

CTTTCCTTGA CTCAGCCGCT GCCTGGTCTT CTTCAGACCT GTTCTGAATT CTAAACTCTG    8100

AGGGGGTCGG ATGACGTGGC CATTCTTTGC CTAAAGCATT GAGTTTACTG CAAGGTCAGA    8160

AAAGCATGCA AAGCCCTCAG AATGGCTGCA AAGAGCTCCA ACAAAACAAT TTAGAACTTT    8220

ATTAAGGAAT AGGGGGAAGC TAGGAAGAAA CTCAAAACAT CAAGATTTTA AATACGCTTC    8280

TTGGTCTCCT TGCTATAATT ATCTGGGATA AGCATGCTGT TTTCTGTCTG TCCCTAACAT    8340

GCCCTGTGAT TATCCGCAAA CAACACACCC AAGGGCAGAA CTTTGTTACT TAAACACCAT    8400

CCTGTTTGCT TCTTTCCTCA GGAACTGTGG CTGCACCATC TGTCTTCATC TTCCCGCCAT    8460

CTGATGAGCA GTTGAAATCT GGAACTGCCT CTGTTGTGTG CCTGCTGAAT AACTTCTATC    8520

CCAGAGAGGC CAAAGTACAG TGGAAGGTGG ATAACGCCCT CCAATCGGGT AACTCCCAGG    8580

AGAGTGTCAC AGAGCAGGAC AGCAAGGACA GCACCTACAG CCTCAGCAGC ACCCTGACGC    8640

TGAGCAAAGC AGACTACGAG AAACACAAAG TCTACGCCTG CGAAGTCACC CATCAGGGCC    8700

TGAGCTCGCC CGTCACAAAG AGCTTCAACA GGGGAGAGTG TTAGAGGGAG AAGTGCCCCC    8760

ACCTGCTCCT CAGTTCCAGC CTGACCCCCT CCCATCCTTT GGCCTCTGAC CCTTTTTCCA    8820

CAGGGGACCT ACCCCTATTG CGGTCCTCCA GCTCATCTTT CACCTCACCC CCTCCTCCT    8880
```

```
CCTTGGCTTT AATTATGCTA ATGTTGGAGG AGAATGAATA AATAAAGTGA ATCTTTGCAC     8940

CTGTGGTTTC TCTCTTTCCT CAATTTAATA ATTATTATCT GTTGTTTACC AACTACTCAA     9000

TTTCTCTTAT AAGGGACTAA ATATGTAGTC ATCCTAAGGC GCATAACCAT TTATAAAAAT     9060

CATCCTTCAT TCTATTTTAC CCTATCATCC TCTGCAAGAC AGTCCTCCCT CAAACCCACA     9120

AGCCTTCTGT CCTCACAGTC CCCTGGGCCG TGGTAGGAGA GACTTGCTTC CTTGTTTTCC     9180

CCTCCTCAGC AAGCCCTCAT AGTCCTTTTT AAGGGTGACA GGTCTTACGG TCATATATCC     9240

TTTGATTCAA TTCCCTGGGA ATCAACCAAG GCAAATTTTT CAAAAGAAGA AACCTGCNAN     9300

NNNNNNNNNN NNNNNNNNNN NNNNNNNNNN NNNNNNNNNN NNNNNNNNNN NNNNNNNNNN     9360

NNNNNNNNNN NNNNNNNNNN NNNNNNNNNN NNNNNNNNNN NNNNNNNNNN NNNNNNNNNN     9420

NNNNNNNNNN NNNNNNNNNN NNNNNNNNNN NNNNNNNNNN NNNNNNNNNN NNNNNNNNNN     9480

NNNNNNNNNN NNNNNNNNNN NNNNNNNNNN NNNNNNNNNN NNNNNNNNNN NNNNNNNNNN     9540

NNNNNNNNNN NNNNNNNNNN NNNNNNNNNN NNNNNNNNNN NNNNNNNNNN NNNNNNNNNN     9600

NNNNNNNNNN NNNNNNNNNN NNNNNNNNNN NNNNNNNNNN NNNNNNNNNN NNNNNNNNNN     9660

NNNNNNNNNN NNNNNNNNNN NNNNNNNNNN NNNNNNNNNN NNNNNNNNNN NNNNNNNNNN     9720

NNNNNNNNNN NNNNNNNNNN NNNNNNNNNN NNNNNNNNNN NNNNNNNNNN NNNNNNNNNN     9780

NNNNNNNNNN NNNNNNNNNN NNNNNNNNNN NNNNNNNNNN NNNNNNNNNN NNNNNNNNNN     9840

NNNNNNNNNN NNNNNNNNNN NNNNNNNNNN NNNNNNNNNN NNNNNNNNNN NNNNNNNNNN     9900

NNNNNNNNNN NNNNNNNNNN NNNNNNNNNN NNNNNNNNNN NNNNNNNNNN NNNNNNNNNN     9960

NNNNNNNNNN NNNNNNNNNN NNNNNNNNNN NNNNNNNNNN NNNNNNNNNN NNNNNNNNNN    10020

NNNNNNNNNN NNNNNNNNNN NNNNNNNNNN NNNNNNNNNN NNNNNNNNNN NNNNNNNNNN    10080

NNNNNNNNNN NNNNNNNNNN NNNNNNNNNN NNNNNNNNNN NNNNNNNNNN NNNNNNNNNN    10140

NNNNNNNNNN NNNNNNNNNN NNNNNNNNNN NNNNNNNNNN NNNNNNNNNN NNNNNNNNNN    10200

NNNNNNNNNN NNNNNNNNNN NNNNNNNNNN NNNNNNNNNN NNNNNNNNNN NNNNNNNNNN    10260

NNNNNNNNNN NNNNNNNNNN NNNNNNNNNN NNNNNNNNNN NNNNNNNNNN NNNNNNNNNN    10320

NNNNNNNNNN NNNNNNNNNN NNNNNNNNNN NNNNNNNNNN NNNNNNNNNN NNNNNNNNNN    10380

NNNNNNNNNN NNNNNNNNNN NNNNNNNNNN NNNNNNNNNN NNNNNNNNNN NNNNNNNNNN    10440

NNNNNNNNNN NNNNNNNNNN NNNNNNNNNN NNNNNNNNNN NNNNNNNNNN NNNNNNNNNN    10500

NNNNNNNNNN NNNNNNNNNN NNNNNNNNNN NNNNNNNNNN NNNNNNNNNN NNNNNNNNNN    10560

NNNNNNNNNN NNNNNNNNNN NNNNNNNNNN NNNNNNNNNN NNNNNNNNNN NNNNNNNNNN    10620

NNNNNNNNNN NNNNNNNNNN NNNNNNNNNN NNNNNNNNNN NNNNNNNNNN NNNNNNNNNN    10680

NNNNNNNNNN NNNNNNNNNN NNNNNNNNNN NNNNNNNNNN NNNNNNNNNN NNNNNNNNNN    10740

NNNNNNNNNN NNNNNNNNNN NNNNNNNNNN NNNNNNNNNN NNNNNNNNNN NNNNNNNNNN    10800

NNNNNNNNNN NNNNNNNNNN NNNNNNNNNN NNNNNNNNNN NNNNNNNNNN NNNNNNNNNN    10860

NNNNNNNNNN NNNNNNNNNN NNNNNNNNNN NNNNNNNNNN NNNNNNNNNN NNNNNNNNNN    10920

NNNNNNNNNN NNNNNNNNNN NNNNNNNNNN NNNNNNNNNN NNNNNNNNNN NNNNNNNNNN    10980

NNNNNNNNNN NNNNNNNNNN NNNNNNNNNN NNNNNNNNNN NNNNNNNNNN NNNNNNNNNN    11040

NNNNNNNNNN NNNNNNNNNN NNNNNNNNNN NNNNNNNNNN NNNNNNNNNN NNNNNNNNNN    11100

NNNNNNNNNN NNNNNNNNNN NNNNNNNNNN NNNNNNNNNN NNNNNNNNNN NNNNNNNNNN    11160

NNNNNNNNNN NNNNNNNNNN NNNNNNNNNN NNNNNNNNNN NNNNNNNNNN NNNNNNNNNN    11220

NNNNNNNNNN NNNNNNNNNN NNNNNNNNNN NNNNNNNNNN NNNNNNNNNN NNNNNNNNNN    11280
```

```
NNNNNNNNNN NNNNNNNNNN NNNNNNNNNN NNNNNNNNNN NNNNNNNNNN NNNNNNNNNN    11340
NNNNNNNNNN NNNNNNNNNN NNNNNNNNNN NNNNNNNNNN NNNNNNNNNN NNNNNNNNNN    11400
NNNNNNNNNN NNNNNNNNNN NNNNNNNNNN NNNNNNNNNN NNNNNNNNNN NNNNNNNGAT    11460
TCNNNNNNNN NNNNNNNNNN NNNNNNNNNN NNNNNNNNNN NNNNNNNNNN NNNNNNNNNN    11520
NNNNNNNNNN NNNNNNNNNN NNNNNNNNNN NNNNNNNNNN NNNNNNNNNN NNNNNNNNNN    11580
NNNNNNNNNN NNNNNNNNNN NNNNNNNNNN NNNNNNNNNN NNNNNNNNNN NNNNNNNNNN    11640
NNNNNNNNNN NNNNNNNNNN NNNNNNNNNN NNNNNNNNNN NNNNNNNNNN NNNNNNNNNN    11700
NNNNNNNNNN NNNNNNNNNN NNNNNNNNNN NNNNNNNNNN NNNNNNNNNN NNNNNNNNNN    11760
NNNNNNNNNN NNNNNNNNNN NNNNNNNNNN NNNNNNNNNN NNNNNNNNNN NNNNNNNNNN    11820
NNNNNNNNNN NNNNNNNNNN NNNNNNNNNN NNNNNNNNNN NNNNNNNNNN NNNNNNNNNN    11880
NNNNNNNNNN NNNNNNNNNN NNNNNNNNNN NNNNNNNNNN NNNNNNNNNN NNNNNNNNNN    11940
NNNNNNNNNN NNNNNNNNNN NNNNNNNNNN NNNNNNNNNN NNNNNNNNNN NNNNNNNNNN    12000
NNNNNNNNNN NNNNNNNNNN NNNNNNNNNN NNNNNNNNNN NNNNNNNNNN NNNNNNNNNN    12060
NNNNNNNNNN NNNNNNNNNN NNNNNNNNNN NNGGATCCAG ACATGATAAG ATACATTGAT    12120
GAGTTTGGAC AAACCACAAC TAGAATGCAG TGAAAAAAAT GCTTTATTTG TGAAATTTGT    12180
GATGCTATTG CTTTATTTGT AACCATTATA AGCTGCAATA AACAAGTTAA CAACAACAAT    12240
TGCATTCATT TTATGTTTCA GGTTCAGGGG GAGGTGTGGG AGGTTTTTTA AGCAAGTAA     12300
AACCTCTACA AATGTGGTAT GGCTGATTAT GATCTCTAGT CAAGGCACTA TACATCAAAT    12360
ATTCCTTATT AACCCCTTTA CAAATTAAAA AGCTAAAGGT ACACAATTTT TGAGCATAGT    12420
TATTAATAGC AGACACTCTA TGCCTGTGTG GAGTAAGAAA AAACAGTATG TTATGATTAT    12480
AACTGTTATG CCTACTTATA AAGGTTACAG AATATTTTTC CATAATTTTC TTGTATAGCA    12540
GTGCAGCTTT TTCCTTTGTG GTGTAAATAG CAAAGCAAGC AAGAGTTCTA TTACTAAACA    12600
CAGCATGACT CAAAAAACTT AGCAATTCTG AAGGAAAGTC CTTGGGGTCT TCTACCTTTC    12660
TCTTCTTTTT TGGAGGAGTA GAATGTTGAG AGTCAGCAGT AGCCTCATCA TCACTAGATG    12720
GCATTTCTTC TGAGCAAAAC AGGTTTTCCT CATTAAAGGC ATTCCACCAC TGCTCCCATT    12780
CATCAGTTCC ATAGGTTGGA ATCTAAAATA CACAAACAAT TAGAATCAGT AGTTTAACAC    12840
ATTATACACT TAAAAATTTT ATATTTACCT TATAGCTTTA AATCTCTGTA GGTAGTTTGT    12900
CCAATTATGT CACACCACAG AAGTAAGGTT CCTTCACAAA GATCGATCCG GGCCCACTC    12960
ATAAATCCAG TTGCCGCCAC GGTAGCCAAT CACCGTATCG TATAAATCAT CGCGGTACGT    13020
TCGGCATCGC TCATCACAAT ACGTGCCTGG ACGTCGAGGA TTTCGCGTGG GTCAATGCCG    13080
CGCCAGATCC ACATCAGACG GTTAATCATG CGATACCAGT GAGGGATGGT TTTACCATCA    13140
AGGGCCGACT GCACAGGCGG TTGTGCGCCG TGATTAAAGC GGCGGACTAG CGTCGAGGTT    13200
TCAGGATGTT TAAAGCGGGG TTTGAACAGG GTTTCGCTCA GGTTTGCCTG TGTCATGGAT    13260
GCAGCCTCCA GAATACTTAC TGGAAACTAT TGTAACCCGC CTGAAGTTAA AAAGAACAAC    13320
GCCCGGCAGT GCCAGGCGTT GAAAAGATTA GCGACCGGAG ATTGGCGGGA CGAATACGAC    13380
GCCCATATCC CACGGCTGTT CAATCCAGGT ATCTTGCGGG ATATCAACAA CATAGTCATC    13440
AACCAGCGGA CGACCAGCCG GTTTTGCGAA GATGGTGACA AAGTGCGCTT TTGGATACAT    13500
TTCACGAATC GCAACCGCAG TACCACCGGT ATCCACCAGG TCATCAATAA CGATGAAGCC    13560
TTCGCCATCG CCTTCTGCGC GTTTCAGCAC TTTAAGCTCG CGCTGGTTGT CGTGATCGTA    13620
GCTGGAAATA CAAACGGTAT CGACATGACG AATACCCAGT TCACGCGCCA GTAACGCACC    13680
```

-continued

```
CGGTACCAGA CCGCCACGGC TTACGGCAAT AATGCCTTTC CATTGTTCAG AAGGCATCAG    13740

TCGGCTTGCG AGTTTACGTG CATGGATCTG CAACATGTCC CAGGTGACGA TGTATTTTTC    13800

GCTCATGTGA AGTGTCCCAG CCTGTTTATC TACGGCTTAA AAAGTGTTCG AGGGGAAAAT    13860

AGGTTGCGCG AGATTATAGA GATCTGGCGC ACTAAAAACC AGTATTTCAC ATGAGTCCGC    13920

GTCTTTTTAC GCACTGCCTC TCCCTGACGC GGGATAAAGT GGTATTCTCA AACATATCTC    13980

GCAAGCCTGT CTTGTGTCC                                                 13999
```

(2) INFORMATION FOR SEQ ID NO:25:

(i) SEQUENCE CHARACTERISTICS:
        (A) LENGTH: 128 amino acids
        (B) TYPE: amino acid
        (D) TOPOLOGY: linear (ii) MOLECULE TYPE: protein (v) FRAGMENT TYPE: internal (xi) SEQUENCE DESCRIPTION: SEQ ID NO:25:

```
Met Asp Phe Gln Val Gln Ile Phe Ser Phe Leu Leu Ile Ser Ala Ser
 1               5                  10                  15

Val Ile Leu Ser Arg Gly Gln Ile Val Leu Thr Gln Ser Pro Ala Ile
             20                  25                  30

Met Ser Ala Ser Pro Gly Glu Lys Val Thr Met Thr Cys Ser Ala Ser
         35                  40                  45

Ser Ser Ile Asp Tyr Ile His Trp Tyr Gln Gln Lys Ser Gly Thr Ser
     50                  55                  60

Pro Lys Arg Trp Ile Tyr Asp Thr Ser Lys Leu Ala Ser Gly Val Pro
65                  70                  75                  80

Ala Arg Phe Ser Gly Ser Gly Ser Gly Thr Ser Tyr Ser Leu Thr Ile
                 85                  90                  95

Ser Ser Met Glu Pro Glu Asp Ala Ala Thr Tyr Tyr Cys His Gln Arg
            100                 105                 110

Asn Ser Tyr Pro Trp Thr Phe Gly Gly Gly Thr Arg Leu Glu Ile Arg
        115                 120                 125
```

(2) INFORMATION FOR SEQ ID NO:26:

(i) SEQUENCE CHARACTERISTICS:
        (A) LENGTH: 106 amino acids
        (B) TYPE: amino acid
        (D) TOPOLOGY: linear (ii) MOLECULE TYPE: protein (v) FRAGMENT TYPE: internal (xi) SEQUENCE DESCRIPTION: SEQ ID NO:26:

```
Thr Val Ala Ala Pro Ser Val Phe Ile Phe Pro Pro Ser Asp Glu Gln
 1               5                  10                  15

Leu Lys Ser Gly Thr Ala Ser Val Val Cys Leu Leu Asn Asn Phe Tyr
             20                  25                  30

Pro Arg Glu Ala Lys Val Gln Trp Lys Val Asp Asn Ala Leu Gln Ser
         35                  40                  45

Gly Asn Ser Gln Glu Ser Val Thr Glu Gln Asp Ser Lys Asp Ser Thr
     50                  55                  60

Tyr Ser Leu Ser Ser Thr Leu Thr Leu Ser Lys Ala Asp Tyr Glu Lys
65                  70                  75                  80

His Lys Val Tyr Ala Cys Glu Val Thr His Gln Gly Leu Ser Ser Pro
```

```
                85                  90                  95
Val Thr Lys Ser Phe Asn Arg Gly Glu Cys
            100                 105

(2) INFORMATION FOR SEQ ID NO:27:

(i) SEQUENCE CHARACTERISTICS:
        (A) LENGTH: 10785 base pairs
        (B) TYPE: nucleic acid
        (C) STRANDEDNESS: double
        (D) TOPOLOGY: circular (ii) MOLECULE TYPE: DNA (genomic)

(vii) IMMEDIATE SOURCE:
        (B) CLONE: pAH4625

(ix) FEATURE:
        (A) NAME/KEY: misc_feature
        (B) LOCATION: 1..10785
        (D) OTHER INFORMATION: /note= "Function = "Expression
            Vector Coding Sequence""

(xi) SEQUENCE DESCRIPTION: SEQ ID NO:27:

GATCCGATCC NNNNNNNNNN NNNNNNNNNN NNNNNNNNNN NNNNNNNNNN NNNNNNNNNN      60

NNNNNNNNNN NNNNNNNNNN NNNNNNNNNN NNNNNNNNNN NNNNNNNNNN NNNNNNNNNN     120

NNNNNNNNNN NNNNNNNNNN NNNNNNNNNN NNNNNNNNNN NNNNNNNNNN NNNNNNNNNN     180

NNNNNNNNNN NNNNNNNNNN NNNNNNNNNN NNNNNNNNNN NNNNNNNNNN NNNNNNNNNN     240

NNNNNNNNNN NNNNNNNNNN NNNNNNNNNN NNNNNNNNNN NNNNNNNNNN NNNNNNNNNN     300

NNNNNNNNNN NNNNNNNNNN NNNNNNNNNN NNNNNNNNNN NNNNNNNNNN NNNNNNNNNN     360

NNNNNNNNNN NNNNNNNNNN NNNNNNNNNN NNNNNNNNNN NNNNNNNNNN NNNNNNNNNN     420

NNNNNNNNNN NNNNNNNNNN NNNNNNNNNN NNNNNNNNNN NNNNNNNNNN NNNNNNNNNN     480

NNNNNNNNNN NNNNNNNNNN NNNNNNNNNN NNNNNNNNNN NNNNNNNNNN NNNNNNNNNN     540

NNNNNNNNNN NNNNNNNNNN NNNNNNNNNN NNNNNNNNNN NNNNNNNNNN NNNNNNNNNN     600

NNNNNNNNNN NNNNNNNNNN NNNNNNNNNN NNNNNNNNNN NNNNNNNNNN NNNNNNNNNN     660

NNNNNNNNNN NNNNNNNNNN NNNNNNNNNN NNNNNNNNNN NNNNNNNNNN NNNNNNNNNN     720

NNNNNNNNNN NNNNNNNNNN NNNNNNNNNN NNNNNNNNNN NNNNNNNNNN NNNNNNNNNN     780

NNNNNNNNNN NNNNNNNNNN NNNNNNNNNN NNNNNNNNNN NNNNNNNNNN NNNNNNNNNN     840

NNNNNNNNNN NNNNNNNNNN NNNNNNNNNN NNNNNNNNNN NNNNNNNNNN NNNNNNNNNN     900

NNNNNNNNNN NNNNNNNNNN NNNNNNNNNN NNNNNNNNNN NNNNNNNNNN NNNNNNNNNN     960

NNNNNNNNNN NNNNNNNNNN NNNNNNNNNN NNNNNNNNNN NNNNNNNNNN NNNNNNNNNN    1020

NNNNNNNNNN NNNNNNNNNN NNNNNNNNNN NNNNNNNNNN NNNNNNNNNN NNNNNNNNNN    1080

NNNNNNNNNN NNNNNNNNNN NNNNNNNNNN NNNNNNNNNN NNNNNNNNNN NNNNNNNNNN    1140

NNNNNNNNNN NNNNNNNNNN NNNNNNNNNN NNNNNNNNNN NNNNNNNNNN NNNNNNNNNN    1200

NNNNNNNNNN NNNNNNNNNN NNNNNNNNNN NNNNNNNNNN NNNNNNNNNN NNNNNNNNNN    1260

NNNNNNNNNN NNNNNNNNNN NNNNNNNNNN NNNNNNNNNN NNNNNNNNNN NNNNNNNNNN    1320

NNNNNNNNNN NNNNNNNNNN NNNNNNNNNN NNNNNNNNNN NNNNNNNNNN NNNNNNNNNN    1380

NNNNNNNNNN NNNNNNNNNN NNNNNNNNNN NNNNNNNNNN NNNNNNNNNN NNNNNNNNNN    1440

NNNNNNNNNN NNNNNNNNNN NNNNNNNNNN NNNNNNNNNN NNNNNNNNNN NNNNNNNNNN    1500

NNNNNNNNNN NNNNNNNNNN NNNNNNNNNN NNNNNNNNNN NNNNNNNNNN NNNNNNNNNN    1560

NNNNNNNNNN NNNNNNNNNN NNNNNNNNNN NNNNNNNNNN NNNNNNNNNN NNNNNNNNNN    1620
```

```
NNNNNNNNNN NNNNNNNNNN NNNNNNNNNN NNNNNNNNNN NNNNNNNNNN NNNNNNNNNN    1680

NNNNNNNNNN NNNNNNNNNN NNNNNNNNNN ATATAGCACA AAGACATGCA AATAATATTT    1740

CCCTATGCTC ATAAAAACAG CCCTGACCAT GAAGCTTTGA CAGACGCACA ACCCTGGACT    1800

CCCAAGTCTT TCTCTTCAGT GACAAACACA GACATAGGAT ATCCACCATG GAATGGAGCT    1860

GGGTAATGCT CTTCCTCCTG TCAGGAACTG CAGGTGTCCG CTCTGAGGTC CAGCTGCAAC    1920

AGTCTGGACC TGAACTGGTG AAGCCTGGAG CTTCAATGAA GATTTCCTGC AAGGCTTCTG    1980

GTTACTCATT CACTGGCTAC ACCATGAACT GGGTGAAGCA GAGCCATGGA GAGAACCTTG    2040

AGTGGATTGG ACGTATTAAT CCTCACAATG GTGGTACTGA CTACAACCAG AAGTTCAAGG    2100

ACAAGGCCCC TTTAACTGTA GACAAGTCAT CCAACACAGC CTACATGGAG CTCCTCAGTC    2160

TGACATCTGA GGACTCTGCA GTCTATTACT GTGCAAGAGG CTACTATTAC TATTCTTTGG    2220

ACTACTGGGG TCAAGGAACC TCAGTCACCG TCTCCTCAGC TAGCACCAAG GGCCCATCGG    2280

TCTTCCCCCT GGCGCCCTGC TCCAGGAGCA CCTCCGAGAG CACAGCGGCC CTGGGCTGCC    2340

TGGTCAAGGA CTACTTCCCC GAACCGGTGA CGGTGTCGTG GAACTCAGGC GCTCTGACCA    2400

GCGGCGTGCA CACCTTCCCA GCTGTCCTAC AGTCCTCAGG ACTCTACTCC CTCAGCAGCG    2460

TGGTGACCGT GCCCTCCAGC AACTTCGGCA CCCAGACCTA CACCTGCAAC GTAGATCACA    2520

AGCCCAGCAA CACCAAGGTG GACAAGACAG TTGGTGAGAG GCCAGCTCAG GGAGGGAGGG    2580

TGTCTGCTGG AAGCCAGGCT CAGCCCTCCT GCCTGGACGC ACCCCGGCTG TGCAGCCCCA    2640

GCCCAGGGCA GCAAGGCAGG CCCCATCTGT CTCCTCACCC GGAGGCCTCT GCCCGCCCCA    2700

CTCATGCTCA GGGAGAGGGT CTTCTGGCTT TTTCCACCAG GCTCCAGGCA GGCACAGGCT    2760

GGGTGCCCCT ACCCCAGGCC CTTCACACAC AGGGGCAGGT GCTTGGCTCA GACCTGCCAA    2820

AAGCCATATC CGGGAGGACC CTGCCCCTGA CCTAAGCCGA CCCCAAAGGC CAAACTGTCC    2880

ACTCCCTCAG CTCGGACACC TTCTCTCCTC CCAGATCCGA GTAACTCCCA ATCTTCTCTC    2940

TGCAGAGCGC AAATGTTGTG TCGAGTGCCC ACCGTGCCCA GGTAAGCCAG CCCAGGCCTC    3000

GCCCTCCAGC TCAAGGCGGG ACAGGTGCCC TAGAGTAGCC TGCATCCAGG GACAGGCCCC    3060

AGCTGGGTGC TGACACGTCC ACCTCCATCT CTTCCTCAGC ACCACCTGTG GCAGGACCGT    3120

CAGTCTTCCT CTTCCCCCCA AAACCCAAGG ACACCCTCAT GATCTCCCGG ACCCCTGAGG    3180

TCACGTGCGT GGTGGTGGAC GTGAGCCACG AAGACCCCGA GGTCCAGTTC AACTGGTACG    3240

TGGACGGCGT GGAGGTGCAT AATGCCAAGA CAAAGCCACG GGAGGAGCAG TTCAACAGCA    3300

CGTTCCGTGT GGTCAGCGTC CTCACCGTTG TGCACCAGGA CTGGCTGAAC GGCAAGGAGT    3360

ACAAGTGCAA GGTCTCCAAC AAAGGCCTCC CAGCCCCCAT CGAGAAAACC ATCTCCAAAA    3420

CCAAAGGTGG GACCCGCGGG GTATGAGGGC CACATGGACA GAGGCCGGCT CGGCCCACCC    3480

TCTGCCCTGG GAGTGACCGC TGTGCCAACC TCTGTCCCTA CAGGGAGGAG ATGACCAAGA    3540

ACCAGGTCAG CCTGACCTGC CTGGTCAAAG GCTTCTACCC CAGCGACATC GCCGTGGAGT    3600

GGGAGAGCAA TGGGCAGCCG GAGAACAACT ACAAGACCAC ACCTCCCATG CTGGACTCCG    3660

ACGGCTCCTT CTTCCTCTAC AGCAAGCTCA CCGTGGACAA GAGCAGGTGG CAGCAGGGGA    3720

ACGTCTTCTC ATGCTCCGTG ATGCATGAGG CTCTGCACAA CCACTACACG CAGAAGAGCC    3780

TCTCCCTGTC TCCGGGTAAA TGAGTGCCAC GGCCGGCAAG CCCCCGCTCC CCAGGCTCTC    3840

GGGGTCGCGT GAGGATGCTT GGCACGTACC CCGTGTACAT ACTTCCCAGG CACCCAGCAT    3900

GGAAATAAAG CACCCAGCGC TGCCCTGGGC CCCTGCGAGA CTGTGATGGT TCTTTCCGTG    3960

GGTCAGGCCG AGTCTGAGGC CTGAGTGGCA TGAGGGAGGC AGAGTGGGTC ANNNNNNNNN    4020
```

| | |
|---|---:|
| NNNNNNNNNN NNNNNNNNNN NNNNNNNNNN NNNNNNNNNN NNNNNNNNNN NNNNNNNNNN | 4080 |
| NNNNNNNNNN NNNNNNNNNN NNNNNNNNNN NNNNNNNNNN NNNNNNNNNN NNNNNNNNNN | 4140 |
| NNNNNNNNNN NNNNNNNNNN NNNNNNNNNN NNNNNNNNNN NNNNNNNNNN NNNNNNNNNN | 4200 |
| NNNNNNNNNN NNNNNNNNNN NNNNNNNNNN NNNNNNNNNN NNNNNNNNNN NNNNNNNNNN | 4260 |
| NNNNNNNNNN NNNNNNNNNN NNNNNNNNNN NNNNNNNNNN NNNNNNNNNN NCAGCTGNNN | 4320 |
| NNNNNNNNNN NNNNNNNNNN NNNNNNNNNN NNNNNNNNNN NNNNNNNNNN NNNNNNNNNN | 4380 |
| NNNNNNNNNN NNNNNNNNNN NNNNNNNNNN NNNNNNNNNN NNNNNNNNNN NNNNNNNNNN | 4440 |
| NNNNNNNNNN NNNNNNNNNN NNNNNNNNNN NNNNNNNNNN NNNNNNNNNN NNNNNNNNNN | 4500 |
| NNNNNNNNNN NNNNNNNGGA TCCAGACATG ATAAGATACA TTGATGAGTT TGGACAAACC | 4560 |
| ACAACTAGAA TGCAGTGAAA AAAATGCTTT ATTTGTGAAA TTTGTGATGC TATTGCTTTA | 4620 |
| TTTGTAACCA TTATAAGCTG CAATAAACAA GTTAACAACA ACAATTGCAT TCATTTTATG | 4680 |
| TTTCAGGTTC AGGGGGAGGT GTGGGAGGTT TTTTAAAGCA AGTAAAACCT CTACAAATGT | 4740 |
| GGTATGGCTG ATTATGATCT CTAGTCAAGG CACTATACAT CAAATATTCC TTATTAACCC | 4800 |
| CTTTACAAAT TAAAAAGCTA AAGGTACACA ATTTTTGAGC ATAGTTATTA ATAGCAGACA | 4860 |
| CTCTATGCCT GTGTGGAGTA AGAAAAAACA GTATGTTATG ATTATAACTG TTATGCCTAC | 4920 |
| TTATAAAGGT TACAGAATAT TTTTCCATAA TTTTCTTGTA TAGCAGTGCA GCTTTTTCCT | 4980 |
| TTGTGGTGTA AATAGCAAAG CAAGCAAGAG TTCTATTACT AAACACAGCA TGACTCAAAA | 5040 |
| AACTTAGCAA TTCTGAAGGA AAGTCCTTGG GGTCTTCTAC CTTTCTCTTC TTTTTTGGAG | 5100 |
| GAGTAGAATG TTGAGAGTCA GCAGTAGCCT CATCATCACT AGATGGCATT TCTTCTGAGC | 5160 |
| AAAACAGGTT TTCCTCATTA AAGGCATTCC ACCACTGCTC CCATTCATCA GTTCCATAGG | 5220 |
| TTGGAATCTA AAATACACAA ACAATTAGAA TCAGTAGTTT AACACATTAT ACACTTAAAA | 5280 |
| ATTTTATATT TACCTTATAG CTTTAAATCT CTGTAGGTAG TTTGTCCAAT TATGTCACAC | 5340 |
| CACAGAAGTA AGGTTCCTTC ACAAAGATCC GGNNNNNNNN NNNNNNNNNN NNNNNNNTCA | 5400 |
| TGCTTGCTCC TTGAGGGCGT TAACGCGCAA GGTAACGGCA TTTTTATGGG CGGTCAGACG | 5460 |
| TTCGGCGGCG GCCAGTGTTT CTATGGTTGA AGCCACCGCG GAGAACCCCT CTTTCGACAG | 5520 |
| TTCCTGTACG GTCATACGCT TCTGGAAATC TGCCAGCCCG AGGCTGGAAC AGGTGGCGGT | 5580 |
| GTAACCGTAA GTCGGTAGAA CGTGGTTGGT TCCGGAGGCG TAATCACCTG CCGATTCCGG | 5640 |
| TGACCAGTCA CCAAGAAATA CCGAACCGGC GCTGGTGATG CTATCGACCA GTTCACGGGC | 5700 |
| GTTGCGGGTC TGAATGATCA GGTGCTCCGG GCCGTACTGA TTAGAGATCT CCACGCACTG | 5760 |
| CGCTGAATCT TTAGTCACGA TCAGGCGGCT GGCGTTCAGT GCCTGGCGGG CGGTTTCGGC | 5820 |
| ACGCGGCAGT TCCGCCAGTT GGCGTTCGAC GGCCTCGGCA ACGCGACGCG CCATATCAGC | 5880 |
| AGCGGGCGTC AGTAAAATCA CCTGTGAGTC CGGGCCGTGT TCAGCCTGAG AGAGCAAATC | 5940 |
| AGAAGCCACG AAATCCGGCG TTGCGCCGCT GTCAGCAATC ACCAGCACTT CCGACGGGCC | 6000 |
| TGCGGGCATA TCGATCTCCG CACCGTCCAG ACGCTGGCTC ACCTGACGTT TCGCTTCGGT | 6060 |
| GACAAAGGCG TTACCCGGCC CGAAGATTTT GTCCACTTTT GGCACGGATT CCGTACCAAA | 6120 |
| CGCCAGTGCG GCAATGGCCT GTGCGCCGCC GACGTTGAAC ACGTCCTGCA CACCGCACAG | 6180 |
| CTGCGCCGCA TAAAGGATCT CATCGGCAAT CGGCGGCGGT GAGCACAGCA CCACTTTTTT | 6240 |
| ACAGCCCGCA ATACGCGCCG GAGTCGCCAG CATTAATACC GTTGAGAAGA GCGGGCGGA | 6300 |
| GCCGCCAGGA ATATACAACC CAACTGAAGC TACCGGACGC GTGACCTGCT GGCAACGCAC | 6360 |
| GCCTGGCTGC GTTTCTACAT CTACCGGCGG CAGTTTTTGC GCAGTGTGGA AGGTTTCAAT | 6420 |

```
ATTCTTTACT GCCACCGCCA TCGCCTGTTT TAGCTCGTCG CTCAGGCGTT CGCTGGCGGC    6480
GGCGATCTCC TCTGCAGACA CCTTCAGCGC GGTAACCGTG GTTTTATCAA ACTTCGCGCT    6540
GTATTCCCGC AGGGCCTCAT CGCCGCGTGC TTTCACGTTA TCGAGAATAT CGTTAACAGT    6600
GCGGGTAATG CTTTCAGAGG CGGAAATCGC CGGGCGCGTT AACAGCTGGC GTTGTTGCAC    6660
CGCAGTACAG CTATTCCAGT CAATGATTGT GTTAAAGCTC ATNNNNCCGG ATCAGCTTTT    6720
TGCAAAAGCC TAGGCCTCCA AAAAAGCCTC CTCACTACTT CTGGAATAGC TCAGAGGCCG    6780
AGGCGCCTCG GCCTCTGCAT AAATAAAAAA AATTAGTCAG CCATGGGGCG GAGAATGGGC    6840
GGAACTGGGC GGAGTTAGGG GCGGGATGGG CGGAGTTAGG GGCGGGACTA TGGTTGCTGA    6900
CTAATTGAGA TGCATGCTTT GCATACTTCT GCCTGCTGGG GAGCCTGGGG ACTTTCCACA    6960
CCTGGTTGCT GACTAATTGA GATGCATGCT TTGCATACTT CTGCCTGCTG GGAGCCTGG    7020
GGACTTTCCA CACCCTAACT GACACACATT CCACAGCTGC CTCGCGCGTT TCGGTGATGA    7080
CGGTGAAAAC CTCTGACACA TGCAGCTCCC GGAGACGGTC ACAGCTTGTC TGTAAGCGGA    7140
TGCCGGGAGC AGACAAGCCC GTCAGGGCGC GTCAGCGGGT GTTGGCGGGT GTCGGGCGC    7200
AGCCATGACC CAGTCACGTA GCGATAGCGG AGTGTATACT GGCTTAACTA TGCGGCATCA    7260
GAGCAGATTG TACTGAGAGT GCACCATATG CGGTGTGAAA TACCGCACAG ATGCGTAAGG    7320
AGAAAATACC GCATCAGGCG CTCTTCCGCT TCCTCGCTCA CTGACTCGCT GCGCTCGGTC    7380
GTTCGGCTGC GGCGAGCGGT ATCAGCTCAC TCAAAGGCGG TAATACGGTT ATCCACAGAA    7440
TCAGGGGATA ACGCAGGAAA GAACATGTGA GCAAAAGGCC AGCAAAAGGC CAGGAACCGT    7500
AAAAAGGCCG CGTTGCTGGC GTTTTTCCAT AGGCTCCGCC CCCCTGACGA GCATCACAAA    7560
AATCGACGCT CAAGTCAGAG GTGGCGAAAC CCGACAGGAC TATAAAGATA CCAGGCGTTT    7620
CCCCCTGGAA GCTCCCTCGT GCGCTCTCCT GTTCCGACCC TGCCGCTTAC CGGATACCTG    7680
TCCGCCTTTC TCCCTTCGGG AAGCGTGGCG CTTTCTCAAT GCTCACGCTG TAGGTATCTC    7740
AGTTCGGTGT AGGTCGTTCG CTCCAAGCTG GGCTGTGTGC ACGAACCCCC CGTTCAGCCC    7800
GACCGCTGCG CCTTATCCGG TAACTATCGT CTTGAGTCCA ACCCGGTAAG ACACGACTTA    7860
TCGCCACTGG CAGCAGCCAC TGGTAACAGG ATTAGCAGAG CGAGGTATGT AGGCGGTGCT    7920
ACAGAGTTCT TGAAGTGGTG GCCTAACTAC GGCTACACTA GAAGGACAGT ATTTGGTATC    7980
TGCGCTCTGC TGAAGCCAGT TACCTTCGGA AAAAGAGTTG GTAGCTCTTG ATCCGGCAAA    8040
CAAACCACCG CTGGTAGCGG TGGTTTTTTT GTTTGCAAGC AGCAGATTAC GCGCAGAAAA    8100
AAAGGATCTC AAGAAGATCC TTTGATCTTT TCTACGGGGT CTGACGCTCA GTGGAACGAA    8160
AACTCACGTT AAGGGATTTT GGTCATGAGA TTATCAAAAA GGATCTTCAC CTAGATCCTT    8220
TTAAATTAAA AATGAAGTTT TAAATCAATC TAAAGTATAT ATGAGTAAAC TTGGTCTGAC    8280
AGTTACCAAT GCTTAATCAG TGAGGCACCT ATCTCAGCGA TCTGTCTATT TCGTTCATCC    8340
ATAGTTGCCT GACTCCCCGT CGTGTAGATA ACTACGATAC GGGAGGGCTT ACCATCTGGC    8400
CCCAGTGCTG CAATGATACC GCGAGACCCA CGCTCACCGG CTCCAGATTT ATCAGCAATA    8460
AACCAGCCAG CCGGAAGGGC CGAGCGCAGA AGTGGTCCTG CAACTTTATC CGCCTCCATC    8520
CAGTCTATTA ATTGTTGCCG GGAAGCTAGA GTAAGTAGTT CGCCAGTTAA TAGTTTGCGC    8580
AACGTTGTTG CCATTGCTGC AGGCATCGTG GTGTCACGCT CGTCGTTTGG TATGGCTTCA    8640
TTCAGCTCCG GTTCCCAACG ATCAAGGCGA GTTACATGAT CCCCCATGTT GTGCAAAAAA    8700
GCGGTTAGCT CCTTCGGTCC TCCGATCGTT GTCAGAAGTA AGTTGGCCGC AGTGTTATCA    8760
CTCATGGTTA TGGCAGCACT GCATAATTCT CTTACTGTCA TGCCATCCGT AAGATGCTTT    8820
```

```
TCTGTGACTG GTGAGTACTC AACCAAGTCA TTCTGAGAAT AGTGTATGCG GCGACCGAGT    8880

TGCTCTTGCC CGGCGTCAAC ACGGGATAAT ACCGCGCCAC ATAGCAGAAC TTTAAAAGTG    8940

CTCATCATTG GAAAACGTTC TTCGGGGCGA AAACTCTCAA GGATCTTACC GCTGTTGAGA    9000

TCCAGTTCGA TGTAACCCAC TCGTGCACCC AACTGATCTT CAGCATCTTT TACTTTCACC    9060

AGCGTTTCTG GGTGAGCAAA AACAGGAAGG CAAAATGCCG CAAAAAAGGG AATAAGGGCG    9120

ACACGGAAAT GTTGAATACT CATACTCTTC CTTTTTCAAT ATTATTGAAG CATTTATCAG    9180

GGTTATTGTC TCATGAGCGG ATACATATTT GAATGTATTT AGAAAAATAA ACAAATAGGG    9240

GTTCCGCGCA CATTTCCCCG AAAAGTGCCA CCTGACGTCT AAGAAACCAT TATTATCATG    9300

ACATTAACCT ATAAAAATAG GCGTATCACG AGGCCCTTTC GTCTTCAAGA ATTCAGAGAG    9360

GTCTGGTGGA GCCTGCAAAA GTCCAGCTTT CAAAGGAACA CAGAAGTATG TGTATGGAAT    9420

ATTAGAAGAT GTTGCTTTTA CTCTTAAGTT GGTTCCTAGG AAAAATAGTT AAATACTGTG    9480

ACTTTAAAAT GTGAGAGGGT TTTCAAGTAC TCATTTTTTT AAATGTCCAA AATTTTTGTC    9540

AATCAATTTG AGGTCTTGTT TGTGTAGAAC TGACATTACT TAAAGTTTAA CCGAGGAATG    9600

GGAGTGAGGC TCTCTCATAC CCTATTCAGA ACTGACTTTT AACAATAATA AATTAAGTTT    9660

AAAATATTTT TAAATGAATT GAGCAATGTT GAGTTGAGTC AAGATGGCCG ATCAGAACCG    9720

GAACACCTGC AGCAGCTGGC AGGAAGCAGG TCATGTGGCA AGGCTATTTG GGGAAGGGAA    9780

AATAAAACCA CTAGGTAAAC TTGTAGCTGT GGTTTGAAGA AGTGGTTTTG AAACACTCTG    9840

TCCAGCCCCA CCAAACCGAA AGTCCAGGCT GAGCAAAACA CCACCTGGGT AATTTGCATT    9900

TCTAAAATAA GTTGAGGATT CAGCCGAAAC TGGAGAGGTC CTCTTTTAAC TTATTGAGTT    9960

CAACCTTTTA ATTTTAGCTT GAGTAGTTCT AGTTTCCCCA AACTTAAGTT TATCGACTTC   10020

TAAAATGTAT TTAGAATTCC TTTGCCTAAT ATTAATGAGG ACTTAACCTG TGGAAATATT   10080

TTGATGTGGG AAGCTGTTAC TGTTAAAACT GAGGTTATTG GGGTAACTGC TATGTTAAAC   10140

TTGCATTCAG GGACACAAAA AACTCATGAA AATGGTGCTG GAAAACCCAT TCAAGGGTCA   10200

AATTTTCATT TTTTTGCTGT TGGTGGGGAA CCTTTGGAGC TGCAGGGTGT GTTAGCAAAC   10260

TACAGGACCA AATATCCTGC TCAAACTGTA ACCCCAAAAA ATGCTACAGT TGACAGTCAG   10320

CAGATGAACA CTGACCACAA GGCTGTTTTG GATAAGGATA ATGCTTATCC AGTGGAGTGC   10380

TGGGTTCCTG ATCCAAGTAA AAATGAAAAC ACTAGATATT TTGGAACCTA CACAGGTGGG   10440

GAAAATGTGC CTCCTGTTTT GCACATTACT AACACAGCAA CCACAGTGCT GCTTGATGAG   10500

CAGGGTGTTG GGCCCTTGTG CAAAGCTGAC AGCTTGTATG TTTCTGCTGT TGACATTTGT   10560

GGGCTGTTTA CCAACACTTC TGGAACACAG CAGTGGAAGG GACTTCCCAG ATATTTTAAA   10620

ATTACCCTTA GAAAGCGGTC TGTGAAAAAC CCCTACCCAA TTTCCTTTTT GTTAAGTGAC   10680

CTAATTAACA GGAGGACACA GAGGGTGGAT GGGCAGCCTA TGATTGGAAT GTCCTCTCAA   10740

GTAGAGGAGG TTAGGGTTTA TGAGGACACA GAGGAGCTTC CTGGG                  10785
```

(2) INFORMATION FOR SEQ ID NO:28:

(i) SEQUENCE CHARACTERISTICS:
        (A) LENGTH: 235 amino acids
        (B) TYPE: amino acid
        (D) TOPOLOGY: linear (ii) MOLECULE TYPE: protein (v) FRAGMENT TYPE: N-terminal (xi) SEQUENCE DESCRIPTION: SEQ ID NO:28:

```
Met Glu Trp Ser Trp Val Met Leu Phe Leu Leu Ser Gly Thr Ala Gly
1               5                   10                  15

Val Arg Ser Glu Val Gln Leu Gln Gln Ser Gly Pro Glu Leu Val Lys
            20                  25                  30

Pro Gly Ala Ser Met Lys Ile Ser Cys Lys Ala Ser Gly Tyr Ser Phe
        35                  40                  45

Thr Gly Tyr Thr Met Asn Trp Val Lys Gln Ser His Gly Glu Asn Leu
    50                  55                  60

Glu Trp Ile Gly Arg Ile Asn Pro His Asn Gly Gly Thr Asp Tyr Asn
65                  70                  75                  80

Gln Lys Phe Lys Asp Lys Ala Pro Leu Thr Val Asp Lys Ser Ser Asn
                85                  90                  95

Thr Ala Tyr Met Glu Leu Leu Ser Leu Thr Ser Glu Asp Ser Ala Val
            100                 105                 110

Tyr Tyr Cys Ala Arg Gly Tyr Tyr Tyr Ser Leu Asp Tyr Trp Gly
        115                 120                 125

Gln Gly Thr Ser Val Thr Val Ser Ser Ala Ser Thr Lys Gly Pro Ser
    130                 135                 140

Val Phe Pro Leu Ala Pro Cys Ser Arg Ser Thr Ser Glu Ser Thr Ala
145                 150                 155                 160

Ala Leu Gly Cys Leu Val Lys Asp Tyr Phe Pro Glu Pro Val Thr Val
                165                 170                 175

Ser Trp Asn Ser Gly Ala Leu Thr Ser Gly Val His Thr Phe Pro Ala
            180                 185                 190

Val Leu Gln Ser Ser Gly Leu Tyr Ser Leu Ser Ser Val Val Thr Val
            195                 200                 205

Pro Ser Ser Asn Phe Gly Thr Gln Thr Tyr Thr Cys Asn Val Asp His
        210                 215                 220

Lys Pro Ser Asn Thr Lys Val Asp Lys Thr Val
225                 230                 235

(2) INFORMATION FOR SEQ ID NO:29:

(i) SEQUENCE CHARACTERISTICS:
        (A) LENGTH: 12 amino acids
        (B) TYPE: amino acid
        (D) TOPOLOGY: linear (ii) MOLECULE TYPE: protein (v) FRAGMENT TYPE: internal (xi) SEQUENCE DESCRIPTION: SEQ ID NO:29:

Glu Arg Lys Cys Cys Val Glu Cys Pro Pro Cys Pro
1               5                   10

(2) INFORMATION FOR SEQ ID NO:30:

(i) SEQUENCE CHARACTERISTICS:
        (A) LENGTH: 109 amino acids
        (B) TYPE: amino acid
        (D) TOPOLOGY: linear (ii) MOLECULE TYPE: protein (v) FRAGMENT TYPE: internal (xi) SEQUENCE DESCRIPTION: SEQ ID NO:30:

Ala Pro Pro Val Ala Gly Pro Ser Val Phe Leu Phe Pro Pro Lys Pro
1               5                   10                  15
```

```
Lys Asp Thr Leu Met Ile Ser Arg Thr Pro Glu Val Thr Cys Val Val
             20                  25                  30

Val Asp Val Ser His Glu Asp Pro Glu Val Gln Phe Asn Trp Tyr Val
             35                  40                  45

Asp Gly Val Glu Val His Asn Ala Lys Thr Lys Pro Arg Glu Glu Gln
 50                      55                  60

Phe Asn Ser Thr Phe Arg Val Val Ser Val Leu Thr Val Val His Gln
 65                  70                  75                  80

Asp Trp Leu Asn Gly Lys Glu Tyr Lys Cys Lys Val Ser Asn Lys Gly
                 85                  90                  95

Leu Pro Ala Pro Ile Glu Lys Thr Ile Ser Lys Thr Lys
                100                 105
```

(2) INFORMATION FOR SEQ ID NO:31:

(i) SEQUENCE CHARACTERISTICS:
        (A) LENGTH: 434 amino acids
        (B) TYPE: amino acid
        (D) TOPOLOGY: linear (ii) MOLECULE TYPE: protein (ix) FEATURE:
        (A) NAME/KEY: Protein
        (B) LOCATION: 1..434
        (D) OTHER INFORMATION: /note= "Translation from
            complementary DNA."

(xi) SEQUENCE DESCRIPTION: SEQ ID NO:31:

```
Met Ser Phe Asn Thr Ile Ile Asp Trp Asn Ser Cys Thr Ala Val Gln
 1               5                  10                  15

Gln Arg Gln Leu Leu Thr Arg Pro Ala Ile Ser Ala Ser Glu Ser Ile
             20                  25                  30

Thr Arg Thr Val Asn Asp Ile Leu Asp Asn Val Lys Ala Arg Gly Asp
             35                  40                  45

Glu Ala Leu Arg Glu Tyr Ser Ala Lys Phe Asp Lys Thr Thr Val Thr
 50                  55                  60

Ala Leu Lys Val Ser Ala Glu Glu Ile Ala Ala Ala Ser Glu Arg Leu
 65                  70                  75                  80

Ser Asp Glu Leu Lys Gln Ala Met Ala Val Ala Val Lys Asn Ile Glu
                 85                  90                  95

Thr Phe His Thr Ala Gln Lys Leu Pro Pro Val Asp Val Glu Thr Gln
                100                 105                 110

Pro Gly Val Arg Cys Gln Gln Val Thr Arg Pro Val Ala Ser Val Gly
                115                 120                 125

Leu Tyr Ile Pro Gly Gly Ser Ala Pro Leu Phe Ser Thr Val Leu Met
130                 135                 140

Leu Ala Thr Pro Ala Arg Ile Ala Gly Cys Lys Lys Val Val Leu Cys
145                 150                 155                 160

Ser Pro Pro Pro Ile Ala Asp Glu Ile Leu Tyr Ala Ala Gln Leu Cys
                165                 170                 175

Gly Val Gln Asp Val Phe Asn Val Gly Gly Ala Gln Ala Ile Ala Ala
                180                 185                 190

Leu Ala Phe Gly Thr Glu Ser Val Pro Lys Val Asp Lys Ile Phe Gly
                195                 200                 205

Pro Gly Asn Ala Phe Val Thr Glu Ala Lys Arg Gln Val Ser Gln Arg
                210                 215                 220

Leu Asp Gly Ala Glu Ile Asp Met Pro Ala Gly Pro Ser Glu Val Leu
225                 230                 235                 240
```

```
Val Ile Ala Asp Ser Gly Ala Thr Pro Asp Phe Val Ala Ser Asp Leu
                245                 250                 255

Leu Ser Gln Ala Glu His Gly Pro Asp Ser Gln Val Ile Leu Leu Thr
            260                 265                 270

Pro Ala Ala Asp Met Ala Arg Arg Val Ala Glu Ala Val Glu Arg Gln
        275                 280                 285

Leu Ala Glu Leu Pro Arg Ala Glu Thr Ala Arg Gln Ala Leu Asn Ala
    290                 295                 300

Ser Arg Leu Ile Val Thr Lys Asp Ser Ala Gln Cys Val Glu Ile Ser
305                 310                 315                 320

Asn Gln Tyr Gly Pro Glu His Leu Ile Ile Gln Thr Arg Asn Ala Arg
                325                 330                 335

Glu Leu Val Asp Ser Ile Thr Ser Ala Gly Ser Val Phe Leu Gly Asp
            340                 345                 350

Trp Ser Pro Glu Ser Ala Gly Asp Tyr Ala Ser Gly Thr Asn His Val
        355                 360                 365

Leu Pro Thr Tyr Gly Tyr Thr Ala Thr Cys Ser Ser Leu Gly Leu Ala
    370                 375                 380

Asp Phe Gln Lys Arg Met Thr Val Gln Glu Leu Ser Lys Glu Gly Phe
385                 390                 395                 400

Ser Ala Val Ala Ser Thr Ile Glu Thr Leu Ala Ala Glu Arg Leu
                405                 410                 415

Thr Ala His Lys Asn Ala Val Thr Leu Arg Val Asn Ala Leu Lys Glu
                420                 425                 430

Gln Ala
```

(2) INFORMATION FOR SEQ ID NO:32:

(i) SEQUENCE CHARACTERISTICS:
        (A) LENGTH: 12127 base pairs
        (B) TYPE: nucleic acid
        (C) STRANDEDNESS: double
        (D) TOPOLOGY: circular (ii) MOLECULE TYPE: DNA (genomic)

(vii) IMMEDIATE SOURCE:
        (B) CLONE: pAH4807

(ix) FEATURE:
        (A) NAME/KEY: misc_feature
        (B) LOCATION: 1..12127
        (D) OTHER INFORMATION: /note= "Function = "Expression
           Vector Coding Sequence""

(xi) SEQUENCE DESCRIPTION: SEQ ID NO:32:

```
GATCCGATCC NNNNNNNNNN NNNNNNNNNN NNNNNNNNNN NNNNNNNNNN NNNNNNNNNN      60

NNNNNNNNNN NNNNNNNNNN NNNNNNNNNN NNNNNNNNNN NNNNNNNNNN NNNNNNNNNN     120

NNNNNNNNNN NNNNNNNNNN NNNNNNNNNN NNNNNNNNNN NNNNNNNNNN NNNNNNNNNN     180

NNNNNNNNNN NNNNNNNNNN NNNNNNNNNN NNNNNNNNNN NNNNNNNNNN NNNNNNNNNN     240

NNNNNNNNNN NNNNNNNNNN NNNNNNNNNN NNNNNNNNNN NNNNNNNNNN NNNNNNNNNN     300

NNNNNNNNNN NNNNNNNNNN NNNNNNNNNN NNNNNNNNNN NNNNNNNNNN NNNNNNNNNN     360

NNNNNNNNNN NNNNNNNNNN NNNNNNNNNN NNNNNNNNNN NNNNNNNNNN NNNNNNNNNN     420

NNNNNNNNNN NNNNNNNNNN NNNNNNNNNN NNNNNNNNNN NNNNNNNNNN NNNNNNNNNN     480

NNNNNNNNNN NNNNNNNNNN NNNNNNNNNN NNNNNNNNNN NNNNNNNNNN NNNNNNNNNN     540

NNNNNNNNNN NNNNNNNNNN NNNNNNNNNN NNNNNNNNNN NNNNNNNNNN NNNNNNNNNN     600
```

```
NNNNNNNNNN NNNNNNNNNN NNNNNNNNNN NNNNNNNNNN NNNNNNNNNN NNNNNNNNNN      660

NNNNNNNNNN NNNNNNNNNN NNNNNNNNNN NNNNNNNNNN NNNNNNNNNN NNNNNNNNNN      720

NNNNNNNNNN NNNNNNNNNN NNNNNNNNNN NNNNNNNNNN NNNNNNNNNN NNNNNNNNNN      780

NNNNNNNNNN NNNNNNNNNN NNNNNNNNNN NNNNNNNNNN NNNNNNNNNN NNNNNNNNNN      840

NNNNNNNNNN NNNNNNNNNN NNNNNNNNNN NNNNNNNNNN NNNNNNNNNN NNNNNNNNNN      900

NNNNNNNNNN NNNNNNNNNN NNNNNNNNNN NNNNNNNNNN NNNNNNNNNN NNNNNNNNNN      960

NNNNNNNNNN NNNNNNNNNN NNNNNNNNNN NNNNNNNNNN NNNNNNNNNN NNNNNNNNNN     1020

NNNNNNNNNN NNNNNNNNNN NNNNNNNNNN NNNNNNNNNN NNNNNNNNNN NNNNNNNNNN     1080

NNNNNNNNNN NNNNNNNNNN NNNNNNNNNN NNNNNNNNNN NNNNNNNNNN NNNNNNNNNN     1140

NNNNNNNNNN NNNNNNNNNN NNNNNNNNNN NNNNNNNNNN NNNNNNNNNN NNNNNNNNNN     1200

NNNNNNNNNN NNNNNNNNNN NNNNNNNNNN NNNNNNNNNN NNNNNNNNNN NNNNNNNNNN     1260

NNNNNNNNNN NNNNNNNNNN NNNNNNNNNN NNNNNNNNNN NNNNNNNNNN NNNNNNNNNN     1320

NNNNNNNNNN NNNNNNNNNN NNNNNNNNNN NNNNNNNNNN NNNNNNNNNN NNNNNNNNNN     1380

NNNNNNNNNN NNNNNNNNNN NNNNNNNNNN NNNNNNNNNN NNNNNNNNNN NNNNNNNNNN     1440

NNNNNNNNNN NNNNNNNNNN NNNNNNNNNN NNNNNNNNNN NNNNNNNNNN NNNNNNNNNN     1500

NNNNNNNNNN NNNNNNNNNN NNNNNNNNNN NNNNNNNNNN NNNNNNNNNN NNNNNNNNNN     1560

NNNNNNNNNN NNNNNNNNNN NNNNNNNNNN NNNNNNNNNN NNNNNNNNNN NNNNNNNNNN     1620

NNNNNNNNNN NNNNNNNNNN NNNNNNNNNN NNNNNNNNNN NNNNNNNNNN NNNNNNNNNN     1680

NNNNNNNNNN NNNNNNNNNN NNNNNNNNNN ATATAGCACA AAGACATGCA AATAATATTT     1740

CCCTATGCTC ATAAAAACAG CCCTGACCAT GAAGCTTTGA CAGACGCACA ACCCTGGACT     1800

CCCAAGTCTT TCTCTTCAGT GACAAACACA GACATAGGAT ATCCACCATG GAATGGAGCT     1860

GGGTAATGCT CTTCCTCCTG TCAGGAACTG CAGGTGTCCG CTCTGAGGTC CAGCTGCAAC     1920

AGTCTGGACC TGAACTGGTG AAGCCTGGAG CTTCAATGAA GATTTCCTGC AAGGCTTCTG     1980

GTTACTCATT CACTGGCTAC ACCATGAACT GGGTGAAGCA GAGCCATGGA GAGAACCTTG     2040

AGTGGATTGG ACGTATTAAT CCTCACAATG GTGGTACTGA CTACAACCAG AAGTTCAAGG     2100

ACAAGGCCCC TTTAACTGTA GACAAGTCAT CCAACACAGC CTACATGGAG CTCCTCAGTC     2160

TGACATCTGA GGACTCTGCA GTCTATTACT GTGCAAGAGG CTACTATTAC TATTCTTTGG     2220

ACTACTGGGG TCAAGGAACC TCAGTCACCG TCTCCTCAAC CAAGGGCCCA TCGGTCTTCC     2280

CCCTGGCGCC CTGCTCCAGG AGCACCTCTG GGGGCACAGC GGCCCTGGGC TGCCTGGTCA     2340

AGGACTACTT CCCCGAACCG GTGACGGTGT CGTGGAACTC AGGCGCCCTG ACCAGCGGCG     2400

TGCACACCTT CCCGGCTGTC CTACAGTCCT CAGGACTCTA CTCCCTCAGC AGCGTGGTGA     2460

CCGTGCCCTC CAGCAGCTTG GGCACCCAGA CCTACACCTG CAACGTGAAT CACAAGCCCA     2520

GCAACACCAA GGTGGACAAG AGAGTTGGTG AGAGGCCAGC GCAGGGAGGG AGGGTGTCTG     2580

CTGGAAGCCA GGCTCAGCCC TCCTGCCTGG ACGCATCCCG GCTGTGCAGT CCCAGCCCAG     2640

GGCACCAAGG CAGGCCCCGT CTGACTCCTC ACCCGGAGGC CTCTGCCCGC CCCACTCATG     2700

CTCAGGGAGA GGGTCTTCTG GCTTTTTCCA CCAGGCTCCG GGCAGGCACA GGCTGGATGC     2760

CCCTACCCCA GGCCCTTCAC ACACAGGGGC AGGTGCTGCG CTCAGAGCTG CCAAGAGCCA     2820

TATCCAGGAG GACCCTGCCC CTGACCTAAG CCCACCCCAA AGGCCAAACT CTCTACTCAC     2880

TCAGCTCAGA CACCTTCTCT CTTCCCAGAT CTGAGTAACT CCCAATCTTC TCTCTGCAGA     2940

GCTCAAAACC CCACTTGGTG ACACAACTCA CACATGCCCA CGGTGCCCAG GTAAGCCAGC     3000
```

-continued

```
CCAGGCCTCG CCCTCCAGCT CAAGGCGGGA CAAGAGCCCT AGAGTGGCCT GAGTCCAGGG      3060
ACAGGCCCCA GCAGGGTGCT GACGCATCCA CCTCCATCCC AGATCCCCGT AACTCCCAAT      3120
CTTCTCTCTG CAGAGCCCAA ATCTTGTGAC ACACCTCCCC CGTGCCCAAG GTGCCCAGGT      3180
AAGCCAGCCC AGGCCTCGCC CTCCAGCTCA AGGCAGGACA GGTGCCCTAG AGTGGCCTGA      3240
GTCCAGGGAC AGGCCCCAGC AGGGTGCTGA CGCATCCACC TCCATCCCAG ATCCCCGTAA      3300
CTCCCAATCT TCTCTCTGCA GAGCCCAAAT CTTGTGACAC ACCTCCCCCG TGCCCAAGGT      3360
GCCCAGGTAA GCCAGCCCAG GCCTCGCCCT CCAGCTCAAG GCAGGACAGG TGCCCTAGAG      3420
TGGCCTGAGT CCAGGGACAG GCCCCAGCAG GGTGCTGACG CATCCACCTC CATCCCAGAT      3480
CCCCGTAACT CCCAATCTTC TCTCTGCAGA GCCCAAATCT TGTGACACAC CTCCCCCGTG      3540
CCCAAGGTGC CCAGGTAAGC CAGCCCAGGC CTCGCCCTCC AGCTCAAGGC AGGACAGGTG      3600
CCCTAGAGTG GCCTGCATCC AGGGACAGGT CCCAGTCGGG TGCTGACACA TCTGCCTCCA      3660
TCTCTTCCTC AGCACCTGAA CTCCTGGGAG GACCGTCAGT CTTCCTCTTC CCCCCAAAAC      3720
CCAAGGATAC CCTTATGATT TCCCGGACCC CTGAGGTCAC GTGCGTGGTG GTGGACGTGA      3780
GCCACGAAGA CCCCGAGGTC CAGTTCAAGT GGTACGTGGA CGGCGTGGAG GTGCATAATG      3840
CCAAGACAAA GCTGCGGGAG GAGCAGTACA ACAGCACGTT CCGTGTGGTC AGCGTCCTCA      3900
CCGTCCTGCA CCAGGACTGG CTGAACGGCA AGGAGTACAA GTGCAAGGTC TCCAACAAAG      3960
CCCTCCCAGC CCCCATCGAG AAAACCATCT CCAAAGCCAA AGGTGGGACC CGCGGGGTAT      4020
GAGGGCCACG TGGACAGAGG CCAGCTTGAC CCACCCTCTG CCCTGGGAGT GACCGCTGTG      4080
CCAACCTCTG TCCCTACAGG ACAGCCCCGA GAACCACAGG TGTACACCCT GCCCCCATCC      4140
CGGGAGGAGA TGACCAAGAA CCAGGTCAGC CTGACCTGCC TGGTCAAAGG CTTCTACCCC      4200
AGCGACATCG CCGTGGAGTG GGAGAGCAAT GGGCAGCCGG AGAACAACTA CAACACCACG      4260
CCTCCCATGC TGGACTCCGA CGGCTCCTTC TTCCTCTACA GCAAGCTCAC CGTGGACAAG      4320
AGCAGGTGGC AGCAGGGGAA CATCTTCTCA TGCTCCGTGA TGCATGAGGC TCTGCACAAC      4380
CGCTACACCC AGAAGAGCCT CTCCCTGTCT CCGGGTAAAT GAGTGCGACA GCCGGCAAGC      4440
CCCCGCTCCC CGGGCTCTCG GGGTCGCGCG AGGATGCTTG GCACGTACCC CGTGTACATA      4500
CTTCCCGGGC ACCCAGCATG GAAATAAAGC ACCCAGCGCT GCCCTGGGCC CCTGTGAGAC      4560
TGTGATGGTT CTTTCCACGG GTCAGGCCGA GTCTGAGGCC TGAGTGACAT GAGGGAGGCA      4620
GAGCGGGTCN NNNNNNNNN NNNNNNNNNN NNNNNNNNNN NNNNNNNNNN NNNNNNNNNN      4680
NNNNNNNNNN NNNNNNNNNN NNNNNNNNNN NNNNNNNNNN NNNNNNNNNN NNNNNNNNNN      4740
NNNNNNNNNN NNNNNNNNNN NNNNNNNNNN NNNNNNNNNN NNNNNNNNNN NNNNNNNNNN      4800
NNNNNNNNNN NNNNNNNNNN NNNNNNNNNN NNNNNNNNNN NNNNNNNNNN NNNNNNNNNN      4860
NNNNNNNNNN NNNNNNNNNN NNNNNNNNNN NNNNNNNNNN NNNNNNNNNN NNNNNNNNNN      4920
NNNNNNNNNN NNNNNNNNNN NNNNNNNNNN NNNNNNNNNN NNNNNNNNNN NNNNNNNNNN      4980
NNNNNNNNNN NNNNNNNNNN NNNNNNNNNN NNNNNNNNNN NNNNNNNNNN NNNNNNNNNN      5040
NNNNNNNNNN NNNNNNNNNN NNNNNNNNNN NNNNNNNNNN NNNNNNNNNN NNNNNNNNNN      5100
NNNNNNNNNN NNNNNNNNNN NNNNNNNNNN NNNNNNNNNN NNNNNNNNNN NNNNNNNNNN      5160
NNNNNNNNNN NNNNNNNNNN NNNNNNNNNN NNNNNNNNNN NNNNNNNNNN NNNNNNNNNN      5220
NNNNNNNNNN NNNNNNNNNN NNNNNNNNNN NNNNNNNNNN NNNNNNNNNN NNNNNNNNNN      5280
NNNNNNNNNN NNNNNNNNNN NNNNNNNNNN NNNNNNNNNN NNNNNNNNNN NNNNNNNNNN      5340
NNNNNNNNNN NNNNNNNNNN NNNNNNNNNN NNNNNNNNNN NNNNNNNNNN NNNNNNNNNN      5400
```

| | |
|---|---|
| NNNNNNNNNN NNNNNNNNNN NNNNNNNNNN NNNNNNNNNN NNNNNNNNNN NNNNNNNNNN | 5460 |
| NNNNNNNNNN NNNNNNNNNN NNNNNNNNNN NNNNNNNNNN NNNNNNNNNN NNNNNNNNNN | 5520 |
| NNNNNNNNNN NNNNNNNNNN NNNNNNNNNN NNNNCAGCTG NNNNNNNNNN NNNNNNNNNN | 5580 |
| NNNNNNNNNN NNNNNNNNNN NNNNNNNNNN NNNNNNNNNN NNNNNNNNNN NNNNNNNNNN | 5640 |
| NNNNNNNNNN NNNNNNNNNN NNNNNNNNNN NNNNNNNNNN NNNNNNNNNN NNNNNNNNNN | 5700 |
| NNNNNNNNNN NNNNNNNNNN NNNNNNNNNN NNNNNNNNNN NNNNNNNNNN NNNNNNNNNN | 5760 |
| NNNNNNNNNN NNNNNNNNNN NNNNNNNNNN NNNNNNNNNN NNNNNNNNNN NNNNNNNNNN | 5820 |
| NNNNNNNNNN NNNNNNNNNN NNNNNNNNNN NNNNNNNNNG GATCCAGACA TGATAAGATA | 5880 |
| CATTGATGAG TTTGGACAAA CCACAACTAG AATGCAGTGA AAAAAATGCT TTATTTGTGA | 5940 |
| AATTTGTGAT GCTATTGCTT TATTTGTAAC CATTATAAGC TGCAATAAAC AAGTTAACAA | 6000 |
| CAACAATTGC ATTCATTTTA TGTTTCAGGT TCAGGGGAG GTGTGGGAGG TTTTTTAAAG | 6060 |
| CAAGTAAAAC CTCTACAAAT GTGGTATGGC TGATTATGAT CTCTAGTCAA GGCACTATAC | 6120 |
| ATCAAATATT CCTTATTAAC CCCTTTACAA ATTAAAAAGC TAAAGGTACA CAATTTTTGA | 6180 |
| GCATAGTTAT TAATAGCAGA CACTCTATGC CTGTGTGGAG TAAGAAAAAA CAGTATGTTA | 6240 |
| TGATTATAAC TGTTATGCCT ACTTATAAAG GTTACAGAAT ATTTTTCCAT AATTTTCTTG | 6300 |
| TATAGCAGTG CAGCTTTTTC CTTTGTGGTG TAAATAGCAA AGCAAGCAAG AGTTCTATTA | 6360 |
| CTAAACACAG CATGACTCAA AAAACTTAGC AATTCTGAAG GAAAGTCCTT GGGGTCTTCT | 6420 |
| ACCTTTCTCT TCTTTTTTGG AGGAGTAGAA TGTTGAGAGT CAGCAGTAGC CTCATCATCA | 6480 |
| CTAGATGGCA TTTCTTCTGA GCAAAACAGG TTTTCCTCAT TAAAGGCATT CCACCACTGC | 6540 |
| TCCCATTCAT CAGTTCCATA GGTTGGAATC TAAAATACAC AAACAATTAG AATCAGTAGT | 6600 |
| TTAACACATT ATACACTTAA AAATTTTATA TTTACCTTAT AGCTTTAAAT CTCTGTAGGT | 6660 |
| AGTTTGTCCA ATTATGTCAC ACCACAGAAG TAAGGTTCCT TCACAAAGAT CCGGNNNNNN | 6720 |
| NNNNNNNNNN NNNNNNNNNT CATGCTTGCT CCTTGAGGGC GTTAACGCGC AAGGTAACGG | 6780 |
| CATTTTTATG GGCGGTCAGA CGTTCGGCGG CGGCCAGTGT TTCTATGGTT GAAGCCACCG | 6840 |
| CGGAGAACCC CTCTTTCGAC AGTTCCTGTA CGGTCATACG CTTCTGGAAA TCTGCCAGCC | 6900 |
| CGAGGCTGGA ACAGGTGGCG GTGTAACCGT AAGTCGGTAG AACGTGGTTG GTTCCGGAGG | 6960 |
| CGTAATCACC TGCCGATTCC GGTGACCAGT CACCAAGAAA TACCGAACCG GCGCTGGTGA | 7020 |
| TGCTATCGAC CAGTTCACGG GCGTTGCGGG TCTGAATGAT CAGGTGCTCC GGGCCGTACT | 7080 |
| GATTAGAGAT CTCCACGCAC TGCGCTGAAT CTTTAGTCAC GATCAGGCGG CTGGCGTTCA | 7140 |
| GTGCCTGGCG GGCGGTTTCG GCACGCGGCA GTTCCGCCAG TTGGCGTTCG ACGGCCTCGG | 7200 |
| CAACGCGACG CGCCATATCA GCAGCGGGCG TCAGTAAAAT CACCTGTGAG TCCGGGCCGT | 7260 |
| GTTCAGCCTG AGAGAGCAAA TCAGAAGCCA CGAAATCCGG CGTTGCGCCG CTGTCAGCAA | 7320 |
| TCACCAGCAC TTCCGACGGG CCTGCGGGCA TATCGATCTC CGCACCGTCC AGACGCTGGC | 7380 |
| TCACCTGACG TTTCGCTTCG GTGACAAAGG CGTTACCCGG CCCGAAGATT TTGTCCACTT | 7440 |
| TTGGCACGGA TTCCGTACCA AACGCCAGTG CGGCAATGGC CTGTGCGCCG CCGACGTTGA | 7500 |
| ACACGTCCTG CACACCGCAC AGCTGCGCCG CATAAAGGAT CTCATCGGCA ATCGGCGGCG | 7560 |
| GTGAGCACAG CACCACTTTT TTACAGCCCG CAATACGCGC CGGAGTCGCC AGCATTAATA | 7620 |
| CCGTTGAGAA GAGCGGGGCG GAGCCGCCAG GAATATACAA CCCAACTGAA GCTACCGGAC | 7680 |
| GCGTGACCTG CTGGCAACGC ACGCCTGGCT GCGTTTCTAC ATCTACCGGC GGCAGTTTTT | 7740 |
| GCGCAGTGTG GAAGGTTTCA ATATTCTTTA CTGCCACCGC CATCGCCTGT TTTAGCTCGT | 7800 |

```
CGCTCAGGCG TTCGCTGGCG GCGGCGATCT CCTCTGCAGA CACCTTCAGC GCGGTAACCG    7860
TGGTTTTATC AAACTTCGCG CTGTATTCCC GCAGGGCCTC ATCGCCGCGT GCTTTCACGT    7920
TATCGAGAAT ATCGTTAACA GTGCGGGTAA TGCTTTCAGA GGCGGAAATC GCCGGGCGCG    7980
TTAACAGCTG GCGTTGTTGC ACCGCAGTAC AGCTATTCCA GTCAATGATT GTGTTAAAGC    8040
TCATNNNNCC GGATCAGCTT TTTGCAAAAG CCTAGGCCTC CAAAAAAGCC TCCTCACTAC    8100
TTCTGGAATA GCTCAGAGGC CGAGGCGCCT CGGCCTCTGC ATAAATAAAA AAAATTAGTC    8160
AGCCATGGGG CGGAGAATGG GCGGAACTGG GCGGAGTTAG GGGCGGGATG GGCGGAGTTA    8220
GGGGCGGGAC TATGGTTGCT GACTAATTGA GATGCATGCT TTGCATACTT CTGCCTGCTG    8280
GGGAGCCTGG GGACTTTCCA CACCTGGTTG CTGACTAATT GAGATGCATG CTTTGCATAC    8340
TTCTGCCTGC TGGGGAGCCT GGGGACTTTC CACACCCTAA CTGACACACA TTCCACAGCT    8400
GCCTCGCGCG TTTCGGTGAT GACGGTGAAA ACCTCTGACA CATGCAGCTC CCGGAGACGG    8460
TCACAGCTTG TCTGTAAGCG GATGCCGGGA GCAGACAAGC CCGTCAGGGC GCGTCAGCGG    8520
GTGTTGGCGG GTGTCGGGGC GCAGCCATGA CCCAGTCACG TAGCGATAGC GGAGTGTATA    8580
CTGGCTTAAC TATGCGGCAT CAGAGCAGAT TGTACTGAGA GTGCACCATA TGCGGTGTGA    8640
AATACCGCAC AGATGCGTAA GGAGAAAATA CCGCATCAGG CGCTCTTCCG CTTCCTCGCT    8700
CACTGACTCG CTGCGCTCGG TCGTTCGGCT GCGGCGAGCG GTATCAGCTC ACTCAAAGGC    8760
GGTAATACGG TTATCCACAG AATCAGGGGA TAACGCAGGA AAGAACATGT GAGCAAAAGG    8820
CCAGCAAAAG GCCAGGAACC GTAAAAAGGC CGCGTTGCTG GCGTTTTTCC ATAGGCTCCG    8880
CCCCCCTGAC GAGCATCACA AAAATCGACG CTCAAGTCAG AGGTGGCGAA ACCCGACAGG    8940
ACTATAAAGA TACCAGGCGT TTCCCCCTGG AAGCTCCCTC GTGCGCTCTC CTGTTCCGAC    9000
CCTGCCGCTT ACCGGATACC TGTCCGCCTT TCTCCCTTCG GGAAGCGTGG CGCTTTCTCA    9060
ATGCTCACGC TGTAGGTATC TCAGTTCGGT GTAGGTCGTT CGCTCCAAGC TGGGCTGTGT    9120
GCACGAACCC CCCGTTCAGC CCGACCGCTG CGCCTTATCC GGTAACTATC GTCTTGAGTC    9180
CAACCCGGTA AGACACGACT TATCGCCACT GGCAGCAGCC ACTGGTAACA GGATTAGCAG    9240
AGCGAGGTAT GTAGGCGGTG CTACAGAGTT CTTGAAGTGG TGGCCTAACT ACGGCTACAC    9300
TAGAAGGACA GTATTTGGTA TCTGCGCTCT GCTGAAGCCA GTTACCTTCG GAAAAAGAGT    9360
TGGTAGCTCT TGATCCGGCA AACAAACCAC CGCTGGTAGC GGTGGTTTTT TTGTTTGCAA    9420
GCAGCAGATT ACGCGCAGAA AAAAAGGATC TCAAGAAGAT CCTTTGATCT TTTCTACGGG    9480
GTCTGACGCT CAGTGGAACG AAAACTCACG TTAAGGGATT TTGGTCATGA GATTATCAAA    9540
AAGGATCTTC ACCTAGATCC TTTTAAATTA AAAATGAAGT TTTAAATCAA TCTAAAGTAT    9600
ATATGAGTAA ACTTGGTCTG ACAGTTACCA ATGCTTAATC AGTGAGGCAC CTATCTCAGC    9660
GATCTGTCTA TTTCGTTCAT CCATAGTTGC CTGACTCCCC GTCGTGTAGA TAACTACGAT    9720
ACGGGAGGGC TTACCATCTG GCCCCAGTGC TGCAATGATA CCGCGAGACC CACGCTCACC    9780
GGCTCCAGAT TTATCAGCAA TAAACCAGCC AGCCGGAAGG GCCGAGCGCA GAAGTGGTCC    9840
TGCAACTTTA TCCGCCTCCA TCCAGTCTAT TAATTGTTGC CGGGAAGCTA GAGTAAGTAG    9900
TTCGCCAGTT AATAGTTTGC GCAACGTTGT TGCCATTGCT GCAGGCATCG TGGTGTCACG    9960
CTCGTCGTTT GGTATGGCTT CATTCAGCTC CGGTTCCCAA CGATCAAGGC GAGTTACATG   10020
ATCCCCCATG TTGTGCAAAA AAGCGGTTAG CTCCTTCGGT CCTCCGATCG TTGTCAGAAG   10080
TAAGTTGGCC GCAGTGTTAT CACTCATGGT TATGGCAGCA CTGCATAATT CTCTTACTGT   10140
CATGCCATCC GTAAGATGCT TTTCTGTGAC TGGTGAGTAC TCAACCAAGT CATTCTGAGA   10200
```

```
ATAGTGTATG CGGCGACCGA GTTGCTCTTG CCCGGCGTCA ACACGGGATA ATACCGCGCC    10260

ACATAGCAGA ACTTTAAAAG TGCTCATCAT TGGAAAACGT TCTTCGGGGC GAAAACTCTC    10320

AAGGATCTTA CCGCTGTTGA GATCCAGTTC GATGTAACCC ACTCGTGCAC CCAACTGATC    10380

TTCAGCATCT TTTACTTTCA CCAGCGTTTC TGGGTGAGCA AAAACAGGAA GGCAAAATGC    10440

CGCAAAAAAG GGAATAAGGG CGACACGGAA ATGTTGAATA CTCATACTCT TCCTTTTTCA    10500

ATATTATTGA AGCATTTATC AGGGTTATTG TCTCATGAGC GGATACATAT TTGAATGTAT    10560

TTAGAAAAAT AAACAAATAG GGGTTCCGCG CACATTTCCC CGAAAAGTGC CACCTGACGT    10620

CTAAGAAACC ATTATTATCA TGACATTAAC CTATAAAAAT AGGCGTATCA CGAGGCCCTT    10680

TCGTCTTCAA GAATTCAGAG AGGTCTGGTG GAGCCTGCAA AAGTCCAGCT TTCAAAGGAA    10740

CACAGAAGTA TGTGTATGGA ATATTAGAAG ATGTTGCTTT TACTCTTAAG TTGGTTCCTA    10800

GGAAAAATAG TTAAATACTG TGACTTTAAA ATGTGAGAGG GTTTTCAAGT ACTCATTTTT    10860

TTAAATGTCC AAAATTTTTG TCAATCAATT TGAGGTCTTG TTTGTGTAGA ACTGACATTA    10920

CTTAAAGTTT AACCGAGGAA TGGGAGTGAG GCTCTCTCAT ACCCTATTCA GAACTGACTT    10980

TTAACAATAA TAAATTAAGT TTAAAATATT TTTAAATGAA TTGAGCAATG TTGAGTTGAG    11040

TCAAGATGGC CGATCAGAAC CGGAACACCT GCAGCAGCTG GCAGGAAGCA GGTCATGTGG    11100

CAAGGCTATT TGGGGAAGGG AAAATAAAAC CACTAGGTAA ACTTGTAGCT GTGGTTTGAA    11160

GAAGTGGTTT TGAAACACTC TGTCCAGCCC CACCAAACCG AAAGTCCAGG CTGAGCAAAA    11220

CACCACCTGG GTAATTTGCA TTTCTAAAAT AAGTTGAGGA TTCAGCCGAA ACTGGAGAGG    11280

TCCTCTTTTA ACTTATTGAG TTCAACCTTT TAATTTTAGC TTGAGTAGTT CTAGTTTCCC    11340

CAAACTTAAG TTTATCGACT TCTAAAATGT ATTTAGAATT CCTTTGCCTA ATATTAATGA    11400

GGACTTAACC TGTGGAAATA TTTTGATGTG GGAAGCTGTT ACTGTTAAAA CTGAGGTTAT    11460

TGGGGTAACT GCTATGTTAA ACTTGCATTC AGGGACACAA AAAACTCATG AAAATGGTGC    11520

TGGAAAACCC ATTCAAGGGT CAAATTTTCA TTTTTTTGCT GTTGGTGGGG AACCTTTGGA    11580

GCTGCAGGGT GTGTTAGCAA ACTACAGGAC CAAATATCCT GCTCAAACTG TAACCCCAAA    11640

AAATGCTACA GTTGACAGTC AGCAGATGAA CACTGACCAC AAGGCTGTTT TGGATAAGGA    11700

TAATGCTTAT CCAGTGGAGT GCTGGGTTCC TGATCCAAGT AAAAATGAAA ACACTAGATA    11760

TTTTGGAACC TACACAGGTG GGGAAAATGT GCCTCCTGTT TTGCACATTA CTAACACAGC    11820

AACCACAGTG CTGCTTGATG AGCAGGGTGT TGGGCCCTTG TGCAAAGCTG ACAGCTTGTA    11880

TGTTTCTGCT GTTGACATTT GTGGGCTGTT TACCAACACT TCTGGAACAC AGCAGTGGAA    11940

GGGACTTCCC AGATATTTTA AAATTACCCT TAGAAAGCGG TCTGTGAAAA ACCCCTACCC    12000

AATTTCCTTT TTGTTAAGTG ACCTAATTAA CAGGAGGACA CAGAGGGTGG ATGGGCAGCC    12060

TATGATTGGA ATGTCCTCTC AAGTAGAGGA GGTTAGGGTT TATGAGGACA CAGAGGAGCT    12120

TCCTGGG                                                             12127
```

(2) INFORMATION FOR SEQ ID NO:33:

(i) SEQUENCE CHARACTERISTICS:
        (A) LENGTH: 233 amino acids
        (B) TYPE: amino acid
        (D) TOPOLOGY: linear (ii) MOLECULE TYPE: protein (v) FRAGMENT TYPE: N-terminal (xi) SEQUENCE DESCRIPTION: SEQ ID NO:33:

```
Met Glu Trp Ser Trp Val Met Leu Phe Leu Leu Ser Gly Thr Ala Gly
1               5                   10                  15

Val Arg Ser Glu Val Gln Leu Gln Gln Ser Gly Pro Glu Leu Val Lys
                20                  25                  30

Pro Gly Ala Ser Met Lys Ile Ser Cys Lys Ala Ser Gly Tyr Ser Phe
            35                  40                  45

Thr Gly Tyr Thr Met Asn Trp Val Lys Gln Ser His Gly Glu Asn Leu
        50                  55                  60

Glu Trp Ile Gly Arg Ile Asn Pro His Asn Gly Gly Thr Asp Tyr Asn
65                  70                  75                  80

Gln Lys Phe Lys Asp Lys Ala Pro Leu Thr Val Asp Lys Ser Ser Asn
                85                  90                  95

Thr Ala Tyr Met Glu Leu Leu Ser Leu Thr Ser Glu Asp Ser Ala Val
            100                 105                 110

Tyr Tyr Cys Ala Arg Gly Tyr Tyr Tyr Ser Leu Asp Tyr Trp Gly
            115                 120                 125

Gln Gly Thr Ser Val Thr Val Ser Ser Thr Lys Gly Pro Ser Val Phe
        130                 135                 140

Pro Leu Ala Pro Cys Ser Arg Ser Thr Ser Gly Gly Thr Ala Ala Leu
145                 150                 155                 160

Gly Cys Leu Val Lys Asp Tyr Phe Pro Glu Pro Val Thr Val Ser Trp
                165                 170                 175

Asn Ser Gly Ala Leu Thr Ser Gly Val His Thr Phe Pro Ala Val Leu
            180                 185                 190

Gln Ser Ser Gly Leu Tyr Ser Leu Ser Ser Val Val Thr Val Pro Ser
        195                 200                 205

Ser Ser Leu Gly Thr Gln Thr Tyr Thr Cys Asn Val Asn His Lys Pro
210                 215                 220

Ser Asn Thr Lys Val Asp Lys Arg Val
225                 230

(2) INFORMATION FOR SEQ ID NO:34:

(i) SEQUENCE CHARACTERISTICS:
        (A) LENGTH: 17 amino acids
        (B) TYPE: amino acid
        (D) TOPOLOGY: linear (ii) MOLECULE TYPE: protein (v) FRAGMENT TYPE: internal (xi) SEQUENCE DESCRIPTION: SEQ ID NO:34:

Glu Leu Lys Thr Pro Leu Gly Asp Thr Thr His Thr Cys Pro Arg Cys
1               5                   10                  15

Pro (2) INFORMATION FOR SEQ ID NO:35:

(i) SEQUENCE CHARACTERISTICS:
        (A) LENGTH: 15 amino acids
        (B) TYPE: amino acid
        (D) TOPOLOGY: linear (ii) MOLECULE TYPE: protein (v) FRAGMENT TYPE: internal (xi) SEQUENCE DESCRIPTION: SEQ ID NO:35:

Glu Pro Lys Ser Cys Asp Thr Pro Pro Cys Pro Arg Cys Pro
```

(2) INFORMATION FOR SEQ ID NO:36:

(i) SEQUENCE CHARACTERISTICS:
        (A) LENGTH: 15 amino acids
        (B) TYPE: amino acid
        (D) TOPOLOGY: linear (ii) MOLECULE TYPE: protein (v) FRAGMENT TYPE: internal (xi) SEQUENCE DESCRIPTION: SEQ ID NO:36:

```
Glu Pro Lys Ser Cys Asp Thr Pro Pro Cys Pro Arg Cys Pro
1               5                   10                  15
```

(2) INFORMATION FOR SEQ ID NO:37:

(i) SEQUENCE CHARACTERISTICS:
        (A) LENGTH: 15 amino acids
        (B) TYPE: amino acid
        (D) TOPOLOGY: linear (ii) MOLECULE TYPE: protein (v) FRAGMENT TYPE: internal (xi) SEQUENCE DESCRIPTION: SEQ ID NO:37:

```
Glu Pro Lys Ser Cys Asp Thr Pro Pro Cys Pro Arg Cys Pro
1               5                   10                  15
```

(2) INFORMATION FOR SEQ ID NO:38:

(i) SEQUENCE CHARACTERISTICS:
        (A) LENGTH: 110 amino acids
        (B) TYPE: amino acid
        (D) TOPOLOGY: linear (ii) MOLECULE TYPE: protein (v) FRAGMENT TYPE: internal (xi) SEQUENCE DESCRIPTION: SEQ ID NO:38:

```
Ala Pro Glu Leu Leu Gly Gly Pro Ser Val Phe Leu Phe Pro Lys
1               5                   10                  15

Pro Lys Asp Thr Leu Met Ile Ser Arg Thr Pro Glu Val Thr Cys Val
                20                  25                  30

Val Val Asp Val Ser His Glu Asp Pro Glu Val Gln Phe Lys Trp Tyr
                35                  40                  45

Val Asp Gly Val Glu Val His Asn Ala Lys Thr Lys Leu Arg Glu Glu
        50                  55                  60

Gln Tyr Asn Ser Thr Phe Arg Val Val Ser Val Leu Thr Val Leu His
65                  70                  75                  80

Gln Asp Trp Leu Asn Gly Lys Glu Tyr Lys Cys Lys Val Ser Asn Lys
                85                  90                  95

Ala Leu Pro Ala Pro Ile Glu Lys Thr Ile Ser Lys Ala Lys
                100                 105                 110
```

(2) INFORMATION FOR SEQ ID NO:39:

(i) SEQUENCE CHARACTERISTICS:
        (A) LENGTH: 107 amino acids
        (B) TYPE: amino acid
        (D) TOPOLOGY: linear (ii) MOLECULE TYPE: protein (v) FRAGMENT TYPE: internal (xi) SEQUENCE DESCRIPTION: SEQ ID NO:39:

```
Gly Gln Pro Arg Glu Pro Gln Val Tyr Thr Leu Pro Pro Ser Arg Glu
1               5                   10                  15

Glu Met Thr Lys Asn Gln Val Ser Leu Thr Cys Leu Val Lys Gly Phe
            20                  25                  30

Tyr Pro Ser Asp Ile Ala Val Glu Trp Glu Ser Asn Gly Gln Pro Glu
        35                  40                  45

Asn Asn Tyr Asn Thr Thr Pro Pro Met Leu Asp Ser Asp Gly Ser Phe
50                  55                  60

Phe Leu Tyr Ser Lys Leu Thr Val Asp Lys Ser Arg Trp Gln Gln Gly
65                  70                  75                  80

Asn Ile Phe Ser Cys Ser Val Met His Glu Ala Leu His Asn Arg Tyr
                85                  90                  95

Thr Gln Lys Ser Leu Ser Leu Ser Pro Gly Lys
            100                 105
```

(2) INFORMATION FOR SEQ ID NO:40:

(i) SEQUENCE CHARACTERISTICS:
        (A) LENGTH: 434 amino acids
        (B) TYPE: amino acid
        (D) TOPOLOGY: linear (ii) MOLECULE TYPE: protein (ix) FEATURE:
        (A) NAME/KEY: Protein
        (B) LOCATION: 1..434
        (D) OTHER INFORMATION: /note= "Translation from
            complementary DNA."

(xi) SEQUENCE DESCRIPTION: SEQ ID NO:40:

```
Met Ser Phe Asn Thr Ile Ile Asp Trp Asn Ser Cys Thr Ala Val Gln
1               5                   10                  15

Gln Arg Gln Leu Leu Thr Arg Pro Ala Ile Ser Ala Ser Glu Ser Ile
            20                  25                  30

Thr Arg Thr Val Asn Asp Ile Leu Asp Asn Val Lys Ala Arg Gly Asp
        35                  40                  45

Glu Ala Leu Arg Glu Tyr Ser Ala Lys Phe Asp Lys Thr Thr Val Thr
50                  55                  60

Ala Leu Lys Val Ser Ala Glu Glu Ile Ala Ala Ser Glu Arg Leu
65                  70                  75                  80

Ser Asp Glu Leu Lys Gln Ala Met Ala Val Ala Val Lys Asn Ile Glu
            85                  90                  95

Thr Phe His Thr Ala Gln Lys Leu Pro Pro Val Asp Val Glu Thr Gln
        100                 105                 110

Pro Gly Val Arg Cys Gln Gln Val Thr Arg Pro Val Ala Ser Val Gly
    115                 120                 125

Leu Tyr Ile Pro Gly Gly Ser Ala Pro Leu Phe Ser Thr Val Leu Met
130                 135                 140

Leu Ala Thr Pro Ala Arg Ile Ala Gly Cys Lys Lys Val Val Leu Cys
145                 150                 155                 160

Ser Pro Pro Pro Ile Ala Asp Glu Ile Leu Tyr Ala Ala Gln Leu Cys
                165                 170                 175

Gly Val Gln Asp Val Phe Asn Val Gly Gly Ala Gln Ala Ile Ala Ala
            180                 185                 190
```

```
Leu Ala Phe Gly Thr Glu Ser Val Pro Lys Val Asp Lys Ile Phe Gly
        195                 200                 205

Pro Gly Asn Ala Phe Val Thr Glu Ala Lys Arg Gln Val Ser Gln Arg
        210                 215                 220

Leu Asp Gly Ala Glu Ile Asp Met Pro Ala Gly Pro Ser Glu Val Leu
225                 230                 235                 240

Val Ile Ala Asp Ser Gly Ala Thr Pro Asp Phe Val Ala Ser Asp Leu
                245                 250                 255

Leu Ser Gln Ala Glu His Gly Pro Asp Ser Gln Val Ile Leu Leu Thr
            260                 265                 270

Pro Ala Ala Asp Met Ala Arg Arg Val Ala Glu Ala Val Glu Arg Gln
            275                 280                 285

Leu Ala Glu Leu Pro Arg Ala Glu Thr Ala Arg Gln Ala Leu Asn Ala
        290                 295                 300

Ser Arg Leu Ile Val Thr Lys Asp Ser Ala Gln Cys Val Glu Ile Ser
305                 310                 315                 320

Asn Gln Tyr Gly Pro Glu His Leu Ile Ile Gln Thr Arg Asn Ala Arg
                325                 330                 335

Glu Leu Val Asp Ser Ile Thr Ser Ala Gly Ser Val Phe Leu Gly Asp
            340                 345                 350

Trp Ser Pro Glu Ser Ala Gly Asp Tyr Ala Ser Gly Thr Asn His Val
            355                 360                 365

Leu Pro Thr Tyr Gly Tyr Thr Ala Thr Cys Ser Ser Leu Gly Leu Ala
        370                 375                 380

Asp Phe Gln Lys Arg Met Thr Val Gln Glu Leu Ser Lys Glu Gly Phe
385                 390                 395                 400

Ser Ala Val Ala Ser Thr Ile Glu Thr Leu Ala Ala Ala Glu Arg Leu
                405                 410                 415

Thr Ala His Lys Asn Ala Val Thr Leu Arg Val Asn Ala Leu Lys Glu
            420                 425                 430

Gln Ala (2) INFORMATION FOR SEQ ID NO:41:

(i) SEQUENCE CHARACTERISTICS:
        (A) LENGTH: 10844 base pairs
        (B) TYPE: nucleic acid
        (C) STRANDEDNESS: double
        (D) TOPOLOGY: circular (ii) MOLECULE TYPE: DNA (genomic)

(v) FRAGMENT TYPE: N-terminal (vii) IMMEDIATE SOURCE:
        (B) CLONE: pAH4808

(ix) FEATURE:
        (A) NAME/KEY: misc_feature
        (B) LOCATION: 1..10844
        (D) OTHER INFORMATION: /note= "Function = "Expression
            Vector Coding Sequence""

(xi) SEQUENCE DESCRIPTION: SEQ ID NO:41:

CGTTGTCAGA AGTAAGTTGG CCGCAGTGTT ATCACTCATG GTTATGGCAG CACTGCATAA      60

TTCTCTTACT GTCATGCCAT CCGTAAGATG CTTTTCTGTG ACTGGTGAGT ACTCAACCAA     120

GTCATTCTGA GAATAGTGTA TGCGGCGACC GAGTTGCTCT TGCCCGGCGT CAACACGGGA     180

TAATACCGCG CCACATAGCA GAACTTTAAA AGTGCTCATC ATTGGAAAAC GTTCTTCGGG     240

GCGAAAACTC TCAAGGATCT TACCGCTGTT GAGATCCAGT TCGATGTAAC CCACTCGTGC     300
```

```
ACCCAACTGA TCTTCAGCAT CTTTTACTTT CACCAGCGTT TCTGGGTGAG CAAAAACAGG    360

AAGGCAAAAT GCCGCAAAAA AGGGAATAAG GGCGACACGG AAATGTTGAA TACTCATACT    420

CTTCCTTTTT CAATATTATT GAAGCATTTA TCAGGGTTAT TGTCTCATGA GCGGATACAT    480

ATTTGAATGT ATTTAGAAAA ATAAACAAAT AGGGGTTCCG CGCACATTTC CCCGAAAAGT    540

GCCACCTGAC GTCTAAGAAA CCATTATTAT CATGACATTA ACCTATAAAA ATAGGCGTAT    600

CACGAGGCCC TTTCGTCTTC AAGAATTCAG AGAGGTCTGG TGGAGCCTGC AAAAGTCCAG    660

CTTTCAAAGG AACACAGAAG TATGTGTATG GAATATTAGA AGATGTTGCT TTTACTCTTA    720

AGTTGGTTCC TAGGAAAAAT AGTTAAATAC TGTGACTTTA AAATGTGAGA GGGTTTTCAA    780

GTACTCATTT TTTTAAATGT CCAAAATTTT TGTCAATCAA TTTGAGGTCT TGTTTGTGTA    840

GAACTGACAT TACTTAAAGT TTAACCGAGG AATGGGAGTG AGGCTCTCTC ATACCCTATT    900

CAGAACTGAC TTTTAACAAT AATAAATTAA GTTAAAATA TTTTTAAATG AATTGAGCAA     960

TGTTGAGTTG AGTCAAGATG GCCGATCAGA ACCGGAACAC CTGCAGCAGC TGGCAGGAAG   1020

CAGGTCATGT GGCAAGGCTA TTTGGGGAAG GGAAAATAAA ACCACTAGGT AAACTTGTAG   1080

CTGTGGTTTG AAGAAGTGGT TTTGAAACAC TCTGTCCAGC CCCACCAAAC CGAAAGTCCA   1140

GGCTGAGCAA AACACCACCT GGGTAATTTG CATTTCTAAA ATAAGTTGAG GATTCAGCCG   1200

AAACTGGAGA GGTCCTCTTT TAACTTATTG AGTTCAACCT TTTAATTTTA GCTTGAGTAG   1260

TTCTAGTTTC CCCAAACTTA AGTTTATCGA CTTCTAAAAT GTATTTAGAA TTCCTTTGCC   1320

TAATATTAAT GAGGACTTAA CCTGTGGAAA TATTTTGATG TGGGAAGCTG TTACTGTTAA   1380

AACTGAGGTT ATTGGGGTAA CTGCTATGTT AAACTTGCAT TCAGGACACA AAAAAACTCA   1440

TGAAAATGGT GCTGGAAAAC CCATTCAAGG GTCAAATTTT CATTTTTTTG CTGTTGGTGG   1500

GGAACCTTTG GAGCTGCAGG GTGTGTTAGC AAACTACAGG ACCAAATATC CTGCTCAAAC   1560

TGTAACCCCA AAAAATGCTA CAGTTGACAG TCAGCAGATG AACACTGACC ACAAGGCTGT   1620

TTTGGATAAG GATAATGCTT ATCCAGTGGA GTGCTGGGTT CCTGATCCAA GTAAAAATGA   1680

AAACACTAGA TATTTTGGAA CCTACACAGG TGGGGAAAAT GTGCCTCCTG TTTTGCACAT   1740

TACTAACACA GCAACCACAG TGCTGCTTGA TGAGCAGGGT GTTGGGCCCT TGTGCAAAGC   1800

TGACAGCTTG TATGTTTCTG CTGTTGACAT TTGTGGGCTG TTTACCAACA CTTCTGGAAC   1860

ACAGCAGTGG AAGGGACTTC CCAGATATTT TAAAATTACC CTTAGAAAGC GGTCTGTGAA   1920

AAACCCCTAC CCAATTTCCT TTTTGTTAAG TGACCTAATT AACAGGAGGA CACAGAGGGT   1980

GGATGGGCAG CCTATGATTG GAATGTCCTC TCAAGTAGAG GAGGTTAGGG TTTATGAGGA   2040

CACAGAGGAG CTTCCTGGGG ATCCGATCCN NNNNNNNNNN NNNNNNNNNN NNNNNNNNNN   2100

NNNNNNNNNN NNNNNNNNNN NNNNNNNNNN NNNNNNNNNN NNNNNNNNNN NNNNNNNNNN   2160

NNNNNNNNNN NNNNNNNNNN NNNNNNNNNN NNNNNNNNNN NNNNNNNNNN NNNNNNNNNN   2220

NNNNNNNNNN NNNNNNNNNN NNNNNNNNNN NNNNNNNNNN NNNNNNNNNN NNNNNNNNNN   2280

NNNNNNNNNN NNNNNNNNNN NNNNNNNNNN NNNNNNNNNN NNNNNNNNNN NNNNNNNNNN   2340

NNNNNNNNNN NNNNNNNNNN NNNNNNNNNN NNNNNNNNNN NNNNNNNNNN NNNNNNNNNN   2400

NNNNNNNNNN NNNNNNNNNN NNNNNNNNNN NNNNNNNNNN NNNNNNNNNN NNNNNNNNNN   2460

NNNNNNNNNN NNNNNNNNNN NNNNNNNNNN NNNNNNNNNN NNNNNNNNNN NNNNNNNNNN   2520

NNNNNNNNNN NNNNNNNNNN NNNNNNNNNN NNNNNNNNNN NNNNNNNNNN NNNNNNNNNN   2580

NNNNNNNNNN NNNNNNNNNN NNNNNNNNNN NNNNNNNNNN NNNNNNNNNN NNNNNNNNNN   2640

NNNNNNNNNN NNNNNNNNNN NNNNNNNNNN NNNNNNNNNN NNNNNNNNNN NNNNNNNNNN   2700
```

```
NNNNNNNNNN NNNNNNNNNN NNNNNNNNNN NNNNNNNNNN NNNNNNNNNN NNNNNNNNNN    2760

NNNNNNNNNN NNNNNNNNNN NNNNNNNNNN NNNNNNNNNN NNNNNNNNNN NNNNNNNNNN    2820

NNNNNNNNNN NNNNNNNNNN NNNNNNNNNN NNNNNNNNNN NNNNNNNNNN NNNNNNNNNN    2880

NNNNNNNNNN NNNNNNNNNN NNNNNNNNNN NNNNNNNNNN NNNNNNNNNN NNNNNNNNNN    2940

NNNNNNNNNN NNNNNNNNNN NNNNNNNNNN NNNNNNNNNN NNNNNNNNNN NNNNNNNNNN    3000

NNNNNNNNNN NNNNNNNNNN NNNNNNNNNN NNNNNNNNNN NNNNNNNNNN NNNNNNNNNN    3060

NNNNNNNNNN NNNNNNNNNN NNNNNNNNNN NNNNNNNNNN NNNNNNNNNN NNNNNNNNNN    3120

NNNNNNNNNN NNNNNNNNNN NNNNNNNNNN NNNNNNNNNN NNNNNNNNNN NNNNNNNNNN    3180

NNNNNNNNNN NNNNNNNNNN NNNNNNNNNN NNNNNNNNNN NNNNNNNNNN NNNNNNNNNN    3240

NNNNNNNNNN NNNNNNNNNN NNNNNNNNNN NNNNNNNNNN NNNNNNNNNN NNNNNNNNNN    3300

NNNNNNNNNN NNNNNNNNNN NNNNNNNNNN NNNNNNNNNN NNNNNNNNNN NNNNNNNNNN    3360

NNNNNNNNNN NNNNNNNNNN NNNNNNNNNN NNNNNNNNNN NNNNNNNNNN NNNNNNNNNN    3420

NNNNNNNNNN NNNNNNNNNN NNNNNNNNNN NNNNNNNNNN NNNNNNNNNN NNNNNNNNNN    3480

NNNNNNNNNN NNNNNNNNNN NNNNNNNNNN NNNNNNNNNN NNNNNNNNNN NNNNNNNNNN    3540

NNNNNNNNNN NNNNNNNNNN NNNNNNNNNN NNNNNNNNNN NNNNNNNNNN NNNNNNNNNN    3600

NNNNNNNNNN NNNNNNNNNN NNNNNNNNNN NNNNNNNNNN NNNNNNNNNN NNNNNNNNNN    3660

NNNNNNNNNN NNNNNNNNNN NNNNNNNNNN NNNNNNNNNN NNNNNNNNNN NNNNNNNNNN    3720

NNNNNNNNNN NNNNNNNNNN NNNNNNNNNN NNNNNNNNNN NNNNNNNNNA TATAGCACAA    3780

AGACATGCAA ATAATATTTC CCTATGCTCA TAAAAACAGC CCTGACCATG AAGCTTTGAC    3840

AGACGCACAA CCCTGGACTC CCAAGTCTTT CTCTTCAGTG ACAAACACAG ACATAGGATA    3900

TCCACCATGG AATGGAGCTG GGTAATGCTC TTCCTCCTGT CAGGAACTGC AGGTGTCCGC    3960

TCTGAGGTCC AGCTGCAACA GTCTGGACCT GAACTGGTGA AGCCTGGAGC TTCAATGAAG    4020

ATTTCCTGCA AGGCTTCTGG TTACTCATTC ACTGGCTACA CCATGAACTG GGTGAAGCAG    4080

AGCCATGGAG AGAACCTTGA GTGGATTGGA CGTATTAATC CTCACAATGG TGGTACTGAC    4140

TACAACCAGA AGTTCAAGGA CAAGGCCCCT TTAACTGTAG ACAAGTCATC CAACACAGCC    4200

TACATGGAGC TCCTCAGTCT GACATCTGAG GACTCTGCAG TCTATTACTG TGCAAGAGGC    4260

TACTATTACT ATTCTTTGGA CTACTGGGGT CAAGGAACCT CAGTCACCGT CTCCTCAGCT    4320

AGCACCAAGG GCCCATCCGT CTTCCCCCTG GCGCCCTGCT CCAGGAGGAC CTCCGAGAGC    4380

ACAGCCGCCC TGGGCTGCCT GGTCAAGGAC TACTTCCCCG AACCGGTGAC GGTGTCGTGG    4440

AACTCAGGCG CCCTGACCAG CGGCGTGCAC ACCTTCCCGG CTGTCCTACA GTCCTCAGGA    4500

CTCTACTCCC TCAGCAGCGT GGTGACCGTG CCCTCCAGCA GCTTGGGCAC GAAGACCTAC    4560

ACCTGCAACG TAGATCACAA GCCCAGCAAC ACCAAGGTGG ACAAGAGAGT TGGTGAGAGG    4620

CCAGCACAGG GAGGGAGGGT GTCTGCTGGA AGCCAGGCTC AGCCCTCCTG CCTGGACGCA    4680

CCCCGGCTGT GCAGCCCCAG CCCAGGGCAG CAAGGGCCCC ATCTGTCTCC TCACCCGGAG    4740

GCCTCTGACC ACCCCACTCA TGCTCAGGGA GAGGGTCTTC TGGATTTTTC CACCAGGCTC    4800

CCGGCACCAC AGGCTGGATG CCCCTACCCC AGGCCCTGCG CATACAGGGC AGGTGCTGCG    4860

CTCAGACCTG CCAAGAGCCA TATCCGGGAG GACCCTGCCC CTGACCTAAG CCCACCCCAA    4920

AGGCCAAACT CTCCACTCCC TCAGCTCAGA CACCTTCTCT CCTCCCAGAT CTGAGTAACT    4980

CCCAATCTTC TCTCTGCAGA GTCCAAATAT GGTCCCCCAT GCCCATCATG CCCAGGTAAG    5040

CCAACCCAGG CCTCGCCCTC CAGCTCAAGG CGGGACAGGT GCCCTAGAGT AGCCTGCATC    5100
```

```
CAGGGACAGG CCCCAGCCGG GTGCTGACGC ATCCACCTCC ATCTCTTCCT CAGCACCTGA    5160
GTTCCTGGGG GGACCATCAG TCTTCCTGTT CCCCCCAAAA CCCAAGGACA CTCTCATGAT    5220
CTCCCGGACC CCTGAGGTCA CGTGCGTGGT GGTGGACGTG AGCCAGGAAG ACCCCGAGGT    5280
CCAGTTCAAC TGGTACGTGG ATGGCGTGGA GGTGCATAAT GCCAAGACAA AGCCGCGGGA    5340
GGAGCAGTTC AACAGCACGT ACCGTGTGGT CAGCGTCCTC ACCGTCCTGC ACCAGGACTG    5400
GCTGAACGGC AAGGAGTACA AGTGCAAGGT CTCCAACAAA GGCCTCCCGT CCTCCATCGA    5460
GAAAACCATC TCCAAAGCCA AAGGTGGGAC CCACGGGGTG CGAGGGCCAC ACGGACAGAG    5520
GCCAGCTCGG CCCACCCTCT GCCCTGGGAG TGACCGCTGT GCCAACCTCT GTCCCTACAG    5580
GGCAGCCCCG AGAGCCACAG GTGTACACCC TGCCCCCATC CCAGGAGGAG ATGACCAAGA    5640
ACCAGGTCAG CCTGACCTGC CTGGTCAAAG GCTTCTACCC CAGCGACATC GCCGTGGAGT    5700
GGGAGAGCAA TGGGCAGCCG GAGAACAACT ACAAGACCAC GCCTCCCGTG CTGGACTCCG    5760
ACGGCTCCTT CTTCCTCTAC AGCAGGCTAA CCGTGGACAA GAGCAGGTGG CAGGAGGGGA    5820
ATGTCTTCTC ATGCTCCGTG ATGCATGAGG CTCTGCACAA CCACTACACG CAGAAGAGCC    5880
TCTCCCTGTC TCCGGGTAAA TGAGTGCCAG GGCCGGCAAG CCCCCGCTCC CCGGGCTCTC    5940
GGGGTCGCGC GAGGATGCTT GGCACGTACC CCGTCTACAT ACTTCCCAGG CACCCAGCAT    6000
GGAAATAAAG CACCCACCAC TGCCCTGGGC CCCTGTGAGA CTGTGATGGT TCTTTCCACG    6060
GGTCAGGCCG AGTCTGAGGC CTGAGTGACA TGAGGGAGGC AGAGCGGGTC CCACTGTCCC    6120
CACACTGGNN NNNNNNNNNN NNNNNNNNNN NNNNNNNNNN NNNNNNNNNN NNNNNNNNNN    6180
NNNNNNNNNN NNNNNNNNNN NNNNNNNNNN NNNNNNNNNN NNNNNNNNNN NNNNNNNNNN    6240
NNNNNNNNNN NNNNNNNNNN NNNNNNNNNN NNNNNNNNNN NNNNNNNNNN NNNNNNNNNN    6300
NNNNNNNNNN NNNNNNNNNN NNNNNNNNNC AGCTGNNNNN NNNNNNNNNN NNNNNNNNNN    6360
NNNNNNNNNN NNNNNNNNNN NNNNNNNNNN NNNNNNNNNN NNNNNNNNNN NNNNNNNNNN    6420
NNNNNNNNNN NNNNNNNNNN NNNNNNNNNN NNNNNNNNNN NNNNNNNNNN NNNNNNNNNN    6480
NNNNNNNNNN NNNNNNNNNN NNNNNNNNNN NNNNNNNNNN NNNNNNNNNN NNNNNNNNNN    6540
NNNNNNNNNN NNNNNNNNNN NNNNNNNNNN NNNNNNNNNN NNNNNNNNNN NNNNNNNNNN    6600
NNNNNNNNNN NNNNNNNNNN NNNNNNNNNN NNNNNGGATC CAGACATGAT AAGATACATT    6660
GATGAGTTTG ACAAACCAC AACTAGAATG CAGTGAAAAA AATGCTTTAT TTGTGAAATT     6720
TGTGATGCTA TTGCTTTATT TGTAACCATT ATAAGCTGCA ATAAACAAGT TAACAACAAC    6780
AATTGCATTC ATTTTATGTT TCAGGTTCAG GGGGAGGTGT GGGAGGTTTT TTAAAGCAAG    6840
TAAAACCTCT ACAAATGTGG TATGGCTGAT TATGATCTCT AGTCAAGGCA CTATACATCA    6900
AATATTCCTT ATTAACCCCT TTACAAATTA AAAAGCTAAA GGTACACAAT TTTTGAGCAT    6960
AGTTATTAAT AGCAGACACT CTATGCCTGT GTGGAGTAAG AAAAAACAGT ATGTTATGAT    7020
TATAACTGTT ATGCCTACTT ATAAAGGTTA CAGAATATTT TTCCATAATT TCCTTGTATA    7080
GCAGTGCAGC TTTTTCCTTT GTGGTGTAAA TAGCAAAGCA AGCAAGAGTT CTATTACTAA    7140
ACACAGCATG ACTCAAAAAA CTTAGCAATT CTGAAGGAAA GTCCTTGGGG TCTTCTACCT    7200
TTCTCTTCTT TTTTGGAGGA GTAGAATGTT GAGAGTCAGC AGTAGCCTCA TCATCACTAG    7260
ATGGCATTTC TTCTGAGCAA AACAGGTTTT CCTCATTAAA GGCATTCCAC CACTGCTCCC    7320
ATTCATCAGT TCCATAGGTT GGAATCTAAA ATACACAAAC AATTAGAATC AGTAGTTTAA    7380
CACATTATAC ACTTAAAAAT TTTATATTTA CCTTATAGCT TTAAATCTCT GTAGGTAGTT    7440
TGTCCAATTA TGTCACACCA CAGAAGTAAG GTTCCTTCAC AAAGATCCGG NNNNNNNNNN    7500
```

```
NNNNNNNNNN NNNNNTCATG CTTGCTCCTT GAGGGCGTTA ACGCGCAAGG TAACGGCATT      7560

TTTATGGGCG GTCAGACGTT CGGCGGCGGC CAGTGTTTCT ATGGTTGAAG CCACCGCGGA      7620

GAACCCCTCT TTCGACAGTT CCTGTACGGT CATACGCTTC TGGAAATCTG CCAGCCCGAG      7680

GCTGGAACAG GTGGCGGTGT AACCGTAAGT CGGTAGAACG TGGTTGGTTC CGGAGGCGTA      7740

ATCACCTGCC GATTCCGGTG ACCAGTCACC AAGAAATACC GAACCGGCGC TGGTGATGCT      7800

ATCGACCAGT TCACGGGCGT TGCGGGTCTG AATGATCAGG TGCTCCGGGC CGTACTGATT      7860

AGAGATCTCC ACGCACTGCG CTGAATCTTT AGTCACGATC AGGCGGCTGG CGTTCAGTGC      7920

CTGGCGGGCG GTTTCGGCAC GCGGCAGTTC CGCCAGTTGG CGTTCGACGG CCTCGGCAAC      7980

GCGACGCGCC ATATCAGCAG CGGGCGTCAG TAAAATCACC TGTGAGTCCG GCCGTGTTC       8040

AGCCTGAGAG AGCAAATCAG AAGCCACGAA ATCCGGCGTT GCGCCGCTGT CAGCAATCAC      8100

CAGCACTTCC GACGGGCCTG CGGGCATATC GATCTCCGCA CCGTCCAGAC GCTGGCTCAC      8160

CTGACGTTTC GCTTCGGTGA CAAAGGCGTT ACCCGGCCCG AAGATTTTGT CCACTTTTGG      8220

CACGGATTCC GTACCAAACG CCAGTGCGGC AATGGCCTGT GCGCCGCCGA CGTTGAACAC      8280

GTCCTGCACA CCGCACAGCT GCGCCGCATA AAGGATCTCA TCGGCAATCG GCGGCGGTGA      8340

GCACAGCACC ACTTTTTTAC AGCCCGCAAT ACGCGCCGGA GTCGCCAGCA TTAATACCGT      8400

TGAGAAGAGC GGGGCGGAGC CGCCAGGAAT ATACAACCCA ACTGAAGCTA CCGGACGCGT      8460

GACCTGCTGG CAACGCACGC CTGGCTGCGT TTCTACATCT ACCGGCGGCA GTTTTTGCGC      8520

AGTGTGGAAG GTTTCAATAT TCTTTACTGC CACCGCCATC GCCTGTTTTA GCTCGTCGCT      8580

CAGGCGTTCG CTGGCGGCGG CGATCTCCTC TGCAGACACC TTCAGCGCGG TAACCGTGGT      8640

TTTATCAAAC TTCGCGCTGT ATTCCCGCAG GGCCTCATCG CCGCGTGCTT TCACGTTATC      8700

GAGAATATCG TTAACAGTGC GGGTAATGCT TTCAGAGGCG GAAATCGCCG GGCGCGTTAA      8760

CAGCTGGCGT TGTTGCACCG CAGTACAGCT ATTCCAGTCA ATGATTGTGT TAAAGCTCAT      8820

NNNNCCGGAT CAGCTTTTTG CAAAAGCCTA GGCCTCCAAA AAAGCCTCCT CACTACTTCT      8880

GGAATAGCTC AGAGGCCGAG GCGCCTCGGC CTCTGCATAA ATAAAAAAAA TTAGTCAGCC      8940

ATGGGGCGGA GAATGGGCGG AACTGGGCGG AGTTAGGGGC GGGATGGGCG GAGTTAGGGG      9000

CGGGACTATG GTTGCTGACT AATTGAGATG CATGCTTTGC ATACTTCTGC CTGCTGGGGA      9060

GCCTGGGGAC TTTCCACACC TGGTTGCTGA CTAATTGAGA TGCATGCTTT GCATACTTCT      9120

GCCTGCTGGG GAGCCTGGGG ACTTTCCACA CCCTAACTGA CACACATTCC ACAGCTGCCT      9180

CGCGCGTTTC GGTGATGACG GTGAAAACCT CTGACACATG CAGCTCCCGG AGACGGTCAC      9240

AGCTTGTCTG TAAGCGGATG CCGGGAGCAG ACAAGCCCGT CAGGGCGCGT CAGCGGGTGT      9300

TGGCGGGTGT CGGGGCGCAG CCATGACCCA GTCACGTAGC GATAGCGGAG TGTATACTGG      9360

CTTAACTATG CGGCATCAGA GCAGATTGTA CTGAGAGTGC ACCATATGCG GTGTGAAATA      9420

CCGCACAGAT GCGTAAGGAG AAAATACCGC ATCAGGCGCT CTTCCGCTTC CTCGCTCACT      9480

GACTCGCTGC GCTCGGTCGT TCGGCTGCGG CGAGCGGTAT CAGCTCACTC AAAGGCGGTA      9540

ATACGGTTAT CCACAGAATC AGGGGATAAC GCAGGAAAGA ACATGTGAGC AAAAGGCCAG      9600

CAAAAGGCCA GGAACCGTAA AAAGGCCGCG TTGCTGGCGT TTTTCCATAG GCTCCGCCCC      9660

CCTGACGAGC ATCACAAAAA TCGACGCTCA AGTCAGAGGT GGCGAAACCC GACAGGACTA      9720

TAAAGATACC AGGCGTTTCC CCCTGGAAGC TCCCTCGTGC GCTCTCCTGT TCCGACCCTG      9780

CCGCTTACCG GATACCTGTC CGCCTTTCTC CCTTCGGGAA GCGTGGCGCT TTCTCAATGC      9840

TCACGCTGTA GGTATCTCAG TTCGGTGTAG GTCGTTCGCT CCAAGCTGGG CTGTGTGCAC      9900
```

```
GAACCCCCCG TTCAGCCCGA CCGCTGCGCC TTATCCGGTA ACTATCGTCT TGAGTCCAAC    9960

CCGGTAAGAC ACGACTTATC GCCACTGGCA GCAGCCACTG GTAACAGGAT TAGCAGAGCG   10020

AGGTATGTAG GCGGTGCTAC AGAGTTCTTG AAGTGGTGGC CTAACTACGG CTACACTAGA   10080

AGGACAGTAT TTGGTATCTG CGCTCTGCTG AAGCCAGTTA CCTTCGGAAA AGAGTTGGT    10140

AGCTCTTGAT CCGGCAAACA AACCACCGCT GGTAGCGGTG GTTTTTTTGT TTGCAAGCAG   10200

CAGATTACGC GCAGAAAAAA AGGATCTCAA GAAGATCCTT TGATCTTTTC TACGGGGTCT   10260

GACGCTCAGT GGAACGAAAA CTCACGTTAA GGGATTTTGG TCATGAGATT ATCAAAAAGG   10320

ATCTTCACCT AGATCCTTTT AAATTAAAAA TGAAGTTTTA AATCAATCTA AGTATATAT    10380

GAGTAAACTT GGTCTGACAG TTACCAATGC TTAATCAGTG AGGCACCTAT CTCAGCGATC   10440

TGTCTATTTC GTTCATCCAT AGTTGCCTGA CTCCCCGTCG TGTAGATAAC TACGATACGG   10500

GAGGGCTTAC CATCTGGCCC CAGTGCTGCA ATGATACCGC GAGACCCACG CTCACCGGCT   10560

CCAGATTTAT CAGCAATAAA CCAGCCAGCC GGAAGGGCCG AGCGCAGAAG TGGTCCTGCA   10620

ACTTTATCCG CCTCCATCCA GTCTATTAAT TGTTGCCGGG AAGCTAGAGT AAGTAGTTCG   10680

CCAGTTAATA GTTTGCGCAA CGTTGTTGCC ATTGCTGCAG GCATCGTGGT GTCACGCTCG   10740

TCGTTTGGTA TGGCTTCATT CAGCTCCGGT TCCCAACGAT CAAGGCGAGT TACATGATCC   10800

CCCATGTTGT GCAAAAAAGC GGTTAGCTCC TTCGGTCCTC CGAT                    10844

(2) INFORMATION FOR SEQ ID NO:42:

(i) SEQUENCE CHARACTERISTICS:
        (A) LENGTH: 235 amino acids
        (B) TYPE: amino acid
        (D) TOPOLOGY: linear (ii) MOLECULE TYPE: protein (v) FRAGMENT TYPE: N-terminal (xi) SEQUENCE DESCRIPTION: SEQ ID NO:42:

Met Glu Trp Ser Trp Val Met Leu Phe Leu Leu Ser Gly Thr Ala Gly
1               5                   10                  15

Val Arg Ser Glu Val Gln Leu Gln Gln Ser Gly Pro Glu Leu Val Lys
                20                  25                  30

Pro Gly Ala Ser Met Lys Ile Ser Cys Lys Ala Ser Gly Tyr Ser Phe
            35                  40                  45

Thr Gly Tyr Thr Met Asn Trp Val Lys Gln Ser His Gly Glu Asn Leu
        50                  55                  60

Glu Trp Ile Gly Arg Ile Asn Pro His Asn Gly Gly Thr Asp Tyr Asn
65                  70                  75                  80

Gln Lys Phe Lys Asp Lys Ala Pro Leu Thr Val Asp Lys Ser Ser Asn
                85                  90                  95

Thr Ala Tyr Met Glu Leu Leu Ser Leu Thr Ser Glu Asp Ser Ala Val
            100                 105                 110

Tyr Tyr Cys Ala Arg Gly Tyr Tyr Tyr Ser Leu Asp Tyr Trp Gly
        115                 120                 125

Gln Gly Thr Ser Val Thr Val Ser Ser Ala Ser Thr Lys Gly Pro Ser
    130                 135                 140

Val Phe Pro Leu Ala Pro Cys Ser Arg Arg Thr Ser Glu Ser Thr Ala
145                 150                 155                 160

Ala Leu Gly Cys Leu Val Lys Asp Tyr Phe Pro Glu Pro Val Thr Val
                165                 170                 175
```

```
Ser Trp Asn Ser Gly Ala Leu Thr Ser Gly Val His Thr Phe Pro Ala
            180                 185                 190

Val Leu Gln Ser Ser Gly Leu Tyr Ser Leu Ser Ser Val Val Thr Val
        195                 200                 205

Pro Ser Ser Leu Gly Thr Lys Thr Tyr Thr Cys Asn Val Asp His
    210                 215                 220

Lys Pro Ser Asn Thr Lys Val Asp Lys Arg Val
225                 230                 235

(2) INFORMATION FOR SEQ ID NO:43:

(i) SEQUENCE CHARACTERISTICS:
        (A) LENGTH: 12 amino acids
        (B) TYPE: amino acid
        (D) TOPOLOGY: linear (ii) MOLECULE TYPE: protein (v) FRAGMENT TYPE: internal (xi) SEQUENCE DESCRIPTION: SEQ ID NO:43:

Glu Ser Lys Tyr Gly Pro Pro Cys Pro Ser Cys Pro
1               5                   10

(2) INFORMATION FOR SEQ ID NO:44:

(i) SEQUENCE CHARACTERISTICS:
        (A) LENGTH: 110 amino acids
        (B) TYPE: amino acid
        (D) TOPOLOGY: linear (ii) MOLECULE TYPE: protein (v) FRAGMENT TYPE: internal (xi) SEQUENCE DESCRIPTION: SEQ ID NO:44:

Ala Pro Glu Phe Leu Gly Gly Pro Ser Val Phe Leu Phe Pro Pro Lys
1               5                   10                  15

Pro Lys Asp Thr Leu Met Ile Ser Arg Thr Pro Glu Val Thr Cys Val
            20                  25                  30

Val Val Asp Val Ser Gln Glu Asp Pro Glu Val Gln Phe Asn Trp Tyr
        35                  40                  45

Val Asp Gly Val Glu Val His Asn Ala Lys Thr Lys Pro Arg Glu Glu
50                  55                  60

Gln Phe Asn Ser Thr Tyr Arg Val Val Ser Val Leu Thr Val Leu His
65                  70                  75                  80

Gln Asp Trp Leu Asn Gly Lys Glu Tyr Lys Cys Lys Val Ser Asn Lys
                85                  90                  95

Gly Leu Pro Ser Ser Ile Glu Lys Thr Ile Ser Lys Ala Lys
            100                 105                 110

(2) INFORMATION FOR SEQ ID NO:45:

(i) SEQUENCE CHARACTERISTICS:
        (A) LENGTH: 107 amino acids
        (B) TYPE: amino acid
        (D) TOPOLOGY: linear (ii) MOLECULE TYPE: protein (v) FRAGMENT TYPE: internal (xi) SEQUENCE DESCRIPTION: SEQ ID NO:45:

Gly Gln Pro Arg Glu Pro Gln Val Tyr Thr Leu Pro Pro Ser Gln Glu
1               5                   10                  15
```

```
Glu Met Thr Lys Asn Gln Val Ser Leu Thr Cys Leu Val Lys Gly Phe
            20                  25                  30

Tyr Pro Ser Asp Ile Ala Val Glu Trp Glu Ser Asn Gly Gln Pro Glu
            35                  40                  45

Asn Asn Tyr Lys Thr Thr Pro Pro Val Leu Asp Ser Asp Gly Ser Phe
 50                      55                  60

Phe Leu Tyr Ser Arg Leu Thr Val Asp Lys Ser Arg Trp Gln Glu Gly
 65                  70                  75                  80

Asn Val Phe Ser Cys Ser Val Met His Glu Ala Leu His Asn His Tyr
                 85                  90                  95

Thr Gln Lys Ser Leu Ser Leu Ser Pro Gly Lys
            100                 105

(2) INFORMATION FOR SEQ ID NO:46:

(i) SEQUENCE CHARACTERISTICS:
        (A) LENGTH: 434 amino acids
        (B) TYPE: amino acid
        (D) TOPOLOGY: linear (ii) MOLECULE TYPE: protein (ix) FEATURE:
        (A) NAME/KEY: Protein
        (B) LOCATION: 1..434
        (D) OTHER INFORMATION: /note= "Translation from
            complementary DNA."

(xi) SEQUENCE DESCRIPTION: SEQ ID NO:46:

Met Ser Phe Asn Thr Ile Ile Asp Trp Asn Ser Cys Thr Ala Val Gln
 1               5                  10                  15

Gln Arg Gln Leu Leu Thr Arg Pro Ala Ile Ser Ala Ser Glu Ser Ile
            20                  25                  30

Thr Arg Thr Val Asn Asp Ile Leu Asp Asn Val Lys Ala Arg Gly Asp
            35                  40                  45

Glu Ala Leu Arg Glu Tyr Ser Ala Lys Phe Asp Lys Thr Thr Val Thr
 50                  55                  60

Ala Leu Lys Val Ser Ala Glu Glu Ile Ala Ala Ala Ser Glu Arg Leu
 65                  70                  75                  80

Ser Asp Glu Leu Lys Gln Ala Met Ala Val Ala Val Lys Asn Ile Glu
                 85                  90                  95

Thr Phe His Thr Ala Gln Lys Leu Pro Pro Val Asp Val Glu Thr Gln
            100                 105                 110

Pro Gly Val Arg Cys Gln Gln Val Thr Arg Pro Val Ala Ser Val Gly
            115                 120                 125

Leu Tyr Ile Pro Gly Gly Ser Ala Pro Leu Phe Ser Thr Val Leu Met
 130                 135                 140

Leu Ala Thr Pro Ala Arg Ile Ala Gly Cys Lys Lys Val Val Leu Cys
145                 150                 155                 160

Ser Pro Pro Pro Ile Ala Asp Glu Ile Leu Tyr Ala Ala Gln Leu Cys
                 165                 170                 175

Gly Val Gln Asp Val Phe Asn Val Gly Gly Ala Gln Ala Ile Ala Ala
            180                 185                 190

Leu Ala Phe Gly Thr Glu Ser Val Pro Lys Val Asp Lys Ile Phe Gly
            195                 200                 205

Pro Gly Asn Ala Phe Val Thr Glu Ala Lys Arg Gln Val Ser Gln Arg
 210                 215                 220

Leu Asp Gly Ala Glu Ile Asp Met Pro Ala Gly Pro Ser Glu Val Leu
```

```
225                 230                 235                 240
Val Ile Ala Asp Ser Gly Ala Thr Pro Asp Phe Val Ala Ser Asp Leu
                245                 250                 255
Leu Ser Gln Ala Glu His Gly Pro Asp Ser Gln Val Ile Leu Leu Thr
                260                 265                 270
Pro Ala Ala Asp Met Ala Arg Arg Val Ala Glu Ala Val Glu Arg Gln
            275                 280                 285
Leu Ala Glu Leu Pro Arg Ala Glu Thr Ala Arg Gln Ala Leu Asn Ala
        290                 295                 300
Ser Arg Leu Ile Val Thr Lys Asp Ser Ala Gln Cys Val Glu Ile Ser
305                 310                 315                 320
Asn Gln Tyr Gly Pro Glu His Leu Ile Ile Gln Thr Arg Asn Ala Arg
                325                 330                 335
Glu Leu Val Asp Ser Ile Thr Ser Ala Gly Ser Val Phe Leu Gly Asp
                340                 345                 350
Trp Ser Pro Glu Ser Ala Gly Asp Tyr Ala Ser Gly Thr Asn His Val
            355                 360                 365
Leu Pro Thr Tyr Gly Tyr Thr Ala Thr Cys Ser Ser Leu Gly Leu Ala
        370                 375                 380
Asp Phe Gln Lys Arg Met Thr Val Gln Glu Leu Ser Lys Glu Gly Phe
385                 390                 395                 400
Ser Ala Val Ala Ser Thr Ile Glu Thr Leu Ala Ala Ala Glu Arg Leu
                405                 410                 415
Thr Ala His Lys Asn Ala Val Thr Leu Arg Val Asn Ala Leu Lys Glu
                420                 425                 430
Gln Ala
```